(12) United States Patent
Hettmann et al.

(10) Patent No.: US 9,988,462 B2
(45) Date of Patent: *Jun. 5, 2018

(54) MATERIAL AND METHODS FOR TREATING OR PREVENTING HER-3 ASSOCIATED DISEASES

(71) Applicants: Daiichi Sankyo Europe GmbH, Munich (DE); AMGEN, INC., Thousand Oaks, CA (US)

(72) Inventors: Thore Hettmann, Munich (DE); Daniel J. Freeman, Newbury Park, CA (US); Robert Radinsky, Thousand Oaks, CA (US); Mike Rothe, Krailling (DE)

( * ) Notice: Subject to any disclaimer, the term of this patent is extended or adjusted under 35 U.S.C. 154(b) by 1 day.

This patent is subject to a terminal disclaimer.

(21) Appl. No.: 15/000,005

(22) Filed: Jan. 18, 2016

(65) Prior Publication Data

US 2016/0222126 A1 Aug. 4, 2016

Related U.S. Application Data

(60) Continuation of application No. 13/870,796, filed on Apr. 25, 2013, now Pat. No. 9,803,025, which is a division of application No. 12/944,764, filed on Nov. 12, 2010, now Pat. No. 9,101,760, application No. 15/000,005, filed on Jan. 18, 2016, which is a continuation-in-part of application No. 12/365,784, filed on Feb. 4, 2009, now Pat. No. 9,249,230, which is a division of application No. 11/649,722, filed on Jan. 3, 2007, now Pat. No. 7,705,130.

(60) Provisional application No. 61/261,149, filed on Nov. 13, 2009, provisional application No. 60/755,103, filed on Dec. 30, 2005.

(51) Int. Cl.
| | |
|---|---|
| A61K 39/395 | (2006.01) |
| A61K 51/10 | (2006.01) |
| C07K 16/40 | (2006.01) |
| A61K 45/06 | (2006.01) |
| C07K 16/28 | (2006.01) |
| C07K 16/32 | (2006.01) |
| A61N 5/10 | (2006.01) |
| A61K 47/68 | (2017.01) |
| A61K 31/506 | (2006.01) |
| A61K 31/4709 | (2006.01) |
| A61K 31/5377 | (2006.01) |
| A61K 31/496 | (2006.01) |
| A61K 39/00 | (2006.01) |

(52) U.S. Cl.
CPC ........... *C07K 16/40* (2013.01); *A61K 39/395* (2013.01); *A61K 39/3955* (2013.01); *A61K 39/39558* (2013.01); *A61K 45/06* (2013.01); *A61K 47/6871* (2017.08); *A61N 5/10* (2013.01); *C07K 16/2863* (2013.01); *C07K 16/32* (2013.01); *A61K 31/4709* (2013.01); *A61K 31/496* (2013.01); *A61K 31/506* (2013.01); *A61K 31/5377* (2013.01); *A61K 2039/505* (2013.01); *A61K 2039/507* (2013.01); *C07K 2317/21* (2013.01); *C07K 2317/24* (2013.01); *C07K 2317/31* (2013.01); *C07K 2317/54* (2013.01); *C07K 2317/55* (2013.01); *C07K 2317/565* (2013.01); *C07K 2317/622* (2013.01); *C07K 2317/626* (2013.01); *C07K 2317/76* (2013.01); *C07K 2317/92* (2013.01)

(58) Field of Classification Search
CPC ............ A61K 39/395; A61K 39/39533; A61K 39/39558; A61K 2039/507; A61K 47/6801; A61K 47/6849; A61K 51/10; A61K 51/1096; C07K 16/2863
See application file for complete search history.

(56) References Cited

U.S. PATENT DOCUMENTS

| | | | |
|---|---|---|---|
| 4,399,216 | A | 8/1983 | Axel et al. |
| 4,740,461 | A | 4/1988 | Kaufman et al. |
| 4,816,397 | A | 3/1989 | Boss et al. |
| 4,816,567 | A | 3/1989 | Cabilly et al. |
| 4,912,040 | A | 3/1990 | Kaufman et al. |
| 4,959,455 | A | 9/1990 | Clark et al. |
| 5,183,884 | A | 2/1993 | Kraus et al. |
| 5,480,968 | A | 1/1996 | Kraus et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,591,669 | A | 1/1997 | Krimpenfort et al. |
| 5,643,763 | A | 2/1997 | Dunn et al. |
| 5,612,205 | A | 3/1997 | Kay et al. |
| 5,625,126 | A | 4/1997 | Lonberg et al. |

(Continued)

FOREIGN PATENT DOCUMENTS

| | | | |
|---|---|---|---|
| EP | 0463151 | B1 | 7/1991 |
| EP | 546073 | B1 | 3/1992 |

(Continued)

OTHER PUBLICATIONS

Carter P. (2001) Nature Reviews 1:118-129.

(Continued)

*Primary Examiner* — Misook Yu
*Assistant Examiner* — Anne L Holleran

(57) ABSTRACT

Described herein are materials and methods for treating subjects having a HER-3 associated disease, by administering a first agent that binds to HER-3, in combination with a second agent that binds and/or inhibits another member of the HER family. The first and the second agent may be a biologic, such as an antigen-binding protein, or a small molecular tyrosine kinase inhibitor, for example.

31 Claims, 21 Drawing Sheets

(56) References Cited

U.S. PATENT DOCUMENTS

| | | | |
|---|---|---|---|
| 5,625,825 | A | 4/1997 | Restoker et al. |
| 5,633,425 | A | 5/1997 | Lonberg et al. |
| 5,661,016 | A | 8/1997 | Lonberg et al. |
| 5,721,367 | A | 2/1998 | Kay et al. |
| 5,770,429 | A | 5/1998 | Lonberg et al. |
| 5,766,863 | A | 6/1998 | Godowski et al. |
| 5,789,215 | A | 8/1998 | Berns et al. |
| 5,789,650 | A | 8/1998 | Lonberg et al. |
| 5,814,318 | A | 9/1998 | Lonberg et al. |
| 5,837,815 | A | 11/1998 | Lev et al. |
| 5,874,299 | A | 2/1999 | Lonberg et al. |
| 5,877,397 | A | 3/1999 | Lonberg et al. |
| 5,916,771 | A | 6/1999 | Hori et al. |
| 5,939,598 | A | 8/1999 | Kucherlapati et al. |
| 5,968,511 | A | 10/1999 | Akita et al. |
| 5,981,175 | A | 11/1999 | Loring et al. |
| 6,023,010 | A | 2/2000 | Krimpenfort et al. |
| 6,075,181 | A | 6/2000 | Kucherlapati et al. |
| 6,114,595 | A | 9/2000 | Moore |
| 6,150,584 | A | 11/2000 | Kucherlapati et al. |
| 6,162,963 | A | 12/2000 | Kucherlapati et al. |
| 6,207,418 | B1 | 3/2001 | Hori et al. |
| 6,255,458 | B1 | 7/2001 | Lonberg et al. |
| 6,833,268 | B1 | 12/2004 | Green et al. |
| 6,949,245 | B1 | 9/2005 | Silwkowski |
| 7,285,649 | B2 | 10/2007 | Akita et al. |
| 7,705,130 | B2 | 4/2010 | Rothe et al. |
| 2002/0064805 | A1 | 5/2002 | Akita et al. |
| 2003/0217373 | A1 | 11/2003 | Green et al. |
| 2004/0050683 | A1 | 3/2004 | Olivier |
| 2004/0071696 | A1 | 4/2004 | Adams et al. |
| 2008/0124345 | A1 | 5/2008 | Rothe et al. |

FOREIGN PATENT DOCUMENTS

| | | |
|---|---|---|
| JP | 3 068 180 B2 | 3/1991 |
| JP | 3 068 506 B2 | 3/1991 |
| JP | 3 068 507 B2 | 3/1991 |
| WO | WO 92/03918 | 3/1992 |
| WO | WO 92/22645 | 12/1992 |
| WO | WO 92/22647 | 12/1992 |
| WO | 9402602 | 2/1994 |
| WO | WO 0503707 | 6/1994 |
| WO | WO 96/34096 | 10/1996 |
| WO | WO 97/13852 | 4/1997 |
| WO | WO 97/35885 A1 | 10/1997 |
| WO | WO 98/24884 | 6/1998 |
| WO | WO 98/24893 | 6/1998 |
| WO | WO9826054 A2 | 6/1998 |
| WO | WO 98/50433 | 11/1998 |
| WO | WO0040971 A1 | 7/2000 |
| WO | WO 00/76310 | 12/2000 |
| WO | WO 00/78347 | 12/2000 |
| WO | WO0078347 A1 | 12/2000 |
| WO | WO0100245 A2 | 1/2001 |
| WO | WO0115730 A1 | 3/2001 |
| WO | WO 03013602 | 2/2003 |
| WO | WO 03048730 A2 | 6/2003 |
| WO | WO 03080835 | 10/2003 |
| WO | WO 04011900 | 2/2004 |
| WO | WO 2004/050683 | 6/2004 |
| WO | WO 04091384 | 10/2004 |
| WO | 2007077028 A2 | 7/2007 |
| WO | WO2007077028 A2 | 7/2007 |
| WO | WO 2008/100624 A2 | 8/2008 |
| WO | WO 2011/022727 A2 | 2/2011 |

OTHER PUBLICATIONS

Ethier et al. (1996) Cancer Research 56:899-907.
Fendly et al. (1990) Cancer Research 50:1550-1558.
Fiddes et al. (1995) Cell Growth and Differentiation 6:1567-1577.
Gammet et al. (1995) J. Biol. Chem. 270(32):19022-19027.
Levi et al. (1995) J. Neurosci. 15:1329-1340.
Lewis et al. (1996) Cancer Res. 56:1457-1465.
Presta et al. (1992) Curr. Op. Struct. Biol. 2:593-596.
Rajkumar et al. (1994) Breast Cancer Research and Treatment 29:3-9.
Hamann et al. (2002) Bioconjug. Chem. 13:40-46.
Hazra et al. (1994) Cell Biophys. 24-25:1-7.
Janmaat et al. (2005) Mol. Pharmacol. 68:502-510.
Jimeno et al. (2006) J. Translational Med. 4:3.
Kraus et al. (1989) Proc. Natl. Acad. Sci. US 86:9193-9197.
Kraus et al. (1993) Proc. Natl. Acad. Sci. US 90:2900-2904.
Li et al. (1999) Int. J. Mol. Med. 3:647-53.
Liu et al. (1996) Proc. Natl. Acad. Sci. US 93:8618-8623.
Mandler et al. (2000) J. Natl. Cancer Inst. 92:1549-1551.
Otani et al. (2000) Jpn. J. Cancer Res. 91:837-44.
Plowman et al. (1990) Proc. Natl. Acad. Sci. US 87:4905-4909.
Hsieh et al. (2007) British Journal of Cancer 97:453-457.
Treder et al. (2008) European Journal of Cancer (Suppl.) 6(12):99; Poster 309 "Fully human anti-HER3 mAb U3-1287 (AMG 888) demonstrates unique in vitro and in vivo activities versus other HER family inhibitors in NSCLC models".
Witzig (2001) Cancer Chemother. Pharmacol. 48 (Suppl. 1):91-95.
Freeman et al., AACR Meeting Abstracts Online, 2008, URL<http://www.aacrmeetingabstracts.org/cgi/content/meeting_abstract/2008/1_Annual_Meeting/LB-21 ?maxtoshow=&hits I O&RESULTFORMAT=&fulltext=LB-21&andorexactfulltext=and &searchid=I&FIRSTINDEX=O&sortspec=relevance &resourcetype=HWCIT>[Sep. 26, 2014 search]. Cancer Res., 68(9): Abstract LB-21, AACR, Apr. 2008.
Gadducci et al., Critical Reviews in Oncology/Hematology, 2006, vol. 58, p. 242-256.
Iorio et al., Cancer Research, Mar. 15, 2009, vol. 69, No. 6, p. 2195-2200.
Merrimack Pharmaceuticals: "A study of MM-121 combination therapy in patients with advanced non-small cell lung cancer", ClinicaiTrials.gov, Oct. 13, 2009 (Oct. 13, 2009), Retrieved from the Internet: URL:http://www.clinicaltrials.gov/ct2/show/record/NCT00994123? term=MM-121 &rank=1[retrieved on Jun. 25, 2014] ; -&"View of NCT00994123 on 2009_10_13",ClinicaiTrials.gov archive Oct. 2009 (Oct. 13, 2009), Retrieved from the Internet: URL:http://clinicaltrials.gov/archive/NCT00994123/2009_10_13 [retrieved on Jun. 25, 2014].
Alberts, Bruce, Molekularbiologie der Zelle, 1995, 3rd ed., pp. 897-899.
Baselga et al., 2009, Nature Reviews Cancer 9:463-475.
Bohn et al., 2000, Journal of Neurochemistry 74:564-573.
Bowie et al., 1990, Science 247:1306-1310.
Braasch and Corey, 2002, Biochemistry 41:4503-4510.
Burgess et al., 1990, J. Cell Biology 111:2129-2138.
Dikic et al., 1996, Nature 383:547-550.
Emkey et al., 1997, The Journal of Biological Chemistry 272:31182-31189.
Fiddes Rodney et al., 1998, Oncogene 16:2803-2813.
Gschwind, Fischer and Ullrich, 2004, Nature Reviews: Cancer 4:361-370.
Hobbs et al., 2004, J. Invest. Dermatol. 123:503-515.
Hurwitz et al., 1995, Proc. Natl. Acad. Sci. 92:3353-3357.
Ohta et al., 1995, Igaku No Ayumi (Progress in Medicine) 175:701-704.
Johansen et al., 2005, Br. J. Dermatol. 152:37-42.
Kraus et al., 1989, Proc. Natl. Acad. Sci. USA 86:9193-9197.
Lazar et al., 1988, Molecular and Cellular Biology 8:1247-1252.
Noshinkei Geka Journal (Journal of Neurosurgery) 8, No. 4, p. 279, Apr. 20, 1999.
Opalinska and Gerwitz, 2002, Nature Reviews 1:503-514, Jul. 2002.
Pandey et al.,1999, The Journal of Biol. Chemistry 274:10140-10144.
Peter Blume-Jensen et al., 2001, Insight Review Articles, Nature 411:355-356.
Ram et al., 2000, Cell Growth & Differentiation 11:173-183.
Seikagaku Jiten (Dictionary of biochemistry), third edition, p. 1359, Published on Nov. 20, 1998, K.K. Tokyo Kagaku Dojin.
Shi et al., 2010, Proc. Natl. Acad. Sci USA 107:7692-7697.

(56) References Cited

OTHER PUBLICATIONS

Shoji and Nakashima, 2004, Current Pharmaceutical Design 10:785-796.
Sierke et al., 1097, Biochem. J. 322:757-763.
Sasaki et al., 1999, Tanpakushitsu Kakusan Koso (Protein, Nucleic acid, Enzyme) 44:112-122.
Thermo Scientific data sheet on "c-erbB-3/HER-3 Ab-5 (Clone: H3.105.5; same as Ab105)."
Upstate Biotechnology Catalog, 1999, pp. 1, 2 and 63.
Upstate Biotechnology Catalog, 2000, pp. 1-3 and 74.
Upstate Certificate of Analysis; Anti-erbB-3/HER-3, clone H3.105.5.
Vadlamudi et al., 1999, Oncogene 18:305-314.
Van Der Horst et al., 2005, Int. J. Cancer: 113:689-698.
Waterman, et al., 1999, EMBO J. 18:3348-3358.
Zrihan-Licht et al., 2000, Oncogene 19:1318-1328.
Casset et al., 2003, Biochemical and Biophysical Research Communications 307:198-205.
Chen et al., 1999, Journal of Molecular Biology 293:865-881.
DePacalis et al., 2002, The Journal of Immunology 169:3076-3084.
Holm et al., 2007, Molecular Immunology 44:1075-1084.
MaCallum et al., 1996, , Journal of Molecular Biology 262:732-745.
Rudkoff et al., 1982, Proc. Natl. Acad. Sci. USA 79:1079-1983.
Vajdos et al., 2002, Journal of Molecular Biology 320: 415-428.
Wu et al., 1999. Journal of Molecular Biology 294:151-162.
Alberts et al.; The Receptors for Most Growth Factors Are Transmembrane Tyrosine-Specific Protein Kinases; Chapter 15.3.2; Molecular Biology of the Cell, Third Edition; Copyright 1994, Garland Publishing Co., pp. 760-761.
Alimandi et al.; "Cooperative Signaling of Erbb3 and Erbb2 In Neoplastic Transformation and Human Mammary Carcinomas"; *Oncogene*; 1995; 1813-1821; 10.
Baldrick, P.; "Pharmaceutical Excipient Development: The Need for Preclinical Guidance."; *Regulatory Toxicology and Pharmacology*; 2000; 210-218; 32.
Binz et al.; "Engineered Proteins As Specific Binding Reagents"; *Current Opinion in Biotechnology*; 2005; 459-469; 16.
Binz et al.; "Engineering Novel Binding Proteins From Nonimmunoglobulin Domains"; *Nature Biotechnology*; 2005; 1257-1268; vol. 23.
Binz et al; "The Matrix Reloaded: Specific Binding Proteins Based on Non- immunoglobulin Domains"; Department of Biochemistry, University of Zurich; pp. 1-20, suppl. info. for Nature Biotech., 2005; 1257-1268: vol. 23.
Bowie et al..; "A Method to Identify Protein Sequences That Fold into a Known Three-Dimensional Structure"; *Science*; 1991, 164-170; vol. 253.
Carraway et al.; "A New Acquaintance for Erbb3 and Erbb4: A Role for Receptor Heterodimerization In Growth Signaling"; *Cell*; vol. 78, 1994; pp. 5-8.
Charman, W. N.; "Lipids, Lipophillic Drugs, and Oral Drug Delivery-Some Emerging Concepts;" *Journal of Pharmaceutical Sciences*; 2000; 967-978; vol. 89, No. 8.
Chen et al.; "An Immunological Approach Reveals Biological Differences Between the Two NDF/Heregulin Receptors, Erbb-3 and Erbb-4"; *J. Bilol. Chem.*; vol. 271, No. 13, 1996; 7620-7629.
Chen et al.; "$V_H$ Gene Expression and Regulation in the Mutant Alicia Rabbit"; *Journal of Immunology*; 1993; 2783-2793; vol. 150; No. 7.
Choi et al.; "Transgenic Mice Containing a Human Heavy Chain Immunoglobulin Gene Fragment Cloned in a Yeast Artificial Chromosome"; Nature Genetics; 1993; 117-123; vol. 4.
Chothia et al.; "Canonical Structures for the Hypervariable Regions of Immunoglobulins"; *J Mol. Biol.*; Aug. 20, 1987; 901-917; 196(4).
Chothia et al.; "Conformations of Immunoglobulin Hypervariable Regions"; *Nature*; vol. 342 (Dec. 21-28, 1989) , 877-883.
Clackson et al.; "Making Antibody Fragments Using Phage Display Libraries"; *Nature*; vol. 352 (Aug. 15, 1991), 624-628.

DeFazio et al.; "Expression of C-Erbb Receptors, Heregulin and Oesterogen Receptor in Human Breast Cell Lines"; *Int. J. Cancer*; (2000); 87; 487-498.
Feldhaus et al; "Yeast Display of Antibody Fragments: A Discovery and Characterization Platform"; *J. Immunol. Methods*; 290 (2004); 69-80.
Fendly et al.; "Murine Monoclonal Antibodies Defining Neutralizing Epitopes on Tumor Necrosis Factor"; *Hybridoma*; vol. 6, No. 4, 1987; 359-370.
Fishwild et al.; "High-Avidity Human Iggk Monoclonal Antibodies From a Novel Strain of Minilocus Transgenic Mice"; *Nature Biotechnology*; vol. 14 (Jul. 1996); 845-851.
Green et al.; "Regulation of B Cell Development By Variable Gene Complexity in Mice Reconstituted with Human Immunoglobulin Yeast Artificial Chromosomes"; *J. Exp. Med*; vol. 188, No. 3 (1998), 483-495.
Groves et al.; "Applications of Ribosome Display to Antibody Drug Discovery"; *Expert Opin. Biol. Ther.*; 2005; 125-135.
Hamman et al.; "An Anti-CD33 Antibody-Calicheamicin Conjugate for Treatment of Acute Myeloid Leukemia. Choice of Linker"; *Bioconjug. Chem*; 13 (2002), 40-46.
Hazra et al.; "Linking Radiosilver to Monoclonal Antibodies Reduced By Ascorbic Acid"; *Cell Biophys.*; vols. 24-25 (1994), 1-7.
Heldin, C-H.; "Dimerization of Cell Surface Receptors in Signal Transduction"; *Cell*, 1995, vol. 80; 213-223.
Holliger et al.; "Diabodies: Small Bivalent and Bispecific Antibody Fragments"; *Proc. Natl. Acad. Sci. U.S.A.*: 90 (1993), 6444-6448.
Holt et al.; "Domain Antibodies: Proteins for Therapy"; *Trends In Biotechnology*; 21; Nov. 2003; 484-90.
Hudziak et al.; "p185$^{HER2}$ Monoclonal Antibody Has Antiproliferative Effects In Vitro and Sensitizes Human Breast Tumor Cells to Tumor Necrosis Factor"; *Molecular and Cellular Biology*; Mar. 1989; vol. 9, No. 3; 1165-1172.
Idusogie et al.; "Engineered Antibodies With Increased Activity to Recruit Complement"; *Journal of Immunology.*; 2001; 166:2571-2575.
Ishida et al.; "Production of Human Monoclonal and Polyclonal Antibodies In Transchromo Animals"; *Cloning and Stem Cells*; vol. 4 (2002), 91-102.
Jia et al.; "A Novel Method of Multiplexed Competitive Antibody Binning for the Characterization of Monoclonal Antibodies"; *Journal of Immunological Methods*; 288 (2004), 91-98.
Jones et al.; "Replacing the Complementarity-Determining Regions in a Human Antibody With Those From a Mouse"; *Nature*; 321 (1986), 522-525.
Jostock et al.; "Screening of Molecular Repertoires by Microbial Surface Display"; *Combinatoral Chemistry & High Throughput Screening*; 2005; 8; 127-133.
Kearney et al.; "A New Mouse Myeloma Cell Line That Has Lost Immunoglobulin Expression But Permits the Construction of Antibody-Secreting Hybrid Cell Lines"; *Journal of Immunology*; vol. 123, No. 4 (1979), 1548-1550.
Köhler et al.; "Continuous Cultures of Fused Cells Secreting Antibody of Predefined Specificity"; *Nature*; 256 (1975), 495-497.
Kraus et al.; "Isolation and Characterization of ERBB3, A Third Member of the ERBB/Epidermal Growth Receptor Family: Evidence for Overexpression in a Subset of Human Mammary Tumors"; vol. 86; Dec. 1989; 9193-9197.
Kraus et al.; "Demonstration of Ligand-Dependent Signaling by the erbB-3 Tyrosine Kinase and its Constitutive Activation in Human Breast Tumor Cells"; *Proc. Natl. Acad. Sci. U.S.A.*; vol. 90; (1993); 2900-2904.
Li et al.; "Induction of Growth Inhibition and Apoptosis in Pancreatic Cancer Cells by Auristatin-PE and Gemcitabine"; *International Journal of Molecular Medicine*; 3 (1999), 647-53.
Liu et al.; "Eradication of Large Colon Tumor Xenografts By Targeted Delivery of Maytansinoids"; *Proc. Natl. Acad. Sci. USA*; vol. 93 (1996); 8618-8623.
Lonberg et al.; "Antigen-Specific Human Antibodies From Mice Comprising Four Distinct Genetic Modifications"; *Nature*; vol. 368; (1994); 856-859.
Mandler et al.; "Immunoconjugates of Geldanamycin and Anti-HER2 Monoclonal Antibodies: Antiproliferative Activity on Human

(56) References Cited

OTHER PUBLICATIONS

Breast Carcinoma Cell Lines"; *Journal of the National Cancer Institute*; vol. 92, No. 19; (2000); 1573-1581.
Marks et al.; "By-passing Immunization Human Antibodies from V-Gene Libraries Displayed on Phage"; *J. Mol. Biol.*; 222 (1991), 581-597.
Martin et al.; "Structural Families in Loops of Homologous Proteins: Automatic Classification, Modeling and Application to Antibodies"; *J. Mol. Biol.*; (1996); 263; 800-815.
Mendez et al.; "Functional Transplant of Megabase Human Immunoglobulin Loci Recapitulates Human Antibody Response in Mice"; *Nature Genetics*; vol. 15; (1997); 146-156.
Morrison et al.; "Chimeric Human Antibody Molecules: Mouse Antigen-Binding Domains With Human Constant Region Domains"; *Proc. Natl. Acad. Sci. U.S.A.*; vol. 81; (Nov. 1984); 6851-6855.
Muyldermans, S.; "Single Domain Camel Antibodies: Current Status"; *Reviews in Molecular Biotechnology*; 74; (2001); 277-302.
Naidu et al.; "Expression of c-erbB3 Protein in Primary Breast Carcinomas"; *British Journal of Cancer*; (1996); 78(10); 1385-1390.
Otani et al.; "TZT-1027, An Antimicrotubule Agent, Attacks Tumor Vasculature and Induces Tumor Cell Death"; *Jpn J Cancer Res.*; 91; (Aug. 2000); 837-844.
Plowman et al.; "Molecular Cloning and Expression of an Additional Epidermal Growth Factor Receptor-Related Gene"; *Proc. Natl. Acad. Sci. U.S.A.*; vol. 87; (Jul. 1990);4905-4909.
Pluckthün, A.; "Antibodies From *Escherichia coli*" in *The Pharmacology of Monoclonal Antibodies*;, Chapter II, Rosenburg and Moore, Eds., Springer Verlag, N.Y.; 113 (1994), 269-315).
Powell et al.; "Compendium of Excipients for Parental Formulations"; *PDA Journal of Pharmaceutical Science & Technology.*; vol. 52, No. 5; (Sep.-Oct. 1998), 238-311.
Presta, L. G.; "Antibody Engineering"; *Current Opinion in Structural Bioloyg*; 1992, 2:593-596.
Price et al.; "Methods for the Study of Protein-Protein Interactions in Cancer Cell Biology"; *Methods in Molecular Biology*; vol. 218; (2002); 255-267.
Rajkumar et al.; "A Monoclonal Antibody to the Human C-ERB3 Protein Stimulates the Anchorage-Independent Growth of Breast Cancer Cell Lines"; *British Journal of Cancer*, vol. 70, No. 3, 1994; 459-465.
Rajkumar et al.; "c-cerbB3 Expression in Breast Tumor Derived Cell Lines"; *The Breast* (1995), 4; 84-91.
Reichmann et al.; "Reshaping Human Antibodies for Therapy"; *Nature*; vol. 332; (Mar. 1998); 323-327.
Shields et al.; "High Resolution Mapping of the Binding Site on Human IgG1 for FcγRI, FcγRII, FcγRIII, and FcRn and Design of IgG1 Variants with Improved Binding to the FcγR*"; *The Journal of Biological Chemistry*; vol. 276, No. 9; 2001; 6591-6604.
Skerra, A.; "Engineered Protein Scaffolds for Molecular Recognition"; *Journal of Molecular Recognition*; (2000); 13; 167-187.
Sliwkovsky et al; "Coexpression of erbB2 and erbB3 Proteins Reconstitutes a High Affinity Receptor for Heregulin"; *J. of Biol. Chem.*; 1994, vol. 269, No. 20; 14661-14665.
Stebbing et al.; "Herceptin (trastuzamab) in Advanced Breast Cancer"; *Cancer Treatment Reviews*; 2000; 26; 287-290.
Taylor et al.; "Human Immunoglobulin Transgenes Undergo Rearrangement, Somatic Mutation and Class Switching in Mice that Lack Endogenous IgM"; *International Immunology*; vol. 6, No. 4; (1994); 579-591.
Taylor et al.; "A Transgenic Mouse That Expresses a Diversity of Human Sequence Heavy and Light Chain Immunoglobulins"; *Nucleic Acids Research*; (1992); vol. 20, No. 23; 6287-6295.
Thornton et al.; "Prediction of Progress At Last"; *Nature*; vol. 354, (Nov. 1991); 105-106.
Tuaillon at al.; "Human Immunoglobulin Heavy-Chain Minilocus Recombination in Transgenic Mice: Gene-Segment Use in u and y Transcripts"; *Proc. Natl. Acad. Sci.*; (Apr. 1993); vol. 90; 3720-3724.
Tuaillon et al.; "Analysis of Direct and Inverted $_{DJH}$ Rearrangments in a Human Ig Heavy Chain Transgenic Minilocusi[1]"; (1995).
Ulrich et al.; "Signal Transduction by Receptors with Tyrosine Kinase Activity"; *Cell*; vol. 61, 1990; 203-212.
Wallasch et al.; "Heregulin-Dependent Regulation of HER2/Neu Oncogenic Signaling by Heterodimerization with HER3"; *The EMBO Journal*; (1995); vol. 14 No. 17; 4267-4275.
Wallasch; C.; "Bedeutung von HER3 Fur Die Signal Definition Von HER2"; Dissertation Max-Planck Institute of Biochemistry, Munich, Germany, 1996.
Wang, W.; "Lyophilization and Development of Solid Protein Pharmaceuticals"; *International Journal of Pharmaceutics.*; 203; (2000), 1-60.
Witzig, T.; "Radioimmunotherapy for Patients with Relapsed B-Cell Non-Hodgkin Lymphoma"; *Cancer Chemother. Pharmacol.*; (2001); 48 (Suppl 1); S91-S95.
Zhang et al.; "Transformation of NIH 3T3 Cells by HER3 or HER4 Receptors Requires the Presence of HER1 or HER2"; *J. of Biol. Chemistry*; 1996, vol. 271, No. 7; 3884-3890.
International Search Report in counterpart international application No. PCT/EP2006/012632 dated Jun. 26, 2007, 4 pgs.

\* = versus control treatment
\*\* = versus either single agent alone

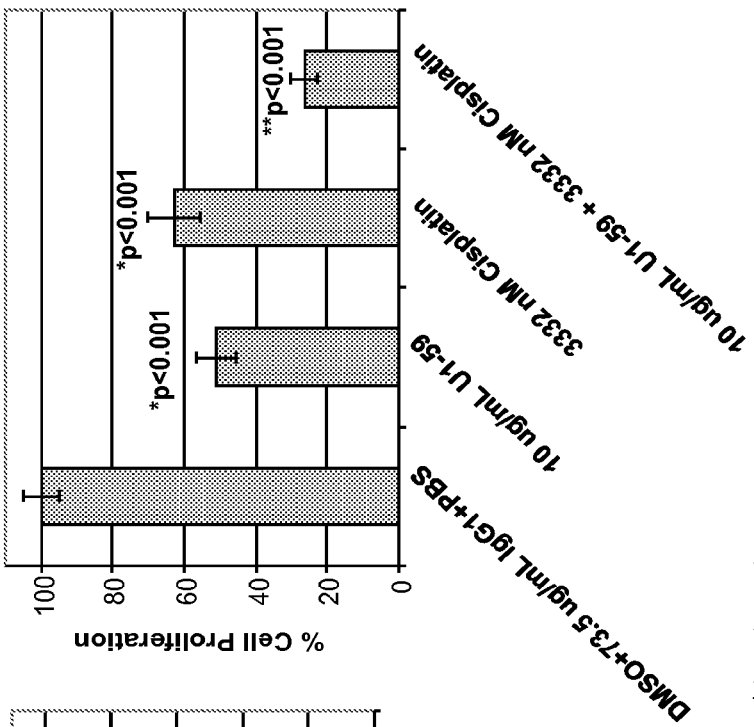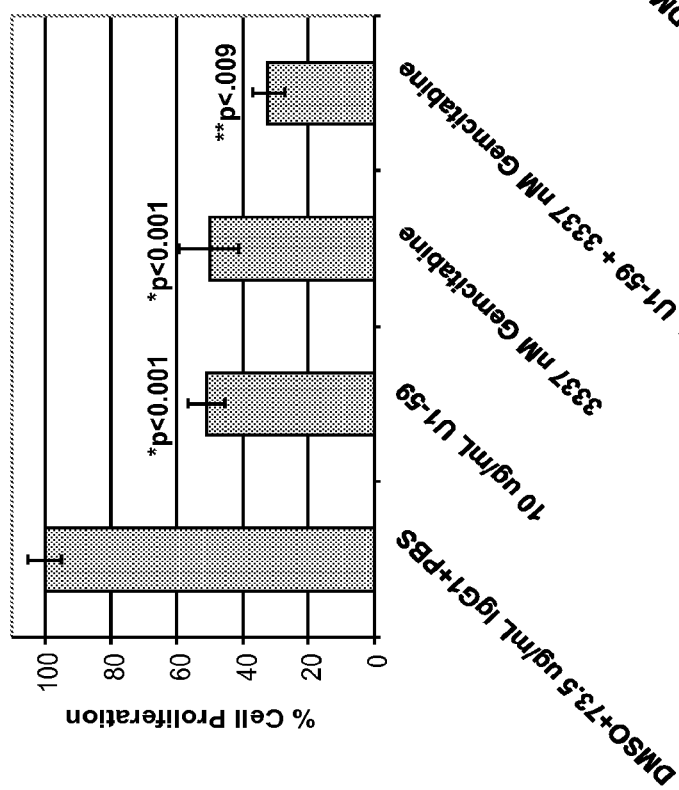

SEQUENCE LISTING

<160> NUMBER OF SEQ ID NOS: 390

<210> SEQ ID NO 1
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 1
gaggtgcagc tggtggagtc tggaggaggc ttgatccagc ctggggggtc cctgagactc    60

```
tcctgtgcag cctctgggtt caccgtcagt agcaactaca tgagctgggt ccgccaggct    120
ccagggaagg ggctggattg ggtctcagtt atttatagcg gtggtagcac atactacgca    180
gactccgtga agggccgatt caccatctcc agagacaatt ccaagaacac gctgtatctt    240
caaatgaaca gcctgagagc cgaggacacg gccgtgtatt actgtgcgag agggcagtgg    300
ctggacgtct ggggccaagg gaccacggtc accgtctcct ca                       342
```

<210> SEQ ID NO 2
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 2

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Asp Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gln Trp Leu Asp Val Trp Gly Gln Gly Thr Thr Val Thr Val
            100                 105                 110

Ser Ser
```

<210> SEQ ID NO 3
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 3

```
gatattgtga tgactcagtc tccactctcc ctgcccgtca cccctggaga gccggcctcc     60
atctcctgca ggtcaagtca gagcctcctg catagtaatg gatacaacta tttggattgg    120
tacctgcaga ggccagggca gtctccacaa ctcctgttct atttgggttt tcatcgggcc    180
tccggggtcc ctgacaggtt cagtggcagt ggatcaggca cagattttac actgaaaatc    240
agcagagtgg aggctgagga tgttggggtt tattactgca ggcaagctct acaaactccg    300
ctcactttcg gcggagggac caaggtggag atcaaa                              336
```

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 4

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Arg Pro Gly Gln Ser
        35                  40                  45

Pro Gln Leu Leu Phe Tyr Leu Gly Phe His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Arg Gln Ala
                85                  90                  95

Leu Gln Thr Pro Leu Thr Phe Gly Gly Gly Thr Lys Val Glu Ile Lys
            100                 105                 110
```

<210> SEQ ID NO 5
<211> LENGTH: 374
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 5

```
caggtgcagc tgcaggagtc gggcccagga ctggtgaagc cttcacagac cctgtccctc      60
acctgtactg tctctggtgg ctccatcagc agtggtggtt actactggag ctggatccgc     120
cagcacccag ggaagggcct ggagtggatt gggtacatct attccagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagat     300
agggaactgg aactttacta ctactactac ggtatggacg tctggggcca aggaccacg      360 gtcaccgtct cctc                                                        374
```

<210> SEQ ID NO 6
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 6

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Ser Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Glu Leu Glu Leu Tyr Tyr Tyr Tyr Gly Met
            100                 105                 110

Asp Val Trp Gly Gln Gly Thr Thr Val Thr Val Ser
```

<210> SEQ ID NO 7
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 7

```
gatattgtga tgactcagtc tccactctcc ctgcccgtca cccctggaga gccggcctcc    60
atctcctgca ggtctagtca gagcctcctg tatagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggaatt tattactgca tgcaagctct acaaactccg   300
ctcactttcg gcggagggac caaggtggag atcaaa                             336
```

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 9
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 9

```
cagatcacct tgaaggagtc tggtcctacg ctggtgaaac ccacacagac cctcacgctg    60
acctgcacct tctctgggtt ctcactcagc actagtggag tgggtgtggg ctggatccgt   120
cagcccccag gaaaggccct ggactggctt gcactcattt attggaatga tgataagcgc   180
tacagcccat ctctgaagag caggctcacc atcaccaagg acacctccaa aaaccaggtg   240
gtccttacaa tgaccaacat ggatcttgtg acacagcca catattactg tgtacacaga   300
gacgaagttc gagggtttga ctactgggc cagggaaccc tggtcaccgt ctcctca      357
```

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 10

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Asp
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Leu Val Asp Thr Ala Thr Tyr Tyr
                85                  90                  95

Cys Val His Arg Asp Glu Val Arg Gly Phe Asp Tyr Trp Gly Gln Gly
            100                 105                 110

Thr Leu Val Thr Val Ser Ser
        115

<210> SEQ ID NO 11
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 11
gatgttgtga tgactcagtc tccactctcc ctgcccgtca cccttggaca gccggcctcc      60
atctcctgca ggtctagtca aagcctcgta tacagtgatg gatacaccta cttgcattgg     120
tttcagcaga ggccaggcca atctccaagg cgcctatttt ataaggtttc taactgggac     180
tctggggtcc cagacagatt cagcggcagt gggtcaggca ctgatttcac actgaaaatc     240
agcagggtgg aggctgagga tgttggggtt tattactgca tgcaaggtgc acactggccg     300
atcaccttcg gccaagggac acgactggag attaaa                               336

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Tyr Thr Tyr Leu His Trp Phe Gln Gln Arg Pro Gly Gln Ser
        35                  40                  45

```
Pro Arg Arg Leu Ile Tyr Lys Val Ser Asn Trp Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ala His Trp Pro Ile Thr Phe Gly Gln Gly Thr Arg Leu Glu Ile Lys
            100                 105                 110
```

```
<210> SEQ ID NO 13
<211> LENGTH: 374
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 13
caggtgcagc tgcaggagtc gggcccagga ctggtgaagc cttcacagac cctgtccctc     60
acctgcactg tctctggtgg ctccatcagc agtggtgggt actactggag ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtatttctg tgcgagagat    300
cgggaacttg agggttactc caactactac ggtgtggacg tctggggcca agggaccacg    360
gtcaccgtct cctc                                                      374
```

```
<210> SEQ ID NO 14
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 14

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Phe
                 85                  90                  95

Cys Ala Arg Asp Arg Glu Leu Glu Gly Tyr Ser Asn Tyr Tyr Gly Val
            100                 105                 110

Asp Val Trp Gly Gln Gly Thr Thr Val Thr Val Ser
        115                 120
```

```
<210> SEQ ID NO 15
<211> LENGTH: 321
<212> TYPE: DNA
<213> ORGANISM: Artificial Sequence
<220> FEATURE:
<223> OTHER INFORMATION: Description of Artificial Sequence: Synthetic
```

-continued polynucleotide construct

<400> SEQUENCE: 15

```
gacatccaga tgacccagtc tccatcctcc ctgtctgcat ctgtaggaga cagagtcacc    60
atcacttgcc gggcaagtca ggccattagc aactatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag cctgcagcct   240
gaagattttg caacttatta ctgtcaacag aataatagtc tcccgatcac cttcggccaa   300
gggacacgac tggagattaa a                                             321
```

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide construct

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Asn Ser Leu Pro Ile
                85                  90                  95

Thr Phe Gly Gln Gly Thr Arg Leu Glu Ile Lys
            100                 105

<210> SEQ ID NO 17
<211> LENGTH: 354
<212> TYPE: DNA
<213> ORGANISM: Artificial Sequence
<220> FEATURE:
<223> OTHER INFORMATION: Description of Artificial Sequence: Synthetic
    polynucleotide construct

<400> SEQUENCE: 17

```
gaggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga taccagatac   180
agcccgtcct tccaaggcca ggtcaccatc tcagccgaca gtccatcagc accgcctac    240
ctgcagtgga gcagcctgaa ggcctcggac accgccatgt attactgtgc gagacatgaa   300
aactacggtg actacaacta ctggggccag ggaaccctgg tcaccgtctc ctca         354
```

<210> SEQ ID NO 18
<211> LENGTH: 118
<212> TYPE: PRT
<213> ORGANISM: Artificial Sequence
<220> FEATURE:
<223> OTHER INFORMATION: Description of Artificial Sequence: Synthetic
    polypeptide construct

<400> SEQUENCE: 18

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Glu Asn Tyr Gly Asp Tyr Asn Tyr Trp Gly Gln Gly Thr
            100                 105                 110

Leu Val Thr Val Ser Ser
        115
```

<210> SEQ ID NO 19
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 19

```
gacatccaga tgacccagtc tccatcctcc ctgtctgcat ctgtcggaga cagagtcacc      60
atcacttgcc gggcaagtca gagcattcgc agctatttaa attggtatca gcagaaacca     120
gggaaagccc ctaagctcct gatctatgct gcttccagtt tgcaaagtgg ggtcccatca     180
aggttcagtg gcagtggatc tgggacagat ttcactctca ccatcagcag tctgcaacct     240
gaagattttg cactttactg ctgtcaacag agtaacggtt ccccgctcac tttcggcgga     300
gggaccaagg tggagatcaa a                                               321
```

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide construct

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Leu Tyr Cys Cys Gln Gln Ser Asn Gly Ser Pro Leu
                85                  90                  95
```

Thr Phe Gly Gly Gly Thr Lys Val Glu Ile Lys
            100                 105

<210> SEQ ID NO 21
<211> LENGTH: 380
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 21
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct attacagtgg gagcacctac     180
tacaacccgt ccctcaggag tcgagttacc atatcagtag acacgtctaa gaaccagttc     240
tccctgaagc tgagctctgt gactgccgcg gacacggccg tgtattactg tgcgagagat     300
agagagagag agtgggatga ttacggtgac ccccaaggta tggacgtctg gggccaaggg     360
accacggtca ccgtctcctc                                                 380

<210> SEQ ID NO 22
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Glu Arg Glu Trp Asp Asp Tyr Gly Asp Pro Gln
            100                 105                 110

Gly Met Asp Val Trp Gly Gln Gly Thr Thr Val Thr Val Ser
        115                 120                 125

<210> SEQ ID NO 23
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 23
gacatccaga tgacccagtc tccatcctcc ctgtctgcat ctgtaggaga cagagtcacc      60
atcacttgcc gggcaagtca gagcattagc agctatttac attggtatca gcagaaacca     120
gggaaagccc ctaagctcct gatccatgct gcatccagtt tacaaagtgg ggtcccatca     180

```
aggttcagtg gcagtggatc tgggacagat ttcactctca ccatcagtag tctgcaacct    240
gaagattttg caacttacta ctgtcaacag agttacagta acccgctcac tttcggcgga    300
gggaccaagg tggagatcca a                                              321
```

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu His Trp Tyr Gln Gln Lys Pro Gly Lys Ala Pro Lys Leu Leu Ile
        35                  40                  45

His Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Leu
                85                  90                  95

Thr Phe Gly Gly Gly Thr Lys Val Glu Ile Gln
            100                 105
```

<210> SEQ ID NO 25
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 25

```
gaggtgcagc tggtgcagtc tggagcagag gtgaaaaagc ccggggagtc tctgaagatc    60
tcctgtaagg gttctggata cagctttacc agctactgga tcggctgggt gcgccagatg    120
cccgggaaag gcctggagtg gatggggatc atctggcctg gtgactctga taccatatac    180
agcccgtcct tccaaggcca ggtcaccatc tcagccgaca gtccatcagc accgcctac     240 ctgcagtgga gcagcctgaa ggcctcggac accgccatgt attactgtgc gagacatgaa    300
aactacggtg actacaacta ctggggccag ggaaccctgg tcaccgtctc ctca          354
```

<210> SEQ ID NO 26
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 26

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30
```

Trp Ile Gly Trp Val Arg Gln Met Pro Gly Lys Gly Leu Glu Trp Met
            35                  40                  45

Gly Ile Ile Trp Pro Gly Asp Ser Asp Thr Ile Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Glu Asn Tyr Gly Asp Tyr Asn Tyr Trp Gly Gln Gly Thr
            100                 105                 110

Leu Val Thr Val Ser Ser
        115

<210> SEQ ID NO 27
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 27
gacatccaga tgacccagtc tccatcctcc ctgtctgcat ctgtgggaga cagagtcacc      60
atcacttgcc gggcaagtca gagcattcga agttatttaa attggtatca gcagaaaccg     120
gggaatgccc ctaaactcct gatctatgct gcatccagtt tgcaaagtgg ggtcccatca     180
aggttcagtg gcagtggatc tgggacagat ttcactctca ccatcagcag tctgcaacct     240
gaagattttg cactttacta ctgtcaacag agtatcagtt ccccgctcac tttcggcgga     300
gggaccaagg tggagatcaa a                                               321

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 28

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Arg Ser Tyr
             20                  25                  30

Leu Asn Trp Tyr Gln Gln Lys Pro Gly Asn Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Leu Tyr Tyr Cys Gln Gln Ser Ile Ser Ser Pro Leu
                 85                  90                  95

Thr Phe Gly Gly Gly Thr Lys Val Glu Ile Lys
            100                 105

<210> SEQ ID NO 29
<211> LENGTH: 374
<212> TYPE: DNA
<213> ORGANISM: Artificial Sequence
<220> FEATURE:

<223> OTHER INFORMATION: Description of Artificial Sequence: Synthetic
      polynucleotide construct

<400> SEQUENCE: 29
caggtgcagc tggtgcagtc tggggctgag gtgaagaagc ctggggcctc agtgaaggtc      60
tcctgcaagg cttctggata caccttcacc agttatgata tcaactgggt gcgacaggcc     120
actggacaag gcttgagtg gatgggatgg atgaaccctaacagtggtga cactggctat       180 gcacaggtgt tccagggcag agtcaccatg acctggaaca cctccataag cacagcctac     240
atggaactga gcagcctgag atctgaggac acggccgtgt attactgtgc gagatttggg     300
gatctcccgt atgactacag ttactacgaa tggttcgacc cctggggcca gggaaccctg     360
gtcaccgtct cctc                                                       374

<210> SEQ ID NO 30
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asp Thr Gly Tyr Ala Gln Val Phe
    50                  55                  60

Gln Gly Arg Val Thr Met Thr Trp Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Gly Asp Leu Pro Tyr Asp Tyr Ser Tyr Tyr Glu Trp Phe
            100                 105                 110

Asp Pro Trp Gly Gln Gly Thr Leu Val Thr Val Ser
        115                 120

<210> SEQ ID NO 31
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 31
gacatccaga tgacccagtc tccatcctcc ctgtctgcat ctgtaggaga cagagtcacc      60
atcacttgcc gggcaagcca gagcattagc agctatttaa attggtatca gcagagacca    120
gggaaagccc ctaagctcct gatctatgca gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccgctcac tttcggcgga    300
gggaccaagg tggagatcaa a                                              321

<210> SEQ ID NO 32

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Arg Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 33
<211> LENGTH: 386
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 33
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc aagtggtat     180
aatgattatg cagtatctgt gaaaagtcga ataaccatca cccagacac atccaagaac     240
cagttctccc tgcagctgaa ctctgtgact cccgaggaca cggctgtgta ttactgtgca     300
agagatctct acgattttgg gagtggttat ccctactact acggtatgga cgtctggggc     360
caagggacca cggtcaccgt ctcctc                                          386

<210> SEQ ID NO 34
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 34

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn

```
                65                  70                  75                  80
Gln Phe Ser Leu Gln Leu Asn Ser Val Thr Pro Glu Asp Thr Ala Val
                    85                  90                  95

Tyr Tyr Cys Ala Arg Asp Leu Tyr Asp Phe Trp Ser Gly Tyr Pro Tyr
                100                 105                 110

Tyr Tyr Gly Met Asp Val Trp Gly Gln Gly Thr Thr Val Thr Val Ser
            115                 120                 125

<210> SEQ ID NO 35
<211> LENGTH: 383
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 35
caggtacagc tgcagcagtc aggtccagga ctggtgaagc cctcgcagac cctctcactc        60
acctgtgcca tctccgggga cagtgtctct agcaacagtg ctgcttggaa ctggatcagg       120
cagtccccat cgagaggcct tgagtggctg gaaggacat actacaggtc caagtggtat        180
aatgattatg cagtatctgt gaaaagtcga ataaccatca acccagacac atccaagaac       240
cagttctccc tgcagctgaa ctctgtgact cccgaggaca cggctgtgta ttactgtgca       300
agagattact atggttcggg gagtttctac tactactacg gtatggacgt ctggggccaa       360
gggaccacgg tcaccgtctc ctc                                               383

<210> SEQ ID NO 36
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 36

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                    85                  90                  95

Tyr Tyr Cys Ala Arg Asp Tyr Tyr Gly Ser Gly Ser Phe Tyr Tyr Tyr
                100                 105                 110

Tyr Gly Met Asp Val Trp Gly Gln Gly Thr Thr Val Thr Val Ser
            115                 120                 125

<210> SEQ ID NO 37
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct
```

<400> SEQUENCE: 37

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaaggtcct gatctatgct gcatccaatt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctcggac gttcggccaa     300
gggaccaagg tggaaatcaa a                                               321
```

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 38

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Val Leu Ile
        35                  40                  45
Tyr Ala Ala Ser Asn Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Arg
                85                  90                  95
Thr Phe Gly Gln Gly Thr Lys Val Glu Ile Lys
            100                 105
```

<210> SEQ ID NO 39
<211> LENGTH: 371
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 39

```
caggtgcagc tgcaggagtc gggcccagga ctggtgaagc cttcggagac cctgtccctc      60
acctgcactg tctctggtgg ctccatcagt agttactact ggagctggat ccggcagccc     120
gccgggaagg gactggagtg gattgggcat atctatacca gtgggagcac caactacaac     180
ccctccctca gagtcgagt caccatgtca gtagacacgt ccaagaacca gttctccctg     240
aagctgagct ctgtgaccgc cgcggacacg gccgtgtatt actgtgcgag agaagcgatt     300
tttggagtgg gccctacta ctactacggt atggacgtct ggggccaagg gaccacggtc     360
accgtctcct c                                                          371
```

<210> SEQ ID NO 40
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide construct

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly His Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ala Ile Phe Gly Val Gly Pro Tyr Tyr Tyr Tyr Gly Met Asp
            100                 105                 110

Val Trp Gly Gln Gly Thr Thr Val Thr Val Ser
        115                 120

<210> SEQ ID NO 41
<211> LENGTH: 377
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 41
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctaatattggtgg cacaaactgt     180 gcacagaagt ttcagggcag ggtcaccatg accagggaca cgtccatcag cacagcctac     240
atggagctga gcaggctgag atctgacgac acggccgtgt attactgtgc gagaggggga     300
cggtatagca gcagctggtc ctactactac tacggtatgg acgtctgggg ccaagggacc     360
acggtcaccg tctcctc                                                    377

<210> SEQ ID NO 42
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ile Gly Gly Thr Asn Cys Ala Gln Lys Phe
    50                  55                  60

Gln Gly Arg Val Thr Met Thr Arg Asp Thr Ser Ile Ser Thr Ala Tyr
65                  70                  75                  80

```
Met Glu Leu Ser Arg Leu Arg Ser Asp Asp Thr Ala Val Tyr Tyr Cys
                85                  90                  95

Ala Arg Gly Gly Arg Tyr Ser Ser Trp Tyr Tyr Tyr Gly
            100                 105                 110

Met Asp Val Trp Gly Gln Gly Thr Thr Val Thr Val Ser
        115                 120                 125

<210> SEQ ID NO 43
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 43
gatattctga tgacccagac tccactctct ctgtccgtca cccctggaca gccggcctcc      60
atctcctgca gtctagtca gagcctcctg cttagtgatg gagggaccta tttgtattgg     120
tacctgcaga agccaggcca gcctccacag ctcctgatct atgaagtttc caaccggttc     180
tctggagtgc cagataggtt cagtggcagc gggtcaggga cagatttcac actgaaaatc     240
agccgggtgg aggctgagga tgttggggtt tattactgca tgcaaagtat gcagcttccg     300
atcaccttcg gccaagggac acgactggaa attaaa                               336

<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 44

Asp Ile Leu Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Leu Ser
            20                  25                  30

Asp Gly Gly Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Met Gln Leu Pro Ile Thr Phe Gly Gln Gly Thr Arg Leu Glu Ile Lys
            100                 105                 110

<210> SEQ ID NO 45
<211> LENGTH: 380
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 45
caggtgcagc tgcaggagtc gggcccagga ctggtgaagc cttcggagac cctgtccctc      60
acctgcactg tctctggtgg ctccgtcagc agtggtggtt actactggag ctggatccgg     120
```

```
cagcccccag ggaagggact ggagtggatt gggtatatct attacagtgg gagcaccaac    180
tacaacccct ccctcaagag tcgagtcacc atatcagtag acacgtccaa gaaccagttc    240
tccctgaagc tgagctctgt gaccgctgcg gacacggccg tgtattactg tgcgagaggg    300
ggggacagta actacgagga ttactactac tactacggta tggacgtctg gggccaaggg    360
accacggtca ccgtctcctc                                                380

<210> SEQ ID NO 46
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gly Asp Ser Asn Tyr Glu Asp Tyr Tyr Tyr Tyr Tyr
            100                 105                 110

Gly Met Asp Val Trp Gly Gln Gly Thr Thr Val Thr Val Ser
        115                 120                 125

<210> SEQ ID NO 47
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 47
gacatccaga tgacccagtc tccatcctcc ctgtctgcat ctgtaggaga cagagtcacc     60
atcacttgcc gggcaagtca gagcattagc atctatttac attggtatca gcagaaacca    120
gggaaagccc ctaagctctt gatctctgct gcatccagtt tgcaaagtgg ggtcccgtca    180
aggttcagtg gcagtggatc tgggacagat ttcactctca ccatcagaag tctgcaacct    240
gaagattttg caacttacta ctgtcaacag agttacactt ccccgatcac cttcggccaa    300
gggacacgac tggagattaa a                                              321

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 48
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ile Tyr
            20                  25                  30

Leu His Trp Tyr Gln Gln Lys Pro Gly Lys Ala Pro Lys Leu Leu Ile
            35                  40                  45

Ser Ala Ala Ser Ser Leu Gln Ser Gly Val Pro Ser Arg Phe Ser Gly
50                  55                  60

Ser Gly Ser Gly Thr Asp Phe Thr Leu Thr Ile Arg Ser Leu Gln Pro
65                  70                  75                  80

Glu Asp Phe Ala Thr Tyr Tyr Cys Gln Gln Ser Tyr Thr Ser Pro Ile
                85                  90                  95

Thr Phe Gly Gln Gly Thr Arg Leu Glu Ile Lys
                100                 105

<210> SEQ ID NO 49
<211> LENGTH: 380
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 49
caggtgcagc tgcaggagtc gggcccagga ctggtgaagc cttcggagac cctgtccctc        60
acctgcactg tctctggtgg ctccatcagt agttactact ggagctggat ccggcagccc       120
ccagggaagg gactggagtg gattgggtat atctattaca gtgggagcac caactacaac       180
ccctccctca gagtcgagt caccatatca gtagacacgt ccaagcacca gttctccctg       240
aagctgagct ctgtgaccgc tgcggacacg gccgtgtatt actgtgcgag agattcgagt       300
tactatgata gtagtggtta ttacttatac tactacgcta tggacgtctg ggggccaaggg      360 accacggtca ccgtctcctc                                                    380

<210> SEQ ID NO 50
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys His Gln Phe Ser Leu
65                  70                  75                  80

Lys Leu Ser Ser Val Thr Ala Ala Asp Thr Ala Val Tyr Tyr Cys Ala
                85                  90                  95

Arg Asp Ser Ser Tyr Tyr Asp Ser Ser Gly Tyr Tyr Leu Tyr Tyr Tyr
                100                 105                 110

Ala Met Asp Val Trp Gly Gln Gly Thr Thr Val Thr Val Ser

<210> SEQ ID NO 51
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 51
gacatcgtga tgacccagtc tccagactcc ctggctgtgt ctctgggcga gagggccacc    60
atcaactgca gtccagcca gagtgtttta tacagctcca acaataagaa ctacttagct   120
tggtaccagc agaaaccagg acagcctcct aagctgctca tttcctgggc atctacccgg   180
gaatccgggg tccctgaccg attcagtggc agcgggtctg ggacagattt cactctcacc   240
atcagcagcc tgcaggctga agatgtggca gtttattact gtcagcaata ttatactact   300
cctctcactt tcggccctgg gaccaaagtg gatatcaaa                          339

<210> SEQ ID NO 52
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Leu Thr Phe Gly Pro Gly Thr Lys Val Asp Ile
            100                 105                 110

Lys

<210> SEQ ID NO 53
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 53
gaggtgcaac tggtggagtc tgggggaggc ttggtacagc ctggggggtc cctgagactc    60
tcctgtgcag cctctggatt caccttcagt atctatagca tgaactgggt ccgccaggct   120
ccagggaagg ggctggagtg ggtttcatac attagtagta gtagtagtac catatactac   180
gcagactctg tgaagggccg attcaccatc tccagagaca tgccaagaa ctcactgtat   240 ctgcaaatga acagcctgag agacgaggac acggctgtgt attactgtgc gagagatagg   300
ggtgacttcg atgctttga tatctggggc aagggacaa tggtcaccgt ctcttca        357

<210> SEQ ID NO 54
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Arg Gly Asp Phe Asp Ala Phe Asp Ile Trp Gly Gln Gly
            100                 105                 110

Thr Met Val Thr Val Ser Ser
        115

<210> SEQ ID NO 55
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 55
gacatccaga tgacccagtc tccatcctcc ctgtctgcat ctgtaggaga cagagtcacc        60
atcacttgcc aggcgagtca ggacattacc aactatttga attggtatca gcagaaacca       120
gggaaagccc ctaagctcct gatctacgat gcatccaatt tggaaacagg gtcccatca        180 aggttcagtg gaagtggatc tgggacagat tttactttca ccatcagcag cctgcagcct       240
gaagatattg caacatataa ctgtcaacag tgtgaaaatt tcccgatcac cttcggccaa       300
gggacacgac tggagattaa a                                                 321

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile

```
                35                  40                  45
Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Asn Cys Gln Gln Cys Glu Asn Phe Pro Ile
                 85                  90                  95

Thr Phe Gly Gln Gly Thr Arg Leu Glu Ile Lys
            100                 105
```

<210> SEQ ID NO 57
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 57

```
gatattgtga tgactcagtc tccactctcc ctgcccgtca cccctggaga gccggcctcc      60
atctcctgca ggtctagtca gagcctcctg tatagtaatg gatacaagta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattattgca tgcaggctct acaaactccg    300
atcaccttcg gccaagggac acgactggag attaaa                              336
```

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 58

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
             20                  25                  30

Asn Gly Tyr Lys Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Ile Thr Phe Gly Gln Gly Thr Arg Leu Glu Ile Lys
            100                 105                 110
```

<210> SEQ ID NO 59
<211> LENGTH: 374
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 59

```
caggtgcagc tgcaggagtc gggcccagga ctggtgaagc cttcggagac cctgtccctc    60
acctgcactg tctctggtgg ctccgtcagc agtggtggtt actactggaa ctggatccgg   120
cagcccccag ggaagggact ggagtggatt gggtatatca attacagtgg gagcaccaac   180
tacaacccct ccctcaagag tcgagtcacc atatcagtag acacgtccaa gaaccagttc   240
tccctgaagc tgagctctgt gaccgctgcg gacacggccg tgtattactg cgagagat    300 cgagaactgg aactttacta ctactactac ggtatggacg tctggggcca agggaccacg   360
gtcaccgtct cctc                                                     374
```

<210> SEQ ID NO 60
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 60

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Asn Trp Ile Arg Gln Pro Pro Gly Lys Gly Leu Glu
        35                  40                  45

Trp Ile Gly Tyr Ile Asn Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Glu Leu Glu Leu Tyr Tyr Tyr Tyr Gly Met
            100                 105                 110

Asp Val Trp Gly Gln Gly Thr Thr Val Thr Val Ser
        115                 120
```

<210> SEQ ID NO 61
<211> LENGTH: 374
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 61

```
caggtgcagc tgcaggagtc gggcccagga ctggtgaagc cttctgagac cctgtccctc    60
acctgcactg tctctggtgg ctccgtcagc agtggtggtt actactggaa ctggatccgg   120
cagcccccag ggaagggact ggagtggatt gggtatatca attacagtgg gagcaccaac   180
tacaacccct ccctcaagag tcgagtcacc atatcagtag acacgtccaa gaaccagttc   240
tccctgaagc tgagctctgt gaccgctgcg gacacggccg tgtattactg cgagagat    300 cgagaactgg aactttacta ctactactac ggtatggacg tctggggcca agggaccacg   360
gtcaccgtct cctc                                                     374
```

<210> SEQ ID NO 62
<211> LENGTH: 124
<212> TYPE: PRT

```
<213> ORGANISM: Artificial Sequence
<220> FEATURE:
<223> OTHER INFORMATION: Description of Artificial Sequence: Synthetic
      polypeptide construct

<400> SEQUENCE: 62

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Asn Trp Ile Arg Gln Pro Pro Gly Lys Gly Leu Glu
        35                  40                  45

Trp Ile Gly Tyr Ile Asn Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Glu Leu Glu Leu Tyr Tyr Tyr Tyr Gly Met
            100                 105                 110

Asp Val Trp Gly Gln Gly Thr Thr Val Thr Val Ser
        115                 120

<210> SEQ ID NO 63
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 63
gatattgtga tgactcagtc tccactctcc ctgcccgtca cccctggaga gccggcctcc      60
atctcctgca ggtctagtca gagcctcctg tatagtaatg gatacaagta tttggattgg    120
tacctgcaga agccagggca gtctccacag ctcatgatct atttgggttc taatcgggcc    180
tccggggtcc ctgacaggtt cagtggcagt ggatcaggca cagattttac actgaaaatc    240
agcagagtgg aggctgagga tgttggggtt tattattgca tgcaggctct acaaactccg    300
atcaccttcg gccaagggac acgactggag attaaa                              336

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Lys Tyr Leu Asp Trp Tyr Leu Gln Lys Pro Gly Gln Ser
        35                  40                  45

Pro Gln Leu Met Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 65
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 65
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg gctggagtg gtggcagtt atatggtatg atggaagtaa taaatactat     180
gcagactccg tgaagggccg attcaccatc tccagagaca attccaagaa cacgctgtat    240
ctgcaaatga acagcctgag agccgaggac acggctgtgt attactgtgc gagagcagct    300
cgccttgact actactacgg tatggacgtc tggggccaag ggaccacggt caccgtctcc    360
tca                                                                  363

<210> SEQ ID NO 66
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Arg Leu Asp Tyr Tyr Tyr Gly Met Asp Val Trp Gly
            100                 105                 110

Gln Gly Thr Thr Val Thr Val Ser Ser
        115                 120

<210> SEQ ID NO 67
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 67
gacatccaga tgacccagtc tccatcctcc ctgtctgcat ctgtaggaga cagagtctcc     60

```
atcacttgcc gggcaagtca gagcattaac agctatttaa attggtttca gcagaagcca    120
gggaaagccc ctcagctcct gatctttggt gcatccggtt tgcaaagtgg ggtcccatca    180
aggttcagtg gcagtggatc tgggacagat ttcactctca ccatcaacag tctgcaacct    240
gaagattttg caacttacta ctgtcaacag agttacagtt ccccgctcac cttcggccaa    300
gggacacgac tggagattaa a                                              321
```

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide construct

<400> SEQUENCE: 68

```
Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Ser Ile Asn Ser Tyr
            20                  25                  30

Leu Asn Trp Phe Gln Gln Lys Pro Gly Lys Ala Pro Gln Leu Leu Ile
        35                  40                  45

Phe Gly Ala Ser Gly Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Ser Pro Leu
                85                  90                  95

Thr Phe Gly Gln Gly Thr Arg Leu Glu Ile Lys
            100                 105
```

<210> SEQ ID NO 69
<211> LENGTH: 351
<212> TYPE: DNA
<213> ORGANISM: Artificial Sequence
<220> FEATURE:
<223> OTHER INFORMATION: Description of Artificial Sequence: Synthetic
    polynucleotide construct

<400> SEQUENCE: 69

```
caggtgcagc tacagcagtg gggcgcagga ctgttgaagc cttcggagac cctgtccctc    60
acctgcgctg tctatggtgg gtccttcagt ggttactact ggagctggat ccgccagccc    120
ccagggaagg ggctggagtg gattgggaa atcaatcata gtggaagcac caactacaac    180
ccgtccctca agagtcgagt caccatatca gtagaaacgt ccaagaacca gttctccctg    240
aagctgagct ctgtgaccgc cgcggacacg gctgtgtatt actgtgcgag agataagtgg    300
acctggtact cgatctctg gggccgtggc accctggtca ctgtctcctc a             351
```

<210> SEQ ID NO 70
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide construct

<400> SEQUENCE: 70

```
Gln Val Gln Leu Gln Gln Trp Gly Ala Gly Leu Leu Lys Pro Ser Glu
1               5                   10                  15
```

```
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
 50                  55                  60

Ser Arg Val Thr Ile Ser Val Glu Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser
        115

<210> SEQ ID NO 71
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 71
gacatcgaga tgacccagtc tccagactcc ctggctgtgt ctctgggcga gagggccacc      60
atcaactgca ggtccagcca gagtgtttta tacagctcca gcaataggaa ctacttagct     120
tggtaccagc agaaacccagg acagcctcct aagctgctca tttactgggc ttctacccgg    180
gaatccgggg tccctgaccg attcagtggc agcgggtctg ggacagattt cactctcacc     240
atcagcagcc tgcaggctga agatgtggca gtttattact gtcagcaata ttatagtact     300
cctcggacgt tcggccaagg gaccaaggtg gaaatcaaa                            339

<210> SEQ ID NO 72
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 72

Asp Ile Glu Met Thr Gln Ser Pro Asp Ser Leu Ala Val Ser Leu Gly
 1               5                  10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys
```

<210> SEQ ID NO 73
<211> LENGTH: 374
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 73

```
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatg gggaacatct attacagtgg gagcacctac     180
tacaacccgt ccctcaagag tcgagttacc atatcagtag acacgtctga gaccagttc      240 tccctgaagc tgaactctgt gactgccgcg gacacggccg tatattactg tgcgagaggg     300
ggaactggaa ccaattacta ctactactac ggtatggacg tctggggcca agggaccacg     360
gtcaccgtct cctc                                                       374
```

<210> SEQ ID NO 74
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide construct

<400> SEQUENCE: 74

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Met Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Glu Asn Gln Phe
65                  70                  75                  80

Ser Leu Lys Leu Asn Ser Val Thr Ala Ala Asp Thr Ala Val Tyr Tyr
                85                  90                  95

Cys Ala Arg Gly Gly Thr Gly Thr Asn Tyr Tyr Tyr Tyr Gly Met
            100                 105                 110

Asp Val Trp Gly Gln Gly Thr Thr Val Thr Val Ser
        115                 120

<210> SEQ ID NO 75
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 75

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gctgggccac tggcatccca     180
aacaggttca gtggcagtgg gtctgggaca gacttcactc tcaccatcag cagactggag     240
```

```
cctgaagatt ttgcagtgta ttactgtcag cagtatggta gctcaccgct cactttcggc    300
ggagggacca aggtggagat caaa                                          324
```

<210> SEQ ID NO 76
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 76

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Trp Ala Thr Gly Ile Pro Asn Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105
```

<210> SEQ ID NO 77
<211> LENGTH: 377
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 77

```
caggtgcagc tgcaggagtc gggcccagga ctggtgaagc cttcacagac cctgtccctc    60
acctgcactg tctctggtgt ctccatcagc agtggtggtt actactggag ctggatccgc   120
cagcacccag ggatgggcct ggagtggatt gggtacatct attacagtgg gagcacctac   180
tacaacccgt ccctcaagag tcgagtcacc atatcagaag acacgtctaa gaaccagttc   240
tccctgaagc tgagctctgt gactgccgcg gacacggccg tgtattactg tgcgagagat   300
tccgagtccg agtatagcag ctcgtcgaac tacggtatgg acgtctgggg ccaagggacc   360
acggtcaccg tctcctc                                                  377
```

<210> SEQ ID NO 78
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 78

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Ser Gly
            20                  25                  30

Gly Tyr Tyr Trp Ser Trp Ile Arg Gln His Pro Gly Met Gly Leu Glu
```

```
                35                  40                  45
Trp Ile Gly Tyr Ile Tyr Tyr Ser Gly Ser Thr Tyr Tyr Asn Pro Ser
        50                  55                  60

Leu Lys Ser Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Glu Ser Glu Tyr Ser Ser Ser Asn Tyr Gly
            100                 105                 110

Met Asp Val Trp Gly Gln Gly Thr Thr Val Thr Val Ser
        115                 120                 125

<210> SEQ ID NO 79
<211> LENGTH: 377
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 79
caggtgcagc tgcaggagtc gggcccagga ctggtgaagc cttcacagac cctgtccctc      60
acctgcactg tctctggtgt ctccatcagc agtggtggtt actactggag ctggatccgc     120
cagcacccag ggatgggcct ggagtggatt gggtacatct attacagtgg agcacctac      180 tacaacccgt ccctcaagag tcgagtcacc atatcagaag acacgtctaa gaaccagttc     240
tccctgaagc tgagctctgt gactgccgcg gacacggccg tgtattactg tgcgagagat     300
tccgagtccg agtatagcag ctcgtcgaac tacggtatgg acgtctgggg ccaagggacc     360
acggtcaccg tctcctc                                                    377

<210> SEQ ID NO 80
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 80

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Ser Gly
            20                  25                  30

Gly Tyr Tyr Trp Ser Trp Ile Arg Gln His Pro Gly Met Gly Leu Glu
        35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Glu Ser Glu Tyr Ser Ser Ser Asn Tyr Gly
            100                 105                 110

Met Asp Val Trp Gly Gln Gly Thr Thr Val Thr Val Ser
        115                 120                 125

<210> SEQ ID NO 81
```

<211> LENGTH: 321
<212> TYPE: DNA
<213> ORGANISM: Artificial Sequence
<220> FEATURE:
<223> OTHER INFORMATION: Description of Artificial Sequence: Synthetic
    polynucleotide construct

<400> SEQUENCE: 81
gacatccaga tgacccagtc tccatcctcc ctgtctgcat ctgtaggaga cagaatcacc    60
atcacttgcc gggcaagtca gaccattagc agctatttaa attggtatca gcagaaacca   120
gggaaagccc ctaagctcct gatctatgct gcatccagtt tgcaaggtgg ggtcccatca   180
aggttcagtg gcagtgtatc tgggacagat ttcaccctca ccgtcagcag tctgcaacct   240
gaagattttg caacttacta ctgtcaacag agttacagta accgctcac tttcggcgga    300 gggaccaagg tggagatcaa a                                             321

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide construct

<400> SEQUENCE: 82

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Val Ser Gly Thr Asp Phe Thr Leu Thr Val Ser Ser Leu Gln Pro
65                  70                  75                  80

Glu Asp Phe Ala Thr Tyr Tyr Cys Gln Gln Ser Tyr Ser Asn Pro Leu
                85                  90                  95

Thr Phe Gly Gly Gly Thr Lys Val Glu Ile Lys
            100                 105

<210> SEQ ID NO 83
<211> LENGTH: 371
<212> TYPE: DNA
<213> ORGANISM: Artificial Sequence
<220> FEATURE:
<223> OTHER INFORMATION: Description of Artificial Sequence: Synthetic
    polynucleotide construct

<400> SEQUENCE: 83
gaggtgcagc tggtgcagtc tggagcagag gtgaaaaagc ccggggagtc tctgaagatc    60
tcctgtaagg gttctggata cagttttacc agctactgga tcggctgggt gcgccagatg   120
cccgggaaag gcctggagtg gatggggatc atctatcctg gtgactctga taccagatac   180
agcccgtcct tccaaggcca ggtcaccatg tcagccgaca gtccatcag taccgcctac   240 ctgcagctga gcagccatga aggcctcgga caccgccatg tattactgtg cgagacagat   300
ggctggaaac tacgtacatc acgggtgatc gagacgtcct ggggccaagg gaccacggtc   360
accgtctcct c                                                        371

```
<210> SEQ ID NO 84
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 84

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
50                  55                  60

Gln Gly Gln Val Thr Met Ser Ala Asp Lys Ser Ile Ser Thr Ala Tyr
65                  70                  75                  80

Leu Gln Leu Ser Ser His Glu Gly Leu Gly His Arg His Val Leu Leu
                85                  90                  95

Cys Glu Thr Asp Gly Trp Lys Leu Arg Thr Ser Arg Val Ile Glu Thr
            100                 105                 110

Ser Trp Gly Gln Gly Thr Thr Val Thr Val Ser
        115                 120

<210> SEQ ID NO 85
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 85
gaaattgtgt tgacgcagtc tccaggcacc ctgtctttgt ctccagggga aagagccacc      60
ctctcctgca gggccagtca gagtgttatc agcatctact tagcctggta ccagcagaaa     120
cctggccagg ctcccaggct cctcatctat ggtgcatccg caggggccac tggcatccca     180
gacaggttca gtggcagtgg gtctgggaca gacttcactc tcaccatcag cagactggag     240
cctgaagatt ttgcagtgta ttactgtcag cagtatggta gctcaccgtg cagttttggc     300
caggggacca aactggagat caaa                                            324

<210> SEQ ID NO 86
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 86

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ile Ser Ile
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Cys Ser Phe Gly Gln Gly Thr Lys Leu Glu Ile Lys
            100                 105
```

<210> SEQ ID NO 87
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 87

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagcacccag ggaagggcct ggagtggatt gggtacatct attacagtgg gagcacctac   180
tacaacccgt ccctcaggag tcgagttacc atatcagtag acacgtctaa gaaccagttc   240
tccctgaagc tgagctctgt gactgccgcg gacacggccg tgtattactg tgcgagagcg   300
gattacgatt tttggagtgg ttattttgac tactggggcc agggaaccct ggtcaccgtc   360
tcctca                                                              366
```

<210> SEQ ID NO 88
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 88

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Arg Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 89
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 89

```
gacatccaga tgacccagtc tccatcctcc ctgtctgcat ctgtaggaga cagagtcacc    60
atcacttgcc gggcaagtca gggcattaga aatgatttag gctggtatca gcagatacct   120
gggaaagccc ctaagcgcct gatctatgct gcatccagtt tgcaaagtgg ggtcccatca   180
aggttcagcg gcagtggatc tgggacagaa ttcactctca caatcaacag cctgcagcct   240
gaagattttg caacttatta ctgtctacag cataatggtt acccgtggac gttcggccaa   300
gggaccaagg tggaaatcaa ac                                            322
```

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide construct

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys
            100                 105
```

<210> SEQ ID NO 91
<211> LENGTH: 366
<212> TYPE: DNA
<213> ORGANISM: Artificial Sequence
<220> FEATURE:
<223> OTHER INFORMATION: Description of Artificial Sequence: Synthetic
    polynucleotide construct

<400> SEQUENCE: 91

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagcacccag gaagggcct ggagtggatt ggatacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagcg   300
gattacgatt tttggagtgg ttattttgac tactggggcc agggaaccct ggtcaccgtc   360
tcctca                                                              366
```

<210> SEQ ID NO 92
<211> LENGTH: 122
<212> TYPE: PRT
<213> ORGANISM: Artificial Sequence
<220> FEATURE:
<223> OTHER INFORMATION: Description of Artificial Sequence: Synthetic
    polypeptide construct

<400> SEQUENCE: 92

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 93
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 93
gacttccaga tgacccagtc tccatcctcc ctgtctgcat ctgtaggaga cagagtcacc      60
atcacttgcc gggcaagtca ggacattcga aatgatttag ctggtatcg gcagaaacct     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa ac                                             322

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 94

Asp Phe Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Arg Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 95
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 95
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt ggatacatct attacagtgg agcacctac      180 tacaacccgt ccctcaagag tcgagttacc atatcaatag acacgtctaa gaaccagttc     240
tccctgaagc tgagctctgt gactgccgcg gacacggccg tgtattactg tgcgagagcg     300
gattacgatt tttggaatgg ttattttgac tactggggcc agggaaccct ggtcaccgtc     360
tcctca                                                                366

<210> SEQ ID NO 96
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 96

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Asn Gly Tyr Phe Asp Tyr Trp
            100                 105                 110

Gly Gln Gly Thr Leu Val Thr Val Ser Ser
        115                 120

<210> SEQ ID NO 97
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 97
gacatccaga tgacccagtc tccatcctcc ctgtctgcat ctgtaggaga cagagtcacc      60
atcacttgcc gggcaagtca ggacattaga aatgatttag ctggtatcg gcagaaacct     120 gggaaagccc ctaagcgcct gatctatgct gcatccagtt tgcaaagtgg ggtcccatca     180

```
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa a                                              321
```

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Arg Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 99
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 99

```
caggtgcagc tgcaggagtc gggcccagga ctggtgaagc ctacacagac cctgtccctc    60
acctgcactg tctctggtgg ctccatcagc agtggtgatt actactggag ctggatccgc    120
cagcacccag ggaagggcct ggagtggatt gggtacatct attacagtgg gagcacctac    180
tacaacccgt ccctcaagag tcgacttacc atatcagtag acacgtctaa gaaccagttc    240
tccctgaagc tgagctctgt gactgccgcg gacacggccg tgtattactg tgcgagagca    300
gattacgatt tttggagtgg ttactttgac tactggggcc agggaaccct ggtcaccgtc    360
tcctca                                                               366
```

<210> SEQ ID NO 100
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 100

```
Gln Val Gln Leu Gln Glu Ser Gly Pro Gly Leu Val Lys Pro Thr Gln
1               5                   10                  15

Thr Leu Ser Leu Thr Cys Thr Val Ser Gly Gly Ser Ile Ser Ser Gly
```

```
                    20                  25                  30

Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
            115                 120

<210> SEQ ID NO 101
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 101
gacatccaga tgacccagtc tccatcctcc ctgtctgcat ctgtaggaga cagagtcacc      60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataataatt acccgtggac gttcggccaa    300
gggaccaagg tggaaatcaa a                                              321

<210> SEQ ID NO 102
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Glu Ile Lys
            100                 105

<210> SEQ ID NO 103
<211> LENGTH: 366
<212> TYPE: DNA
```

<213> ORGANISM: Artificial Sequence
<220> FEATURE:
<223> OTHER INFORMATION: Description of Artificial Sequence: Synthetic polynucleotide construct

<400> SEQUENCE: 103

```
caggtgcagc tgcaggagtc gggcccagga ctggtgaagc cttcacagac cctgtccctc    60
acctgcactg tctctggtgg ctccatcagt agtggtgatt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagt tgagctctgt gactgccgcg gacacggccg tgtattactg tgcgagagcc   300
gattacgatt tttggagtgg ttattttgac tactggggcc agggaaccct ggtcaccgtc   360
tcctca                                                              366
```

<210> SEQ ID NO 104
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide construct

<400> SEQUENCE: 104

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 105
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 105

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataataatt acccgtggac gttcggccaa   300
gggaccaagg tggaaatcaa a                                             321
```

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Glu Ile Lys
            100                 105

<210> SEQ ID NO 107
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 107
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagag     300
gacgacggta tggacgtctg gggccaaggg accacggtca ccgtctcctc a              351

<210> SEQ ID NO 108
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 108

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe

```
                65                  70                  75                  80
Ser Leu Lys Leu Ser Ser Val Thr Ala Ala Asp Thr Ala Val Tyr Tyr
                    85                  90                  95

Cys Ala Arg Glu Asp Asp Gly Met Asp Val Trp Gly Gln Gly Thr Thr
                100                 105                 110

Val Thr Val Ser Ser
        115

<210> SEQ ID NO 109
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 109
gatattgtga tgactcagtc tccactctcc ctgcccgtca cccctggaga gccggcctcc      60
atttcctgca ggtctagtca gagcctcctg catagtaatg gatacaacta tttggaatgg     120
tacctgcaga agccagggca gtccccacag ttcatgattt atttggggtc taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactccg     300
atcaccttcg gccaagggac acgactggag attaaa                               336

<210> SEQ ID NO 110
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 110

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Glu Trp Tyr Leu Gln Lys Pro Gly Gln Ser
            35                  40                  45

Pro Gln Phe Met Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
                100                 105                 110

<210> SEQ ID NO 111
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 111
caggtgcagc tgcaggagtc gggcccagga ctggtgaagc cttcacagac cctgtccctc      60
```

```
acctgcactg tctctggtgg ctccatcagc agtggtgatt actactggag ctggatccgc      120
cagtacccag ggaagggcct ggagtggatt gggtacatct attacagtgg agcacctac      180 tacaacccgt ccctcaagag tcgagttacc atatcagtag acacgtctaa gaaccagttc      240
tccctgaagc tgaggtctgt gactgccgcg gacacggccg tgtattactg tgcgagagcg      300
gattacgatt tttggagtgg ttattttgac tactggggcc agggaaccct ggtcaccgtc      360
tcctca                                                                 366
```

<210> SEQ ID NO 112
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 112

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Tyr Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 113
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 113

```
gacatccaga tgacccagtc tccatcctcc ctgtctgcat ctgtaggaga cagagtcacc      60
atcacttgcc gggcaagtca gggcattaga aatgatttag ctggtatca gcagaaacca      120 gggaaagccc ctaagcgcct gatctatgct gcatccagtt tgcaaagtgg ggtcccatca      180
aggttcagcg gcagtggatc tgggacagaa ttcactctca caatcagcag cctgcagcct      240
gaagattttg caacttatta ctgtctacag cataatactt acccgtggac gttcggccaa      300
gggaccaagg tggaaatcaa ac                                               322
```

<210> SEQ ID NO 114
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys
            100                 105

<210> SEQ ID NO 115
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 115
caggtgcagc tgcaggagtc gggcccagga ctggtgaagc cttcggagac cctgtccctc      60
acctgcactg tctctggtgg ctccgtcagc agtggtggtt actactggag ctggatccgg     120 cagccccag ggaagggact ggagtggatt gggtatatct attacagtgg gagcaccaac      180
tacaacccct ccctcaagag tcgagtcacc atatcagtag acacgtccaa gaaccagttc     240
tccctgaagc tgagctctgt gaccgctgcg gacacggccg tgtattactg tgcgagagat     300
ggggacgtgg atacagctat ggtcgatgct tttgatatct ggggccaagg gacaatggtc     360
accgtctcct ca                                                         372

<210> SEQ ID NO 116
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 116

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Asp Val Asp Thr Ala Met Val Asp Ala Phe Asp
            100                 105                 110

<210> SEQ ID NO 117
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 117

```
gaaattgtat tgacgcagtc tccaggcacc ctgtctttgt ctccagggga aagagccacc    60
ctctcctgca gggccagtca gagtttaagc ggcaactact tagcctggta ccagcagaag   120
cctggccagg ctcccaggct catcatctgt ggtgcatcca gcagggccac tggcatccca   180
gacaggttca gtggcagtgg gtctgggaca gacttcactc tcaccatcac aagactggag   240
cctgaagatt ttgcagtgta ttactgtcag cagtatgata ggtcaccgct cactttcggc   300
ggagggacca aggtggagat caaa                                          324
```

Ile Trp Gly Gln Gly Thr Met Val Thr Val Ser Ser
        115                 120

<210> SEQ ID NO 118
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide construct

<400> SEQUENCE: 118

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Leu Ser Gly Asn
            20                  25                  30
Tyr Leu Ala Trp Tyr Gln Gln Lys Pro Gly Gln Ala Pro Arg Leu Ile
        35                  40                  45
Ile Cys Gly Ala Ser Ser Arg Ala Thr Gly Ile Pro Asp Arg Phe Ser
    50                  55                  60
Gly Ser Gly Ser Gly Thr Asp Phe Thr Leu Thr Ile Thr Arg Leu Glu
65                  70                  75                  80
Pro Glu Asp Phe Ala Val Tyr Tyr Cys Gln Gln Tyr Asp Arg Ser Pro
                85                  90                  95
Leu Thr Phe Gly Gly Gly Thr Lys Val Glu Ile Lys
            100                 105

<210> SEQ ID NO 119
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 119

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagga   300
```

```
gattacgatt tttggagtgg agagtttgac tactggggcc agggaaccct ggtcaccgtc    360
tcctca                                                              366

<210> SEQ ID NO 120
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 120

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Asp Tyr Asp Phe Trp Ser Gly Glu Phe Asp Tyr Trp
            100                 105                 110

Gly Gln Gly Thr Leu Val Thr Val Ser Ser
        115                 120

<210> SEQ ID NO 121
<211> LENGTH: 386
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 121
caggtgcagc tgcaggagtc gggcccagga ctggtgaagc cttcacagac cctgtccctc    60
acctgcactg tctctggtgg ctccatcagc agtggtggtt actactggag ctggatccgc    120
cagcacccag gaagggcct ggagtggatt gggtacatct atgacagtgg gagcacctac    180
tacaacccgt ccctcaagag tcgagttacc atatcagtag acacgtctaa gaaccagttc    240
tccctgaagc tgaggtctgt gactgccgcg gacacggccg tgtattactg tgcgagagat    300
caggggcagg acgatacag ctatggttac ggctactact acggtatgga cgtctggggc     360
caagggacca cggtcaccgt ctcctc                                         386

<210> SEQ ID NO 122
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 122

Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
         35                  40                  45

Trp Ile Gly Tyr Ile Tyr Asp Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
             85                  90                  95

Cys Ala Arg Asp Gln Gly Gln Asp Gly Tyr Ser Tyr Gly Tyr Gly Tyr
            100                 105                 110

Tyr Tyr Gly Met Asp Val Trp Gly Gln Gly Thr Thr Val Thr Val Ser
        115                 120                 125

<210> SEQ ID NO 123
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 123
gacatccaga tgacccagtc tccatcctcc ctgtctgcat ctgtaggaga cagagtcacc      60
atcacttgcc aggcgagtca ggacattagc aattatttaa attggtatca gcagaaacca    120
gggaaagccc ctaaactcct gatctacgtt gcatccaatt tggaaacagg ggtcccatca    180
aggttcagtg aagtggatc tgggacagat tttactttca ccatcagcag cctgcagcct     240
gaagatattg caacatatta ctgtcaacag tgtgataatc tccctctcac tttcggcgga    300
gggaccaagg tggagatcaa a                                              321

<210> SEQ ID NO 124
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 124

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Val Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Cys Asp Asn Leu Pro Leu
             85                  90                  95

Thr Phe Gly Gly Gly Thr Lys Val Glu Ile Lys
            100                 105

<210> SEQ ID NO 125
<211> LENGTH: 365
```

```
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 125
caggtgcagc tgcaggagtc gggcccagga ctggtgaagc cttcacagac cctgtccctc    60
acctgcactg tctctggtgg ctccatcagc agtggtgatt actactggag ctggatccgc   120
cagcacccag ggaagggcct ggagtggatt ggatacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagcg   300
gattacgatt tttggagtgg ttattttgac tactggggcc agggaaccct ggtcaccgtc   360
tcctc                                                               365

<210> SEQ ID NO 126
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 126

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser
        115                 120

<210> SEQ ID NO 127
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 127
gacatccaga tgacccagtc tccatcctcc ctgtctgcat ctgtaggaga cagagtcacc    60
atcacttgcc gggcaagtca ggacattaga aatgatttag ctggtatcg gcagaaacct   120 gggaaagccc ctaagcgcct gatctatgct gcatcccgtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgtggac gttcggccaa   300
gggaccaagg tggaaatcaa ac                                            322
```

<210> SEQ ID NO 128
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Arg Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 129
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 129
caggtgcagc tgcaggagtc gggcccagga ctggtgaagc cttcacagac cctgtccctc    60
acctgcactg tctctggtgg ctccatcagc agtggtgatt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagcc   300
gattacgatt tttggagtgg ttattttgac tactgggggcc agggaaccct ggtcaccgtc   360
tcctca                                                              366

<210> SEQ ID NO 130
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 130

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser

```
                50                  55                  60
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Ser Gly Tyr Phe Asp Tyr Trp
                100                 105                 110

Gly Gln Gly Thr Leu Val Thr Val Ser Ser
        115                 120

<210> SEQ ID NO 131
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 131
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaaatgg ggtcccatca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa ac                                             322

<210> SEQ ID NO 132
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 132

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Asn Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
                100                 105

<210> SEQ ID NO 133
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 133
```

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg cgagagcg     300 gattacgatt tttggagtgg ttattttgac tactggggcc agggaatcct ggtcaccgtc   360
tcctc                                                               365
```

<210> SEQ ID NO 134
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 134

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Ile Leu Val Thr Val Ser
        115                 120
```

<210> SEQ ID NO 135
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 135

```
gacatccaga tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagcgcct gatttatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgtggac gttcggccaa   300
gggaccaagg tggaaatcaa ac                                            322
```

<210> SEQ ID NO 136
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide construct

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 137
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 137
caggtgcagc tgcaggagtc gggcccagga ctggtgaagc cttcacagac cctgtccctc      60
acctgcactg tctctggtgg ctccatcagt agtggtgatt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagt tgagctctgt gactgccgcg gacacggccg tgtattactg tgcgagagcc     300
gattacgatt tttggaatgg ttattttgac tactggggcc agggaaccct ggtcaccgtc     360
tcctca                                                                366

<210> SEQ ID NO 138
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 138

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Asn Gly Tyr Phe Asp Tyr Trp
            100                 105                 110

Gly Gln Gly Thr Leu Val Thr Val Ser Ser
        115                 120

<210> SEQ ID NO 139
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 139
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataataatt acccgtggac gttcggccaa    300
gggaccaagg tggaaatcaa a                                              321

<210> SEQ ID NO 140
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Glu Ile Lys
            100                 105

<210> SEQ ID NO 141
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 141
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt gggtacatct attacagtgg gagcacctac    180

```
tacaacccgt ccctcaagag tcgagttacc atatcagtag acacgtctaa gaaccagttc    240
tccctgaagc tgagctctgt gactgccgcg gacacggccg tgtattactg tgcgagagcc    300
gattacgatt tttggagtgg ttattttgac tactggggcc agggaaccct ggtcaccgtc    360
tcctca                                                               366
```

<210> SEQ ID NO 142
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 142

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 143
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 143

```
gacatccagc tgacccagtc tccatcctcc ctgtctgcat ctgtaggaga cagagtcacc    60
atcacttgcc gggcaagtca gggcattaga aatgatttag ctggtatca gcagaaacca    120 gggaaagccc ctaagcgcct gatctatgct gcatccagtt tgcaaaatgg ggtcccatca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa ac                                            322
```

<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 144

```
Asp Ile Gln Leu Thr Gln Ser Pro Ser Ser Leu Ser Ala Ser Val Gly
1               5                   10                  15
```

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Asn Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 145
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 145
caggtgcagc tgcaggagtc gggcccagga ctggtgaagc cttcacagac cctgtccctc      60
acctgcactg tctctggtgg ctccatcagc agtggtgatt actactggag ctggatccgc     120
cagtacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgggctctgt gactgccgcg gacacggccg tgtatttctg tgcgagagcc     300
gattacgatt tttggagtgg ttattttgac ttctggggcc agggaaccct ggtcaccgtc     360
tcctc                                                                 365

<210> SEQ ID NO 146
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 146

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Tyr Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Gly Ser Val Thr Ala Ala Asp Thr Ala Val Tyr Phe
                85                  90                  95

Cys Ala Arg Ala Asp Tyr Asp Phe Trp Ser Gly Tyr Phe Asp Phe Trp
            100                 105                 110

Gly Gln Gly Thr Leu Val Thr Val Ser
        115                 120

<210> SEQ ID NO 147
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 147
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatggtt acccgtggac gttcggccaa   300
gggaccaagg tggaaatcaa ac                                            322

<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys
            100                 105

<210> SEQ ID NO 149
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 149
caggtgcagc tgcaggagtc gggcccagga ctggtgaagc cttcacagac cctgtccctc    60
acctgcactg tctctggtgg ctccatcagc agtggtgatt actactggag ctggatccgc   120
cagtacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgggctctgt gactgccgcg gacacggccg tgtatttctg tgcgagagcc   300
gattacgatt ttggagtgg ttattttgac ttctggggcc agggaaccct ggtcaccgtc   360
tcctc                                                              365

```
<210> SEQ ID NO 150
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 150

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Tyr Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Gly Ser Val Thr Ala Ala Asp Thr Ala Val Tyr Phe
                85                  90                  95

Cys Ala Arg Ala Asp Tyr Asp Phe Trp Ser Gly Tyr Phe Asp Phe Trp
            100                 105                 110

Gly Gln Gly Thr Leu Val Thr Val Ser
        115                 120

<210> SEQ ID NO 151
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 151
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatggtt acccgtggac gttcggccaa    300
gggaccaagg tggaaatcaa ac                                             322

<210> SEQ ID NO 152
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45
```

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
 65              70                  75                      80

Glu Asp Phe Ala Thr Tyr Tyr Cys Leu Gln His Asn Gly Tyr Pro Trp
                    85                  90                  95

Thr Phe Gly Gln Gly Thr Lys Val Glu Ile Lys
            100                 105

<210> SEQ ID NO 153
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 153
caggtgcagc tgcaggagtc gggcccagga ctggtgaagc cttcacagac cctgtccctc      60
acctgcactg tctctggtgg ctccatcagt agtggtgatt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagcg     300
gattacgatt tttggagtgg ttattttgac cctggggcc agggaaccct ggtcaccgtc      360
tcctca                                                                366

<210> SEQ ID NO 154
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 154

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Ser Trp
            100                 105                 110

Gly Gln Gly Thr Leu Val Thr Val Ser Ser
        115                 120

<210> SEQ ID NO 155
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 155

```
gacatccaga tgacccagtc tccatcctcc ctgtctgcat ctgtaggaga cagagtcacc      60
atcacttgcc gggcaagtca gggcattaga aatgatttag ctggtatca  gcagatacct    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatggtt acccgtggac gttcggccaa    300
gggaccaagg tggaaatcaa a                                              321
```

<210> SEQ ID NO 156
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide construct

<400> SEQUENCE: 156

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys
            100                 105
```

<210> SEQ ID NO 157
<211> LENGTH: 366
<212> TYPE: DNA
<213> ORGANISM: Artificial Sequence
<220> FEATURE:
<223> OTHER INFORMATION: Description of Artificial Sequence: Synthetic
    polynucleotide construct

<400> SEQUENCE: 157

```
caggttcagc tggtgcagtc tggagctgag gtgaagaagc ctggggcctc agtgaaggtc      60
tcctgcaagg cttctggtta ccctttacc  aactatggta tcagctgggt gcggcaggcc    120
cctggacaag gcttgagtg  gatgggatgg atcagcgctt acgatggtta cagaaactat    180
gcacagaagc tccagggcag agtcaccatg accacagaca catccacgac cactgcctac    240
atggagctga ggagcctgag atctgacgac acggccgtgt attactgtgc gagagatgtt    300
caagactacg gtgactacga ctactttgac tactggggcc agggaaccct ggtcaccgtc    360
tcctca                                                               366
```

<210> SEQ ID NO 158
<211> LENGTH: 122
<212> TYPE: PRT
<213> ORGANISM: Artificial Sequence
<220> FEATURE:

<223> OTHER INFORMATION: Description of Artificial Sequence: Synthetic
polypeptide construct

<400> SEQUENCE: 158

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly Tyr Arg Asn Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Val Gln Asp Tyr Gly Asp Tyr Asp Tyr Phe Asp Tyr Trp
            100                 105                 110

Gly Gln Gly Thr Leu Val Thr Val Ser Ser
        115                 120
```

<210> SEQ ID NO 159
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide construct

<400> SEQUENCE: 159

```
gacatccaga tgacccagtc tccatcctcc ctgtctgcat ctgtaggaga cagagtcacc     60
atcacttgcc gggcaagtca gagcattagc agttatttaa attggtatca gcagaaacca    120
gggaaagccc ctaacctcct gatctatgct gcatccagtt tgcaaagtgg ggtcccatca    180
agattcaggg gcagtggatc tgggacagat ttcactctca ccatcagcag tctgcaacct    240
gaagattttg caacttacta ctgtcaacag agttacagta cccccatcac cttcggccaa    300
gggacacgac tggagattaa a                                              321
```

<210> SEQ ID NO 160
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide construct

<400> SEQUENCE: 160

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
```

```
                    85                  90                  95
Thr Phe Gly Gln Gly Thr Arg Leu Glu Ile Lys
            100                 105

<210> SEQ ID NO 161
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 161
caggtgcagc tgcaggagtc gggcccagga ctggtgaagc ctttacagac cctgtccctc    60
acctgcactg tctctggtgg ctccatcagc agtggtgatt actactggag ctggatccgc   120
cagcacccag ggaagggcct ggagtggatt gggtacatct attacagtgg gaccacctac   180
tacaacccgt ccctcaagag tcgagttacc atatcagtag acacgtctaa gaaccagttc   240
gccctgaagc tgaactctgt gactgccgcg gacacggccg tgtattactg tgcgagagcc   300
gattacgatt tttggagtgg ttattttgac tactggggcc agggaaccct ggtcaccgtc   360
tcctca                                                              366

<210> SEQ ID NO 162
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 162

Gln Val Gln Leu Gln Glu Ser Gly Pro Gly Leu Val Lys Pro Leu Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ala Leu Lys Leu Asn Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 163
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 163
gacatccaga tgacccagtc tccatcctcc ctgtctgcat ctgtaggaga cagagtcacc    60
atcacttgcc gggcaggtca ggcattaga aatgatttag gctggtatca gcagaaacca   120
```

```
gggaaagccc ctcagcgcct gatctatgct gcatccagtt tgcaaagtgg ggtcccatca      180
aggttcagcg gcagtggatc tgggacagaa ttctctctca caatctccag cctgcagcct      240
gaagattttg caacttatta ctgtctacag cataatagtt acccgtggac gttcggccaa      300
gggaccaagg tggaaatcaa ac                                               322
```

<210> SEQ ID NO 164
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 164

```
Asp Ile Gln Met Thr Gln Ser Pro Ser Ser Leu Ser Ala Ser Val Gly
1               5                   10                  15

Asp Arg Val Thr Ile Thr Cys Arg Ala Gly Gln Gly Ile Arg Asn Asp
            20                  25                  30

Leu Gly Trp Tyr Gln Gln Lys Pro Gly Lys Ala Pro Gln Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 165
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 165

```
caggtgcagc tggtggagtc tgggggaggc ttggtcaagc ctggagggtc cctgagactc      60
tcctgtgcag cctctggatt caccttcagt gactactaca tgagctggat ccgccaggct      120
ccagggaagg gactggagtg ggtttcatat attagtagta gtggtaataa catataccac      180
gcagactctg tgaagggccg attcaccatc tccagggaca acgccaagaa ctcactgtat      240
ctgcaaatga acagcctgag agccgaggac acggccgtgt attactgtgc gagagagaga      300
tatagtggct acgacgaccc tgatggtttt gatatctggg gccaagggac aatggtcacc      360
gtctcttca                                                              369
```

<210> SEQ ID NO 166
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 166

```
Gln Val Gln Leu Val Glu Ser Gly Gly Gly Leu Val Lys Pro Gly Gly
1               5                   10                  15
```

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asn Asn Ile Tyr His Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Ser Gly Tyr Asp Asp Pro Asp Gly Phe Asp Ile
            100                 105                 110

Trp Gly Gln Gly Thr Met Val Thr Val Ser Ser
            115                 120

<210> SEQ ID NO 167
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 167
gacatccaga tgacccagtc tccatcctcc ctgtctgcat ctgtaggaga cagagtcacc      60
atcacttgcc aggcgagtca ggacattagc aactatttaa gttggtttca gcagaaacca    120
gggaaagccc ctaagctcct gatccacgat gcatccaatt tggaaacagg ggtcccttca    180
aggttcagtg gaagtggatc tgggacagat tttactttca ccatcagcag cctgcagcct    240
gaagatattg caacatatta ctgtcaacag tatgataatc ccccgtgcag ttttggccag    300
gggaccaagc tggagatcaa a                                              321

<210> SEQ ID NO 168
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 168

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Ser Trp Phe Gln Gln Lys Pro Gly Lys Ala Pro Lys Leu Leu Ile
        35                  40                  45

His Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Pro Pro Cys
                 85                  90                  95

Ser Phe Gly Gln Gly Thr Lys Leu Glu Ile Lys
            100                 105

<210> SEQ ID NO 169

<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 169
caggtgcagc tgcaggagtc gggcccagga ctggtgaagc cttcacagac cctgtccctc    60
acctgcactg tctctggtgg ctccatcagc agtggttatt actactggag ctggatccgc   120
cagcacccag ggaagggcct ggagtggatt gggtacatct attacagtgg gaccacctac   180
tacaatccgt ccttcaagag tcgagttacc atatcagtag acacgtctaa gaaccagttc   240
tccctgaaac tgagctctgt gactgccgcg gacacggccg tgtattactg cgcagagcc   300 gattacgatt tttggagtgg tcactttgac tactggggcc agggaaccct ggtcaccgtc   360
tcctca                                                              366

<210> SEQ ID NO 170
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 170

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Tyr Tyr Tyr Trp Ser Trp Ile Arg Gln His Pro Gly Lys Gly Leu Glu
        35                  40                  45

Trp Ile Gly Tyr Ile Tyr Tyr Ser Gly Thr Thr Tyr Tyr Asn Pro Ser
    50                  55                  60

Phe Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly His Phe Asp Tyr Trp
            100                 105                 110

Gly Gln Gly Thr Leu Val Thr Val Ser Ser
        115                 120

<210> SEQ ID NO 171
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 171
gacatccaga tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgtggac gttcggccaa   300

-continued

```
gggaccaagg tggaaatcaa a                                              321
```

<210> SEQ ID NO 172
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 173
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 173

```
caggttcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gacttgagtg gatgggatgg atcagcgctt acgatggtca cacaaactat   180
gcacagaagc tccagggcag agtcaccatg accacagaca catccacgaa cacagcctac   240
atggagctga ggagcctgag atctgacgac acggccgttt attactgtgc gagagacccc   300
catgactaca gtaactacga ggcttttgac ttctggggcc agggaaccct ggtcaccgtc   360
tcctc                                                               365
```

<210> SEQ ID NO 174
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 174

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly His Thr Asn Tyr Ala Gln Lys Leu
 50                  55                  60

Gln Gly Arg Val Thr Met Thr Thr Asp Thr Ser Thr Asn Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Pro His Asp Tyr Ser Asn Tyr Glu Ala Phe Asp Phe Trp
             100                 105                 110

Gly Gln Gly Thr Leu Val Thr Val Ser
            115                 120

<210> SEQ ID NO 175
<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 175
atgaggtccc ctgctcagct cctggggctc ctgctactct ggctccgagg tgccagatgt     60
gacatccaga tgacccagtc tccatcctcc ctgtctgcat ctgtaggaga cagagtcacc    120
atcacttgcc gggcaagtca gagcattagc agttatttaa attggtatca gcagaaacca    180
gggaaagccc ctaacctcct gatctatgct gcatccagtt tgcaaagtgg ggtcccatca    240
agattcagtg gcagtggatc tgggacagat ttcactctca ccatcagcag tctgcaacct    300
gaagattttg caacttacta ctgtcaacag agttacagta cccccatcac cttcggccaa    360
gggacacgac tggagattaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgcc                           519

<210> SEQ ID NO 176
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 176

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Asn Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Ile
                 85                  90                  95

Thr Phe Gly Gln Gly Thr Arg Leu Glu Ile Lys
            100                 105

<210> SEQ ID NO 177
<211> LENGTH: 534

<212> TYPE: DNA
<213> ORGANISM: Artificial Sequence
<220> FEATURE:
<223> OTHER INFORMATION: Description of Artificial Sequence: Synthetic
    polynucleotide construct

<400> SEQUENCE: 177

```
accatggact ggacctggag ggtccttttc ttggtggcag cagcaacagg tgcccactcc      60
caggttcagc tggtgcagtc tggagctgag gtgaagaagc ctggggcctc agtgaaggtc     120
tcctgcaagg cttctggtta caccttacc aactatggta tcagctgggt gcggcaggcc     180
cctggacaag gcttgagtg gatgggatgg atcagcgctt acgatggtta cagaaactat     240
gcacagaagc tccagggcag agtcaccatg accacagaca catccacgac cactgcctac     300
atggagctga ggagcctgag atctgacgac acggccgtgt attactgtgc gagagatgtt     360
caagactacg gtgactacga ctactttgac tactggggcc agggaaccct ggtcaccgtc     420
tcctcagctt ccaccaaggg cccatccgtc ttccccctgg tgccctgctc caggagcacc     480
tccgagagca cagccgccct gggctgcctg gtcaaggact acttccccga accg           534
```

<210> SEQ ID NO 178
<211> LENGTH: 122
<212> TYPE: PRT
<213> ORGANISM: Artificial Sequence
<220> FEATURE:
<223> OTHER INFORMATION: Description of Artificial Sequence: Synthetic
    polypeptide construct

<400> SEQUENCE: 178

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asp Gly Tyr Arg Asn Tyr Ala Gln Lys Leu
    50                  55                  60
Gln Gly Arg Val Thr Met Thr Thr Asp Thr Ser Thr Thr Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Val Gln Asp Tyr Gly Asp Tyr Asp Tyr Phe Asp Tyr Trp
            100                 105                 110
Gly Gln Gly Thr Leu Val Thr Val Ser Ser
        115                 120

<210> SEQ ID NO 179
<211> LENGTH: 504
<212> TYPE: DNA
<213> ORGANISM: Artificial Sequence
<220> FEATURE:
<223> OTHER INFORMATION: Description of Artificial Sequence: Synthetic
    polynucleotide construct

<400> SEQUENCE: 179

```
cagctcctgg ggctcctgct actctggctc cgaggtgcca gatgtgacat ccagatgacc      60
cagtctccat cctccctgtc tgcatctgta ggagacagag tcaccatcac ttgccgggca     120
agtcagagca ttagcagtta tttaaattgg tatcagcaga aaccagggaa agcccctaac     180
ctcctgatct atgctgcatc cagtttgcaa agtggggtcc catcaagatt cagtggcagt     240
```

```
ggatctggga cagatttcac tctcaccatc agcagtctgc aacctgaaga ttttgcaact    300
tactactgtc aacagagtta cagtacccccc atcaccttcg gccaagggac acgactggag    360
attaaacgaa ctgtggctgc accatctgtc ttcatcttcc cgccatctga tgagcagttg    420
aaatctggaa ctgcctctgt tgtgtgcctg ctgaataact ctatcccag agaggccaaa    480 gtacagtgga aggtggataa cgcc                                            504
```

```
<210> SEQ ID NO 180
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 180
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

```
<210> SEQ ID NO 181
<211> LENGTH: 493
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 181
catctgtggt tcttcctcct gctggtggca gctcccagat gggtcctgtc ccaggtgcag    60
ctgcaggagt cgggcccagg actggtgaag ccttcacaga ccctgtccct cacctgcact    120
gtctctggtg gctccatcaa cagtggtgat tactactgga gctggatccg ccagcaccca    180
gggaagggcc tggagtggat tgggtacatc tattacagtg ggagcaccta ctacaacccg    240
tccctcaaga gtcgagttac catatcagta gacacgtcta agaaccagtt ctccctgaag    300
ctgagctctg tgactgccgc ggacacggcc gtgtattact gtgcgagagc agattacgat    360
ttttggagtg gttactttga ctactgggc agggaaccc tggtcaccgt ctcctcagcc    420
tccaccaagg gcccatcggt cttccccctg gcaccctcct ccaagagcac ctctgggggc    480
acaacggccc tgg                                                        493
```

```
<210> SEQ ID NO 182
<211> LENGTH: 122
<212> TYPE: PRT
<213> ORGANISM: Artificial Sequence
<220> FEATURE:
<223> OTHER INFORMATION: Description of Artificial Sequence: Synthetic
```

-continued polypeptide construct

<400> SEQUENCE: 182

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 183
<211> LENGTH: 518
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 183
atgagggtcc ctgctcagct cctggggctc ctgctgctct ggttcccagg tgccaggtgt      60
gacatccaga tgacccagtc tccatcctcc ctgtctgcat ctgtaggaga cagagtcacc     120
atcacttgcc gggcaagtca gggcattaga aatgatttag ctggtatca gcagaaacca     180 gggaaagccc ctaagcgcct gatctatgct gcatccagtt tgcaaagtgg ggtcccatca     240
aggttcagcg gcagtggatc tgggacagaa ttcactctca caatcagcag cctgcagcct     300
gaagattttg caacttatta ctgtctacag cataatagtt acccgtggac gttcggccaa     360
gggaccaagg tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgc                             518

<210> SEQ ID NO 184
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105
```

<210> SEQ ID NO 185
<211> LENGTH: 436
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 185

```
tggttcttcc ttctgctggt ggcagctccc agatgggtcc tgtcccaggt gcagctgcag      60
gagtcgggcc caggactggt gaagccttca cagaccctgt ccctcacctg cactgtctct     120
ggtggctcca tcagcagtgg tggttactac tggagctgga tccgccagca cccagggaag     180
ggcctggagt ggattgggta catctattac agtgggagca cctactacaa cccgtccctc     240
aagagtcgag ttaccatatc agtagacacg tctaagaacc agttctccct gaagctgagc     300
tctgtgactg ccgcggacac ggccgtgtat tactgtgcga gagatggcta tgatagtagt     360
ggttattacc acggctactt tgactactgg ggccagggaa ccctggtcac cgtctcctca     420
gcctccacca agggcc                                                     436
```

<210> SEQ ID NO 186
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 186

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
             35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Gly Tyr Asp Ser Ser Gly Tyr Tyr His Gly Tyr Phe
            100                 105                 110

Asp Tyr Trp Gly Gln Gly Thr Leu Val Thr Val Ser Ser
            115                 120                 125
```

<210> SEQ ID NO 187
<211> LENGTH: 521
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 187

```
caggtcttca tttctctgtt gctctggatc tctggtgcct acggggacat cgtgatgacc    60
cagtctccag actccctggc tgtgtctctg ggcgagaggg ccaccatcaa ctgcaagtcc   120
agccagagtg ttttatacag ctccaacaat aagaactact tagcttggta ccagcagaaa   180
ccaggacagc ctcctaagct gctcatttac tgggcatcta cccgggaatc cggggtccct   240
gaccgattca gtggcagcgg gtctgggaca gatttcactc tcaccatcag cagcctgcag   300
gctgaagatg tggcagttta ttactgtcag caatattata gtactccgct cactttcggc   360
ggagggacca aggtggagat caaacgaact gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg c                       521
```

<210> SEQ ID NO 188
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 188

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Ser Thr Pro Leu Thr Phe Gly Gly Gly Thr Lys Val Glu Ile
            100                 105                 110
Lys
```

<210> SEQ ID NO 189
<211> LENGTH: 455
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 189

```
ctgtggttct tcctcctgct ggtggcagct cccagatggg tcctgtccca ggtgcagctg    60
caggagtcgg gcccaggact ggtgaagcct tcacagaccc tgtccctcac ctgcactgtc   120
tctggtggct ccatcagtag tggtgattac tactggagct ggatccgcca gcacccaggg   180
aagggcctgg agtggattgg gtacatctat tacagtggga gcacctacta caacccgtcc   240
ctcaagagtc gagttaccat atcagtagac acgtctaaga accagttctc cctgaagttg   300
agctctgtga ctgccgcgga cacggccgtg tattactgtg cgagagccga ttacgatttt   360
```

```
tggagtggtt attttgacta ctggggccag ggaaccctgg tcaccgtctc ctcagcctcc    420
accaagggcc catcggtctt ccccctggca ccctc                              455
```

<210> SEQ ID NO 190
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 190

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 191
<211> LENGTH: 442
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 191

```
gtgcccgctc agcgcctggg gctcctgctg ctctggttcc caggtgccag gtgtgacatc    60
cagatgaccc agtctccatc ctccctgtct gcatctgtag gagacagagt caccatcact    120
tgccgggcaa gtcagggcat tagaaatgat ttaggctggt atcagcagaa accagggaaa    180
gcccctaagc gcctgatcta tgctgcatcc agtttgcaaa gtggggtccc atcaaggttc    240
agcggcagtg gatctgggac agaattcact ctcacaatca gcagcctgca gcctgaagat    300
tttgcaactt attactgtct acagcataat aattacccgt ggacgttcgg ccaagggacc    360
aaggtggaaa tcaaacgaac tgtggctgca ccatctgtct tcatcttccc gccatctgat    420
gagcagttga aatctggaac tg                                             442
```

<210> SEQ ID NO 192
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 192

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Gly Ile Arg Asn Asp
              20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Asn Tyr Pro Trp
                 85                  90                  95

Thr Phe Gly Gln Gly Thr Lys Val Glu Ile Lys
            100                 105

<210> SEQ ID NO 193
<211> LENGTH: 427
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 193
tggttcttcc ttctgctggt ggcagctccc agatgggtcc tgtcccaggt gcagctgcag     60
gagtcgggcc caggactggt gaagccttca cagaccctgt ccctcacctg cactgtctct    120
ggtggctcca tcagcagtgg tgattactac tggagctgga tccgccagca cccagggaag    180
ggcctggagt ggattgggta catctattac agtgggagca cctactacaa cccgtccctc    240
aagagtcgag ttaccatatc agtagacacg tctaagaacc agttctccct gaagctgagc    300
tctgtgactg ccgcggacac ggccgtgtat ttctgtgcga gagccgatta cgattttggg    360
agtggttatt ttgactactg gggccaggga accctggtca ccgtctcctc agcctccacc    420
aagggcc                                                              427

<210> SEQ ID NO 194
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 194

Gln Val Gln Leu Gln Glu Ser Gly Pro Gly Leu Val Lys Pro Ser Gln
1               5                  10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Phe
                 85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser 115                 120

<210> SEQ ID NO 195
<211> LENGTH: 518
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 195
atgagggtcc ccgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga aatgatttag ctggtatca gcagaaacca    180 gggaaagccc ctaagcgcct gatctatgct gcatccagtt tgcaaagtgg ggtcccatca   240
aggttcagcg gcagtggatc tgggacagaa ttcactctca caatcagcag cctgcagcct   300
gaagattttg caacttatta ctgtctacag cataatactt acccgtggac gttcggccaa   360
gggaccaagg tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgc                           518

<210> SEQ ID NO 196
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys
            100                 105

<210> SEQ ID NO 197
<211> LENGTH: 428
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 197
tggttcttcc ttctgctggt ggcagctccc agatgggtcc tgtcccaggt gcagctgcag    60
gagtcgggcc caggactggt gaagccttca cagaccctgt ccctcacctg cactgtctct   120
ggtggctcca tcagcagtgg tgattactac tggagctgga tccgccagca cccagggaag   180

```
ggcctggagt ggattgggta catctattac agtgggagca cctactacaa cccgtccctc    240
aagagtcgag ttaccatatc agtagacacg tctaagaacc agttctccct gaagctgagc    300
tctgtgactg ccgcggacac ggccgtgtat ttctgtgcga gagccgatta cgattttggg    360
aatggttatt ttgactactg gggccaggga accctggtca ccgtctcctc agcctccacc    420
aagggccc                                                             428
```

<210> SEQ ID NO 198
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 198

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Ala Asp Tyr Asp Phe Trp Asn Gly Tyr Phe Asp Tyr Trp
            100                 105                 110

Gly Gln Gly Thr Leu Val Thr Val Ser Ser
        115                 120
```

<210> SEQ ID NO 199
<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 199

```
atgagggtcc ccgctcagct cctggggctc ctgctgctct ggttcccagg tgccaggtgt     60
gacatccaga tgacccagtc tccatcctcc ctgtctgcat ctgtaggaga cagagtcacc    120
atcacttgcc gggcaagtca gggcattaga aatgatttag ctggtatcag cagaaaccca    180
gggaaagccc ctaagcgcct gatctatgct gcttccagtt tgcaaagtgg ggtcccatca    240
aggttcagcg gcagtggatc tgggacagaa ttcactctca caatcagcag cctgcagcct    300
gaagattttg caacttatta ctgtctacag cataatactt acccgtggac gttcggccaa    360
gggaccaagg tggaaatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgcc                           519
```

<210> SEQ ID NO 200
<211> LENGTH: 107
<212> TYPE: PRT

<213> ORGANISM: Artificial Sequence
<220> FEATURE:
<223> OTHER INFORMATION: Description of Artificial Sequence: Synthetic
      polypeptide construct

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys
            100                 105

<210> SEQ ID NO 201
<211> LENGTH: 398
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 201
ttggtggcag cagctacagg cacccacgcc caggtccagc tggtacagtc tggggctgag      60
gtgaagaagc ctgggcctc agtgaaggtc tcctgcaagg tttccggata caccctcact     120
gaattatcca tgtactgggt gcgacaggct cctggaaaag gcttgagtg gatgggaggt     180 tttgatcctg aagatggtga aacaatctac gcacagaagt tccagggcag agtcaccatg     240
accgaggaca catctacaga cacagcctac atggagctga gcagcctgag atctgaggac     300
acggccgtgt attactgtgc aactgggtgg aactacgtct ttgactactg gggccaggga     360
accctggtca ccgtctcctc agcctccacc aagggccc                            398

<210> SEQ ID NO 202
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 202

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met Tyr Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

```
Met Glu Leu Ser Ser Leu Arg Ser Glu Asp Thr Ala Val Tyr Tyr Cys
                 85                  90                  95

Ala Thr Gly Trp Asn Tyr Val Phe Asp Tyr Trp Gly Gln Gly Thr Leu
            100                 105                 110

Val Thr Val Ser Ser
            115

<210> SEQ ID NO 203
<211> LENGTH: 388
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 203
ggatccagtg gggatattgt gatgactcag tctccactct ccctgcccgt cacccctgga      60
gagccggcct ccatctcctg caggtccagt cagagcctcc tgcatagtaa tggatacaac    120
tatttggatt ggtacctgca gaagccaggg cagtctccac agctcctgat ctatttggat    180
tctcatcggg cctccggggt ccctgacagg ttcagtggca gtggatcagg cacagatttt    240
acactgaaaa tcagcagagt ggaggctgag gatgttgggg tttattactg catgcaagct    300
ctacaaactc cgctcacttt cggcggaggg accaaggtgg agatcaaacg aactgtggct    360
gcaccatctg tcttcatctt cccgccat                                       388

<210> SEQ ID NO 204
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 204

Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Asp Ser His Arg Ala Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 205
<211> LENGTH: 446
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 205
tggttcttcc ttctgctggt ggcagctccc agatgggtcc tgtcccaggt gcagctgcag     60
```

```
gagtcgggcc caggactggt gaagccttca cagaccctgt ccctcacctg cactgtctct    120
ggtggctcca tcagcagtgg tgattactac tggagctgga tccgccagca cccagggaag    180
ggcctggagt ggattgggta catctattac agtgggagca cctactacaa cccgtccctc    240
aagagtcgag ttaccatatc agtagacacg tctaagaacc agttctccct gaagctgagc    300
tctgtgactg ccgcggacac ggccgtgtat ttctgtgcga gagccgatta cgattttttgg    360 agtggttatt ttgactactg gggccaggga accctggtca ccgtctcctc agcctccacc    420
aagggcccat cgagtcttcc ccctgg                                          446
```

<210> SEQ ID NO 206
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 206

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 207
<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 207

```
atgagggtcc ccgctcagct cctggggctc ctgctgctct ggttcccagg tgccaggtgt    60
gacatccaga tgacccagtc tccatcctcc ctgtctgcat ctgtaggaga cagagtcacc    120
atcacttgcc gggcaagtca gggcattaga aatgatttag ctggtatcag cagaaaccca    180
gggaaagccc ctaagcgcct gatctatgct gcatccagtt tgcaaagtgg ggtcccatca    240
aggttcagcg gcagtggatc tgggacaaaa ttcactctca ctatcagcag cctgcagcct    300
gaagattttg caacttatta ctgtctacag cataatactt acccgtggac gttcggccaa    360
gggaccaagg tggaaatcag acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgcc                           519
```

<210> SEQ ID NO 208
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 208

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Lys Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Arg
            100                 105
```

<210> SEQ ID NO 209
<211> LENGTH: 564
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 209

```
accatgaaac atctgtggtt cttcctcctg ctggtggcag ctcccagatg ggtcctgtcc      60
caggtgcagc tgcaggagtc gggcccagga ctggtgaagc cttcacagac cctgtccctc     120
acctgcactg tctctggtgg ctccatcagc agtggtgatt actactggag ctggatccgc     180
cagcacccag ggaagggcct ggagtggatt gggtacatct attacagtgg gagcacctac     240
tacaacccgt ccctcaagag tcgagttacc atatcagtag acacgtctaa gaaccagttc     300
tccctgaagc tgagctctgt gactgccgcg gacacggccg tgtattactg tgcgagagcg     360
gattacgatt tttggagtgg ttatttttgac tactggggcc agggaatcct ggtcaccgtc     420
tcctcagcct ccaccaaggg cccatcggtc ttccccctgg cacccctcct caagaacacc     480
tctgggggca cagcggccct gggctgcctg gtcaaggact acttccccga accggtgacg     540
gtgtcctgga actcaggcgc cctg                                             564
```

<210> SEQ ID NO 210
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 210

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30
```

Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Ile Leu Val Thr Val Ser Ser
        115                 120

<210> SEQ ID NO 211
<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 211
atgagggtcc ccgctcagct cctggggctc ctgctgctct ggttcccagg tgccaggtgt      60
gacatccaga tgacccagtc tccatcctcc ctgtctgcat ctgtaggaga cagagtcacc     120
atcacttgcc gggcaagtca gggcattaga aatgatttag gctggtatca gcagaaacca     180
gggaaagccc ctaagcgcct gatctatgct gcatccagtt tgcaaagtgg ggtcccatca     240
aggttcagcg gcagtggatc tgggacagaa ttcactctca caatcagcag cctgcagcct     300
gaagattttg caacttatta ctgtctacag cataatagtt acccgtggac gttcggccaa     360
gggaccaagg tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgcc                            519

<210> SEQ ID NO 212
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 213
<211> LENGTH: 432
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 213

```
tggttcttcc ttctgctggt ggcagctccc agatgggtcc tgtcccaggt gcagctgcag      60
gagtcgggcc caggactggt gaagccttca cagaccctgt ccctcacctg cactgtctct     120
ggtggctcca tcagcagtgg tgattactac tggagctgga tccgccagca cccagggaag     180
ggcctggagt ggattggata catctattac agtgggagca cctactacaa ttcgtccctc     240
aagagtcgag ttaccatatc agtagacacg tctaagaacc agttctccct gaagctgagc     300
tctgtgactg ccgcggacac ggccgtgtat tactgtgcga gagcggatta cgattttgg      360 agtggttatt ttgactactg gggccaggga accctggtca ccgtctcctc agcctccacc     420
aagggcccat cg                                                         432
```

<210> SEQ ID NO 214
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide construct

<400> SEQUENCE: 214

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Ser Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 215
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide construct

<400> SEQUENCE: 215

```
ggtgccaggt gtgacatcca gatgacccag tctccatcct ccctgtctgc atctgtagga      60
gacagagtca ccatcacttg ccgggcaagt cagggcatta gaaatgattt aggctggtat     120
cagcagaaac ctgggaaagc ccctaagcgc ctgatctatg ctgcatccag tttgcaaagt     180
```

```
ggggtcccat caaggttcag cggcagtgga tctgggacag aattcactct cacaatcagc    240
agcctgcagc ctgaagattt tgcaacttat tactgtctac agcacaatag ttacccgtgg    300
acgttcggcc aagggaccaa ggtggaaatc aaacgaactg tggctgcacc atctgtcttc    360
atcttcccgc ca                                                        372
```

<210> SEQ ID NO 216
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 217
<211> LENGTH: 548
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 217

```
aggttcttcc ttctgctggt ggcagctccc agatgggtcc tgtcccaggt gcagctgcag    60
gagtcgggcc caggactggt gaagccttca cagaccctgt ccctcacctg cactgtctct    120
ggtggctcca tcagcagtgg tgattactac tggagctgga tccgccagca cccagggaag    180
ggcctggagt ggattggata catctattac agtgggagca cctactacaa cccgtccctc    240
aagagtcgag ttaccatatc agtagacacg tctaagaacc agttctccct gaagctgagc    300
tctgtgactg ccgcggacac ggccgtgtat tactgtgcga gagccgatta cgattttggg    360
agtggttatt ttgactactg gggccaggga accctggtca ccgtctcctc agcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccct                                                             548
```

<210> SEQ ID NO 218
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 218

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 219
<211> LENGTH: 517
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 219
atgagggtcc ccgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga aatgatttag gctggtatca gcagaaacca   180
gggaaagccc ctaagcgcct gatctatgct gcatccagtt tgcaaagtgg ggtcccatca   240
aggttcagcg gcagtggatc tgggacagaa ttcactctca caatcagcag cctgcagcct   300
gaagattttg caacttatta ctgtctacag cataatagtt acccgtggac gttcggccaa   360
gggaccaagg tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacg                           517

<210> SEQ ID NO 220
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 221
<211> LENGTH: 446
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 221
ctgtggttct tccttctgct ggtggcagct cccagatggg tcctgtccca ggtgcagctg     60
caggagtcgg gcccaggact ggtgaagcct tcacagaccc tgtccctcac ctgcactgtc    120
tctggtggct ccatcagcag tggtgattac tactggagct ggatccgcca gcacccaggg    180
aagggcctgg agtggattgg gtacatctat tacagtggga gcacctacta caacccgtcc    240
ctcaagagtc gagttaccat gtcagtagac acgtctaaga accagttctc cctgaagctg    300
agctctgtga ctgccgcgga cacggccgtg tattactgtg cgagagccga ttacgatttt    360
tggagtggtc actttgactg ctggggccag ggaaccctgg tcaccgtctc ctcagcttcc    420
accaagggcc catccgtctt ccccc                                          446

<210> SEQ ID NO 222
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 222

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly His Phe Asp Cys Trp
            100                 105                 110

Gly Gln Gly Thr Leu Val Thr Val Ser Ser
        115                 120

<210> SEQ ID NO 223
<211> LENGTH: 419
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 223

```
atgagggtcc ccgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga gatgatttag ctggtatca gcagaaacca    180
gggaaagccc ctaagcgcct gatctatgct gaatccagtt tgcaaagtgg ggtcccatca   240
aggttcagcg gcagtggatc tgggacagaa ttcactctca caatcagcag cctgcagcct   300
gaagattttg caacttatta ctgtctacag catcatagtt acccgtggac gttcggccaa   360
gggaccaagg tggaaatcaa acgaactgtg gctgcaccat ctgtcttcat cttcccgcc    419
```

<210> SEQ ID NO 224
<211> LENGTH: 107
<212> TYPE: PRT
<213> ORGANISM: Artificial Sequence
<220> FEATURE:
<223> OTHER INFORMATION: Description of Artificial Sequence: Synthetic
  polypeptide construct

<400> SEQUENCE: 224

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asp Asp
            20                  25                  30
Leu Gly Trp Tyr Gln Gln Lys Pro Gly Lys Ala Pro Lys Arg Leu Ile
        35                  40                  45
Tyr Ala Glu Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His His Ser Tyr Pro Trp
                85                  90                  95
Thr Phe Gly Gln Gly Thr Lys Val Glu Ile Lys
            100                 105
```

<210> SEQ ID NO 225
<211> LENGTH: 504
<212> TYPE: DNA
<213> ORGANISM: Artificial Sequence
<220> FEATURE:
<223> OTHER INFORMATION: Description of Artificial Sequence: Synthetic
  polynucleotide construct

<400> SEQUENCE: 225

```
tggctgagct gggttttcct cgttgctctt taagaggtg tccagtgtca ggtgcagctg     60
gtggagtctg ggggaggcgt ggtccagcct gggaggtccc tgagactctc ctgtgcagcg   120
tctggattca ccttcaatag ctatgacatg cactgggtcc gccaggctcc aggcaagggg   180
ctggagtggg tggcagttat atggtatgat ggaagtaata atactatgc agactccgtg    240
aagggccgat tcaccatctc tagagacaat tccaagaaca cgctgtatct gcaaatgaac   300
agcctgagag ccgaggacac ggctgtgtat tactgtgcga gagaccgctt gtgtactaat   360
ggtgtatgct atgaagacta cggtatggac gtctggggcc aagggaccac ggtcaccgtc   420
tcctcagctt ccaccaaggg cccatccgtc ttccccctgg cgcctgctc caggagcacc    480
tccgagagca gccgccct gggc                                           504
```

```
<210> SEQ ID NO 226
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 226

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Ser Tyr
                20                  25                  30

Asp Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Leu Cys Thr Asn Gly Val Cys Tyr Glu Asp Tyr Gly
            100                 105                 110

Met Asp Val Trp Gly Gln Gly Thr Thr Val Thr Val Ser Ser
        115                 120                 125

<210> SEQ ID NO 227
<211> LENGTH: 504
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 227
atgagggtcc ctgctcagct cctggggctc ctgctgctct ggctctcagg tgccagatgt      60
gacatccaga tgacccagtc tccatcctcc ctgtctgcat ctgtaggaga cagagtcacc     120
atcacttgcc aggcgagtca ggacattagc aactatttaa attggtatca gcagaaacca     180
gggaaagccc ctaaggtcct gatctacgat gcatccaatt tggaaacagg ggtcccatca     240
aggttcagtg gaagtggatc tgggacagat tttactttca ccatcagcag cctgcagcct     300
gaagatgttg caacatatta ctgtcaaaca tatgatactc tcccgctcac tttcggcgga     360
gggaccaagg tggagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtgg                                            504

<210> SEQ ID NO 228
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30
```

Leu Asn Trp Tyr Gln Gln Lys Pro Gly Lys Ala Pro Lys Val Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Ala Thr Tyr Tyr Cys Gln His Tyr Asp Thr Leu Pro Leu
                85                  90                  95

Thr Phe Gly Gly Gly Thr Lys Val Glu Ile Lys
            100                 105

<210> SEQ ID NO 229
<211> LENGTH: 472
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 229
ggactgtgca agaacatgaa acacctgtgg ttcttcctcc tgctggtggc agctcccaga      60
tgggtcctgt cccaggtgca gctgcaggag tcgggcccag gactggtgaa gccttacag     120 accctgtccc tcacctgcac tgtctctggt ggctccatca gcagtggtga ttactactgg     180
agctggatcc gccagcaccc agggaagggc ctggagtgga ttgggtacat ctattacagt     240
gggaccacct actacaaccc gtccctcaag agtcgagtta ccatatcagt agacacgtct     300
aagaaccagt tcgccctgaa gctgaactct gtgactgccg cggacacggc cgtgtattac     360
tgtgcgagag ccgattacga ttttggagt ggttattttg actactgggg ccagggaacc     420
ctggtcaccg tctcctcagc ttccaccaag ggcccatccg tcttccccct gg             472

<210> SEQ ID NO 230
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 230

Gln Val Gln Leu Gln Glu Ser Gly Pro Gly Leu Val Lys Pro Leu Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ala Leu Lys Leu Asn Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 231
<211> LENGTH: 531
<212> TYPE: DNA
<213> ORGANISM: Artificial Sequence
<220> FEATURE:
<223> OTHER INFORMATION: Description of Artificial Sequence: Synthetic
      polynucleotide construct

<400> SEQUENCE: 231

```
atgagggtcc ctgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaggtca gggcattaga aatgatttag ctggtatca gcagaaacca   180 gggaaagccc ctcagcgcct gatctatgct gcatccagtt tgcaaagtgg ggtcccatca   240
aggttcagcg gcagtggatc tgggacagaa ttctctctca caatctccag cctgcagcct   300
gaagattttg caacttatta ctgtctacag cataatagtt acccgtggac gttcggccaa   360
gggaccaagg tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc ttccaatcgg g           531
```

<210> SEQ ID NO 232
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 232

```
Asp Ile Gln Met Thr Gln Ser Pro Ser Ser Leu Ser Ala Ser Val Gly
1               5                   10                  15

Asp Arg Val Thr Ile Thr Cys Arg Ala Gly Gln Gly Ile Arg Asn Asp
            20                  25                  30

Leu Gly Trp Tyr Gln Gln Lys Pro Gly Lys Ala Pro Gln Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 233
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233

```
cgggatccat gtcctagcct aggggc                                         26
```

<210> SEQ ID NO 234
<211> LENGTH: 39
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 234
gctctagatt aatgatgatg atgatgatgt tgtcctaaa                              39

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Gly Ser Ile Asn Ser Gly Asp Tyr Tyr Trp Ser
1               5                   10

<210> SEQ ID NO 236
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Gly Ser Ile Ser Ser Gly Asp Tyr Tyr Trp Ser
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Gly Ser Ile Ser Ser Gly Gly Tyr Tyr Trp Ser
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Tyr Thr Leu Thr Glu Leu Ser Met Tyr
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Gly Ser Val Ser Ser Gly Gly Tyr Tyr Trp Ser
1               5                   10

<210> SEQ ID NO 240
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Phe Thr Phe Asn Ser Tyr Asp Met His
1               5                   10

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Tyr Thr Phe Thr Asn Tyr Gly Ile Ser
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Phe Thr Phe Ser Asp Tyr Tyr Met Ser
1               5                   10

<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Gly Ser Ile Ser Ser Gly Tyr Tyr Tyr Trp Ser
1               5                   10

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Tyr Thr Phe Thr Ser Tyr Gly Ile Ser
1               5                   10

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245
```

```
Gly Phe Ser Leu Ser Thr Ser Gly Val Gly Val Gly
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Phe Thr Val Ser Ser Asn Tyr Met Ser
1               5                   10

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gly Tyr Ser Phe Thr Ser Tyr Trp Ile Gly
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gly Tyr Thr Phe Thr Ser Tyr Asp Ile Asn
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gly Asp Ser Val Ser Ser Asn Ser Ala Ala Trp Asn
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gly Gly Ser Ile Ser Ser Tyr Tyr Trp Ser
1               5                   10

<210> SEQ ID NO 251
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 251

Gly Tyr Thr Phe Thr Gly Tyr Tyr Met His
1               5                   10

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Phe Thr Phe Ser Ile Tyr Ser Met Asn
1               5                   10

<210> SEQ ID NO 253
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gly Gly Ser Val Ser Ser Gly Gly Tyr Tyr Trp Asn
1               5                   10

<210> SEQ ID NO 254
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gly Gly Ser Val Ser Ser Gly Gly Tyr Tyr Trp Asn
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gly Phe Thr Phe Ser Ser Tyr Gly Met His
1               5                   10

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gly Gly Ser Phe Ser Gly Tyr Tyr Trp Ser
1               5                   10
```

-continued

```
<210> SEQ ID NO 257
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gly Val Ser Ile Ser Ser Gly Gly Tyr Tyr Trp Ser
1               5                   10

<210> SEQ ID NO 258
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Tyr Ile Tyr Tyr Ser Gly Ser Thr Tyr Tyr Asn Pro Ser Leu Lys Ser
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Tyr Ile Tyr Tyr Ser Gly Ser Thr Tyr Tyr Asn Pro Ser Leu Arg Ser
1               5                   10                  15

<210> SEQ ID NO 260
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gly Phe Asp Pro Glu Asp Gly Glu Thr Ile Tyr Ala Gln Lys Phe Gln
1               5                   10                  15

Gly

<210> SEQ ID NO 261
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Tyr Ile Tyr Tyr Ser Gly Ser Thr Asn Tyr Asn Pro Ser Leu Lys Ser
1               5                   10                  15

<210> SEQ ID NO 262
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 262

Tyr Ile Tyr Tyr Ser Gly Ser Thr Tyr Tyr Asn Ser Ser Leu Lys Ser
1               5                   10                  15

<210> SEQ ID NO 263
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Tyr Ile Tyr Asp Ser Gly Ser Thr Tyr Asn Pro Ser Leu Lys Ser
1               5                   10                  15

<210> SEQ ID NO 264
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Val Ile Trp Tyr Asp Gly Ser Asn Lys Tyr Tyr Ala Asp Ser Val Lys
1               5                   10                  15

Gly

<210> SEQ ID NO 265
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Tyr Ile Tyr Tyr Ser Gly Thr Thr Tyr Tyr Asn Pro Ser Leu Lys Ser
1               5                   10                  15

<210> SEQ ID NO 266
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Trp Ile Ser Ala Tyr Asp Gly Tyr Arg Asn Tyr Ala Gln Lys Leu Gln
1               5                   10                  15

Gly

<210> SEQ ID NO 267
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Tyr Ile Ser Ser Ser Gly Asn Asn Ile Tyr His Ala Asp Ser Val Lys
1               5                   10                  15

Gly

<210> SEQ ID NO 268
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 268

Tyr Ile Tyr Tyr Ser Gly Thr Thr Tyr Asn Pro Ser Phe Lys Ser
1               5                   10                  15

<210> SEQ ID NO 269
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 269

Trp Ile Ser Ala Tyr Asp Gly His Thr Asn Tyr Ala Gln Lys Leu Gln
1               5                   10                  15

Gly

<210> SEQ ID NO 270
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 270

Leu Ile Tyr Trp Asn Asp Asp Lys Arg Tyr Ser Pro Ser Leu Lys Ser
1               5                   10                  15

<210> SEQ ID NO 271
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 271

Val Ile Tyr Ser Gly Gly Ser Thr Tyr Tyr Ala Asp Ser Val Lys Gly
1               5                   10                  15

<210> SEQ ID NO 272
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 272

Tyr Ile Tyr Ser Ser Gly Ser Thr Tyr Tyr Asn Pro Ser Leu Lys Ser
1               5                   10                  15

<210> SEQ ID NO 273
<211> LENGTH: 17
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 273

Ile Ile Tyr Pro Gly Asp Ser Asp Thr Arg Tyr Ser Pro Ser Phe Gln
1               5                   10                  15

Gly

<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Ile Ile Trp Pro Gly Asp Ser Asp Thr Ile Tyr Ser Pro Ser Phe Gln
1               5                   10                  15

Gly

<210> SEQ ID NO 275
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Trp Met Asn Pro Asn Ser Gly Asp Thr Gly Tyr Ala Gln Val Phe Gln
1               5                   10                  15

Gly

<210> SEQ ID NO 276
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Arg Thr Tyr Tyr Arg Ser Lys Trp Tyr Asn Asp Tyr Ala Val Ser Val
1               5                   10                  15

Lys Ser

<210> SEQ ID NO 277
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

His Ile Tyr Thr Ser Gly Ser Thr Asn Tyr Asn Pro Ser Leu Lys Ser
1               5                   10                  15

<210> SEQ ID NO 278
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 278

Trp Ile Asn Pro Asn Ile Gly Gly Thr Asn Cys Ala Gln Lys Phe Gln
1               5                   10                  15

Gly

<210> SEQ ID NO 279
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Asn Ile Tyr Tyr Ser Gly Ser Thr Tyr Tyr Asn Pro Ser Leu Lys Ser
1               5                   10                  15

<210> SEQ ID NO 280
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Tyr Ile Ser Ser Ser Ser Ser Thr Ile Tyr Tyr Ala Asp Ser Val Lys
1               5                   10                  15

Gly

<210> SEQ ID NO 281
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Tyr Ile Asn Tyr Ser Gly Ser Thr Asn Tyr Asn Pro Ser Leu Lys Ser
1               5                   10                  15

<210> SEQ ID NO 282
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Glu Ile Asn His Ser Gly Ser Thr Asn Tyr Asn Pro Ser Leu Lys Ser
1               5                   10                  15

<210> SEQ ID NO 283
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283
```

```
Ala Asp Tyr Asp Phe Trp Ser Gly Tyr Phe Asp Tyr
1               5                   10

<210> SEQ ID NO 284
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Asp Gly Tyr Asp Ser Ser Gly Tyr Tyr His Gly Tyr Phe Asp Tyr
1               5                   10                  15

<210> SEQ ID NO 285
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Asp Tyr Asp Phe Trp Asn Gly Tyr Phe Asp Tyr
1               5                   10

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gly Trp Asn Tyr Val Phe Asp Tyr
1               5

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Glu Asp Asp Gly Met Asp Val
1               5

<210> SEQ ID NO 288
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Asp Gly Asp Val Asp Thr Ala Met Val Asp Ala Phe Asp Ile
1               5                   10

<210> SEQ ID NO 289
<211> LENGTH: 12
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 289

Gly Asp Tyr Asp Phe Trp Ser Gly Glu Phe Asp Tyr
1               5                   10

<210> SEQ ID NO 290
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Asp Gln Gly Gln Asp Gly Tyr Ser Tyr Gly Tyr Gly Tyr Tyr Gly
1               5                   10                  15

Met Asp Val

<210> SEQ ID NO 291
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ala Asp Tyr Asp Phe Trp Ser Gly Tyr Phe Asp Phe
1               5                   10

<210> SEQ ID NO 292
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ala Asp Tyr Asp Phe Trp Ser Gly Tyr Phe Asp Ser
1               5                   10

<210> SEQ ID NO 293
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Asp Arg Leu Cys Thr Asn Gly Val Cys Tyr Glu Asp Tyr Gly Met Asp
1               5                   10                  15

Val

<210> SEQ ID NO 294
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

```
Asp Val Gln Asp Tyr Gly Asp Tyr Asp Tyr Phe Asp Tyr
1               5                   10

<210> SEQ ID NO 295
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ala Asp Tyr Asp Phe Trp Ser Gly His Phe Asp Cys
1               5                   10

<210> SEQ ID NO 296
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Glu Arg Tyr Ser Gly Tyr Asp Asp Pro Asp Gly Phe Asp Ile
1               5                   10

<210> SEQ ID NO 297
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Ala Asp Tyr Asp Phe Trp Ser Gly His Phe Asp Tyr
1               5                   10

<210> SEQ ID NO 298
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Asp Pro His Asp Tyr Ser Asn Tyr Glu Ala Phe Asp Phe
1               5                   10

<210> SEQ ID NO 299
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Arg Asp Glu Val Arg Gly Phe Asp Tyr
1               5

<210> SEQ ID NO 300
<211> LENGTH: 6
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 300

Gly Gln Trp Leu Asp Val
1               5

<210> SEQ ID NO 301
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Asp Arg Glu Leu Glu Leu Tyr Tyr Tyr Tyr Tyr Gly Met Asp Val
1               5                   10                  15

<210> SEQ ID NO 302
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Asp Arg Glu Leu Glu Gly Tyr Ser Asn Tyr Tyr Gly Val Asp Val
1               5                   10                  15

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

His Glu Asn Tyr Gly Asp Tyr Asn Tyr
1               5

<210> SEQ ID NO 304
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Asp Arg Glu Arg Glu Trp Asp Asp Tyr Gly Asp Pro Gln Gly Met Asp
1               5                   10                  15

Val

<210> SEQ ID NO 305
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Phe Gly Asp Leu Pro Tyr Asp Tyr Ser Tyr Tyr Glu Trp Phe Asp Pro

<210> SEQ ID NO 306
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Asp Leu Tyr Asp Phe Trp Ser Gly Tyr Pro Tyr Tyr Tyr Gly Met Asp
1               5                   10                  15
Val

<210> SEQ ID NO 307
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Asp Tyr Tyr Gly Ser Gly Ser Phe Tyr Tyr Tyr Tyr Gly Met Asp Val
1               5                   10                  15

<210> SEQ ID NO 308
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Glu Ala Ile Phe Gly Val Gly Pro Tyr Tyr Tyr Tyr Gly Met Asp Val
1               5                   10                  15

<210> SEQ ID NO 309
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gly Gly Arg Tyr Ser Ser Ser Trp Ser Tyr Tyr Tyr Tyr Gly Met Asp
1               5                   10                  15
Val

<210> SEQ ID NO 310
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gly Gly Asp Ser Asn Tyr Glu Asp Tyr Tyr Tyr Tyr Gly Met Asp
1               5                   10                  15
Val

```
<210> SEQ ID NO 311
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Asp Ser Ser Tyr Tyr Asp Ser Ser Gly Tyr Tyr Leu Tyr Tyr Tyr Ala
1               5                   10                  15

Met Asp Val

<210> SEQ ID NO 312
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gly Gly Thr Gly Thr Asn Tyr Tyr Tyr Tyr Gly Met Asp Val
1               5                   10                  15

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Asp Arg Gly Asp Phe Asp Ala Phe Asp Ile
1               5                   10

<210> SEQ ID NO 314
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ala Ala Arg Leu Asp Tyr Tyr Tyr Gly Met Asp Val
1               5                   10

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Asp Lys Trp Thr Trp Tyr Phe Asp Leu
1               5

<210> SEQ ID NO 316
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 316

Asp Ser Glu Ser Glu Tyr Ser Ser Ser Asn Tyr Gly Met Asp Val
1               5                   10                  15

<210> SEQ ID NO 317
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gln Met Ala Gly Asn Tyr Tyr Tyr Gly Met Asp Val
1               5                   10

<210> SEQ ID NO 318
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Arg Ala Ser Gln Gly Ile Arg Asn Asp Leu Gly
1               5                   10

<210> SEQ ID NO 319
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Lys Ser Ser Gln Ser Val Leu Tyr Ser Ser Asn Asn Lys Asn Tyr Leu
1               5                   10                  15
Ala

<210> SEQ ID NO 320
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Arg Ala Ser Gln Asp Ile Arg Asn Asp Leu Gly
1               5                   10

<210> SEQ ID NO 321
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Arg Ser Ser Gln Ser Leu Leu His Ser Asn Gly Tyr Asn Tyr Leu Asp
1               5                   10                  15
```

-continued

```
<210> SEQ ID NO 322
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Arg Ser Ser Gln Ser Leu Leu His Ser Asn Gly Tyr Asn Tyr Leu Glu
1               5                   10                  15

<210> SEQ ID NO 323
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Arg Ala Ser Gln Ser Leu Ser Gly Asn Tyr Leu Ala
1               5                   10

<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Gln Ala Ser Gln Asp Ile Ser Asn Tyr Leu Asn
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Arg Ala Gly Gln Gly Ile Arg Asn Asp Leu Gly
1               5                   10

<210> SEQ ID NO 326
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Arg Ala Ser Gln Ser Ile Ser Ser Tyr Leu Asn
1               5                   10

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327
```

Arg Ala Ser Gln Gly Ile Arg Asp Asp Leu Gly
1               5                   10

<210> SEQ ID NO 328
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gln Ala Ser Gln Asp Ile Ser Asn Tyr Leu Ser
1               5                   10

<210> SEQ ID NO 329
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Arg Ser Ser Gln Ser Leu Val Tyr Ser Asp Gly Tyr Thr Tyr Leu His
1               5                   10                  15

<210> SEQ ID NO 330
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Arg Ser Ser Gln Ser Leu Leu Tyr Ser Asn Gly Tyr Asn Tyr Leu Asp
1               5                   10                  15

<210> SEQ ID NO 331
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Arg Ala Ser Gln Ala Ile Ser Asn Tyr Leu Asn
1               5                   10

<210> SEQ ID NO 332
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Arg Ala Ser Gln Ser Ile Arg Ser Tyr Leu Asn
1               5                   10

<210> SEQ ID NO 333
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 333

Arg Ala Ser Gln Ser Ile Ser Ser Tyr Leu His
1               5                   10

<210> SEQ ID NO 334
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Lys Ser Ser Gln Ser Leu Leu Leu Ser Asp Gly Gly Thr Tyr Leu Tyr
1               5                   10                  15

<210> SEQ ID NO 335
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Arg Ala Ser Gln Ser Ile Ser Ile Tyr Leu His
1               5                   10

<210> SEQ ID NO 336
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Arg Ala Ser Gln Ser Val Ser Ser Ser Tyr Leu Ala
1               5                   10

<210> SEQ ID NO 337
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Gln Ala Ser Gln Asp Ile Thr Asn Tyr Leu Asn
1               5                   10

<210> SEQ ID NO 338
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Arg Ser Ser Gln Ser Leu Leu Tyr Ser Asn Gly Tyr Lys Tyr Leu Asp
1               5                   10                  15
```

<210> SEQ ID NO 339
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Arg Ala Ser Gln Ser Ile Asn Ser Tyr Leu Asn
1               5                   10

<210> SEQ ID NO 340
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Arg Ser Ser Gln Ser Val Leu Tyr Ser Ser Ser Asn Arg Asn Tyr Leu
1               5                   10                  15

Ala

<210> SEQ ID NO 341
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Arg Ala Ser Gln Thr Ile Ser Ser Tyr Leu Asn
1               5                   10

<210> SEQ ID NO 342
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Arg Ala Ser Gln Ser Val Ile Ser Ile Tyr Leu Ala
1               5                   10

<210> SEQ ID NO 343
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ala Ala Ser Ser Leu Gln Ser
1               5

<210> SEQ ID NO 344
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Trp Ala Ser Thr Arg Glu Ser
1               5

<210> SEQ ID NO 345
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Leu Asp Ser His Arg Ala Ser
1               5

<210> SEQ ID NO 346
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Leu Gly Ser Asn Arg Ala Ser
1               5

<210> SEQ ID NO 347
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Gly Ala Ser Ser Arg Ala Thr
1               5

<210> SEQ ID NO 348
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Val Ala Ser Asn Leu Glu Thr
1               5

<210> SEQ ID NO 349
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Ala Ala Ser Arg Leu Gln Ser
1               5

<210> SEQ ID NO 350

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Ala Ala Ser Ser Leu Gln Asn
1               5

<210> SEQ ID NO 351
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Asp Ala Ser Asn Leu Glu Thr
1               5

<210> SEQ ID NO 352
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Ala Glu Ser Ser Leu Gln Ser
1               5

<210> SEQ ID NO 353
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Lys Val Ser Asn Trp Asp Ser
1               5

<210> SEQ ID NO 354
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Leu Gly Phe His Arg Ala Ser
1               5

<210> SEQ ID NO 355
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355
```

Ala Ala Ser Asn Leu Gln Ser
1               5

<210> SEQ ID NO 356
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Glu Val Ser Asn Arg Phe Ser
1               5

<210> SEQ ID NO 357
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Gly Ala Ser Ser Trp Ala Thr
1               5

<210> SEQ ID NO 358
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gly Ala Ser Gly Leu Gln Ser
1               5

<210> SEQ ID NO 359
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Ala Ala Ser Ser Leu Gln Gly
1               5

<210> SEQ ID NO 360
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Leu Gln His Asn Ser Tyr Pro Trp Thr
1               5

<210> SEQ ID NO 361
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 361

Leu Gln His Asn Gly Tyr Pro Trp Thr
1               5

<210> SEQ ID NO 362
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Gln Gln Tyr Tyr Ser Thr Pro Leu Thr
1               5

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Leu Gln His Asn Asn Tyr Pro Trp Thr
1               5

<210> SEQ ID NO 364
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Leu Gln His Asn Thr Tyr Pro Trp Thr
1               5

<210> SEQ ID NO 365
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Met Gln Ala Leu Gln Thr Pro Leu Thr
1               5

<210> SEQ ID NO 366
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Met Gln Ala Leu Gln Thr Pro Ile Thr
1               5
```

```
<210> SEQ ID NO 367
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gln Gln Tyr Asp Arg Ser Pro Leu Thr
1               5

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gln Gln Cys Asp Asn Leu Pro Leu Thr
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Gln His Tyr Asp Thr Leu Pro Leu Thr
1               5

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gln Gln Ser Tyr Ser Thr Pro Ile Thr
1               5

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Leu Gln His His Ser Tyr Pro Trp Thr
1               5

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372
```

```
Gln Gln Tyr Asp Asn Pro Pro Cys Ser
1               5

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Met Gln Gly Ala His Trp Pro Ile Thr
1               5

<210> SEQ ID NO 374
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Arg Gln Ala Leu Gln Thr Pro Leu Thr
1               5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gln Gln Asn Asn Ser Leu Pro Ile Thr
1               5

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gln Gln Ser Asn Gly Ser Pro Leu Thr
1               5

<210> SEQ ID NO 377
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Gln Gln Ser Tyr Ser Asn Pro Leu Thr
1               5

<210> SEQ ID NO 378
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 378

Gln Gln Ser Ile Ser Ser Pro Leu Thr
1               5

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Gln Gln Ser Tyr Ser Thr Pro Leu Thr
1               5

<210> SEQ ID NO 380
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Gln Gln Ser Tyr Ser Thr Pro Arg Thr
1               5

<210> SEQ ID NO 381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Met Gln Ser Met Gln Leu Pro Ile Thr
1               5

<210> SEQ ID NO 382
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Gln Gln Ser Tyr Thr Ser Pro Ile Thr
1               5

<210> SEQ ID NO 383
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Gln Gln Tyr Tyr Thr Thr Pro Leu Thr
1               5
```

<210> SEQ ID NO 384
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 384

Gln Gln Tyr Gly Ser Ser Pro Leu Thr
1               5

<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 385

Gln Gln Cys Glu Asn Phe Pro Ile Thr
1               5

<210> SEQ ID NO 386
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 386

Gln Gln Ser Tyr Ser Ser Pro Leu Thr
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 387

Gln Gln Tyr Tyr Ser Thr Pro Arg Thr
1               5

<210> SEQ ID NO 388
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 388

Gln Gln Tyr Gly Ser Ser Pro Cys Ser
1               5

<210> SEQ ID NO 389
<211> LENGTH: 5511
<212> TYPE: DNA
<213> ORGANISM: Homo sapiens
<220> FEATURE:
<221> NAME/KEY: CDS
<222> LOCATION: (194)..(4219)

<400> SEQUENCE: 389

```
acacacacac acccctcccc tgccatccct ccccggactc cggctccggc tccgattgca      60
atttgcaacc tccgctgccg tcgccgcagc agccaccaat tcgccagcgg ttcaggtggc     120
tcttgcctcg atgtcctagc ctaggggccc ccgggccgga cttggctggg ctcccttcac     180
cctctgcgga gtc atg agg gcg aac gac gct ctg cag gtg ctg ggc ttg       229
            Met Arg Ala Asn Asp Ala Leu Gln Val Leu Gly Leu
              1               5                  10 ctt ttc agc ctg gcc cgg ggc tcc gag gtg ggc aac tct cag gca gtg       277
Leu Phe Ser Leu Ala Arg Gly Ser Glu Val Gly Asn Ser Gln Ala Val
         15                  20                  25 tgt cct ggg act ctg aat ggc ctg agt gtg acc ggc gat gct gag aac       325
Cys Pro Gly Thr Leu Asn Gly Leu Ser Val Thr Gly Asp Ala Glu Asn
     30                  35                  40 caa tac cag aca ctg tac aag ctc tac gag agg tgt gag gtg gtg atg       373
Gln Tyr Gln Thr Leu Tyr Lys Leu Tyr Glu Arg Cys Glu Val Val Met
 45                  50                  55                  60 ggg aac ctt gag att gtg ctc acg gga cac aat gcc gac ctc tcc ttc       421
Gly Asn Leu Glu Ile Val Leu Thr Gly His Asn Ala Asp Leu Ser Phe
                 65                  70                  75 ctg cag tgg att cga gaa gtg aca ggc tat gtc ctc gtg gcc atg aat       469
Leu Gln Trp Ile Arg Glu Val Thr Gly Tyr Val Leu Val Ala Met Asn
             80                  85                  90 gaa ttc tct act cta cca ttg ccc aac ctc cgc gtg gtg cga ggg acc       517
Glu Phe Ser Thr Leu Pro Leu Pro Asn Leu Arg Val Val Arg Gly Thr
         95                 100                 105 cag gtc tac gat ggg aag ttt gcc atc ttc gtc atg ttg aac tat aac       565
Gln Val Tyr Asp Gly Lys Phe Ala Ile Phe Val Met Leu Asn Tyr Asn
    110                 115                 120 acc aac tcc agc cac gct ctg cgc cag ctc cgc ttg act cag ctc acc       613
Thr Asn Ser Ser His Ala Leu Arg Gln Leu Arg Leu Thr Gln Leu Thr
125                 130                 135                 140 gag att ctg tca ggg ggt gtt tat att gag aag aac gat aag ctt tgt       661
Glu Ile Leu Ser Gly Gly Val Tyr Ile Glu Lys Asn Asp Lys Leu Cys
                145                 150                 155 cac atg gac aca att gac tgg agg gac atc gtg agg gac cga gat gct       709
His Met Asp Thr Ile Asp Trp Arg Asp Ile Val Arg Asp Arg Asp Ala
            160                 165                 170 gag ata gtg gtg aag gac aat ggc aga agc tgt ccc ccc tgt cat gag       757
Glu Ile Val Val Lys Asp Asn Gly Arg Ser Cys Pro Pro Cys His Glu
        175                 180                 185 gtt tgc aag ggg cga tgc tgg ggt cct gga tca gaa gac tgc cag aca       805
Val Cys Lys Gly Arg Cys Trp Gly Pro Gly Ser Glu Asp Cys Gln Thr
    190                 195                 200 ttg acc aag acc atc tgt gct cct cag tgt aat ggt cac tgc ttt ggg       853
Leu Thr Lys Thr Ile Cys Ala Pro Gln Cys Asn Gly His Cys Phe Gly
205                 210                 215                 220 ccc aac ccc aac cag tgc tgc cat gat gag tgt gcc ggg ggc tgc tca       901
Pro Asn Pro Asn Gln Cys Cys His Asp Glu Cys Ala Gly Gly Cys Ser
                225                 230                 235 ggc cct cag gac aca gac tgc ttt gcc tgc cgg cac ttc aat gac agt       949
Gly Pro Gln Asp Thr Asp Cys Phe Ala Cys Arg His Phe Asn Asp Ser
            240                 245                 250 gga gcc tgt gta cct cgc tgt cca cag cct ctt gtc tac aac aag cta       997
Gly Ala Cys Val Pro Arg Cys Pro Gln Pro Leu Val Tyr Asn Lys Leu
        255                 260                 265 act ttc cag ctg gaa ccc aat ccc cac acc aag tat cag tat gga gga      1045
Thr Phe Gln Leu Glu Pro Asn Pro His Thr Lys Tyr Gln Tyr Gly Gly
    270                 275                 280
```

| | | | | | | | | | | | | | | | |
|---|---|---|---|---|---|---|---|---|---|---|---|---|---|---|---|
| gtt | tgt | gta | gcc | agc | tgt | ccc | cat | aac | ttt | gtg | gtg | gat | caa | aca | tcc | 1093 |
| Val | Cys | Val | Ala | Ser | Cys | Pro | His | Asn | Phe | Val | Val | Asp | Gln | Thr | Ser | |
| 285 | | | | 290 | | | | | 295 | | | | | 300 | | | tgt gtc agg gcc tgt cct cct gac aag atg gaa gta gat aaa aat ggg   1141
Cys Val Arg Ala Cys Pro Pro Asp Lys Met Glu Val Asp Lys Asn Gly
                305                 310                 315 ctc aag atg tgt gag cct tgt ggg gga cta tgt ccc aaa gcc tgt gag   1189
Leu Lys Met Cys Glu Pro Cys Gly Gly Leu Cys Pro Lys Ala Cys Glu
            320                 325                 330 gga aca ggc tct ggg agc cgc ttc cag act gtg gac tcg agc aac att   1237
Gly Thr Gly Ser Gly Ser Arg Phe Gln Thr Val Asp Ser Ser Asn Ile
        335                 340                 345 gat gga ttt gtg aac tgc acc aag atc ctg ggc aac ctg gac ttt ctg   1285
Asp Gly Phe Val Asn Cys Thr Lys Ile Leu Gly Asn Leu Asp Phe Leu
    350                 355                 360 atc acc ggc ctc aat gga gac ccc tgg cac aag atc cct gcc ctg gac   1333
Ile Thr Gly Leu Asn Gly Asp Pro Trp His Lys Ile Pro Ala Leu Asp
365                 370                 375                 380 cca gag aag ctc aat gtc ttc cgg aca gta cgg gag atc aca ggt tac   1381
Pro Glu Lys Leu Asn Val Phe Arg Thr Val Arg Glu Ile Thr Gly Tyr
                385                 390                 395 ctg aac atc cag tcc tgg ccg ccc cac atg cac aac ttc agt gtt ttt   1429
Leu Asn Ile Gln Ser Trp Pro Pro His Met His Asn Phe Ser Val Phe
            400                 405                 410 tcc aat ttg aca acc att gga ggc aga agc ctc tac aac cgg ggc ttc   1477
Ser Asn Leu Thr Thr Ile Gly Gly Arg Ser Leu Tyr Asn Arg Gly Phe
        415                 420                 425 tca ttg ttg atc atg aag aac ttg aat gtc aca tct ctg ggc ttc cga   1525
Ser Leu Leu Ile Met Lys Asn Leu Asn Val Thr Ser Leu Gly Phe Arg
    430                 435                 440 tcc ctg aag gaa att agt gct ggg cgt atc tat ata agt gcc aat agg   1573
Ser Leu Lys Glu Ile Ser Ala Gly Arg Ile Tyr Ile Ser Ala Asn Arg
445                 450                 455                 460 cag ctc tgc tac cac cac tct ttg aac tgg acc aag gtg ctt cgg ggg   1621
Gln Leu Cys Tyr His His Ser Leu Asn Trp Thr Lys Val Leu Arg Gly
                465                 470                 475 cct acg gaa gag cga cta gac atc aag cat aat cgg ccg cgc aga gac   1669
Pro Thr Glu Glu Arg Leu Asp Ile Lys His Asn Arg Pro Arg Arg Asp
            480                 485                 490 tgc gtg gca gag ggc aaa gtg tgt gac cca ctg tgc tcc tct ggg gga   1717
Cys Val Ala Glu Gly Lys Val Cys Asp Pro Leu Cys Ser Ser Gly Gly
        495                 500                 505 tgc tgg ggc cca ggc cct ggt cag tgc ttg tcc tgt cga aat tat agc   1765
Cys Trp Gly Pro Gly Pro Gly Gln Cys Leu Ser Cys Arg Asn Tyr Ser
    510                 515                 520 cga gga ggt gtc tgt gtg acc cac tgc aac ttt ctg aat ggg gag cct   1813
Arg Gly Gly Val Cys Val Thr His Cys Asn Phe Leu Asn Gly Glu Pro
525                 530                 535                 540 cga gaa ttt gcc cat gag gcc gaa tgc ttc tcc tgc cac ccg gaa tgc   1861
Arg Glu Phe Ala His Glu Ala Glu Cys Phe Ser Cys His Pro Glu Cys
                545                 550                 555 caa ccc atg gag ggc act gcc aca tgc aat ggc tcg ggc tct gat act   1909
Gln Pro Met Glu Gly Thr Ala Thr Cys Asn Gly Ser Gly Ser Asp Thr
            560                 565                 570 tgt gct caa tgt gcc cat ttt cga gat ggg ccc cac tgt gtg agc agc   1957
Cys Ala Gln Cys Ala His Phe Arg Asp Gly Pro His Cys Val Ser Ser
        575                 580                 585 tgc ccc cat gga gtc cta ggt gcc aag ggc cca atc tac aag tac cca   2005
Cys Pro His Gly Val Leu Gly Ala Lys Gly Pro Ile Tyr Lys Tyr Pro -continued

```
                  590                 595                 600
gat gtt cag aat gaa tgt cgg ccc tgc cat gag aac tgc acc cag ggg    2053
Asp Val Gln Asn Glu Cys Arg Pro Cys His Glu Asn Cys Thr Gln Gly
605                 610                 615                 620 tgt aaa gga cca gag ctt caa gac tgt tta gga caa aca ctg gtg ctg    2101
Cys Lys Gly Pro Glu Leu Gln Asp Cys Leu Gly Gln Thr Leu Val Leu
                625                 630                 635 atc ggc aaa acc cat ctg aca atg gct ttg aca gtg ata gca gga ttg    2149
Ile Gly Lys Thr His Leu Thr Met Ala Leu Thr Val Ile Ala Gly Leu
        640                 645                 650 gta gtg att ttc atg atg ctg ggc ggc act ttt ctc tac tgg cgt ggg    2197
Val Val Ile Phe Met Met Leu Gly Gly Thr Phe Leu Tyr Trp Arg Gly
655                 660                 665 cgc cgg att cag aat aaa agg gct atg agg cga tac ttg gaa cgg ggt    2245
Arg Arg Ile Gln Asn Lys Arg Ala Met Arg Arg Tyr Leu Glu Arg Gly
670                 675                 680 gag agc ata gag cct ctg gac ccc agt gag aag gct aac aaa gtc ttg    2293
Glu Ser Ile Glu Pro Leu Asp Pro Ser Glu Lys Ala Asn Lys Val Leu
685                 690                 695                 700 gcc aga atc ttc aaa gag aca gag cta agg aag ctt aaa gtg ctt ggc    2341
Ala Arg Ile Phe Lys Glu Thr Glu Leu Arg Lys Leu Lys Val Leu Gly
        705                 710                 715 tcg ggt gtc ttt gga act gtg cac aaa gga gtg tgg atc cct gag ggt    2389
Ser Gly Val Phe Gly Thr Val His Lys Gly Val Trp Ile Pro Glu Gly
                720                 725                 730 gaa tca atc aag att cca gtc tgc att aaa gtc att gag gac aag agt    2437
Glu Ser Ile Lys Ile Pro Val Cys Ile Lys Val Ile Glu Asp Lys Ser
        735                 740                 745 gga cgg cag agt ttt caa gct gtg aca gat cat atg ctg gcc att ggc    2485
Gly Arg Gln Ser Phe Gln Ala Val Thr Asp His Met Leu Ala Ile Gly
750                 755                 760 agc ctg gac cat gcc cac att gta agg ctg ctg gga cta tgc cca ggg    2533
Ser Leu Asp His Ala His Ile Val Arg Leu Leu Gly Leu Cys Pro Gly
765                 770                 775                 780 tca tct ctg cag ctt gtc act caa tat ttg cct ctg ggt tct ctg ctg    2581
Ser Ser Leu Gln Leu Val Thr Gln Tyr Leu Pro Leu Gly Ser Leu Leu
        785                 790                 795 gat cat gtg aga caa cac cgg ggg gca ctg ggg cca cag ctg ctg ctc    2629
Asp His Val Arg Gln His Arg Gly Ala Leu Gly Pro Gln Leu Leu Leu
                800                 805                 810 aac tgg gga gta caa att gcc aag gga atg tac tac ctt gag gaa cat    2677
Asn Trp Gly Val Gln Ile Ala Lys Gly Met Tyr Tyr Leu Glu Glu His
        815                 820                 825 ggt atg gtg cat aga aac ctg gct gcc cga aac gtg cta ctc aag tca    2725
Gly Met Val His Arg Asn Leu Ala Ala Arg Asn Val Leu Leu Lys Ser
830                 835                 840 ccc agt cag gtt cag gtg gca gat ttt ggt gtg gct gac ctg ctg cct    2773
Pro Ser Gln Val Gln Val Ala Asp Phe Gly Val Ala Asp Leu Leu Pro
845                 850                 855                 860 cct gat gat aag cag ctg cta tac agt gag gcc aag act cca att aag    2821
Pro Asp Asp Lys Gln Leu Leu Tyr Ser Glu Ala Lys Thr Pro Ile Lys
        865                 870                 875 tgg atg gcc ctt gag agt atc cac ttt ggg aaa tac aca cac cag agt    2869
Trp Met Ala Leu Glu Ser Ile His Phe Gly Lys Tyr Thr His Gln Ser
                880                 885                 890 gat gtc tgg agc tat ggt gtg aca gtt tgg gag ttg atg acc ttc ggg    2917
Asp Val Trp Ser Tyr Gly Val Thr Val Trp Glu Leu Met Thr Phe Gly
        895                 900                 905 gca gag ccc tat gca ggg cta cga ttg gct gaa gta cca gac ctg cta    2965
Ala Glu Pro Tyr Ala Gly Leu Arg Leu Ala Glu Val Pro Asp Leu Leu
```

```
                Ala Glu Pro Tyr Ala Gly Leu Arg Leu Ala Glu Val Pro Asp Leu Leu
                    910                 915                 920 gag aag ggg gag cgg ttg gca cag ccc cag atc tgc aca att gat gtc        3013
Glu Lys Gly Glu Arg Leu Ala Gln Pro Gln Ile Cys Thr Ile Asp Val
925                 930                 935                 940 tac atg gtg atg gtc aag tgt tgg atg att gat gag aac att cgc cca        3061
Tyr Met Val Met Val Lys Cys Trp Met Ile Asp Glu Asn Ile Arg Pro
                    945                 950                 955 acc ttt aaa gaa cta gcc aat gag ttc acc agg atg gcc cga gac cca        3109
Thr Phe Lys Glu Leu Ala Asn Glu Phe Thr Arg Met Ala Arg Asp Pro
                960                 965                 970 cca cgg tat ctg gtc ata aag aga gag agt ggg cct gga ata gcc cct        3157
Pro Arg Tyr Leu Val Ile Lys Arg Glu Ser Gly Pro Gly Ile Ala Pro
            975                 980                 985 ggg cca gag ccc cat ggt ctg aca aac aag aag cta  gag gaa gta gag       3205
Gly Pro Glu Pro His Gly Leu Thr Asn Lys Lys Leu  Glu Glu Val Glu
                990                 995                  1000 ctg gag cca gaa cta gac cta gac cta gac ttg gaa gca gag gag            3250
Leu Glu Pro Glu Leu Asp Leu Asp Leu Asp Leu Glu Ala Glu Glu
1005                1010                1015 gac aac ctg gca acc acc aca ctg ggc tcc gcc ctc agc cta cca            3295
Asp Asn Leu Ala Thr Thr Thr Leu Gly Ser Ala Leu Ser Leu Pro
1020                1025                1030 gtt gga aca ctt aat cgg cca cgt ggg agc cag agc ctt tta agt            3340
Val Gly Thr Leu Asn Arg Pro Arg Gly Ser Gln Ser Leu Leu Ser
1035                1040                1045 cca tca tct gga tac atg ccc atg aac cag ggt aat ctt ggg gag            3385
Pro Ser Ser Gly Tyr Met Pro Met Asn Gln Gly Asn Leu Gly Glu
1050                1055                1060 tct tgc cag gag tct gca gtt tct ggg agc agt gaa cgg tgc ccc            3430
Ser Cys Gln Glu Ser Ala Val Ser Gly Ser Ser Glu Arg Cys Pro
1065                1070                1075 cgt cca gtc tct cta cac cca atg cca cgg gga tgc ctg gca tca            3475
Arg Pro Val Ser Leu His Pro Met Pro Arg Gly Cys Leu Ala Ser
1080                1085                1090 gag tca tca gag ggg cat gta aca ggc tct gag gct gag ctc cag            3520
Glu Ser Ser Glu Gly His Val Thr Gly Ser Glu Ala Glu Leu Gln
1095                1100                1105 gag aaa gtg tca atg tgt agg agc cgg agc agg agc cgg agc cca            3565
Glu Lys Val Ser Met Cys Arg Ser Arg Ser Arg Ser Arg Ser Pro
1110                1115                1120 cgg cca cgc gga gat agc gcc tac cat tcc cag cgc cac agt ctg            3610
Arg Pro Arg Gly Asp Ser Ala Tyr His Ser Gln Arg His Ser Leu
1125                1130                1135 ctg act cct gtt acc cca ctc tcc cca ccc ggg tta gag gaa gag            3655
Leu Thr Pro Val Thr Pro Leu Ser Pro Pro Gly Leu Glu Glu Glu
1140                1145                1150 gat gtc aac ggt tat gtc atg cca gat aca cac ctc aaa ggt act            3700
Asp Val Asn Gly Tyr Val Met Pro Asp Thr His Leu Lys Gly Thr
1155                1160                1165 ccc tcc tcc cgg gaa ggc acc ctt tct tca gtg ggt ctc agt tct            3745
Pro Ser Ser Arg Glu Gly Thr Leu Ser Ser Val Gly Leu Ser Ser
1170                1175                1180 gtc ctg ggt act gaa gaa gaa gat gaa gat gag gag tat gaa tac            3790
Val Leu Gly Thr Glu Glu Glu Asp Glu Asp Glu Glu Tyr Glu Tyr
1185                1190                1195 atg aac cgg agg aga agg cac agt cca cct cat ccc cct agg cca            3835
Met Asn Arg Arg Arg Arg His Ser Pro Pro His Pro Pro Arg Pro
1200                1205                1210
```

| | | | | | | | | | | | | | | |
|---|---|---|---|---|---|---|---|---|---|---|---|---|---|---|
| agt | tcc | ctt | gag | gag | ctg | ggt | tat | gag | tac | atg | gat | gtg | ggg | tca | 3880 |
| Ser | Ser | Leu | Glu | Glu | Leu | Gly | Tyr | Glu | Tyr | Met | Asp | Val | Gly | Ser | |
| 1215 | | | | 1220 | | | | | 1225 | | | | | | |

| | | | | | | | | | | | | | | |
|---|---|---|---|---|---|---|---|---|---|---|---|---|---|---|
| gac | ctc | agt | gcc | tct | ctg | ggc | agc | aca | cag | agt | tgc | cca | ctc | cac | 3925 |
| Asp | Leu | Ser | Ala | Ser | Leu | Gly | Ser | Thr | Gln | Ser | Cys | Pro | Leu | His | |
| 1230 | | | | 1235 | | | | | 1240 | | | | | | |

| | | | | | | | | | | | | | | |
|---|---|---|---|---|---|---|---|---|---|---|---|---|---|---|
| cct | gta | ccc | atc | atg | ccc | act | gca | ggc | aca | act | cca | gat | gaa | gac | 3970 |
| Pro | Val | Pro | Ile | Met | Pro | Thr | Ala | Gly | Thr | Thr | Pro | Asp | Glu | Asp | |
| 1245 | | | | 1250 | | | | | 1255 | | | | | | |

| | | | | | | | | | | | | | | |
|---|---|---|---|---|---|---|---|---|---|---|---|---|---|---|
| tat | gaa | tat | atg | aat | cgg | caa | cga | gat | gga | ggt | ggt | cct | ggg | ggt | 4015 |
| Tyr | Glu | Tyr | Met | Asn | Arg | Gln | Arg | Asp | Gly | Gly | Gly | Pro | Gly | Gly | |
| 1260 | | | | 1265 | | | | | 1270 | | | | | | |

| | | | | | | | | | | | | | | |
|---|---|---|---|---|---|---|---|---|---|---|---|---|---|---|
| gat | tat | gca | gcc | atg | ggg | gcc | tgc | cca | gca | tct | gag | caa | ggg | tat | 4060 |
| Asp | Tyr | Ala | Ala | Met | Gly | Ala | Cys | Pro | Ala | Ser | Glu | Gln | Gly | Tyr | |
| 1275 | | | | 1280 | | | | | 1285 | | | | | | |

| | | | | | | | | | | | | | | |
|---|---|---|---|---|---|---|---|---|---|---|---|---|---|---|
| gaa | gag | atg | aga | gct | ttt | cag | ggg | cct | gga | cat | cag | gcc | ccc | cat | 4105 |
| Glu | Glu | Met | Arg | Ala | Phe | Gln | Gly | Pro | Gly | His | Gln | Ala | Pro | His | |
| 1290 | | | | 1295 | | | | | 1300 | | | | | | |

| | | | | | | | | | | | | | | |
|---|---|---|---|---|---|---|---|---|---|---|---|---|---|---|
| gtc | cat | tat | gcc | cgc | cta | aaa | act | cta | cgt | agc | tta | gag | gct | aca | 4150 |
| Val | His | Tyr | Ala | Arg | Leu | Lys | Thr | Leu | Arg | Ser | Leu | Glu | Ala | Thr | |
| 1305 | | | | 1310 | | | | | 1315 | | | | | | |

| | | | | | | | | | | | | | | |
|---|---|---|---|---|---|---|---|---|---|---|---|---|---|---|
| gac | tct | gcc | ttt | gat | aac | cct | gat | tac | tgg | cat | agc | agg | ctt | ttc | 4195 |
| Asp | Ser | Ala | Phe | Asp | Asn | Pro | Asp | Tyr | Trp | His | Ser | Arg | Leu | Phe | |
| 1320 | | | | 1325 | | | | | 1330 | | | | | | |

| | | | | | | |
|---|---|---|---|---|---|---|
| ccc | aag | gct | aat | gcc | cag | aga acg taactcctgc tccctgtggc | 4239 |
| Pro | Lys | Ala | Asn | Ala | Gln | Arg Thr | |
| 1335 | | | | 1340 | | | | actcagggag catttaatgg cagctagtgc ctttagaggg taccgtcttc tccctattcc 4299
ctctctctcc caggtcccag ccccttttcc ccagtcccag acaattccat tcaatctttg 4359
gaggctttta acattttga cacaaaattc ttatggtatg tagccagctg tgcactttct 4419
tctctttccc aaccccagga aaggttttcc ttattttgtg tgctttccca gtcccattcc 4479
tcagcttctt cacaggcact cctggagata tgaaggatta ctctccatat cccttcctct 4539
caggctcttg actacttgga actaggctct tatgtgtgcc tttgtttccc atcagactgt 4599
caagaagagg aaagggagga aacctagcag aggaaagtgt aattttggtt tatgactctt 4659
aaccccctag aaagacagaa gcttaaaatc tgtgaagaaa gaggttagga gtagatattg 4719
attactatca taattcagca cttaactatg agccaggcat catactaaac ttcacctaca 4779
ttatctcact tagtccttta tcatccttaa acaattctg tgacatacat attatctcat 4839
tttacacaaa gggaagtcgg gcatggtggc tcatgcctgt aatctcagca ctttgggagg 4899
ctgaggcaga aggattacct gaggcaagga gtttgagacc agcttagcca acatagtaag 4959
acccccatct ctttaaaaaa aaaaaaaaaa aaaaaaaaaa aacttagaa ctgggtgcag 5019
tggctcatgc ctgtaatccc agccagcact tgggaggct gagatgggaa gatcacttga 5079
gcccagaatt agagataagc ctatggaaac atagcaagac actgtctcta caggggaaaa 5139
aaaaaaaga aactgagcct taagagatg aaataaatta agcagtagat ccaggatgca 5199
aaatcctccc aattcctgtg catgtgctct tattgtaagg tgccaagaaa aactgattta 5259
agttacagcc cttgtttaag gggcactgtt tcttgttttt gcactgaatc aagtctaacc 5319
ccaacagcca catcctccta tacctagaca tctcatctca ggaagtggtg gtgggggtag 5379
tcagaaggaa aaataactgg acatctttgt gtaaaccata atccacatgt gccgtaaatg 5439
atcttcactc cttatccgag ggcaaattca caaggatccc caagatccac ttttagaagc 5499
cattctcatc ca 5511

<210> SEQ ID NO 390
<211> LENGTH: 1342
<212> TYPE: PRT
<213> ORGANISM: Homo sapiens

<400> SEQUENCE: 390

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
```

```
              370                 375                 380
Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                    405                 410                 415

Thr Ile Gly Gly Arg Ser Leu Tyr Asn Arg Gly Phe Ser Leu Leu Ile
                420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
        450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                    485                 490                 495

Gly Lys Val Cys Asp Pro Leu Cys Ser Ser Gly Gly Cys Trp Gly Pro
                500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
        530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                    565                 570                 575

Ala His Phe Arg Asp Gly Pro His Cys Val Ser Ser Cys Pro His Gly
                580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
        610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                    645                 650                 655

Met Met Leu Gly Gly Thr Phe Leu Tyr Trp Arg Gly Arg Arg Ile Gln
                660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
        690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                    725                 730                 735

Ile Pro Val Cys Ile Lys Val Ile Glu Asp Lys Ser Gly Arg Gln Ser
                740                 745                 750

Phe Gln Ala Val Thr Asp His Met Leu Ala Ile Gly Ser Leu Asp His
            755                 760                 765

Ala His Ile Val Arg Leu Leu Gly Leu Cys Pro Gly Ser Ser Leu Gln
        770                 775                 780

Leu Val Thr Gln Tyr Leu Pro Leu Gly Ser Leu Leu Asp His Val Arg
785                 790                 795                 800
```

```
Gln His Arg Gly Ala Leu Gly Pro Gln Leu Leu Asn Trp Gly Val
                805                 810                 815

Gln Ile Ala Lys Gly Met Tyr Tyr Leu Glu Glu His Gly Met Val His
                820                 825                 830

Arg Asn Leu Ala Ala Arg Asn Val Leu Leu Lys Ser Pro Ser Gln Val
                835                 840                 845

Gln Val Ala Asp Phe Gly Val Ala Asp Leu Leu Pro Pro Asp Asp Lys
            850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
                900                 905                 910

Ala Gly Leu Arg Leu Ala Glu Val Pro Asp Leu Leu Glu Lys Gly Glu
                915                 920                 925

Arg Leu Ala Gln Pro Gln Ile Cys Thr Ile Asp Val Tyr Met Val Met
                930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
                980                 985                 990

His Gly Leu Thr Asn Lys Lys Leu Glu Glu Val Glu Leu Glu Pro Glu
                995                 1000                1005

Leu Asp Leu Asp Leu Asp Leu Glu Ala Glu Glu Asp Asn Leu Ala
            1010                1015                1020

Thr Thr Thr Leu Gly Ser Ala Leu Ser Leu Pro Val Gly Thr Leu
            1025                1030                1035

Asn Arg Pro Arg Gly Ser Gln Ser Leu Leu Ser Pro Ser Ser Gly
            1040                1045                1050

Tyr Met Pro Met Asn Gln Gly Asn Leu Gly Glu Ser Cys Gln Glu
            1055                1060                1065

Ser Ala Val Ser Gly Ser Ser Glu Arg Cys Pro Arg Pro Val Ser
            1070                1075                1080

Leu His Pro Met Pro Arg Gly Cys Leu Ala Ser Glu Ser Ser Glu
            1085                1090                1095

Gly His Val Thr Gly Ser Glu Ala Glu Leu Gln Glu Lys Val Ser
            1100                1105                1110

Met Cys Arg Ser Arg Ser Arg Ser Arg Ser Pro Arg Pro Arg Gly
            1115                1120                1125

Asp Ser Ala Tyr His Ser Gln Arg His Ser Leu Leu Thr Pro Val
            1130                1135                1140

Thr Pro Leu Ser Pro Pro Gly Leu Glu Glu Glu Asp Val Asn Gly
            1145                1150                1155

Tyr Val Met Pro Asp Thr His Leu Lys Gly Thr Pro Ser Ser Arg
            1160                1165                1170

Glu Gly Thr Leu Ser Ser Val Gly Leu Ser Ser Val Leu Gly Thr
            1175                1180                1185

Glu Glu Glu Asp Glu Asp Glu Glu Tyr Glu Tyr Met Asn Arg Arg
            1190                1195                1200
```

-continued

```
Arg Arg His Ser Pro Pro His Pro Pro Arg Pro Ser Ser Leu Glu
    1205            1210            1215

Glu Leu Gly Tyr Glu Tyr Met Asp Val Gly Ser Asp Leu Ser Ala
    1220            1225            1230

Ser Leu Gly Ser Thr Gln Ser Cys Pro Leu His Pro Val Pro Ile
    1235            1240            1245

Met Pro Thr Ala Gly Thr Thr Pro Asp Glu Asp Tyr Glu Tyr Met
    1250            1255            1260

Asn Arg Gln Arg Asp Gly Gly Gly Pro Gly Gly Asp Tyr Ala Ala
    1265            1270            1275

Met Gly Ala Cys Pro Ala Ser Glu Gln Gly Tyr Glu Glu Met Arg
    1280            1285            1290

Ala Phe Gln Gly Pro Gly His Gln Ala Pro His Val His Tyr Ala
    1295            1300            1305

Arg Leu Lys Thr Leu Arg Ser Leu Glu Ala Thr Asp Ser Ala Phe
    1310            1315            1320

Asp Asn Pro Asp Tyr Trp His Ser Arg Leu Phe Pro Lys Ala Asn
    1325            1330            1335

Ala Gln Arg Thr
    1340
```

MATERIAL AND METHODS FOR TREATING OR PREVENTING HER-3 ASSOCIATED DISEASES

CROSS REFERENCE TO RELATED APPLICATIONS

This application is a continuation of and claims priority to application Ser. No. 13/870,796, filed on Apr. 25, 2013, which is a divisional application of and claims priority to application Ser. No. 12/944,764, filed on Nov. 12, 2010, which claims priority under 35 U.S.C. § 119(e) to Provisional Application No. 61/261,149, filed on Nov. 13, 2009. This application is also a continuation-in-part application of and claims priority to application Ser. No. 12/657,784, filed Feb. 4, 2009 which is a divisional application of application Ser. No. 11/649,722, filed Jan. 3, 2007, which claims priority under 35 U.S.C. § 119(e) to Provisional Application No. 60/755,103, filed Dec. 30, 2005. All prior applications are incorporated by reference.

SEQUENCE LISTING

The instant application contains a Sequence Listing which has been submitted in ASCII format via EFS-Web and is hereby incorporated by reference in its entirety. Said ASCII copy, created on May 17, 2011, is named 01520030.txt and is 288,846 bytes in size.

BACKGROUND

1. Technical Field

This document relates to materials and methods for treating subjects having a disease associated with Human Epidermal Growth Factor Receptor-3 (HER-3) by administering a first agent that binds to HER-3, in combination with a second agent that binds or inhibits another Human Epidermal Growth Factor Receptor (HER) family member. The first and the second agent may be any kind of molecule that binds to HER-3 or binds to and/or inhibits another HER family member, respectively, including, but not limited to a biological compound, such as an antigen binding protein, a small molecular tyrosine kinase inhibitor, an siRNA, or a natural substance.

2. Background

HER-3, also known as ErbB3, is a receptor protein tyrosine kinase that belongs to the epidermal growth factor receptor (EGF-R, also known as HER) family of receptor protein tyrosine kinases, which also includes HER-1 (also known as EGF-R or erbB), HER-2 (also known as erbB2), and HER-4 (also known as erbB4) (Plowman et al. (1990) *Proc. Natl. Acad. Sci. US* 87:4905-4909; Kraus et al. (1989) *Proc. Natl. Acad. Sci. US* 86:9193-9197; and Kraus et al. (1993) *Proc. Natl. Acad. Sci. US* 90:2900-2904). Like the prototypical epidermal growth factor receptor, the transmembrane receptor HER-3 consists of an extracellular ligand-binding domain (ECD), a dimerization domain within the ECD, a transmembrane domain (TMD), an intracellular protein tyrosine kinase domain (TKD), and a C-terminal phosphorylation domain.

The ligand for HER-3, known as heregulin (HRG), binds to the extracellular domain of HER-3 and activates receptor-mediated signaling by promoting dimerization with other human epidermal growth factor receptor (HER) family members, subsequent transphosphorylation of the intracellular HER-3 domain, and activation of downstream signaling cascades. Dimer formation with multiple HER family members expand the signaling potential of HER-3, and is a means for signal diversification as well as signal amplification.

SUMMARY

This document relates to materials and methods for treating subjects having an HER-3 associated disease, by administering an agent that binds to HER-3, in combination with a second agent that binds to and/or inhibits another member of the HER family. The first and the second agent may be any kind of molecule that binds to HER-3 or binds to and/or inhibits another HER family member, respectively, including, but not limited to a biological compound, such as an antigen binding protein, a small molecular tyrosine kinase inhibitor, an siRNA, or a natural substance.

In one aspect, this document features a method of treating or preventing a disease associated with HER-3 in a subject, comprising administering to the subject a first agent and a second agent, wherein the first agent binds to HER-3 and the second agent binds to and/or inhibits the activity of another member of the HER family. The first agent can be a small molecule compound or an antigen-binding protein that binds to HER-3. The first agent can be an antigen-binding protein that binds to HER-3 and comprises a heavy chain amino acid sequence that comprises a CDRH1 selected from the group consisting of SEQ ID NOs:236, 251, 252, and 256; a CDRH2 selected from the group consisting of SEQ ID NOs:258, 278, 280, and 282; and a CDRH3 selected from the group consisting of SEQ ID NOs:283, 285, 309, 313, and 315; and a light chain amino acid sequence that comprises a CDRL1 selected from the group consisting of SEQ ID NOs:320, 334, 337, and 340; a CDRL2 selected from the group consisting of SEQ ID NOs: 343, 356, 351, and 344; and a CDRL3 selected from the group consisting of SEQ ID NOs:360, 381, 385, and 387. The first agent can be an antigen-binding protein that binds to HER-3 and comprises a heavy chain amino acid sequence that comprises at least one of the CDR's selected from the group consisting of (a) CDRH1's as shown in SEQ ID NOs:236, 251, 252, and 256; (b) CDRH2's as shown in SEQ ID NOs:258, 278, 280, and 282; and (c) CDRH3's as shown in SEQ ID NOs:283, 285, 309, 313, and 315. The first agent can be an antigen-binding protein that binds to HER-3 and comprises a light chain amino acid sequence that comprises at least one of the CDR's selected from the group consisting of: (d) CDRL1's as shown in SEQ ID NOs: 320, 334, 337, and 340; (e) CDRL2's as shown in SEQ ID NOs:343, 356, 351, and 344; and (f) CDRL3's as shown in SEQ ID NOs:360, 381, 385, and 387.

The first agent can be an antigen-binding protein that binds to HER-3 and comprises a heavy chain amino acid sequence that comprises at least one of the CDR's selected from the group consisting of (a) CDRH1's as shown in SEQ ID NOs: 236, 251, 252, and 256; (b) CDRH2's as shown in SEQ ID NOs:258, 278, 280, and 282; and (c) CDRH3's as shown in SEQ ID NOs:283, 285, 309, 313, and 315; and a light chain amino acid sequence that comprises at least one of the CDR's selected from the group consisting of: (d) CDRL1's as shown in SEQ ID NOs:320, 334, 337, and 340; (e) CDRL2's as shown in SEQ ID NOs:343, 356, 351, and 344; and (f) CDRL3's as shown in SEQ ID NOs:360, 381, 385, and 387. The first agent can be an antigen-binding protein that binds to HER-3 and comprises a heavy chain amino acid sequence that comprises a CDRH1 selected from the group consisting of SEQ ID NOs: 236, 251, 252, and 256, a CDRH2 selected from the group consisting of SEQ ID NOs: 258, 278, 280, and 282, and a CDRH3 selected from the group consisting of SEQ ID NOs: 283, 285, 309, 313, and 315, or a light chain amino acid sequence that comprises a CDRL1 selected from the group consisting of SEQ ID NOs: 320, 334, 337, and 340, a CDRL2 selected from the group consisting of SEQ ID NOs: 343, 356, 351, and 344, and a CDRL3 selected from the group consisting of SEQ ID NOs: 360, 381, 385, and 387.

The first agent can be an antigen-binding protein that binds to HER-3 and comprises a heavy chain amino acid sequence selected from the group consisting of SEQ ID NOs: 42, 54, 70, 92, and 96. The antigen-binding protein can include a light chain amino acid sequence selected from the group consisting of SEQ ID NOs: 44, 56, 72, 94, and 98.

The first agent can be an antigen-binding protein that binds to HER-3 and comprises a heavy chain amino acid sequence selected from the group consisting of SEQ ID NOs: 42, 54, 70, 92, and 96; and a light chain amino acid sequence selected from the group consisting of SEQ ID NOs: 44, 56, 72, 94, and 98.

The first agent can be an antigen-binding protein that binds to HER-3 and comprises the heavy chain amino acid sequence of SEQ ID NO:42 and the light chain amino acid sequence of SEQ ID NO:44. The first agent can be an antigen-binding protein that binds to HER-3 and comprises the heavy chain amino acid sequence of SEQ ID NO:54 and the light chain amino acid sequence of SEQ ID NO:56. The first agent can be an antigen-binding protein that binds to HER-3 and comprises the heavy chain amino acid sequence of SEQ ID NO:70 and the light chain amino acid sequence of SEQ ID NO:72. The first agent can be an antigen-binding protein that binds to HER-3 and comprises a CDRH3 selected from the group consisting of SEQ ID NOs: 283, 285, 309, 313, and 315. The first agent can be an antigen-binding protein that binds to HER-3 and comprises a CDHL3 selected from the group consisting of SEQ ID NOs: 360, 381, 385, and 387.

The antigen-binding protein can be directed against the extracellular domain of HER-3. Binding of the antigen-binding protein to HER-3 can reduce HER-3-mediated signal transduction, reduce HER-3 phosphorylation, reduce cell proliferation, reduce cell migration, and/or increase the downregulation of HER-3.

The antigen-binding protein that binds to HER-3 can be an antibody. The antibody can be a monoclonal antibody, a polyclonal antibody, a recombinant antibody, a humanized antibody, a human antibody, a chimeric antibody, a multi-specific antibody, or an antibody fragment thereof (e.g., a Fab fragment, a Fab' fragment, a F(ab')2 fragment, a Fv fragment, a diabody, or a single chain antibody molecule). The antibody can be of the IgG1-, IgG2-, IgG3- or IgG4-type.

The first agent can be an antigen-binding protein that binds to HER-3, and the antigen-binding protein can be coupled to an effector group. The effector group can be a radioisotope or radionuclide, a toxin, or a therapeutic or chemotherapeutic group (e.g., a therapeutic or chemotherapeutic group selected from the group consisting of calicheamicin, auristatin-PE, geldanamycin, maytansine and derivatives thereof).

The second agent can be a small molecule compound or an antigen-binding protein. The second agent can be, for example, trastuzumab, lapatinib, neratinib, panitumumab, erlotinib, cetuximab, pertuzumab, and T-DM1.

In another aspect, this document features a method of treating or preventing a disease associated with HER-3 in a subject, comprising administering to the subject a first agent and a second agent, wherein the first agent is an antigen-binding protein that binds to HER-3 and comprises the heavy chain amino acid sequence of SEQ ID NO:42 and the light chain amino acid sequence of SEQ ID NO:44, and wherein the second agent is selected from the group consisting of erlotinib, lapatinib, and neratinib. In addition, this document features methods of treating or preventing a disease associated with HER-3 in a subject, comprising administering to the subject a first agent and a second agent, wherein the first agent is an antigen-binding protein that binds to HER-3 and comprises the heavy chain amino acid sequence of SEQ ID NO:54 and the light chain amino acid sequence of SEQ ID NO:56, or an antigen-binding protein that binds to HER-3 and comprises the heavy chain amino acid sequence of SEQ ID NO:70 and the light chain amino acid sequence of SEQ ID NO:72, and wherein the second agent is selected from the group consisting of erlotinib, lapatinib, and neratinib.

This document also features a method of treating or preventing a disease associated with HER-3 in a subject, comprising administering to the subject a first agent and a second agent, wherein the first agent is an antigen-binding protein that binds to HER-3 and comprises the heavy chain amino acid sequence of SEQ ID NO:42 and the light chain amino acid sequence of SEQ ID NO:44, and wherein the second agent is selected from the group consisting of trastuzumab, T-DM1, panitumumab, and cetuximab.

The methods provided herein can optionally include administering a third or further therapeutic agent and/or radiation therapy. The third or further therapeutic agent can be an anti-neoplastic agent (e.g., an anti-tumor antibody or a chemotherapeutic agent, such as capecitabine, anthracycline, doxorubicin, cyclophosphamide, paclitaxel, docetaxel, cisplatin, gemcitabine, or carboplatin).

The first agent and the second agent can be administered by intravenous, subcutaneous, intramuscular or oral administration. The disease can be a hyperproliferative disease (e.g., a disease selected from the group consisting of breast cancer, ovarian cancer, prostate cancer, colon cancer, renal cancer, lung cancer, pancreatic cancer, epidermoid carcinoma, fibrosarcoma, melanoma, nasopharyngeal carcinoma, and squamous cell carcinoma).

The methods provided herein can include administering the first agent at a dose of about 1 to about 20 mg/kg body weight, at least once every 6 weeks. The methods can include administering the second agent at a dose of about 1 to about 20 mg/kg body weight, at least once every 6 weeks. The methods can further include, prior to the administering, using a method that comprises analysis of a predictive marker to select a subject having a disease associated with HER-3. The methods can further include after the administering, monitoring the therapeutic outcome.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. The disclosures of each of the publications, applications, patents, and other references mentioned herein are hereby incorporated herein by reference in their entireties. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 6A-6D are a series of graphs plotting the effects of a human anti-HER-3 antibody, either alone or in combination with trastuzumab (FIG. 6A), lapatinib (FIG. 6B), gemcitibine (FIG. 6C), or cisplatin (FIG. 6D), on proliferation of MDA-MB-175VII breast cancer cells.

DETAILED DESCRIPTION

Figure 1:
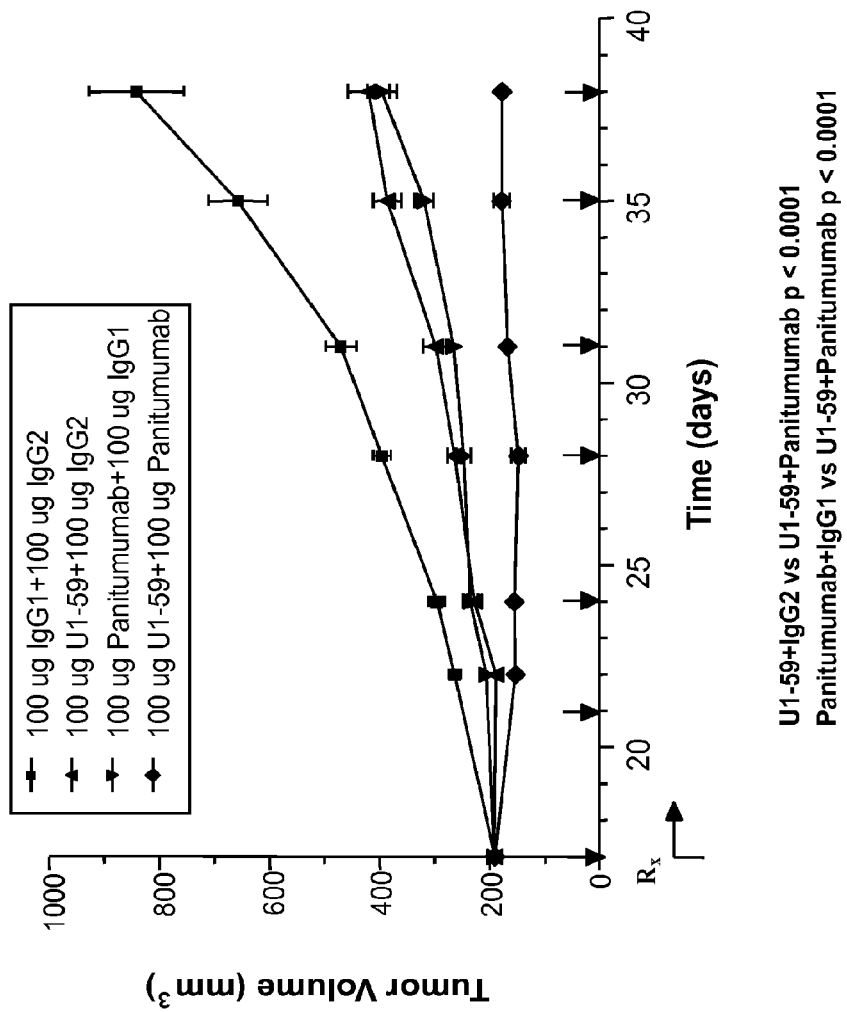
FIG. 1 is a graph plotting the effects of a human anti-HER-3 antibody and panitumumab, either alone or in combination, on non-small cell lung cancer (NSCLC) xenograft tumor (Calu-3) growth.

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of cell and tissue culture, molecular biology, immunology, microbiology, genetics and protein and nucleic acid chemistry and hybridization described herein are those well known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), the disclosure of each reference of which is hereby incorporated herein by reference in its entirety. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

It should be understood that this invention is not limited to the particular methodology, protocols, and reagents, etc., described herein and as such may vary. The terminology used herein is for the purpose of describing particular embodiments only, and is not intended to limit the scope of the disclosed, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean.+/−.1%.

1. General Overview

This document provides materials and methods related to treating or preventing diseases associated with HER-3, using a combination of a first agent that binds to HER-3, and a second agent that binds to/or inhibits the activity of other members of the HER family. The first agent and the second agent may be a biological compound, such as an antigen binding protein, or a small molecular tyrosine kinase inhibitor. For example, provided herein are isolated polypeptides (e.g., binding proteins such as antibodies), and/or small molecular tyrosine kinase inhibitors that bind to and/or inhibit individual or multiple members of the HER family, such as HER-3, HER-2, EGF-R, HER-4, and/or any other members of the HER family. Also provided are compositions comprising a first agent that binds to HER-3, and a second agent that binds to and/or inhibits the activity of one or multiple other HER family members, and methods for using the same to treat or prevent HER-3 associated disease.

Certain first and/or second agents described herein are biologics, such as antigen binding proteins. In certain embodiments, the polypeptide structure of the antigen binding proteins is based on antibodies, including, but not limited to, monoclonal antibodies, bispecific antibodies, minibodies, domain antibodies, synthetic antibodies (sometimes referred to as "antibody mimetics"), chimeric antibodies, humanized antibodies, human antibodies, antibody fusions (sometimes referred to as "antibody conjugates"), and fragments thereof, respectively. The various structures are further described below. In other embodiments, the first and/or second agent is a small molecular tyrosine kinase inhibitor. In yet other embodiments, the first and/or second agent is an siRNA. In yet other embodiments, the first and/or second agent is a natural substance.

The compositions described herein, and the methods of using the same, have been demonstrated improved inhibition of the growth of solid tumors that express HER-3 and at least one other member of the HER family. In particular, administering a combination of a first agent that binds to HER-3 and a second agent that binds to and/or inhibits at least one other member of the HER family has been demonstrated herein to have increased efficacy in inhibiting the growth of a variety of tumors, when compared to the administration of either the first or the second agent alone. Therefore, the compositions and methods disclosed herein have demonstrated utility in improved methods of treating and preventing neoplastic disease, such as cancer.

2. HER-3 Binding Agents

As described herein, the agent that binds to HER-3 can be a biological compound, including, but not limited to, an antigen binding protein, such as an antibody, or a small molecular tyrosine kinase inhibitor. As used herein, an "antigen binding protein" or "binding protein" as used herein means a protein that specifically binds a specified target antigen, such as member of the HER family, e.g., HER-3. An antigen binding protein is said to "specifically bind" its target antigen when the dissociation constant ($K_D$) is $\leq 10^{-8}$ M. The antibody specifically binds antigen with "high affinity" when the $K_D$ is $\leq 5 \times 10^{-9}$ M, and with "very high affinity" when the $K_D$ is $\leq 5 \times 10^{10}$ M. In one embodiment, the antibody has a $K_D$ of $\leq 10^{-9}$ M and an off-rate of about $1 \times 0.10^{-4}$/sec. In one embodiment, the off-rate is about $1 \times 0.10^{5}$/sec. In other embodiments, the antibodies will bind to a specified member of the HER family with a $K_D$ of between about $10^{-8}$ M and $10^{-10}$M, and in yet another embodiment it will bind with a $K_D \leq 2 \times 0.10^{-10}$. Further, as used herein, a small molecule compound is a low molecular weight compound that has been chemically synthesized to inhibit the enzymatic activity of one or more protein kinase, including serine, threonine or tyrosine kinases.

In some embodiments, where the HER-3 binding agent is a biological compound, the agent is an antigen binding protein, such as an antibody that can bind to HER-3. Thus provided herein for use in compositions and methods of treating HER-3 associated diseases are HER binding proteins, including anti-HER-3 antibodies. In some embodiments, an antibody targeted to HER-3 can be directed against the extracellular domain (ECD) of HER-3. For example, an anti-HER-3 antibody as described herein can interact with at least one epitope in the extracellular part of HER-3. The epitopes can be located in the amino terminal L1 domain (aa 19-184), in the S1 (aa 185-327) and S2 (aa 500-632) cysteine-rich domains, in the L2 domain (328-499), which is flanked by the two cysteine-rich domains, or in a combination of HER-3 domains. The epitopes also may be located in combinations of domains such as, without limitation, an epitope comprised by parts of L1 and S1.

A HER-3 binding protein can be further characterized in that its binding to HER-3 reduces HER-3-mediated signal transduction. A reduction of HER-3-mediated signal transduction may, e.g., be caused by a downregulation of HER-3 resulting in an at least partial disappearance of HER-3 molecules from the cell surface or by a stabilization of HER-3 on the cell surface in a substantially inactive form, i.e., a form that exhibits a lower signal transduction compared to the non-stabilized form. Alternatively, a reduction of HER-3-mediated signal transduction also may be caused by influencing, e.g., decreasing or inhibiting, the binding of a ligand or another member of the HER family to HER-3. For example, a reduction of HER-3 mediated signal transduction also can be caused by, decreasing the formation of HER-3 containing dimers with other HER family members (e.g., EGF-R).

A HER-3 binding agent can be a scaffold protein having an antibody-like binding activity (e.g., having activity similar to an anti-HER-3 antibody) or an antibody, i.e., an anti-HER-3 antibody. As used herein, the term "scaffold protein" means a polypeptide or protein with exposed surface areas in which amino acid insertions, substitutions or deletions are highly tolerable. Examples of scaffold proteins that can be used in accordance with the present methods include protein A from *Staphylococcus aureus*, the bilin binding protein from *Pieris brassicae* or other lipocalins, ankyrin repeat proteins, and human fibronectin (reviewed in Binz and Plückthun (2005) *Curr. Opin. Biotechnol.* 16:459-69). Engineering of a scaffold protein can be regarded as grafting or integrating an affinity function onto or into the structural framework of a stably folded protein. Affinity function means a protein binding affinity according to the present document. A scaffold can be structurally separable from the amino acid sequences conferring binding specificity. In general, proteins appearing suitable for the development of such artificial affinity reagents may be obtained by rational, or most commonly, combinatorial protein engineering techniques such as panning against HER-3, either purified protein or protein displayed on the cell surface, for binding agents in an artificial scaffold library displayed in vitro, skills which are known in the art (see, e.g., Skerra (2000) *J. Mol. Recog.* 13:167-87; and Binz and Plückthun, supra). In addition, a scaffold protein having an antibody like binding activity can be derived from an acceptor polypeptide containing the scaffold domain, which can be grafted with binding domains of a donor polypeptide to confer the binding specificity of the donor polypeptide onto the scaffold domain containing the acceptor polypeptide. The inserted binding domains may be, for example, the complementarity determining region (CDR) of an antibody, in particular an anti-HER-3 antibody. Insertion can be accomplished by various methods known to those skilled in the art including, for example, polypeptide synthesis, nucleic acid synthesis of an encoding amino acid as well by various forms of recombinant methods well known to those skilled in the art.

The term "antibody" includes monoclonal antibodies, polyclonal antibodies, recombinant antibodies, humanized antibodies (Jones et al. (1986) *Nature* 321:522-525; Riechmann et al. (1988) *Nature* 332:323-329; and Presta (1992) *Curr. Op. Struct. Biol.* 2:593-596), chimeric antibodies (Morrison et al. (1984) *Proc. Natl. Acad. Sci. US* 81:6851-6855), multispecific antibodies (e.g., bispecific antibodies) formed from at least two antibodies, or antibody fragments thereof. The term "antibody fragment" comprises any portion of the afore-mentioned antibodies, such as their antigen binding or variable regions. Examples of antibody fragments include Fab fragments, Fab' fragments, F(ab')$_2$ fragments, Fv fragments, diabodies (Hollinger et al. (1993) *Proc. Natl. Acad. Sci. US* 90:6444-6448), single chain antibody molecules (Plückthun in: *The Pharmacology of Monoclonal Antibodies* 113, Rosenburg and Moore, eds., Springer Verlag, NY (1994), 269-315) and other fragments as long as they exhibit the desired capability of binding to HER-3.

In addition, the term "antibody," as used herein, includes antibody-like molecules that contain engineered sub-domains of antibodies or naturally occurring antibody variants. These antibody-like molecules may be single-domain antibodies such as $V_H$-only or $V_L$-only domains derived either from natural sources such as camelids (Muyldermans et al. (2001) *Rev. Mol. Biotechnol.* 74:277-302) or through in vitro display of libraries from humans, camelids or other species (Holt et al. (2003) *Trends Biotechnol.* 21:484-90).

An "Fv fragment" is the minimum antibody fragment that contains a complete antigen-recognition and -binding site. This region consists of a dimer of one heavy chain variable domain and one light chain variable domain in tight, non-covalent association. It is in this configuration that the three CDR's of each variable domain interact to define an antigen-binding site on the surface of the $V_H$-$V_L$ dimer. Collectively, the six CDR's confer antigen-binding specificity to the antibody. However, even a single variable domain (or half of an Fv comprising only three CDR's specific for an antigen) has the ability to recognize and bind the antigen, although usually at a lower affinity than the entire binding site. The "Fab fragment" also contains the constant domain of the light chain and the first constant domain (CH1) of the heavy chain. The "Fab fragment" differs from the "Fab' fragment" by the addition of a few residues at the carboxy terminus of the heavy chain CH1 domain, including one or more cysteines from the antibody hinge region. The "F(ab')$_2$ fragment" originally is produced as a pair of "Fab' fragments" which have hinge cysteines between them. Methods of preparing such antibody fragments, such as papain or pepsin digestion, are known to those skilled in the art.

An antibody can be of the IgA-, IgD-, IgE, IgG- or IgM-type, including IgG- or IgM-types such as, without limitation, IgG1-, IgG2-, IgG3-, IgG4-, IgM1- and IgM2-types. For example, in some cases, the antibody is of the IgG1-, IgG2- or IgG4-type.

In certain respects, e.g., in connection with the generation of antibodies as therapeutic candidates against HER-3, it may be desirable that the antibody is capable of fixing complement and participating in complement-dependent cytotoxicity (CDC). There are a number of isotypes of antibodies that are capable of the same including: murine IgM, murine IgG2a, murine IgG2b, murine IgG3, human IgM, human IgG1, human IgG3, and human IgA, for example. It will be appreciated that antibodies that are generated need not initially possess such an isotype but, rather the antibody as generated can possess any isotype and the antibody can be isotype switched by appending the molecularly cloned V region genes or cDNA to molecularly cloned constant region genes or cDNAs in appropriate expression vectors using conventional molecular biological techniques that are well known in the art and then expressing the antibodies in host cells using techniques known in the art. The isotype-switched antibody may also possess an Fc region that has been molecularly engineered to possess superior CDC over naturally occurring variants (Idusogie et al. (2001) *J. Immunol.* 166:2571-2575) and expressed recombinantly in host cells using techniques known in the art. Such techniques include the use of direct recombinant techniques (see, e.g., U.S. Pat. No. 4,816,397), cell-cell fusion techniques (see, e.g., U.S. Pat. Nos. 5,916,771 and 6,207,418), among others. In the cell-cell fusion technique, a myeloma or other cell line such as CHO is prepared that possesses a heavy chain with any desired isotype and another myeloma or other cell line such as CHO is prepared that possesses the light chain. Such cells can thereafter be fused, and a cell line expressing an intact antibody can be isolated. By way of example, a human anti-HER-3 IgG4 antibody that possesses the desired binding to the HER-3 antigen can be readily isotype switched to generate a human IgM, human IgG1 or human IgG3 isotype, while still possessing the same variable region (which defines the antibody's specificity and some of its affinity). Such a molecule might then be capable of fixing complement and participating in CDC.

Moreover, an antibody also may be capable of binding to Fc receptors on effector cells such as monocytes and natural killer (NK) cells, and participating in antibody-dependent cellular cytotoxicity (ADCC). There are a number of antibody isotypes that are capable of the same, including, without limitation, the following: murine IgG2a, murine IgG2b, murine IgG3, human IgG1 and human IgG3. It will be appreciated that the antibodies that are generated need not initially possess such an isotype but, rather the antibody as generated can possess any isotype and the antibody can be isotype switched by appending the molecularly cloned V region genes or cDNA to molecularly cloned constant region genes or cDNAs in appropriate expression vectors using conventional molecular biological techniques that are well known in the art and then expressing the antibodies in host cells using techniques known in the art. The isotype-switched antibody may also possess an Fc region that has been molecularly engineered to possess superior ADCC over naturally occurring variants (Shields et al. (2001) *J. Biol. Chem.* 276:6591-604) and expressed recombinantly in host cells using techniques known in the art. Such techniques include the use of direct recombinant techniques (see, e.g., U.S. Pat. No. 4,816,397), cell-cell fusion techniques (see, e.g., U.S. Pat. Nos. 5,916,771 and 6,207,418), among others. In the cell-cell fusion technique, a myeloma or other cell line such as CHO is prepared that possesses a heavy chain with any desired isotype and another myeloma or other cell line such as CHO is prepared that possesses the light chain. Such cells can thereafter be fused, and a cell line expressing an intact antibody can be isolated. By way of example, a human anti-HER-3 IgG4 antibody that possesses the desired binding to the HER-3 antigen could be readily isotype switched to generate a human IgG1 or human IgG3 isotype, while still possessing the same variable region (which defines the antibody's specificity and some of its affinity). Such molecule might then be capable of binding to FcγR on effectors cells and participating in ADCC.

TABLE 10 herein provides amino acid sequences for a number of CDR's that can be included in antibodies against HER-3. In some embodiments, an isolated binding protein targeted to HER-3 can include a heavy chain amino acid sequence containing at least one CDR selected from the group consisting of: (a) CDRH1's as shown in SEQ ID NOS:2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230, (b) CDRH2's as shown in SEQ ID NOS:2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230, and (c) CDRH3's as shown in SEQ ID NOS:2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230, and/or a light chain amino acid sequence comprising at least one of the CDR's selected from the group consisting of: (d) CDRL1's as shown in SEQ ID NOS:4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232, (c) CDRL2's as shown in SEQ ID NOS:4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232, and (f) CDRL3's as shown in SEQ ID NOS:4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232, as shown in the sequence listing filed herewith.

In some embodiments, an isolated binding protein targeted to HER-3 can include a heavy chain amino acid sequence selected from the group consisting of SEQ ID NOS:2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230, and/or a light chain amino acid sequence selected from the group consisting of SEQ ID NOS:4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232, as shown in the sequence listing filed herewith.

In some embodiments, an anti-HER-3 antibody can include a heavy chain amino acid sequence and a light chain amino acid sequence as shown in SEQ ID NOS:2 and 4, 6 and 8, 10 and 12, 14 and 16, 18 and 20, 22 and 24, 26 and 28, 30 and 32, 36 and 38, 42 and 44, 46 and 48, 50 and 52, 54 and 56, 60 and 58, 62 and 64, 66 and 68, 70 and 72, 74 and 76, 78 and 82, 80 and 82, 84 and 86, 88 and 90, 92 and 94, 96 and 98, 100 and 102, 104 and 106, 108 and 110, 112 and 114, 116 and 118, 122 and 124, 126 and 128, 130 and 132, 134 and 136, 138 and 140, 142 and 144, 146 and 148, 150 and 152, 154 and 156, 158 and 160, 162 and 164, 166 and 168, 170 and 172, 174 and 176, 178 and 180, 182 and 184, 186 and 188, 190 and 192, 194 and 196, 198 and 200, 202 and 204, 206 and 208, 210 and 212, 214 and 216, 218 and 220, 222 and 224, 226 and 228, 230 and 232, or a heavy chain amino acid sequence as shown in any one of SEQ ID NOS:34, 40, 60, 62, and 120, or a light chain amino acid sequence as shown in either of SEQ ID NOS: 58 and 64, as shown in the sequence listing filed herewith.

In some embodiments, a protein targeted to HER-3 can be a scaffold protein having an antibody-like binding activity (e.g., having activity similar to an anti-HER-3 antibody), or an antibody, e.g., an anti-HER-3 antibody. The anti-HER-3 antibody can be selected from the group consisting of antibodies designated U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, and U1-62, or an antibody having at least one heavy or light chain of one of the aforesaid antibodies. The antibodies designated as U1-49 (SEQ ID NO: 42/44), U1-53 (SEQ ID NO: 54/56), and U1-59 (SEQ ID NO: 70/72), or an antibody having at least one heavy or light chain of one of these antibodies, can be particularly useful.

It is to be understood that the amino acid sequence of the HER-3 binding proteins provided herein is not limited to the twenty conventional amino acids (see, *Immunology—A Synthesis* (2$^{nd}$ Edition, Golub and Gren, eds., Sinauer Associates, Sunderland, Mass. (1991), the disclosure of which is hereby incorporated herein by reference in its entirety). For example, the amino acids may include stereoisomers (e.g., D-amino acids) of the twenty conventional amino acids, unnatural amino acids such as α-,α-disubstituted amino acids, N-alkyl amino acids, lactic acid, and other unconventional amino acids. Examples of unconventional amino acids, which may also be suitable components for the binding proteins provided herein, include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids, e.g., 4-hydroxyproline.

Furthermore, minor variations in the amino acid sequences shown in SEQ ID NOS:1-390 (as set forth in the appendix filed herewith) are contemplated as being encompassed by the present disclosure, provided that the variations in the amino acid sequence maintain at least 75% (e.g., at least 80%, 90%, 95%, or 99%) of the sequences shown in SEQ ID NOS:1-390. Variations can occur within the framework regions (i.e., outside the CDRs), within the CDRs, or within the framework regions and the CDRs. In some embodiments, variations in the amino acid sequences shown in SEQ ID NOS:1-390, i.e., deletions, insertions and/or substitutions of at least one amino acid, can occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other binding proteins of known structure and/or function. Methods for identifying protein sequences that fold into a known three-dimensional structure are known in the art. (See, e.g., Bowie et al. (1991) *Science* 253:164; *Proteins, Structures and Molecular Principles*, Creighton, Ed., W H. Freeman and Company, New York (1984); *Introduction to Protein Structure*, Branden and Tooze, eds., Garland Publishing, New York, N.Y. (1991); and Thornton et al. (1991) *Nature* 354:105, the disclosure of each reference of which is hereby incorporated herein by reference in its entirety.) Thus, those of skill in the art can recognize sequence motifs and structural conformations that may be used to define structural and functional domains in accordance with the proteins described herein.

Variations in the amino acid sequences shown in SEQ ID NOS:1-390 can include those that lead to a reduced susceptibility to proteolysis or oxidation, alter glycosylation patterns or alter binding affinities or confer or modify other physicochemical or functional properties of the binding protein. In particular, conservative amino acid replacements are contemplated. Conservative replacements are those that take place within a family of amino acids that are related in their side chains. Amino acid families include the following: acidic family=aspartate, glutamate; basic family=lysine, arginine, histidine; non-polar family=alanine, valine, leucine, isoleucine, proline, phenylalanine, methionine, tryptophan; and uncharged polar family=glycine, asparagine, glutamine, cysteine, serine, threonine, tyrosine. Alternative families include: aliphatic-hydroxy family=serine and threonine; amide-containing family=asparagine and glutamine; aliphatic family=alanine, valine, leucine and isoleucine; and aromatic family=phenylalanine, tryptophan, and tyrosine. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting binding protein, especially if the replacement does not involve an amino acid within a framework site. However, all other possible amino acid replacements also are encompassed herein. Whether an amino acid change results in a functional HER-3 binding protein that reduces signal transduction of HER-3 can readily be determined by assaying the specific HER-3 binding activity of the resulting binding protein by ELISA or FACS, or in vitro or in vivo functional assays.

In some embodiments, a HER-3 binding protein can be coupled to an effector group. Such a binding protein can be especially useful for therapeutic applications. As used herein, the term "effector group" refers to a cytotoxic group such as a radioisotope or radionuclide, a toxin, a therapeutic group or other effector group known in the art. Examples of suitable effector groups are radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I) or non-radio isotopes (e.g., 2D), calicheamicin, dolastatin analogs such as auristatins, and chemotherapeutic agents such as geldanamycin and maytansine derivates, including DM1. Thus, in some cases, a group can be both a labeling group and an effector group. Various methods of attaching effector groups to polypeptides or glycopolypeptides (such as antibodies) are known in the art, and may be used in making and carrying out the compositions and methods described herein. In some embodiments, it may be useful to have effector groups attached to a binding protein by spacer arms of various lengths to, for example, reduce potential steric hindrance.

This document also relates to processes for preparing an isolated HER-3 binding protein, comprising the step of preparing the protein from a host cell that expresses the protein. Host cells that can be used include, without limitation, hybridomas, eukaryotic cells (e.g., mammalian cells such as hamster, rabbit, rat, pig, or mouse cells), plant cells, fungal cells, yeast cells (e.g., *Saccharomyces cerevisiae* or *Pichia pastoris* cells), prokaryotic cells (e.g., *E. coli* cells), and other cells used for production of binding proteins. Various methods for preparing and isolating binding proteins, such as scaffold proteins or antibodies, from host cells are known in the art and may be used in performing the methods described herein. Moreover, methods for preparing binding protein fragments, e.g., scaffold protein fragments or antibody fragments, such as papain or pepsin digestion, modern cloning techniques, techniques for preparing single chain antibody molecules (Plückthun, supra) and diabodies (Hollinger et al., supra), also are known to those skilled in the art and may be used in performing the presently described methods.

In some embodiments, a HER-3 binding protein can be prepared from a hybridoma that secretes the protein. See, e.g., Köhler et al. (1975) *Nature* 256:495.

In some embodiments, a HER-3 binding protein can be prepared recombinantly by optimizing and/or amplifying expression of the binding protein in host cells, and isolating the binding protein from the host cells. To this end, host cells can be transformed or transfected with DNA (e.g., a vector) encoding a HER-3 binding protein, and cultured under conditions appropriate to produce the binding protein. See, e.g., U.S. Pat. No. 4,816,567. Useful host cells include, for example, CHO cells, NS/0 myeloma cells, human embryonic kidney 293 cells, *E. coli* cells, and *Saccharomyces cerevisiae* cells.

HER-3 binding proteins that are antibodies can be prepared from animals genetically engineered to make fully human antibodies, or from an antibody display library made in bacteriophage, yeast, ribosome or E. coli. See, e.g., Clackson et al. (1991) Nature 352:624-628; Marks et al. (1991) J. Mol. Biol. 222:581-597; Feldhaus and Siegel (2004) J. Immunol. Methods 290:69-80; Groves and Osbourn (2005) Expert Opin. Biol. Ther. 5:125-135; and Jostock and Dubel (2005) Comb. Chem. High Throughput Screen 8:127-133.

In some embodiments, antibodies as provided herein can be fully human or humanized antibodies. Human antibodies avoid certain problems associated with xenogeneic antibodies, such as antibodies that possess murine or rat variable and/or constant regions. The presence of xenogeneic-derived proteins can lead to an immune response against the antibody by a patient, subsequently leading to the rapid clearance of the antibody, loss of therapeutic utility through neutralization of the antibody, and/or severe, even life-threatening, allergic reactions. To avoid the using murine or rat-derived antibodies, fully human antibodies can be generated through the introduction of functional human antibody loci into a rodent or another mammal or animal so that the rodent, other mammal or animal produces fully human antibodies.

One method for generating fully human antibodies is to utilize XENOMOUSE® strains of mice that have been engineered to contain 245 kb and 190 kb-sized germline configuration fragments of the human heavy chain locus and kappa light chain locus. Other XENOMOUSE® strains of mice contain 980 kb and 800 kb-sized germline configuration fragments of the human heavy chain locus and kappa light chain locus. Still other XENOMOUSE® strains of mice contain 980 kb and 800 kb-sized germline configuration fragments of the human heavy chain locus and kappa light chain locus plus a 740 kb-sized germline configured complete human lambda light chain locus. See, Mendez et al. (1997) Nature Genetics 15:146-156; and Green and Jakobovits (1998) J. Exp. Med. 188:483-495. XENOMOUSE® strains are available from Amgen, Thousand Oaks, Calif.

The production of XENOMOUSE® mice is further discussed and delineated in US Patent Publication 2003/0217373, filed Nov. 20, 2002; U.S. Pat. Nos. 5,939,598, 6,075,181, 6,114,598, 6,150,584, 6,162,963, 6,673,986, 6,833,268, and 7,435,871, and Japanese Patent Nos. 3068180B2, 3068506B2, and 3068507B2. See, also, European Patent No. EP0463151, PCT Publication Nos. WO 94/02602, WO 96/34096, WO 98/24893, and WO 00/76310. The disclosures of each of the above-cited patents, applications, and references is hereby incorporated herein by reference in its entirety.

Alternatively, a "minilocus" approach can be used. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (e.g., a gamma constant region) are formed into a construct for insertion into an animal. This approach is described in U.S. Pat. Nos. 5,545,806, 5,545,807, 5,569,825, 5,591,669, 5,612,205, 5,625,126, 5,625,825, 5,633,425, 5,643,763, 5,661,016, 5,721,367, 5,770,429, 5,789,215, 5,789,650, 5,814,318, 5,874,299, 5,877,397, 5,981,175, 6,023,010, 6,255,458, the disclosures of which are hereby incorporated herein by reference in their entireties. See, also, EP Patent No. 0546073, and PCT Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of which are hereby incorporated herein by reference in their entireties.

Human antibodies also can be generated from mice in which, through microcell fusion, large pieces of chromosomes, or entire chromosomes, have been introduced. See, EP Patent Application Nos. 773288 and 843961, the disclosures of which are hereby incorporated herein by reference in their entireties. Additionally, KM™ mice, which are the result of cross-breeding of Kirin's Tc mice with Medarex's minilocus (Humab) mice have been generated. These mice possess the HC transchromosome of the Kirin mice and the kappa chain transgene of the Medarex mice (Ishida et al. (2002) Cloning Stem Cells 4:91-102).

Human antibodies also can be derived by in vitro methods. Suitable examples include, but are not limited to, phage display (as commercialized by Cambridge Antibody Technology, Morphosys, Dyax, Biosite/Medarex, Xoma, Symphogen, Alexion (formerly Proliferon), and Affimed), ribosome display (as commercialized by Cambridge Antibody Technology), yeast display, and the like.

As described herein, antibodies were prepared using XENOMOUSE® technology, as described below. Such mice are capable of producing human immunoglobulin molecules and antibodies, and are deficient in the production of murine immunoglobulin molecules and antibodies. Technologies utilized for achieving the same are disclosed in the patents, applications, and references disclosed herein. For example, transgenic production of mice and antibodies therefrom is disclosed in U.S. patent application Ser. No. 08/759,620, filed Dec. 3, 1996, and PCT Publication Nos. WO 98/24893 and WO 00/76310, the disclosures of which are hereby incorporated herein by reference in their entireties. See also Mendez et al. (1997) Nature Genetics 15:146-156, the disclosure of which is hereby incorporated herein by reference in its entirety.

Using technology as described herein, fully human monoclonal antibodies to a variety of antigens can be produced. For example, XENOMOUSE® lines of mice can be immunized with a HER-3 antigen of interest (e.g., HER-3 or a fragment thereof), lymphatic cells (such as B-cells) can be recovered from mice that express antibodies, and the recovered cell lines can be fused with a myeloid-type cell line to prepare immortal hybridoma cell lines. These hybridoma cell lines can be screened and selected to identify hybridoma cell lines that produce antibodies specific to the antigen of interest. Provided herein are methods for the production of multiple hybridoma cell lines that produce antibodies specific to HER-3. Further provided herein are methods for characterizing antibodies produced by such cell lines, including nucleotide and amino acid sequence analyses of the heavy and light chains of such antibodies.

In general, antibodies produced by fused hybridomas as described below are human IgG1 heavy chains with fully human kappa light chains, although some antibodies described herein possess human IgG4 heavy chains as well as IgG1 heavy chains. Antibodies also can be of other human isotypes, including IgG2 and IgG3. The antibodies generally have high affinities, with a $K_D$ typically from about $10^{-6}$ to about $10^{-13}$ M or below, when measured by solid phase and cell-based techniques.

This document also provides isolated nucleic acid molecules that encode HER-3 binding proteins as described herein. The term "isolated nucleic acid molecule," as used herein, refers to a polynucleotide of genomic, cDNA, or synthetic origin, or some combination thereof, which (1) is not associated with all or a portion of a polynucleotide with which the "isolated polynucleotide" is found in nature, (2) is operably linked to a polynucleotide to which it is not linked to in nature, or (3) does not occur in nature as part of a larger sequence. Further, the term "nucleic acid molecule," as used herein, means a polymeric form of nucleotides of at least 10 bases in length, either ribonucleotides or deoxyribonucleotides or a modified form of either type of nucleotide, such as nucleotides with modified or substituted sugar groups and the like. The term also includes single and double stranded forms of DNA.

In some embodiments, a nucleic acid molecule can be operably linked to a control sequence. The term "control sequence," as used herein, refers to polynucleotide sequences that are necessary to effect the expression and processing of coding sequences to which they are ligated. The nature of such control sequences differs depending upon the host organism. In prokaryotes, such control sequences generally include promoters, ribosomal binding sites, and transcription termination sequences. In eukaryotes, generally, such control sequences include promoters and transcription termination sequences. The term "control sequence" is intended to include, at a minimum, all components whose presence is essential for expression and processing, and can also include additional components whose presence is advantageous, for example, leader sequences and fusion partner sequences. Furthermore, the term "operably linked", as used herein, refers to positions of components so described which are in a relationship permitting them to function in their intended manner. Moreover, an expression control sequence operably linked to a coding sequence is ligated in such a way that expression of the coding sequence is achieved under conditions compatible with the expression control sequence.

Also provided herein are vectors comprising a nucleic acid molecule encoding a binding protein as disclosed herein. The nucleic acid molecule can be operably linked to a control sequence. Furthermore, the vector may additionally contain a replication origin or a selection marker gene. Examples of vectors that may be used include, e.g., plasmids, cosmids, phages, and viruses.

This document also provides host cells transformed with a nucleic acid molecule or vector as described herein. Transformation can be accomplished by any known method for introducing polynucleotides into a host cell, including, for example, packaging the polynucleotide in a virus (or into a viral vector) and transducing a host cell with the virus (or vector), or by transfection procedures known in the art, as exemplified by U.S. Pat. Nos. 4,399,216, 4,912,040, 4,740,461, and 4,959,455, the disclosures of which are hereby incorporated herein by reference in their entireties. Methods for introducing heterologous polynucleotides into mammalian cells are well known in the art, and include, without limitation, dextran-mediated transfection, calcium phosphate precipitation, polybrene mediated transfection, protoplast fusion, electroporation, encapsulation of the polynucleotide(s) in liposomes, and direct microinjection of the DNA into nuclei. Examples of host cells that may be used include hybridomas, eukaryotic cells (e.g., mammalian cells such as hamster, rabbit, rat, pig, mouse, or other animal cells), plant cells (e.g., corn and tobacco cells), fungal cells (e.g., *S. cerevisiae* and *P. pastoris* cells), prokaryotic cells such as *E. coli*, and other cells used in the art for production of antibodies. Mammalian cell lines available as hosts for expression are well known in the art and include, for example, many immortalized cell lines available from the American Type Culture Collection (ATCC; Manassas, Va.). These include, without limitation, Chinese hamster ovary (CHO) cells, HeLa cells, baby hamster kidney (BHK) cells, monkey kidney cells (COS), human hepatocellular carcinoma cells (e.g., Hep G2 cells), and a number of other cell lines.

In other embodiments, the agent binding to HER-3 is a small molecule compound. Such compounds can be identified using, for example, physical or virtual libraries of small molecules. In some embodiments, for example, useful small molecule compounds can be identified using consensus virtual screening methods based on known HER-3 inhibitors and models of HER-3 active and inactive state structures. Compounds that appear to be of interest can be further analyzed for structural novelty and desirable physicochemical properties. Candidate compounds identified by virtual screening can be tested in vitro for, e.g., the ability to inhibit growth of cells that overexpress HER-3. In other embodiments, useful small molecule compounds can be identified from a library of small molecule compounds, using high throughput methods to screen large numbers of compounds for the ability to bind to and/or inhibit activity of HER-3 (e.g., in cells that overexpress HER-3). Small molecule HER-3 inhibitors can be synthesized using standard chemical synthesis methods, for example.

In yet anther embodiment, the agent that binds to HER-3 may be a siRNA that interferes with the expression of HER-3. An example of siRNA is EZN-3920 (antisense targeting erbB3 mRNA) (Santaris Pharma, Hoersholm, Denmark).

In yet other embodiments, the agent that binds HER-3 may be a natural substance. For example, Kahalalide F, a marine-derived agent, has been suggested to inhibit HER-3 oncogenic signaling (Jimeno et al. (2006) *J. Translational Med.* 4:3) by down-regulating HER-3 protein expression and AKT signaling (Janmaat et al. (2005) *Mol. Pharmacol.* 68:502-510).

In further embodiments, the agent that binds HRE-3 may be an artificial or naturally-occurring scaffold which is not an anti-HER-3 antibody, but has an antibody-like activity (e.g., has an activity similar to that of an anti-HER-3 antibody)."

3. Agents that Bind to Other HER Family Members

As outlined above, the compositions and methods provided herein for treatment of HER-3 associated disease include a first agent that binds to HER-3, in combination with a second agent that binds and/or inhibits at least one other member of the HER family, including but not limited to, EGF-R, HER-2, HER-4. The second agent can be, without limitation, biological drug, e.g., a binding protein, such as an antibody specifically binding to a member of the HER family, a small molecular compound that binds to and/or alters (e.g., inhibits) the activity of at least one member of the HER family other than (or in addition to) HER-3, an siRNA, or a natural substance. As used herein, the terms "other HER family members" and "another HER family member" refer to HER family members that are not HER-3. Examples are the EGF-R, HER-2, and HER-4, but "HER family member" also includes family members that have not yet been identified.

The second agent can alter the activity (e.g., increase or decrease) the activity of the other HER family member, either through a direct effect or an indirect effect on the HER family member. It is noted, however, that all second agents as provided herein will have an effect on HER family function and activity.

In some cases, for example, the second agent can be an antibody that can bind to another HER family member (e.g., EGF-R, HER-2, or HER-4), or to another molecule that in turn can affect the activity of the other HER family member. Such an antibody can be targeted, for example, to the extracellular domain of the other HER family member, or to any other suitable domain thereof (e.g., a kinase domain or a dimerization domain).

A second agent can be further characterized in that its effect on another HER family member reduces HER-mediated signal transduction. A reduction of HER-mediated signal transduction may, e.g., be caused by downregulation of the targeted HER family member, resulting in an at least partial disappearance of the HER molecule from the cell, or by a stabilization of the HER family member in a substantially inactive form. Alternatively, a reduction of HER-mediated signal transduction may be caused by influencing, e.g., decreasing or inhibiting, the binding of a ligand to the HER family member, the binding of the HER family member to HER-3, or the binding of GRB2 to HER-2 or GRB2 to SHC, or, by inhibiting receptor tyrosine phosphorylation, AKT phosphorylation, PYK2 tyrosine phosphorylation, or ERK2 phosphorylation, or any other cellular component affecting the HER-family mediated signal transduction pathway. For example, a reduction of HER mediated signal transduction can be caused by decreasing the formation of dimers containing HER-3 and another HER family member (e.g., EGF-R, HER-2, or HER-4). Regardless of the mechanism behind the function, it is noted that the second agent can serve to amplify the effect of the first agent that is targeted to HER-3.

In some embodiments, an agent that binds to another HER family member or another protein that in turn affects activity of another HER family member can be a scaffold protein having an antibody like binding activity (e.g., having activity similar to an anti-HER-3 antibody) or an antibody (e.g., an anti-EGF-R, anti-HER-2, or anti-HER-4 antibody). Scaffold proteins and antibodies in this context are as defined and described above for agents targeted to HER-3. Such scaffold can be artificial or naturally-occurring.

It is noted, in some embodiments, the first agent that binds to HER-3, and the second agent that binds to and/or inhibits another HER family member are combined within one compound, such as a bispecific antibody.

Also as described above, the amino acid sequences of proteins that bind to other HER family members, or to other proteins that in turn affect the activity of another HER family member, are not limited to the twenty conventional amino acids. Further, as for the HER-3 binding proteins described herein, an agent that binds to or otherwise affects the activity of another HER family member can be coupled to an effector group.

This document also relates to processes for preparing isolated proteins (e.g., antibodies) that can bind to other HER family members, for example. Such processes include those described above in the context of HER-3 binding proteins. In some embodiments, antibodies (e.g., anti-HER, anti-HER-2, or anti-HER-4 antibodies, respectively) can be prepared from animals engineered to make fully human antibodies, or from an antibody display library made in bacteriophage, yeast, ribosomes, or *E. coli*. Further, an antibody targeted directly or indirectly to another HER family member can be fully human or humanized, as described above.

Also provided herein are isolated nucleic acid molecules (e.g., vectors) expressing proteins that can bind to other HER family members and other proteins that can affect the activity of other HER family members. Protein coding sequences within such nucleic acid molecules can be operably linked to one or more control sequences, as described above. Further, nucleic acid molecules can be transformed or transfected into a host cell as described above.

In some embodiments, the second agent is a small molecular tyrosine kinase inhibitor provided that the agent can affect (either directly or indirectly) the activity of a HER family member other than (or in addition to) HER-3. Such inhibitors can be identified using, for example, physical or virtual libraries of small molecules. In some embodiments, for example, useful small molecule compounds can be identified using consensus virtual screening methods based on known tyrosine kinase inhibitors and models of HER family member structures in active and inactive states. Compounds that are initially identified as being of potential interest can be further analyzed for structural novelty and desirable physicochemical properties. Candidate compounds identified by virtual screening can be tested in vitro for, e.g., the ability to inhibit growth of cells that overexpress a HER family member other than HER-3. In other embodiments, useful small molecule tyrosine kinase inhibitors can be identified from a library of small molecule compounds and using high throughput methods to screen large numbers of the compounds for the ability to bind to and/or inhibit activity of one or more HER family members other than HER-3 (e.g., in cells that overexpress the HER protein). Small molecular tyrosine kinase inhibitors can be synthesized using, for example, standard chemical synthesis methods.

Agents that can affect an activity of EGF-R (HER) include AEE-788 (Novartis, Basel, Switzerland), BIBW-2992(N-[4-(3-chloro-4-fluorophenyl)amino]-7-[[(3S)-tetrahydro-3-furanyl]oxy]-6-quinazolinyl]-4-(dimethylamino)-2-butenamide (Boehringer Ingelheim, Ingelheim, Germany), BMS-599626 (Bristol-Myers Squibb, New York, N.Y.), BMS-690514 (Bristol-Myers Squibb, New York, N.Y.), carnetinib dihydrochloride (N-[4-[N-(3-chloro-4-fluorophenyl) amino]-7-[3-(4-morpholinyl)propoxy]quinazolin-6-yl]acrylamide dihydrochloride (Pfizer, New York, N.Y.), CNX-222 (Avila Therapeutics, Waltham, Mass.), CUDC-101 (Curis, U.S. Pat. No. 7,547,781), Dimercept (Receptor Biologix, Palo Alto, Calif.), lapatinib (ditosilate hydrate (N-[3-chloro-4-[(3-fluorobenzyl)oxy]phenyl]-6-[5-[[[2-(methylsulfonyl) ethyl]amino]methyl]furan-2-yl]quinazolin-4-amine bis(4-methylbenzene-sulfonate)monohydrate (GlaxoSmithKline, London, England), MP-412 (Mitsubishi Tanabe Pharma Co., Osaka, Japan), neratinib ((2E)-N-[4-[[3-chloro-4-[(pyridin-2-yl)methoxy]phenyl]]-3-cyano-7-ethoxyquinolin-6-yl]-4-(dimethylamino)but-2-enamide) (Wyeth, Madison, N.J.), S-222611 (Shionogi, Osaka, Japan), varlitinib (4-N-[3-chloro-4-(thiazol-2-ylmethoxy)phenyl]-6-N-[(4R)-4-methyl-4,5-dihydrooxazol-2-yl]quinazoline-4,6-diamine bis (4-methylbenzenesulfonate) (Array BioPharma, Boulder, Colo.), AGT-2000 (ArmeGen Technologies, Santa Monica, Calif.), AZD-4769 (AstraZeneca, London, England), BIBX-1382 (Boehringer Ingelheim, Ingelheim, Germany), CGP-52411 (4,5-bis(phenylamino)-1H-isoindole-1,3(2H)-dione) (Novartis, Basel, Switzerland), CL-387785 (N-[4-[(3-bromophenyl)amino]-6-quinazolinyl]-2-butynamide) (Wyeth, Madison, N.J.), CP-292597 (Pfizer, New York, N.Y.), DAB-1059 (Mitsubishi Tanabe Pharma Co., Osaka, Japan), erlotinib (hydrochloride(4-(3-ethynylphenylamino)-6,7-bis(2-methoxyethoxy)-quinazoline hydrochloride (OSI Pharmaceuticals, Long Island, N.Y., U.S. Pat. No. 5,747, 498), gefitinib (4-(3-chloro-4-fluorophenylamino)-7-methoxy-6-[3-(4-morpholinyl)propoxy]quinazoline) (AstraZeneca, London, England, U.S. Pat. No. 5,821,246), HMPL-813 (Hutchison China MediTech, Hong Kong), MDP-01, (Med Discovery, Plan-Les-Ouates, Switzerland), MT-062 (Medisyn Technologies, Minneapolis, Minn.), ONC-101 (Oncalis, Schlieren, Switzerland), PD-153035, (4-(3-bromophenylamino)-6,7-dimethoxyquinazoline) (AstraZeneca, London, England), PD-169540 (Pfizer, New York, N.Y.), pelitinib (Wyeth Pharmaceuticals, Madison, N.J.), PF-299804 (Pfizer, New York, N.Y.), PKI-166 (4-(R)-phenethylamino-6-(hydroxyl)phenyl-7H-pyrrolo[2.3-d]-pyrimidine) (Novartis, Basel, Switzerland), vandetanib (N-(4-bromo-2-fluorophenyl)-6-methoxy-7-[(1-methylpiperidin-4-yl)methoxy]quinazolin-4-amine) (AstraZeneca, London, England), VGA-1102 (Taisho Pharmaceuticals, Tokyo, Japan), WHI-P154 (4-(3'-bromo-4'-hydroxyphenyl)-amino-6,7-dimethoxyquinazoline), ZD-1838 (AstraZeneca, London, England), cetuximab (ImClone Systems, New York, N.Y.), panitumumab (Amgen, Thousand Oaks, Calif.).

Agents that can affect an activity of HER2 include AEE-788 (Novartis, Basel, Switzerland), ARRY-333786 (Array BioPharma, Boulder, Colo.), ARRY-380 (Array BioPharma, Boulder, Colo.), BIBW-2992 (N-[4-(3-chloro-4-fluorophenyl)amino]-7-[[(3S)-tetrahydro-3-furanyl]oxy]-6-quinazolinyl]-4-(dimethylamino)-2-butenamide (Boehringer Ingelheim, Ingelheim, Germany), BMS-599626 (Bristol-Myers Squibb, New York, N.Y.), BMS-690514 (Bristol-Myers Squibb, New York, N.Y.), carnetinib dihydrochloride (N-[4-[N-(3-chloro-4-fluorophenyl)amino]-7-[3-(4-morpholinyl)propoxy]quinazolin-6-yl]acrylamide dihydrochloride) (Pfizer, New York, N.Y.), CNF-201 (Biogen Idec, San Diego, Calif.), CNX-222 (Avila Therapeutics, Waltham, Mass.), CP-654577 (OSI Pharmaceuticals, Long Island, N.Y.), CP-724714 (2-methoxy-N-[3-[4-[3-methyl-4-(6-methyl-pyridin-3-yloxy)phenylamino]quinazolin-6-yl]-E-allyl]acetamide) (OSI Pharmaceuticals, Long Island, N.Y.), CUDC-101 (Curis, Cambridge, Mass., U.S. Pat. No. 7,547,781), D-69491 (Baxter International, Deerfield, Ill.), Dimercept (Receptor Biologix, Palo Alto, Calif.), EHT-102 (ExonHit Therapeutics, Paris, France), HER2 antagonist (Centgent Therapeutics, San Diego, Calif.), HER/neu vaccine (Corixa, Seattle, Wash.), Herzyme (Sirna Therapeutics, San Francisco, Calif.), HuMax-Her2 (Genmab, Copenhagen, Denmark), INSM-18 (Insmed, Richmond, Va.), lapatinib (ditosilate hydrate(N-[3-chloro-4-[(3-fluorobenzyl)oxy]phenyl]-6-[5-[[[2-(methyl-sulfonyl)ethyl]amino]methyl]furan-2-yl]quinazolin-4-amine bis(4-methylbenzenesulfonate) monohydrate) (GlaxoSmithKline, London, England), MP-412 (Mitsubishi Tanabe Pharma Co., Osaka, Japan), mu-4-D-5 (Genentech, Oceanside, Calif.), mubritinib (1-[4-[4-[[2-[(E)-2-[4-(trifluoromethyl)phenyl]ethenyl]oxazol-4-yl]methoxy]phenyl]butyl]-1H-1,2,3-triazole) (Takeda Pharmaceuticals, Deerfield, Ill.), neratinib ((2E)-N-[4-[[3-chloro-4-[(pyridin-2-yl)methoxy]phenyl]]-3-cyano-7-ethoxyquinolin-6-yl]-4-(dimethylamino)but-2-enamide): (Wyeth, Madison, N.J.), pertuzumab (Genentech, Oceanside, Calif.), PX-103.1 (Pharmexa, Copenhagen, Denmark), PX-103.2 (Pharmexa, Copenhagen, Denmark), PX-104.1 (Pharmexa, Copenhagen, Denmark), S-222611 (Shionogi, Osaka, Japan), TAK-285 (Takeda Pharmaceuticals, Deerfield, Ill.), trastuzumab (Genentech, Oceanside, Calif.), Trastuzumab-DM1 (ImmunoGen, Waltham, Mass.), varlitinib (4-N-[3-chloro-4-(thiazol-2-ylmethoxy)phenyl]-6-N-[(4R)-4-methyl-4,5-dihydrooxazol-2-yl]quinazoline-4,6-diamine bis(4-methylbenzenesulfonate)) (Array BioPharma, Boulder, Colo.), VM-206 (ViroMed, Minneapolis, Minn.).

Agents that can affect an activity of HER4 include Dimercept (Receptor Biologix, Palo Alto, Calif.), neratinib ((2E)-N-[4-[[3-chloro-4-[(pyridin-2-yl)methoxy]phenyl]amino]-3-cyano-7-ethoxyquinolin-6-yl]-4-(dimethylamino)but-2-enamide) (Wyeth, Madison, N.J.).

Particular non-limiting examples of agents that can bind to and/or alter activity of other HER family members and can be used in the compositions and methods provided herein include, without limitation, panitumumab (Amgen, Thousand Oaks, Calif.), erlotinib (Genentech, South San Francisco, Calif.; OSI Pharmaceuticals, Long Island, N.Y.; Roche, Basel, Switzerland), lapatinib Glaxo Smith Kline, London, U.K.), pertuzumab (Genentech, South San Francisco, Calif.), trastuzumab (Genentech, South San Francisco, Calif.), cetuximab (ImClone, New York, N.Y.; and Bristol Myers Squibb, New York, N.Y.), neratinib (Pfizer Inc., New York, N.Y.), and T-DM1 (Genentech, South San Francisco, Calif.; Roche, Basel, Switzerland), gefitinib (AstraZeneca, London, U.K., and Teva, Petah Tikva, Israel). These are described in further detail below.

Panitumumab, marketed as VECTIBIX®, is a fully human monoclonal antibody specific to EGF-R. In some embodiments, a combination for treatment of HER3-associated disease can be U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, in combination with panitumumab, or U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, in combination with panitumumab, for treatment of neoplastic disease, such as cancer. Examples of cancer types that may be treated with such combinations are breast cancer, gastrointestinal cancer, pancreatic cancer, prostate cancer, ovarian cancer, stomach cancer, endometrial cancer, salivary gland cancer, lung cancer, renal cancer, colon cancer, colorectal cancer, thyroid cancer, bladder cancer, glioma, melanoma, metastatic breast cancer, non-small cell lung cancer, epidermoid carcinoma, fibrosarcoma, melanoma, nasopharyngeal carcinoma, and squamous cell carcinoma.

Erlotinib (marketed as TARCEVA™) is a drug used to treat NSCLC, pancreatic cancer, and several other types of cancer. Erlotinib specifically targets the EGF-R tyrosine kinase, binding reversibly to the ATP binding site of the receptor. In some embodiments, a composition for treatment of HER3-associated disease can be U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with erlotinib, or U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with erlotinib and other agent(s), for treatment of neoplastic disease, such as cancer, including but not limited to breast cancer, gastrointestinal cancer, pancreatic cancer, prostate cancer, ovarian cancer, stomach cancer, endometrial cancer, salivary gland cancer, lung cancer, renal cancer, colon cancer, colorectal cancer, thyroid cancer, bladder cancer, glioma, melanoma, metastatic breast lung cancer, epidermoid carcinoma, fibrosarcoma, melanoma, nasopharyngeal carcinoma, or squamous cell carcinoma. In some preferred embodiments, U1-49, U1-53 or U1-59 can be used in the treatment of patients with cancers including non-small cell lung cancer (NSCLC), locally advanced NSCLC and metastatic NSCLC after failure of at least one prior chemotherapy regimen, in combination with erlotinib.

Lapatinib (marketed as Tykerb) is an orally active small molecule for the treatment of solid tumors such as breast cancer. Lapatinib is a dual tyrosine kinase inhibitor that inhibits tyrosine kinase activity associated with EGF-R and HER2/neu (human EGF-R type 2). In some embodiments, a composition for treatment of HER3-associated disease can be U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with lapatinib, or U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with lapatinib and other agent(s) such as capecitabine, for treatment of neoplastic disease, such as cancer, wherein the cancer is, for example, breast cancer, gastrointestinal cancer, pancreatic cancer, prostate cancer, ovarian cancer, stomach cancer, endometrial cancer, salivary gland cancer, lung cancer, renal cancer, colon cancer, colorectal cancer, thyroid cancer, bladder cancer, glioma, melanoma, metastatic breast cancer, non-small cell lung cancer, epidermoid carcinoma, fibrosarcoma, melanoma, nasopharyngeal carcinoma, or squamous cell carcinoma. In some preferred embodiments, U1-49, U1-53 or U1-59 can be used in the treatment of patients with cancers including breast cancer and metastatic breast cancer whose tumors express or overexpress the HER-2 protein and who have received prior chemotherapy including an anthracycline (for example, doxorubicin or related agent) and/or a taxane (for example, paclitaxel or docetaxel), and trastuzumab, in combination with lapatinib, or, in combination with lapatinib and capecitabine.

Trastuzumab (also known as HERCEPTIN®) is a humanized monoclonal antibody that interferes with the HER2/neu receptor. In some embodiments, a composition for treatment of HER3-associated disease can be U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with trastuzumab, or U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with trastuzumab and other agent(s) such as docetaxel or paclitaxel, for treatment of neoplastic disease, such as cancer, such as breast cancer, gastrointestinal cancer, pancreatic cancer, prostate cancer, ovarian cancer, stomach cancer, endometrial cancer, salivary gland cancer, lung cancer, renal cancer, colon cancer, colorectal cancer, thyroid cancer, bladder cancer, glioma, melanoma, metastatic breast cancer, non-small cell lung cancer, epidermoid carcinoma, fibrosarcoma, melanoma, nasopharyngeal carcinoma, or squamous cell carcinoma. In some preferred embodiments, U1-49, U1-53 or U1-59 can be used in the treatment of patients with cancers including breast cancer and metastatic breast cancer whose tumors express or overexpress the HER-2 protein and who have not received chemotherapy for their (metastatic) disease, in combination with trastuzumab and paclitaxel, or, in combination with trastuzumab and docetaxel.

T-DM1 is an antibody-drug conjugate that includes trastuzumab chemically linked to a potent antimicrotubule drug (DM1) derived from maytansine. Maytansine has been used as a free drug, and has shown effectiveness in, e.g., breast and lung cancer patients. The non-reducible thioether MCC linker is used in T-DM1, providing a stable bond between trastuzumab and DM1, prolonging exposure, and reducing the toxicity of T-DM1 while maintaining activity. In some embodiments, a method for treatment of HER3-associated disease can include administering U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-49, U1-53 or U1-59, in combination with T-DM1 (e.g., either simultaneously or separately), or U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-49, U1-53 or U1-59, in combination with T-DM1 and other agent(s) such as docetaxel or paclitaxel, for treatment of neoplastic disease, such as cancer, including cancers such as gastrointestinal cancer, pancreatic cancer, prostate cancer, ovarian cancer, stomach cancer, endometrial cancer, salivary gland cancer, kidney cancer, colon cancer, thyroid cancer, bladder cancer, glioma, melanoma, lung cancer including non-small cell lung cancer, colorectal cancer, and/or breast cancer including metastatic breast cancer. In some preferred embodiments, U1-49, U1-53 or U1-59 can be used in the treatment of patients with cancers including breast cancer and metastatic breast cancer whose tumors express or overexpress the HER-2 protein and who have not received chemotherapy for their (metastatic) disease, in combination with T-DM1 and paclitaxel, or, in combination with T-DM1 and docetaxel.

Pertuzumab (2C4) (marketed or to be marketed as OMNITARG™) is a monoclonal antibody that inhibits the dimerization of HER2 with other HER receptors. In some embodiments, a composition for treatment of HER3-associated disease can be U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with pertuzumab, or U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with pertuzumab and other agent(s), for treatment of neoplastic disease, such as cancer, including, e.g., breast cancer, gastrointestinal cancer, pancreatic cancer, prostate cancer, ovarian cancer, stomach cancer, endometrial cancer, salivary gland cancer, lung cancer, renal cancer, colon cancer, colorectal cancer, thyroid cancer, bladder cancer, glioma, melanoma, metastatic breast cancer, non-small cell lung cancer, epidermoid carcinoma, fibrosarcoma, melanoma, nasopharyngeal carcinoma, and squamous cell carcinoma.

Cetuximab (marketed as ERBITUX®) is a chimeric (mouse/human) monoclonal antibody that binds to and inhibits EGF-R. In some embodiments, a composition for treatment of HER3-associated disease can be U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with cetuximab, or U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with cetuximab for treatment of neoplastic disease, such as cancer, including, e.g., breast cancer, gastrointestinal cancer, pancreatic cancer, prostate cancer, ovarian cancer, stomach cancer, endometrial cancer, salivary gland cancer, lung cancer, renal cancer, colon cancer, colorectal cancer, thyroid cancer, bladder cancer, glioma, melanoma, metastatic breast cancer, non-small cell lung cancer, epidermoid carcinoma, fibrosarcoma, melanoma, nasopharyngeal carcinoma, and squamous cell carcinoma. In some preferred embodiments, U1-49, U1-53 or U1-59 can be used in the treatment of patients with cancers including colorectal cancer and metastatic colorectal cancer after failure of 5-fluorouracil-based chemotherapy, in combination with cetuximab and irinotecan.

Gefitinib (marketed as IRESSA®) is a drug that acts in a similar manner to erlotinib. Gefitinib selectively inhibits EGF-R's tyrosine kinase domain. In some embodiments, a composition for treatment of HER3-associated disease can be U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with gefitinib, or U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with gefitinib and other agent(s), for treatment of neoplastic disease such as cancer, including, e.g., breast cancer, gastrointestinal cancer, pancreatic cancer, prostate cancer, ovarian cancer, stomach cancer, endometrial cancer, salivary gland cancer, lung cancer, renal cancer, colon cancer, colorectal cancer, thyroid cancer, bladder cancer, glioma, melanoma, metastatic breast cancer, non-small cell lung cancer, epidermoid carcinoma, fibrosarcoma, melanoma, nasopharyngeal carcinoma, and squamous cell carcinoma.

Neratinib is an inhibitor of the HER-2 receptor tyrosine kinase. Neratinib binds irreversibly to the HER-2 receptor and thereby reduces autophosphorylation in cells, apparently by targeting a cysteine residue in the ATP-binding pocket of the receptor. Treatment of cells with neratinib results in inhibition of downstream signal transduction events and cell cycle regulatory pathways, arrest at the G1-S-phase transition of the cell cycle, and ultimately decreased cellular proliferation. In addition, neratinib inhibits the EGF-R kinase and proliferation of EGF-R-dependent cells. In some embodiments, a method for treatment of HER3-associated disease can include administration of U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with neratinib (e.g., simultaneously or separately), or U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62, U1-1, U1-2, U1-3, U1-4, U1-5, U1-6, U1-7, U1-8, U1-9, U1-10, U1-11, U1-12, U1-13, U1-14, U1-15, U1-16, U1-17, U1-18, U1-19, U1-20, U1-21, U1-22, U1-23, U1-24, U1-25, U1-26, U1-27, U1-28, U1-29, U1-30, U1-31, U1-32, U1-33, U1-34, U1-35, U1-36, U1-37, U1-38, U1-39, U1-40, U1-41, U1-42, U1-43, U1-44, U1-45, U1-46, U1-47, U1-48, U1-49, U1-50, U1-51, U1-52, U1-53, U1-55.1, U1-55, U1-57.1, U1-57, U1-58, U1-59, U1-61.1, U1-61, or U1-62,U1-49, U1-53 or U1-59, in combination with neratinib and other agent(s), for treatment of neoplastic disease such as cancer, including, e.g., gastrointestinal cancer, pancreatic cancer, prostate cancer, ovarian cancer, stomach cancer, endometrial cancer, salivary gland cancer, kidney cancer, colon cancer, thyroid cancer, bladder cancer, glioma, melanoma, lung cancer including non-small cell lung cancer, colorectal cancer and/or breast cancer including metastatic breast cancer.

4. Additional Agents to be used in the Compositions and Methods Disclosed Herein Additional agents may be added to the first and second agent binding to HER-3, and binding to and/or inhibiting another member of the HER family, respectively, as disclosed herein. These, in some embodiments, will be chemotherapeutic drugs. The additional agents to be used in the compositions and methods disclosed herein can be also used as the second agent(s) in place of that binding to and/or inhibiting another member of the HER family in the present inventions. In other words, the first agent binding to HER3 can be used in certain treatment in combination with any of the additional agents described hereinafter without/instead for the second agent binding to and/or inhibiting another HER family.

For example, agents that act as microtubule stimulants include NK-105 (paclitaxel) [(−)-(1S,2R,3S,4S,5R,7S,8S,10R,13S)-4,10-diacetoxy-2-benzoyloxy-5,20-epoxy-1,7-dihydroxy-9-oxotax-11-en-13-yl (2R,3S)-3-benzoylamino-2-hydroxy-3-phenylpropionate] (NanoCarrier, Chiba, Japan), milataxel (1,10β-dihydroxy-9-oxo-5β,20-epoxy-3zeta-tax-11-ene-2α,4,7β13α-tetrayl 4-acetate 2-benzoate 13-[(2R,3R)-3-(tert-butoxycarbonylamino)-3-(furan-2-yl)-2-hydroxypropanoate]7-propanoate) (Taxolog, Fairfield, N.J.), laulimalide (Kosan Biosciences, Hayward, Calif. (B-M Squibb)), sarcodictyin A (3-(1-methylimidazol-4-yl)-2(E)-propenoic acid (1R,4aR,6S,7S,10R,12aR)-11-methoxycarbonyl-7,10-epoxy-10-hydroxy-1-isopropyl-4,7-dimethyl-1,2,4a,5,6,7,10,12a-octahydrobenzocyclododecen-6-yl ester) (Pfizer, New York, N.Y.), simotaxel ((2aR,4S,4aS,6R,9S,11S,12S,12aR,12bS)-4,11-dihydroxy-4a,8,13,13-tetramethyl-5-oxo-2a,3,4,4a,5,6,9,10,11,12,12a,12b-dodecahydro-7,11-methano-1H-cyclodeca[3,4]benz[1,2-b]oxete-6,9,12,12b-tetrayl 12b-acetate 12-benzoate 6-cyclopentanecarboxylate 9-[(2R,3R)-2-hydroxy-3-[[(1-methylethoxy)carbonyl]amino]-3-(thiophen-2-yl)propanoate]) (Taxolog, Fairfield, N.J.), SYN-2001 (CLL Pharma, Nice, France), TL-310 (Taxolog, Fairfield, N.J.), TL1836 (Taxolog, Fairfield, N.J.), tesetaxel (2'-[(dimethylamino)methyl]-1-hydroxy-5β,20-epoxy-9α,10α-dihydro[1,3]dioxolo[4',5':9,10]tax-11-ene-2α,4,13α-triyl4-acetate 2-benzoate 13-[(2R,3S)-3-[(tert-butoxycarbonyl)amino]-3-(3-fluoropyridin-2-yl)-2-hydroxypropanoate) (Daiichi Sankyo, Tokyo, Japan), TL-1892 (Taxolog, Fairfield, N.J.), TPI-287 ((2'R,3'S)-2'-hydroxy-N-carboxy-3'-amino-5'-methylhexanoic, N-tert-butyl ester, 13 ester 5β-20-epoxy-1,2α,4,7β,9α,10α,13α-heptahydroxy-4,10-diacetate-2-benzoate-7,9-acrolein acetal-tax-11-ene (Tapestry Pharmaceuticals, Boulder, Colo.), ortataxel (2aR-[2aα,4β,4aβ,6β,9α(2R,3S),10β,11β,12α,12aα,12bα]-3-(tert-butoxycarbonylamino)-2-hydroxy-5-methyl-hexanoic acid 6,12b-diacetoxy-12-benzoyloxy-10,11-carbonyldioxy-4-hydroxy-4a,8,13,13-tetramethyl-5-oxo-2a,3,4,4a,5,6,9,10,11,12,12a,12b-dodecahydro-1H-7,11-methanocyclodeca[3,4]benz[1,2-b]oxet-9-yl ester) (Indena, Milan, Italy), paclitaxel poliglumex (L-pyroglutamylpoly-L-glutamyl-L-glutamic acid partially γ-esterified with (1R,2S)-2-(benzoylamino)-1-[[[(2aR,4S,4aS,6R,9S,11S,12S,12aR,12bS)-6,12b-bis(acetyloxy)-12-(benzoyloxy)-4,11-dihydroxy-4a,8,13,13-tetramethyl-5-oxo-2a,3,4,4a,5,6,9,10,11,12,12a,12b-dodecahydro-7,11-methano-1H-cyclodeca[3,4]benzo[1,2-b]oxet-9-yl]oxy] carbonyl]-2-phenylethyl) (Cell Therapeutics, Seattle, Wash.), paclitaxel protein-bound particles (paclitaxel: (−)-(1S,2R,3S,4S,5R,7S,8S,10R,13S)-4,10-diacetoxy-2-benzoyloxy-5,20-epoxy-1,7-dihydroxy-9-oxotax-11-en-13-yl (2R,3S)-3-benzoylamino-2-hydroxy-3-phenylpropionate) (Abraxis BioScience, Los Angeles, Calif.), paclitaxel (NCI) ((−)-(1S,2R,3S,4S,5R,7S,8S,10R,13S)-4,10-diacetoxy-2-benzoyloxy-5,20-epoxy-1,7-dihydroxy-9-oxotax-11-en-13-yl (2R,3S)-3-benzoylamino-2-hydroxy-3-phenylpropionate) (NCI (NIH)), paclitaxel (NeoPharm, Lake Bluff, Ill.) ((−)-(1S,2R,3S,4S,5R,7S,8S,10R,13S)-4,10-diacetoxy-2-benzoyloxy-5,20-epoxy-1,7-dihydroxy-9-oxotax-11-en-13-yl (2R,3S)-3-benzoylamino-2-hydroxy-3-phenylpropionate) (NeoPharm, Lake Bluff, Ill.), patupilone ((1S,3S,7S,10R,11S,12S,16R)-7,11-dihydroxy-8,8,10,12,16-pentamethyl-3-[(1E)-1-(2-methyl-1,3-thiazol-4-yl)prop-1-en-2-yl]-4,17-dioxabicyclo[14.1.0]heptadecane-5,9-dione) (US Publication No. 2003/0104625, Novartis, Basel, Switzerland), PEG-paclitaxel (Enzo Pharmaceuticals, Long Island, N.Y.), docetaxel hydrate ((−)-(1S,2S,3R,4S,5R,7S,8S,10R,13S)-4-acetoxy-2-benzoyloxy-5,20-epoxy-1,7,10-trihydroxy-9-oxotax-11-ene-13-yl(2R,3S)-3-tert-butoxycarbonylamino-2-hydroxy-3-phenylpropionate trihydrate) (Sanofi-Aventis, Bridgewater, N.J.), eleutherobin (3-(1-methylimidazol-4-yl)-2(E)-propenoic acid (1R,4aR,6S,7S,10R,12aR)-11-(2-O-acetyl-β-D-arabinopyranosyloxymethyl)-7,10-epoxy-1-isopropyl-10-methoxy-4,7-dimethyl-1,2,4a,5,6,7,10,12a-octahydrobenzocyclododecen-6-yl ester) (Bristol-Myers Squibb, New York, N.Y.), IDN-5390 (Indena, Milan, Italy), ixabepilone ((1S,3S,7S,10R,11S,12S,16R)-7,11-dihydroxy-8,8,10,12,16-pentamethyl-3-[(1E)-1-methyl-2-(2-methylthiazol-4-yl)ethenyl]-17-oxa-4-azabicyclo[14.1.0]heptadecane-5,9-dione) (Bristol-Myers Squibb, New York, N.Y.), KOS-1584 (Kosan Biosciences, Hayward, Calif. (B-M Squibb)), KOS-1803 (17-iso-oxazole 26-trifluoro-9,10-dehydro-12,13-desoxy-epothilone B) (Kosan Biosciences, Hayward, Calif. (B-M Squibb)), KOS-862 (Kosan Biosciences, Hayward, Calif. (B-M Squibb); U.S. Pat. Nos. 6,204,388 and 6,303,342), larotaxel (1-hydroxy-9-oxo-5β,20-epoxy-7β,19-cyclotax-11-ene-2α,4,10β,13α-tetrayl 4,10-diacetate 2-benzoate 13-[(2R,3S)-3-[(tert-butoxycarbonyl)amino]-2-hydroxy-3-phenylpropanoate]dehydrate) (Sanofi-Aventis, Bridgewater, N.J., PCT Publication Nos. WO 95/26961 and WO 96/1259), ANG-1005 (Angiopep-2/paclitaxel conjugate) (AngioChem, Montreal, Canada, U.S. Pat. No. 7,557,182), BMS-184476 (Bristol-Myers Squibb, New York, N.Y., EP Publication No. 639577), BMS-188797 (Bristol-Myers Squibb, New York, N.Y.), BMS-275183 (3'-tert-butyl-3'-N-tert-butyloxycarbonyl-4-deacetyl-3'-dephenyl-3'-N-debenzoyl-4-O-methyoxy-carbonyl-paclitaxel) (Bristol-Myers Squibb, New York, N.Y.), BMS-310705 (Bristol-Myers Squibb, New York, N.Y.), BMS-753493 (Bristol-Myers Squibb, New York, N.Y.), cabazitaxel (1-hydroxy-7β,10β-dimethoxy-9-oxo-5β,20-epoxytax-11-ene-2α,4,13α-triyl 4-acetate 2-benzoate 13-[(2R,3S)-3-[[(tertbutoxy)carbonyl]amino]-2-hydroxy-3-phenylpropanoate]) (Sanofi-Aventis, Bridgewater, N.J.), DHA-paclitaxel (Protarga, King of Prussia, Pa., TAXOPREXIN®), disermolide ([3S-[3α,4β,5β,6α(2R*,3Z,5R*,6R*,7S*,8Z,11R*,12S*,13S*,14S*,15R*,16E)]]-6-[14[(aminocarbonyl)oxy]-2,6,12-trihydroxy-5,7,9,11,13,15-hexamethyl-3,8,16,18-nonadecatetraenyl]tetrahydro-4-hydroxy-3,5-dimethyl-2H-pyran-2-one) (Novartis, Basel, Switzerland, U.S. Pat. Nos. 4,939,168 and 5,681,847). Some of these microtubule stimulants have a taxane ring in their chemical structures; such compounds having a taxane ring are referred as "taxanes" herein.

Anthracyclins include actinomycins such as actinomycin D (Dactinomycin: 2-amino-N,N'-bis[(6S,9R,10S,13R,18aS)-6,13-diisopropyl-2,5,9-trimethyl-1,4,7,11,14-pentaoxohexadecahydro-1H-pyrrolo[2,1-i][1,4,7,10,13]oxatetraazacyclohexadecin-10-yl]-4,6-dimethyl-3-oxo-3H-phenoxazine-1,9-dicarboxamide), bleomycin (bleomycin hydrochloride: (3-{[(2'-{(5S,8S,9S,10R,13S)-15-{6-amino-2-[(1S)-3-amino-1-{[(2S)-2,3-diamino-3-oxopropyl]amino}-3-oxopropyl]-5-methylpyrimidin-4-yl}-13-[{[(2R,3S,4S,5S,6S)-3-{[(2R,3S,4S,5R,6R)-4-(carbamoyloxy)-3,5-dihydroxy-6-(hydroxymethyl)tetrahydro-2H-pyran-2-yl]oxy}-4,5-dihydroxy-6-(hydroxymethyl)tetrahydro-2H-pyran-2-yl]oxy}(1H-imidazol-5-yl)methyl]-9-hydroxy-5-[(1R)-1-hydroxyethyl]-8,10-dimethyl-4,7,12,15-tetraoxo-3,6,11,14-tetraazapentadec-1-yl}-2,4'-bi-1,3-thiazol-4-yl)carbonyl]amino}propyl)(dimethyl)sulfonium), daunorubicin hydrochloride (daunorubicin: 8S-cis)-8-Acetyl-10-((3-amino-2,3,6-trideoxy-alpha-L-lyxo-hexopyranosyl)oxy)-7,8,9,10-tetrahydro-6,8,11-trihydroxy-1-methoxy-5,12-naphthacenedione hydrochloride), doxorubicin hydrochloride (doxorubicin: (8S,10S)-10-[(3-amino-2,3,6-trideoxy-α-L-lyxo-hexopyranosyl)oxy]-8-glycoloyl-7,8,9,10-tetrahydro-6,8,11-trihydroxy-1-methoxy-5,12-naphthacenedione hydrochloride) (Alza, Mountain View, Calif.), idarubicin hydrochloride ((7S,9S)-9-acetyl-7,8,9,10-tetrahydro-6,7,9,11-tetrahydroxy-7-O-(2,3,6-trideoxy-3-amino-α-L-lyxo-hexopyranosyl)-5,12-naphthacenedione hydrochloride) (Pfizer, New York, N.Y., U.S. Pat. Nos. 4,046,878 and 4,471,052), and mitomycin ((1aS,8S,8aR,8bR)-6-Amino-4,7-dioxo-1,1a,2,8,8a,8b-hexahydro-8a-methoxy-5-methylazirino[2,3:3,4]pyrrolo[1,2-α]indol-8-yl-methylcarbamate) (Kyowa-Hakko-Kirin, Tokyo, Japan).

Cisplatin and gemcitabine are chemotherapeutic agents. Cisplatin or cis-diamminedichloroplatinum(II) is a platinum-based drug used to treat various types of cancers. The cisplatin platinum complex reacts in vivo, binding to and causing crosslinking of DNA, which ultimately triggers apoptosis. Gemcitabine is a nucleoside analog in which the hydrogen atoms on the 2' carbons of deoxycytidine are replaced by fluorine atoms. Like fluorouracil and other pyrimidine analogues, gemcitabine replaces cytidine during DNA replication, which arrests tumor growth since further nucleosides cannot be attached to the "faulty" nucleoside, resulting in apoptosis. Gemcitabine is marketed as GEMZAR® by Eli Lilly and Company (Indianapolis, Ind.). In some embodiments, a combination for treatment of HER3-associated disease can be: U1-49, U1-53 or U1-59 in combination with a second agent as described herein and cisplatin or gemcitabine and other agent(s), for treatment of cancer which is gastrointestinal cancer, pancreatic cancer, prostate cancer, ovarian cancer, stomach cancer, endometrial cancer, salivary gland cancer, kidney cancer, colon cancer, thyroid cancer, bladder cancer, glioma, melanoma, lung cancer including non-small cell lung cancer, colorectal cancer and/or breast cancer including metastatic breast cancer.

Capecitabine (pentyl[1-(3,4-dihydroxy-5-methyl-tetrahydrofuran-2-yl)-5-fluoro-2-oxo-1H-pyrimidin-4-yl]aminomethanoate, Xeloda, Roche) is an orally-administered chemotherapeutic agent. Capecitabine is a prodrug that is enzymatically converted to 5-fluorouracil in the tumor, where it inhibits DNA synthesis and slows growth of tumor tissue. In some embodiments, a combination for treatment of HER3-associated disease can be: U1-49, U1-53 or U1-59 in combination with a second agent as described herein (e.g., lapatanib) and capecitabine for treatment of cancer, wherein the cancer is gastrointestinal cancer, pancreatic cancer, prostate cancer, ovarian cancer, stomach cancer, endometrial cancer, salivary gland cancer, kidney cancer, colon cancer, thyroid cancer, bladder cancer, glioma, melanoma, lung cancer including non-small cell lung cancer, colorectal cancer and/or breast cancer including metastatic breast cancer. In some cases, such a combination can be administered after failure of prior treatment with an anthracyclin or taxane, for example. In some preferred embodiments, U1-49, U1-53 or U1-59 can be used in the treatment of patients with cancers including breast cancer and metastatic breast cancer whose tumors express or overexpress the HER-2 protein and who have received prior chemotherapy including an anthracycline (for example, doxorubicin or related agent), and/or a taxane (for example, paclitaxel or docetaxel), and trastuzumab, in combination with lapatinib and capecitabine.

Docetaxel ((2R,3S)-N-carboxy-3-phenylisoserine, N-tert-butyl ester, 13-ester with 5,20-epoxy-1,2,4,7,10,13-hexahydroxytax-11-en-9-one 4-acetate 2-benzoate, trihydrate) and paclitaxel ((2α,4α,5β,7β,10β,13α)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl be) are chemotherapeutic agents. Docetaxel is marketed as Taxotere by Sanofi Aventis. Paclitaxel is marketed as Taxol by Bristol-Myers Squibb. In the formulation of Taxol, paclitaxel is dissolved in Cremophor EL and ethanol, as a delivery agent. A formulation in which paclitaxel is bound to albumin is marketed as Abraxane. In some embodiments, a combination for treatment of HER3-associated disease can be: U1-49, U1-53 or U1-59 in combination with a second agent as described herein (e.g., trastuzumab) and docetaxel or paclitaxel and other agent(s) such as trastuzumab, for treatment of cancer, wherein the cancer is gastrointestinal cancer, pancreatic cancer, prostate cancer, ovarian cancer, stomach cancer, endometrial cancer, salivary gland cancer, kidney cancer, colon cancer, thyroid cancer, bladder cancer, glioma, melanoma, lung cancer including non-small cell lung cancer, colorectal cancer and/or breast cancer including metastatic breast cancer. In some preferred embodiments, U1-49, U1-53 or U1-59 can be use in the treatment of patients with cancers including breast cancer and metastatic breast cancer whose tumors express or overexpress the HER-2 protein and who have not received chemotherapy for their (metastatic) disease, in combination with trastuzumab and paclitaxel, in combination with T-DM1 and paclitaxel, in combination with trastuzumab and docetaxel, or, in combination with T-DM1 and docetaxel.

Doxorubicin hydrochloride liposome injection is marketed as Doxil, a liposome formulation comprising doxorubicin chloride. In some embodiments, a combination treatment for HER-3-associated disease can include administering U1-49, U1-53 or U1-59 in combination with a second agent as described herein and doxorubicin hydrochloride liposome injection, with or without one or more other agents such as paclitaxel or platinum-based chemotherapeutic agents, for treatment of cancer such as breast cancer, gastrointestinal cancer, pancreatic cancer, prostate cancer, ovarian cancer, stomach cancer, endometrial cancer, salivary gland cancer, lung cancer, renal cancer, colon cancer, colorectal cancer, thyroid cancer, bladder cancer, glioma, melanoma, metastatic breast cancer, non-small cell lung cancer, epidermoid carcinoma, fibrosarcoma, melanoma, nasopharyngeal carcinoma, and squamous cell carcinoma. In some preferred embodiments, U1-49, U1-53 or U1-59 can be use in the treatment of patients with cancers including ovarian cancer whose disease has progressed or recurred after platinum-based chemotherapy, in combination with doxorubicin HCl liposome injection (Doxil).

Irinotecan hydrochloride hydrate (irinotecan: (+)-(4S)-4,11-diethyl-4-hydroxy-9-[(4-piperidinopiperidino)carbonyloxy]-1H-pyrano[3',4':6,7]indolizino[1-2-b]quinoline-3,14(4H,12H)-dione hydrochloride trihydrate) (Yakult, EP Publication Nos. 137145 and 56692) is marketed as Campto, Camptosar and Ircan. In some embodiments, a combination treatment for HER3-associated disease can include administering U1-49, U1-53 or U1-59 in combination with a second agent as described herein and irinotecan hydrochloride hydrate, or U1-49, U1-53 or U1-59 in combination with a second agent as described herein, irinotecan hydrochloride hydrate, and one or more other agent(s) such as 5-FU(5'-deoxy-5-fluorouridine or 5-fluoro-2,4(1H,3H)-pyrimidinedione), calcium folinate (N-[4-[[(2-amino-5-formyl-1,4,5,6,7,8-hexahydro-4-oxo-6-pteridinyl)methylamino]benzoyl]-L-glutamic acid calcium salt (1:1)) or calcium levofolinate ((−)-calcium N-[4-[[[(6S)-2-amino-5-formyl-1,4,5,6,7,8-hexahydro-4-oxo-6-pteridinyl]methyl]amino]benzoyl]-L-glutamate), and combinations thereof, for treatment of cancer such as breast cancer, gastrointestinal cancer, pancreatic cancer, prostate cancer, ovarian cancer, stomach cancer, endometrial cancer, salivary gland cancer, lung cancer, renal cancer, colon cancer, colorectal cancer, thyroid cancer, bladder cancer, glioma, melanoma, metastatic breast cancer, non-small cell lung cancer, epidermoid carcinoma, fibrosarcoma, melanoma, nasopharyngeal carcinoma, and squamous cell carcinoma.

In some preferred embodiments, U1-49, U1-53 or U1-59 can be use in the treatment of patients with cancers including colorectal cancer and metastatic colorectal cancer after failure of 5-fluorouracil-based chemotherapy, in combination with 5-fluorouracil-based chemotherapy. In some further embodiments, U1-49, U1-53 or U1-59 can be use in the treatment of the treatment of patients with cancers including colorectal cancer and metastatic colorectal cancer with wild-type K-RAS after failure of 5-fluorouracil-based chemotherapy, in combination with cetuximab and irinotecan.

In some embodiments, the additional agents to be use in the compositions and methods disclosed herein, which are exchangeable with the second agent as disclosed herein, may be an artificial or naturally-occurring scaffold which is not an antibody, but has an antibody-like activity (e.g., has an activity similar to that of an antibody).

In some other embodiments, said additional agents, which are exchangeable with the second agent disclosed herein, can be agents inhibit, block or reduce (act as antagonists towards), or, activate, stimulate or accelerate (act as agonist towards) an activity of other targets, including but not limited to those affect cellular growth and/or survival pathways, such as PI3K inhibitors, AKT inhibitors, mTOR inhibitors, RAF/B-RAF inhibitors, RAS inhibitors, MEK inhibitors, Death Receptor inhibitors including DR4 and DR5 agonists such as anti-DR4 or DR5 agonistic antibodies (for example, cedelizumab, tigatuzumab, drozirumab, conatumumab), PPAR gamma agonists (for example, efatutazone, troglitazone, pioglitazone, rosiglitazone), c-MET inhibitors, Hsp-90 inhibitors and telomerase inhibitors.

In some other embodiments, said additional agents, which are exchangeable with the second agent as disclosed herein, can be anti-angiogenics, including but not limited to, VEGF antagonists/inhibitors (for example, bevacizumab, vandetanib).

In some further embodiments, said additional agents, which are exchangeable with the second agent, can be immunotherapeutic such as vaccines or cellular therapeutics.

As further described below, these and other agents can be contained within the compositions provided herein, and can be administered in a variety of different forms, combinations and dosages.

5. Compositions

This document also provides pharmaceutical compositions comprising a HER-3 binding agent as described herein, in combination with a second agent that is directed against another HER family protein or is a chemotherapeutic compound, as well as one or more pharmaceutically acceptable carriers, diluents and/or adjuvants. The term "pharmaceutical composition," as used herein, refers to a chemical compound or composition capable of inducing a desired therapeutic effect when properly administered to a patient (*The McGraw-Hill Dictionary of Chemical Terms*, Parker, Ed., McGraw-Hill, San Francisco (1985)). The potency of the pharmaceutical compositions provided herein typically is based on the binding of the at least one binding protein to HER-3. In some embodiments, this binding can lead to a reduction of the HER-3-mediated signal transduction.

A "pharmaceutically acceptable carrier" (also referred to herein as an "excipient" or a "carrier") is a pharmaceutically acceptable solvent, suspending agent, stabilizing agent, or any other pharmacologically inert vehicle for delivering one or more therapeutic compounds (e.g., HER binding proteins) to a subject, which is nontoxic to the cell or mammal being exposed thereto at the dosages and concentrations employed. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with amino acids include, by way of example and not limitation: water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Pharmaceutically acceptable carriers also include aqueous pH buffered solutions or liposomes (small vesicles composed of various types of lipids, phospholipids and/or surfactants which are useful for delivery of a drug to a mammal). Further examples of pharmaceutically acceptable carriers include buffers such as phosphate, citrate, and other organic acids, antioxidants such as ascorbic acid, low molecular weight (less than about 10 residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Liposomes are vesicles that have a membrane formed from a lipophilic material and an aqueous interior that can contain the composition to be delivered. Liposomes can be particularly useful due to their specificity and the duration of action they offer from the standpoint of drug delivery. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including LIPOFECTIN® (Invitrogen/Life Technologies, Carlsbad, Calif.) and EFFECTENE™ (Qiagen, Valencia, Calif.).

In some embodiments, at least one of the agents contained in a pharmaceutical composition (e.g., a HER-3 binding agent or an agent that binds and/or inhibits another HER family member) can be coupled to an effector such as calicheamicin, duocarmycins, auristatins, maytansinoids, a radioisotope, or a toxic chemotherapeutic agent such as geldanamycin and maytansine. Such conjugates can be particularly useful for targeting cells (e.g., cancer cells) expressing HER-3.

Linking binding proteins to radioisotopes can provide advantages to tumor treatments. Unlike chemotherapy and other forms of cancer treatment, radioimmunotherapy or the administration of a radioisotope-binding protein combination can directly target cancer cells with minimal damage to surrounding normal, healthy tissue. With this "magic bullet," patients can be treated with much smaller quantities of radioisotopes than other forms of treatment available today. Suitable radioisotopes include, for example, yttrium$^{90}$ ($^{90}$Y), indium$^{111}$ ($^{111}$In), $^{131}$I, $^{99}$mTc, radiosilver-111, radiosilver-199, and Bismuth$^{213}$. The linkage of radioisotopes to binding proteins may be performed with, for example, conventional bifunctional chelates. Since silver is monovalent, for radiosilver-111 and radiosilver-199 linkage, sulphur-based linkers may be used (Hazra et al. (1994) *Cell Biophys.* 24-25:1-7). Linkage of silver radioisotopes may involve reducing the immunoglobulin with ascorbic acid. Furthermore, tiuxetan is an MX-DTPA linker chelator attached to ibritumomab to form ibritumomab tiuxetan (Zevalin) (Witzig (2001) *Cancer Chemother. Pharmacol.* 48 (Suppl 1):91-95). Ibritumomab tiuxetan can react with radioisotypes such as indium$^{111}$ ($^{111}$In) or $^{90}$Y to form $^{111}$In-ibritumomab tiuxetan and $^{90}$Y-ibritumomab tiuxetan, respectively.

The binding proteins described herein, particularly when used to treat cancer, can be conjugated with toxic chemotherapeutic drugs such as maytansinoids, (Hamann et al. (2002) *Bioconjug. Chem.* 13:40-46), geldanamycinoids (Mandler et al. (2000) *J. Natl. Cancer Inst.* 92:1549-1551) and maytansinoids, for example, the maytansinoid drug, DM1 (Liu et al. (1996) *Proc. Natl. Acad. Sci. US* 93:8618-8623). Linkers that release the drugs under acidic or reducing conditions or upon exposure to specific proteases may be employed with this technology. A binding protein may be conjugated as described in the art.

In some embodiments, a binding protein can be conjugated to auristatin-PE. Auristatin-PE, e.g., is an antimicrotubule agent that is a structural modification of the marine, shell-less mollusk peptide constituent dolastatin 10. Auristatin-PE has both anti-tumor activity and anti-tumor vascular activity (Otani et al. (2000) *Jpn. J. Cancer Res.* 91:837-44). For example, auristatin-PE inhibits cell growth and induces cell cycle arrest and apoptosis in pancreatic cancer cell lines (Li et al. (1999) *Int. J. Mol. Med.* 3:647-53). Accordingly, to specifically target the anti-tumor activity and anti-tumor vascular activities of auristatin-PE to particular tumors, auristatin-PE may be conjugated to a binding protein as provided herein.

The pharmaceutical compositions provided herein also can contain at least one further active agent. Examples of further active agents include antibodies or low molecular weight inhibitors of other receptor protein kinases, such as IGFR-1 and c-met, receptor ligands such as vascular endothelial factor (VEGF), cytotoxic agents such as doxorubicin, cisplatin or carboplatin, cytokines, or anti-neoplastic agents. Many anti-neoplastic agents are known in the art. In some embodiments, an anti-neoplastic agent can be selected from the group of therapeutic proteins including, but not limited to, antibodies and immunomodulatory proteins. In some embodiments, an anti-neoplastic agent can be selected from the group of small molecule inhibitors and chemotherapeutic agents consisting of mitotic inhibitors, kinase inhibitors, alkylating agents, anti-metabolites, intercalating antibiotics, growth factor inhibitors, cell cycle inhibitors, enzymes, topoisomerase inhibitors, histone deacetylase inhibitors, anti-survival agents, biological response modifiers, anti-hormones (e.g., anti-androgens), microtubule stimulants, anthracyclins, and anti-angiogenesis agents. When the anti-neoplastic agent is radiation, treatment can be achieved either with an internal source (e.g., brachytherapy) or an external source (e.g., external beam radiation therapy). The one or more further active agent(s) can be administered with the HER3-binding agent and the second agent either simultaneously or separately, in a single formulation or in individual (separate) formulations for each active agent.

The pharmaceutical compositions provided herein can be especially useful for diagnosis, prevention, or treatment of a hyperproliferative disease. The hyperproliferative disease can be associated with increased HER family signal transduction. In particular, the disease can be associated with increased HER-3 phosphorylation, increased complex formation between HER-3 and other members of the HER family, increased PI$_3$ kinase activity, increased c-jun terminal kinase activity and/or AKT activity, increased ERK2 and/or PYK2 activity, or any combination thereof. The hyperproliferative disease can be, for example, selected from the group consisting of breast cancer, gastrointestinal cancer, pancreatic cancer, prostate cancer, ovarian cancer, stomach cancer, endometrial cancer, salivary gland cancer, lung cancer, kidney cancer, colon cancer, colorectal cancer, thyroid cancer, bladder cancer, glioma, melanoma, or other HER-3 expressing or overexpressing cancers, and the formation of tumor metastases.

Pharmaceutical compositions can be formulated by mixing one or more active agents with one or more physiologically acceptable carriers, diluents, and/or adjuvants, and optionally other agents that are usually incorporated into formulations to provide improved transfer, delivery, tolerance, and the like. A pharmaceutical composition can be formulated, e.g., in lyophilized formulations, aqueous solutions, dispersions, or solid preparations, such as tablets, dragees or capsules. A multitude of appropriate formulations can be found in the formulary known to all pharmaceutical chemists: *Remington's Pharmaceutical Sciences* (18$^{th}$ ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies as described herein, provided that the active agent in the formulation is not inactivated by the formulation and the formulation is physiologically compatible and tolerable with the route of administration. See, also, Baldrick (2000) *Regul. Toxicol. Pharmacol.* 32:210-218; Wang (2000) *Int. J. Pharm.* 203: 1-60; Charman (2000) *J. Pharm. Sci.* 89:967-978; and Powell et al. (1998) *PDA J. Pharm. Sci. Technol.* 52:238-

311), and the citations therein for additional information related to formulations, excipients and carriers well known to pharmaceutical chemists.

This document also pertains to the use of at least one agent (e.g., an isolated HER-3 binding protein) as described herein, and at least one other active agent (e.g., an agent that binds to another HER family member or a chemotherapeutic compound) in admixture with pharmaceutically acceptable carriers, diluents and/or adjuvants, for the manufacture of a pharmaceutical composition for diagnosis, prevention or treatment of a hyperproliferative disease (e.g., a disease associated with HER-3). The pharmaceutical composition can be a pharmaceutical composition as described herein, and the hyperproliferative disease can be a hyperproliferative disease as described herein.

Methods for formulating and subsequently administering therapeutic compositions are well known to those skilled in the art. Dosing generally is dependent on the severity and responsiveness of the disease state to be treated, with the course of treatment lasting from several days to several months, or until a cure is effected or a diminution of the disease state is achieved. Persons of ordinary skill in the art routinely determine optimum dosages, dosing methodologies and repetition rates. Optimum dosages can vary depending on the relative potency of individual polypeptides, and can generally be estimated based on $EC_{50}$ found to be effective in in vitro and in vivo animal models. Typically, dosage is from 0.1 μg to 100 mg per kg of body weight, and may be given once or more daily, biweekly, weekly, monthly, or even less often. Following successful treatment, it may be desirable to have the patient undergo maintenance therapy to prevent the recurrence of the disease state.

Pharmaceutical compositions can be administered by a number of methods, depending upon whether local or systemic treatment is desired and upon the area to be treated. Administration can be, for example, topical (e.g., transdermal, sublingual, ophthalmic, or intranasal); pulmonary (e.g., by inhalation or insufflation of powders or aerosols); oral; or parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). For treating tissues in the central nervous system, HER-3 binding proteins can be administered by injection or infusion into the cerebrospinal fluid, typically with one or more agents capable of promoting penetration of the polypeptides across the blood-brain barrier.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

HER binding agents can further encompass any pharmaceutically acceptable salts, esters, or salts of such esters, or any other compound which, upon administration to an animal including a human, is capable of providing (directly or indirectly) the biologically active metabolite or residue thereof. Accordingly, for example, this document provides pharmaceutically acceptable salts of small molecules and polypeptides, prodrugs and pharmaceutically acceptable salts of such prodrugs, and other bioequivalents. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the polypeptides provided herein (i.e., salts that retain the desired biological activity of the parent polypeptide without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); and salts formed with organic acids (e.g., acetic acid, citric acid, oxalic acid, palmitic acid, or fumaric acid).

Some embodiments provided herein include pharmaceutical compositions containing (a) one or more HER-3 binding agents; (b) one or more agents that bind to another HER family member; and (c) one or more other agents that function by a different mechanism. For example, one or more agents of (c) are exchangeable with those of (b); anti-inflammatory drugs, including but not limited to non-steroidal anti-inflammatory drugs and corticosteroids, and antiviral drugs, including but not limited to ribivirin, vidarabine, acyclovir and ganciclovir, can be included in compositions. Other non-polypeptide agents (e.g., chemotherapeutic agents) also are within the scope of this document. Such combined compounds can be used together or sequentially.

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

The pharmaceutical formulations, which can be presented conveniently in unit dosage form, can be prepared according to conventional techniques well known in the pharmaceutical industry. Such techniques include the step of bringing into association the active ingredients (e.g., the HER family binding agents provided herein) with the desired pharmaceutical carrier(s) or excipient(s). Typically, the formulations can be prepared by uniformly and bringing the active ingredients into intimate association with liquid carriers or finely divided solid carriers or both, and then, if necessary, shaping the product. Formulations can be sterilized if desired, provided that the method of sterilization does not interfere with the effectiveness of the polypeptide contained in the formulation.

The compositions described herein can be formulated into any of many possible dosage forms such as, but not limited to, tablets, capsules, liquid syrups, soft gels, suppositories, and enemas. The compositions also can be formulated as suspensions in aqueous, non-aqueous or mixed media. Aqueous suspensions further can contain substances that increase the viscosity of the suspension including, for example, sodium carboxymethylcellulose, sorbitol, and/or dextran. Suspensions also can contain stabilizers.

HER binding proteins can be combined with packaging material and sold as kits for treating HER-3 associated diseases. Components and methods for producing articles of manufacture are well known. The articles of manufacture may combine one or more of the polypeptides and compounds set out in the above sections. In addition, the article of manufacture further may include, for example, buffers or other control reagents for reducing or monitoring reduced immune complex formation. Instructions describing how the polypeptides are effective for treating HER-3 associated diseases can be included in such kits. Any of the first agents, the second agents and additional agents could be delivered in nanoparticle(s) or liposome(s), or any other suitable form(s)

6. Methods

This document also provides methods for treating or preventing diseases and conditions associated with expression of HER-3. For example, a method can include contacting a subject or a biological sample from a subject (e.g., a mammal such as a human) with a HER-3 binding protein in combination with a second agent as described herein. The sample may be a cell that shows expression of HER-3, such as a tumor cell, a blood sample or another suitable sample. In some embodiments, the contacting occurs in vivo, such as when a composition containing a HER-3 binding agent and a second agent that binds to another member of the HER family is administered to a subject in need thereof. The diseases or conditions associated with expression of HER-3 that can be treated using the methods described herein include, for example, hyperproliferative diseases such as breast cancer, gastrointestinal cancer, pancreatic cancer, prostate cancer, ovarian cancer, stomach cancer, endometrial cancer, salivary gland cancer, lung cancer, kidney cancer, colon cancer, colorectal cancer, thyroid cancer, bladder cancer, glioma, melanoma, renal cancer, metastatic breast cancer, non-small cell lung cancer, epidermoid carcinoma, fibrosarcoma, melanoma, nasopharyngeal carcinoma, squamous cell carcinoma, and other HER-3-positive, -expressing or -overexpressing cancers.

The term "treatment or prevention," when used herein, refers to both therapeutic treatment and prophylactic or preventative measures, which can be used to prevent, slow, or lessen the effects of the targeted pathologic condition or disorder. Those in need of prevention or treatment can include those already having the disorder, as well as those who may be likely to develop the disorder, or those in whom the disorder is to be prevented. The patient in need of prevention or treatment can be a mammalian patient (i.e., any animal classified as a mammal, including humans, domestic and farm animals, and zoo, sports, or pet animals, such as dogs, cats, cattle, horses, sheep, pigs, goats, rabbits, etc.) In some embodiments, the patient in need of treatment is a human patient.

Methods for preventing or treating diseases or conditions associated with expression of HER-3 in a patient in need thereof can include administering to the patient effective amounts of at least one HER-3 binding agent as described herein and at least one other agent against another HER family member, or a chemotherapeutic compound (e.g., at least one of the "additional/further" agents described above, which are exchangeable with the second agents binding to and/or inhibiting another HER family). Such treatment can, for example, inhibit abnormal cell growth, migration or invasion. The agent against HER-3 and the at least one other agent can be administered simultaneously (e.g., when they are contained in the same composition, or by admixture into a common i.v. bag), or separately (e.g., sequentially). The diseases or conditions associated with the expression of HER-3 that can be treated using the methods provided herein include, for example, the hyperproliferative diseases listed herein. The patient in need of prevention or treatment can be a mammal (e.g., a human, a domestic or farm animal, or a zoo, sport, or pet animal such as a dog, cat, cow, horse, sheep, pig, goat, or rabbit). In some cases, the patient is a human patient.

As used herein, the term "effective amount" is an amount of an agent that results in a decrease or stabilization in one or more symptoms or clinical characteristics of the HER-3 associated condition being treated. For example, administration of an effective amount of a composition as described herein can result in slowing of tumor growth progression, in decreased tumor size, or in decreased activation of HER-3 or HER-3-responsive biomarkers (e.g., Akt, HER-2, ERK, or EGF-R). The slowing or decrease can be any reduction as compared to a previous value (e.g., a 5%, 10%, 20%, 25%, or more than 25% reduction in symptom or characteristic). In some embodiments, an "effective amount" can result in stable disease.

In addition to classical modes of administration of potential binding protein therapeutics, e.g., via the above mentioned formulations, newly developed modalities of administration may also be useful. For example, local administration of $^{131}$I-labeled monoclonal antibody for treatment of primary brain tumors after surgical resection has been reported. Additionally, direct stereotactic intracerebral injection of monoclonal antibodies and their fragments is also being studied clinically and pre-clinically. Intracarotid hyperosmolar perfusion is an experimental strategy to target primary brain malignancy with drug conjugated human monoclonal antibodies.

As described above, the dose of the agents administered can depend on a variety of factors. These include, for example, the nature of the agents, the tumor type, and the route of administration. It should be emphasized that the present methods are not limited to any particular doses. Methods for determining suitable doses are known in the art, and include those described in the Examples herein.

Depending on the type and severity of the condition to be treated, up to about 20 mg/kg of each HER binding antibody can be administered to a patient in need thereof, e.g., by one or more separate administrations or by continuous infusion. A typical daily dosage might range from about 1 µg/day to about 100 mg/day or more, depending on the factors mentioned above. For repeated administrations over several days or longer, depending on the condition to be treated, the treatment can be sustained until a desired suppression of disease symptoms occurs.

In some embodiments, a method as provided herein can include analyzing a particular marker (e.g., HER-3) in a biological sample from a subject to determine whether the subject has a disease associated with HER-3 expression. Such methods can be used to select subjects having diseases associated with HER-3. In such methods, the analyzing step can be done prior to the step of administration, as such screening of patients may avoid treatments that are not likely to be effective. Thus, in some cases, the methods provided herein can further include detecting HER-3 antigen in or on a cell, for determination of HER-3 antigen concentration in patients suffering from a hyperproliferative disease as mentioned above, or for staging of a hyperproliferative disease in a patient. In order to stage the progression of a hyperproliferative disease in a subject under study, or to characterize the response of the subject to a course of therapy, a sample of blood can be taken from the subject and the concentration of the HER-3 antigen present in the sample can be determined. The concentration so obtained can be used to identify in which range of concentrations the value falls. The range so identified can be correlated with a stage of progression or a stage of therapy identified in the various populations of diagnosed subjects, thereby providing a stage for the subject under study. A biopsy of the disease, e.g., cancerous, tissue obtained from the patient also can be used assess the amount of HER-3 antigen present. The amount of HER-3 antigen present in the disease tissue may be assessed using, for example, immunohistochemistry, ELISA, or antibody array using HER-3 antibodies as described herein. Other parameters of diagnostic interest are the dimerization state as well as the dimerization partners of the HER-3 protein and the activation state of it and its partners. Protein analytical methods to determine those parameters are well known in the art and are among others western blot and immunoprecipitation techniques, FACS analysis, chemical crosslinking, bioluminescence resonance energy transfer (BRET), fluorescence resonance energy transfer (FRET) and the like (e.g., Price et al. (2002) *Methods Mol. Biol.* 218: 255-268, or eTag technology (WO 05/03707, WO 04/091384, and WO 04/011900).

In some cases, a method as provided herein can include one or more steps for monitoring the therapeutic outcome of the treatment. For example, a subject can be monitored for symptoms of their disease, to determine whether a reduction in symptoms has occurred. The subject also can be monitored, for example, for potential side effects of the treatment. The monitoring can be done after the administration step, and, in some embodiments, can be done multiple times (e.g., between administrations, if dosages are given more than once). Such methods can be used to assess efficacy and safety of the treatment methods described herein, for example.

The invention will be further described in the following examples, which do not limit the scope of the invention described in the claims.

EXAMPLES

Example 1: HER-3 Antigen and Cell Line Preparation

Recombinant HER-3 proteins were prepared. The extracellular domain of HER-3 (ECD) cDNA was cloned by polymerase chain reaction (PCR) from pcDNA3-HER-3 (expression vector with full length human HER-3, Wallasch et al. (1995) *EMBO J.* 14:4267-4275) with primers based on the sequence of HER-3 (GeneBank Accession No. NM_001982): Forward primer: 5'-CG GGATCCATGTCCTAGCCTAGGGGC-3' (SEQ ID NO: 233); Reverse primer: 5'-GCTCTAGATTA ATGATGATGATGATGATGTTGTCCTAAACAGTCTTG-3' (SEQ ID NO: 234).

The PCR product was digested with BamH1 and XbaI and ligated into pcDNA3 (Invitrogen) digested with BamH1 and XbaI. Plasmids were transfected into HEK293 cells using a $CaPO_4$ method. The HER-3-HIS fusion protein was purified from harvested conditioned media via Ni-NTA affinity chromatography.

RatI HER-3 cells were generated by retroviral gene transfer. Briefly, GP+E 86 cells ($3 \times 10^5$) were seeded on a 60 mm culture disc and transfected with 2 µg/ml pIXSN vector or pIXSN-HER-3 cDNA (C. Wallasch, PhD Thesis, Max-Planck Institute of Biochemistry, Martinsried, Germany) using the calcium phosphate method. After 24 hours, the medium was replaced with fresh medium and the GP+E 86 cells were incubated for 4-8 hours. Subconfluent RatI cells ($2 \times 10^5$ cells per 6 cm dish) were then incubated with supernatants of GP+E 86 cells releasing high titer pLXSN or pLXSN-HER-3, p virus ($>1 \times 10^6$ G418 c.f.u./ml; m.o.i. of 10) for 4-12 hours in the presence of Polybrene (4 mg/ml; Aldrich). After changing the medium, selection of RatI cells with G418 was started. Usually, stable clones were picked after selection for 21 days.

Example 2: HER-3 Expression in Human Cancer Cell Lines

HER-3 expression was quantified in a panel of human cancer cell lines to elucidate the role of HER-3 in human cancer formation. Cancer cell lines were grown as recommended by the ATCC. In detail, $10^5$ cells were harvested with 10 mM EDTA in PBS, washed once with FACS buffer (PBS, 3% FCS, 0.4% azide) and seeded on a 96-well round bottom plate. The cells were spun for 3 minutes at 1000 rpm to remove supernatant and then resuspended with HER-3 antibody 2D1D12 (WO03013602) (3 µg/ml). Cell suspensions were incubated on ice for 1 hour, washed twice with FACS buffer, and resuspended with secondary antibody (100 µl/well) donkey-anti-human-PE (Jackson) diluted 1:50 in FACS buffer. The cell suspensions were incubated on ice and in the dark for 30 minutes, washed twice with FACS buffer and analyzed (FACS, Beckman Coulter). HER-3 was expressed in a variety of human cancer cell lines, including various breast, colon, epidermoid, melanoma, nasopharynx, ovarian, pancreas, and prostate cell lines. See, the figures of US Publication No. 20080124345, which are hereby incorporated herein by reference in their entirety.

Example 3: Immunization and Titering

The HER-3 ECD protein that was prepared as described in Example 1 and C32 cells (Human melanoma; ATCC #CRL-1585) were used as antigen. Monoclonal antibodies against HER-3 were developed by sequentially immunizing XENOMOUSE® mice (strains XMG1 and XMG4; Abgenix, Inc., Fremont, Calif.). XENOMOUSE® animals were immunized via the footpad for all injections. The total volume of each injection was 50 µl per mouse, 25 µl per footpad.

For cohort #1 (10 XMG1 mice), the initial immunization was with 10 µg of HER-3 ECD protein admixed 1:1 (v/v) with TITERMAX GOLD® (Sigma, Oakville, ON) per mouse. The subsequent five boosts were made with 10 µg of HER-3 ECD protein admixed 1:1 (v/v) with 100 µg alum gel (Sigma, Oakville, ON) in pyrogen-free D-PBS. The sixth boost consisted of 10 µg of HER-3 ECD protein admixed 1:1 (v/v) with TITERMAX GOLD®. The seventh injection consisted of 10 µg of HER-3 ECD protein admixed 1:1 v/v with 100 µg alum gel. A final boost was made with 10 µg HER-3 ECD protein in pyrogen-free DPBS, without adjuvant. The XENOMOUSE® mice were immunized on days 0, 4, 7, 11, 15, 20, 24, and 29 for this protocol, and fusions were performed on day 33. The two bleeds were made through Retro-Orbital Bleed procedure on day 13 after the fourth boost and on day 19 after the sixth boost. There was no cohort #2. For Cohort #3 (10 XMG1 mice) and Cohort #4 (10 XMG4 mice), the first injection was with $10^7$ C32 cells in pyrogen-free Dulbecco's PBS (DPBS) admixed 1:1 (v/v) with TITERMAX GOLD® per mouse. The next four boosts were with $10^7$ C32 cells in pyrogen-free DPBS, admixed with 25 µg of Adju-Phos and 10 µg CpG per mouse. The sixth boost was with $10^7$ C32 cells in pyrogen-free DPBS, admixed 1:1 (v/v) with TITERMAX GOLD® per mouse. The seventh, eighth, and ninth boosts were with $10^7$ C32 cells in pyrogen-free DPBS, admixed with 25 µg of Adju-Phos and 10 µg CpG per mouse. The tenth to fourteenth boosts were with 5 µg of HER-3 ECD protein in pyrogen-free DPBS, admixed with 25 µg of Adju-Phos and 10 µg CpG per mouse. A final boost consisted of 5 µg of HER-3 ECD protein in pyrogen-free DPBS, without adjuvant. For both Cohorts #3 and #4, the mice were immunized on days 0, 3, 7, 11, 14, 17, 21, 24, 28, 33, 35, 38, 42 and 45, and fusions were performed on day 49. The three bleeds were made through Retro-Orbital Bleed procedure on day 12 after the fourth boost, on day 19 after the sixth boost, and on day 40 after twelfth boost.

Selection of animals for harvest by titer: For cohort #1, anti-HER-3 antibody titers in the serum from immunized mice were determined by ELISA against HER-3 ECD protein. The specific titer of each XENOMOUSE® animal was determined from the optical density at 650 nm, and is shown in TABLE 1 below. The titer value is the reciprocal of the greatest dilution of sera with an OD reading two-fold that of background. Therefore, the higher the number, the greater the humoral immune response to HER-3 ECD.

TABLE 1

Cohort #1, XMG1

| Mouse ID | After 4 injections | After 6 injections |
|---|---|---|
| P3421 | 8,000 | 11,000 |
| P3422 | 850 | 2,600 |
| P3423 | 2,700 | 5,200 |
| P3424 | 3,200 | 9,100 |
| P3425 | 5,400 | 2,500 |
| P3426 | 700 | 1,500 |
| P3427 | 5,800 | 7,000 |
| P3428 | 3,900 | 4,300 |
| P3429 | 2,200 | 2,500 |
| P34210 | 600 | 850 |
| NC | 250 | 175 |
| PC | 377,000 | 311,000 |
| NC | mAb IL-8, D39.2.1 | |
| PC | xHER-3-2D1D12 | |

For cohorts #3 and #4, anti-HER-3 antibody titers in the serum from immunized mice were determined by FACS using Rat1/HER-3 (antigen positive cell line) cells and Rat1/pLSXN (antigen negative cell line) cells. Data are shown in TABLES 2 and 3, and are presented as geometric mean (GeoMean) fluorescent intensity of cell anti-HER-3 cell staining by serial dilutions of serum samples.

TABLE 2

Cohort #3, XMG1

| | | After 6 injections | | After 12 injections | |
|---|---|---|---|---|---|
| Mouse ID | Sample | pos cells GeoMean | neg cells GeoMean | pos cells GeoMean | neg cells GeoMean |
| Q832-1 | 1:50 | 9 | 10 | 11 | 10 |
| | 1:250 | 6 | 9 | 6 | 6 |
| | 1:1250 | 6 | 7 | 4 | 4 |
| Q832-2 | 1:50 | 8 | 10 | 29 | 42 |
| | 1:250 | 7 | 8 | 11 | 11 |
| | 1:1250 | 5 | 6 | 6 | 5 |
| Q832-3 | 1:50 | 7 | 12 | 11 | 9 |
| | 1:250 | 5 | 7 | 5 | 5 |
| | 1:1250 | 5 | 5 | 4 | 4 |
| Q832-4 | 1:50 | 6 | 10 | 9 | 9 |
| | 1:250 | 6 | 6 | 5 | 5 |
| | 1:1250 | 5 | 5 | 4 | 4 |
| Q832-5 | 1:50 | 11 | 11 | 17 | 13 |
| | 1:250 | 10 | 9 | 7 | 6 |
| | 1:1250 | 6 | 8 | 5 | 4 |
| Q832-6 | 1:50 | 7 | 11 | 15 | 14 |
| | 1:250 | 7 | 7 | 7 | 6 |
| | 1:1250 | 5 | 6 | 6 | 4 |
| Q832-7 | 1:50 | 8 | 11 | 7 | 15 |
| | 1:250 | 6 | 7 | 5 | 5 |
| | 1:1250 | 5 | 5 | 4 | 4 |
| Q832-8 | 1:50 | 7 | 8 | 11 | 20 |
| | 1:250 | 6 | 6 | 7 | 8 |
| | 1:1250 | 5 | 5 | 5 | 4 |
| Q832-9 | 1:50 | 7 | 12 | 15 | 16 |
| | 1:250 | 6 | 8 | 6 | 5 |
| | 1:1250 | 6 | 6 | 4 | 4 |
| Q832-10 | 1:50 | 8 | 13 | 34 | 38 |
| | 1:250 | 6 | 8 | 9 | 8 |
| | 1:1250 | 6 | 6 | 5 | 4 |

TABLE 3

Cohort #4, XMG4

| | | After 6 injections | | After 12 injections | |
|---|---|---|---|---|---|
| Mouse | Sample | pos cells GeoMean | neg cells GeoMean | pos cells GeoMean | neg cells GeoMean |
| Q856-1 | 1:50 | 4 | 6 | 91 | 44 |
| | 1:250 | 4 | 5 | 32 | 18 |
| | 1:1250 | 4 | 4 | 19 | 10 |
| Q856-2 | 1:50 | 4 | 8 | 148 | 54 |
| | 1:250 | 4 | 5 | 89 | 23 |
| | 1:1250 | 4 | 4 | 42 | 9 |
| Q856-3 | 1:50 | 4 | 5 | 72 | 14 |
| | 1:250 | 4 | 4 | 28 | 6 |
| | 1:1250 | 4 | 4 | 18 | 4 |
| Q856-4 | 1:50 | 4 | 5 | 11 | 49 |
| | 1:250 | 4 | 5 | 10 | 17 |
| | 1:1250 | 4 | 4 | 8 | 7 |
| Q856-5 | 1:50 | 4 | 4 | 74 | 20 |
| | 1:250 | 4 | 4 | 30 | 14 |
| | 1:1250 | 4 | 4 | 16 | 6 |
| Q856-6 | 1:50 | 4 | 5 | 86 | 21 |
| | 1:250 | 4 | 4 | 32 | 10 |
| | 1:1250 | 4 | 4 | 16 | 5 |
| Q856-7 | 1:50 | 5 | 6 | 74 | 32 |
| | 1:250 | 4 | 5 | 32 | 14 |
| | 1:1250 | 4 | 4 | 16 | 6 |
| Q856-8 | 1:50 | 4 | 5 | 106 | 14 |
| | 1:250 | 4 | 4 | 45 | 6 |
| | 1:1250 | 4 | 4 | 22 | 4 |
| Q856-9 | 1:50 | 5 | 6 | 53 | 22 |
| | 1:250 | 4 | 4 | 17 | 11 |
| | 1:1250 | 4 | 4 | 11 | 5 |

TABLE 3-continued

| | | Cohort #4, XMG4 | | | |
| | | After 6 injections | | After 12 injections | |
| Mouse | Sample | pos cells GeoMean | neg cells GeoMean | pos cells GeoMean | neg cells GeoMean |
|---|---|---|---|---|---|
| Q856-10 | 1:50 | 4 | 5 | 72 | 53 |
| | 1:250 | 4 | 4 | 26 | 17 |
| | 1:1250 | 4 | 4 | 15 | 7 |

Example 4: Recovery of Lymphocytes, B-Cell Isolations, Fusions and Generation of Hybridomas Immunized mice were sacrificed and the lymph nodes were harvested and pooled from each cohort. The lymphoid cells were dissociated by grinding in DMEM to release the cells from the tissues, and the cells were suspended in DMEM. The cells were counted, and 0.9 ml DMEM per 100 million lymphocytes was added to the cell pellet to resuspend the cells gently but completely. Using 100 μl of CD90+ magnetic beads per 100 million cells, the cells were labeled by incubating the cells with the magnetic beads at 4° C. for 15 minutes. The magnetically-labeled cell suspension containing up to $10^8$ positive cells (or up to $2\times10^9$ total cells) was loaded onto a LS+ column and the column washed with DMEM. The total effluent was collected as the CD90-negative fraction (most of these cells were expected to be B cells).

The fusion was performed by mixing washed enriched B cells from above and nonsecretory myeloma P3X63Ag8.653 cells purchased from ATCC (Cat. No. CRL 1580) (Kearney et al. (1979) *J. Immunol.* 123:1548-1550) at a ratio of 1:1. The cell mixture was gently pelleted by centrifugation at 800 g. After complete removal of the supernatant, the cells were treated with 2 to 4 ml of pronase solution (CalBiochem, Cat. No. 53702; 0.5 mg/ml in PBS) for no more than 2 minutes. Then 3 to 5 ml of FBS was added to stop the enzyme activity, and the suspension was adjusted to 40 ml total volume using electro cell fusion solution, ECFS (0.3 M sucrose, Sigma, Cat. No. 57903, 0.1 mM magnesium acetate, Sigma, Cat. No. M2545, 0.1 mM calcium acetate, Sigma, Cat. No. C4705). The supernatant was removed after centrifugation and the cells were resuspended in 40 ml ECFS. This wash step was repeated and the cells again were resuspended in ECFS to a concentration of $2\times10^6$ cells/ml.

Electro-cell fusion was performed using a fusion generator, model ECM2001, Genetronic, Inc., San Diego, Calif. The fusion chamber size was 2.0 ml, and the following instrument settings were used: Alignment conditions: voltage: 50 V, time: 50 seconds; membrane breaking: voltage: 3000 V, time: 30 μseconds; post-fusion holding time: 3 seconds.

After ECF, the cell suspensions were removed from the fusion chamber under sterile conditions and transferred into a sterile tube containing the same volume of Hybridoma Culture Medium (DMEM (JRH Biosciences), 15% FBS (Hyclone), supplemented with L-glutamine, pen/strep, OPI (oxaloacetate, pyruvate, bovine insulin) (all from Sigma) and IL-6 (Boehringer Mannheim). The cells were incubated for 15 to 30 minutes at 37° C., and then centrifuged at 400 g for five minutes. The cells were gently resuspended in a small volume of Hybridoma Selection Medium (Hybridoma Culture Medium supplemented with 0.5× HA (Sigma, Cat. No. A9666)), and the volume was adjusted appropriately with more Hybridoma Selection Medium, based on a final plating of $5\times10^6$ B cells total per 96-well plate and 200 μl per well. The cells were mixed gently and pipetted into 96-well plates and allowed to grow. On day 7 or 10, half of the medium was removed, and the cells were re-fed with Hybridoma Selection Medium.

Example 5: Selection of Candidate Antibodies by ELISA

After 14 days of culture, primary screening of hybridoma supernatants from the cohort #1 (mice in cohort one were split arbitrarily into fusion #1 and #2) for HER-3-specific antibodies was performed by ELISA using purified his-tagged HER-3 ECD and counter-screening against an irrelevant his-tagged protein by ELISA using goat anti-huIgGFc-HRP (Caltag Inc., Cat. No. H10507, using concentration was 1:2000 dilution) to detect human IgG binding to HER-3 ECD immobilized on ELISA plates. The old culture supernatants from positive hybridoma cells growth wells based on primary screen were removed, and the HER-3 positive hybridoma cells were suspended with fresh hybridoma culture medium and were transferred to 24-well plates. After 2 days in culture, these supernatants were used for a secondary confirmation screen. In the secondary confirmation screen for HER-3 specific fully human IgGk antibodies, the positives in the first screening were screened by ELISA with two sets of detective antibodies: goat anti-huIgGFc-HRP (Caltag Inc., Cat. No. H10507, using a 1:2000 dilution) for human gamma chain detection, and goat anti-hIg kappa-HRP (Southern Biotechnology, Cat. No. 2060-05) for human kappa light chain detection. From cohort #1, 91 fully human IgG/kappa HER-3 specific monoclonal antibodies were generated.

Example 6: Selection of Candidate Antibodies by FMAT/FACS

After 14 days of culture, hybridoma supernatants from the cohorts #3 and #4 (fusions #3 and #4) were screened for HER-3-specific monoclonal antibodies by FMAT. In the primary screen, hybridoma supernatants at 1:10 final dilution were incubated with Rat1-HER-3 cells expressing human HER-3 and 400 ng/ml Cy5-conjugated Goat F(ab')2 anti-human IgG, Fc-specific antibody (Jackson ImmunoResearch, Cat. No. 109-176-098) at room temperature for 6 hours. The binding of antibodies and detection antibodies to cells were measured by FMAT (Applied Biosystems). Non-specific binding of antibodies to the cells was determined by their binding to parental Rat1 cells. A total of 420 hybridomas producing HER-3-specific antibodies were selected from the primary screen of fusion #3. The supernatants from these expanded cultures were tested again using the same FMAT protocol, and 262 of them were confirmed to bind specifically to HER-3 expressing cells. A total of 193 hybridomas producing HER-3 specific antibodies were selected from the primary screen of fusion #4. The supernatants from these expanded cultures were tested by FACS, and 138 of them were confirmed to bind specifically to cells expressing HER-3. In the FACS confirmation assay, Rat1-XHER-3 cells and parental Rat1 cells (as negative control) were incubated with hybridoma supernatants at 1:2 dilution for 1 hour at 40° C. in PBS containing 2% FBS. Following washing with PBS, the binding of antibodies to the cells was detected by 2.5 μg/ml Cy5-conjugated Goat F(ab')2 anti-human IgG, Fc-specific antibody (JIR #109-176-098) and 5 μg/ml PE-conjugated Goat F(ab')2 anti-human kappa-specific antibody (SB #2063-09). After removing unbound antibodies by washing with PBS, the cells were fixed by cytofix (BD #51-2090KZ) at 1:4 dilution and analyzed by FACSCalibur.

Example 7: Selection of Hybridomas for Cloning

Antibodies from cohort #1 were selected for hybridoma cloning based on specificity for HER-3 over HER1 (EGF-R), HER-2 and HER-4 in ELISA using purified recombinant extra-cellular domains (available from, for example, R&D Biosystems, Minneapolis, Minn.), FACS-based analysis of human tumor cell lines expressing different HER family members, and a >5-time increase in mean fluorescent intensity in FACS staining for HER-3 positive cells over background. Based on these criteria, a total of 23 hybridoma lines were selected for cloning by limiting dilution cell plating.

Antibodies from cohorts 3 and 4 were selected for hybridoma cloning based on specificity for HER-3 over HER-1 (EGF-R), HER-2 and HER-4 plus three other criteria. The first criterion was an ELISA screen for antibodies with epitopes contained within the L2 domain of HER-3 (see, Example 8 below).

The second criterion was neutralization of binding of biotinylated heregulin-alpha to HER-3 expressing cells in a FACS based assay. SKBR-3 cells were harvested, washed in culture medium, pelleted via centrifugation and resuspended in culture medium. Resuspended cells were aliquoted into 96-well plates. The plates were centrifuged to pellet the cells. Test antibodies in exhaust hybridoma supernatants were added at 25 µl/well and incubated for 1 hour on ice to allow antibody binding. Fifty µl of a 10 nM heregulin-alpha (R&D Biosystems) solution was added to each well for a final concentration of 5 nM and incubated on ice for 1.5 hours. Cells were washed in 150 µl PBS, pelleted by centrifugation and the supernatant removed. Cells were resuspended in 50 µl of goat anti-HRG-alpha polyclonal antibody at 10 µg/ml and incubated for 45 minutes on ice. Cells were washed in 200 µl PBS, pelleted by centrifugation, and the supernatant was removed. Fifty µl of a solution of rabbit Cy5-labeled anti-goat polyclonal antibody at 5 µg/ml plus 7AAD at 10 µg/ml was added and incubated on ice for 15 minutes. Cells were washed in 200 µl PBS, pelleted by centrifugation and the supernatant removed. The cells were resuspended in 100 µl of FACS buffer and read in the FACS. Test HER-3 antibodies that reduced binding of heregulin-alpha were those that had lowest fluorescence intensity. As positive controls, 1:5 serial dilutions from 10,000 ng/ml to 16 ng/ml of a mouse HER-3 mAb (105.5) or the human IgG1 HER-3 mAb, U1-49 was used. Negative controls were heregulin-alpha alone, cells alone, goat anti-heregulin-alpha polyclonal antibody alone and rabbit Cy5-labeled anti-goat polyclonal antibody alone.

The third criterion was relative ranking for affinity and/or higher relative mean fluorescence intensity in FACS using HER-3 expressing cell lines. Relative ranking for affinity was performed by normalizing HER-3-specific antibody concentrations and plotting versus data from limiting antigen ELISA as follows.

Normalization of antigen specific antibody concentrations using high antigen ELISA: Using an ELISA method, supernatants for concentration of antigen specific antibody were normalized. Using two anti-HER-3 human IgG1 antibodies from cohort 1 of known concentration titrated in parallel, a standard curve was generated and the amount of antigen specific antibody in the test hybridoma supernatants from cohorts 3 and 4 were compared to the standard. In this way, the concentration of human HER-3 IgG antibody in each hybridoma culture was estimated.

Neutravidin plates were made by coating neutravidin at 8 µg/ml in 1×PBS/0.05% sodium azide on Costar 3368 medium binding plates at 50 µl/well with overnight incubation at 4° C. The next day the plates were blocked with 1×PBS/1% skim milk. Photobiotinylated his-tagged-HER-3 ECD at 500 ng/ml in 1×PBS/1% skim milk was bound to the neutravidin plates by incubating for 1 hour at room temperature. Hybridoma supernatant, serially diluted 1:2.5 from a starting dilution of 1:31 to a final dilution of 1:7568 in 1×PBS/1% skim milk/0.05% azide, was added at 50 µl/well, and then incubated for 20 hours at room temperature. Serial dilutions were used to ensure obtaining OD readings for each unknown in the linear range of the assay. Next, a secondary detection antibody, goat anti human IgG Fc HRP at 400 ng/ml in 1×PBX/1% skim milk was added at 50 µl/well. After 1 hour at room temperature, the plates were again washed 5 times with water and 50 µl of one-component TMB substrate were added to each well. The reaction was stopped after 30 minutes by addition of 50 µl 1M hydrochloric acid to each well and the plates were read at wavelength 450 nm. A standard curve was generated from the two IgG1 HER-3 mAbs from cohort #1, serially diluted at 1:2 from 1000 ng/ml to 0.06 ng/ml and assessed in ELISA using the above protocol. For each unknown, OD readings in the linear range of the assay were used to estimate the concentration of human HER-3 IgG in each sample.

The limited antigen analysis is a method that affinity ranks the antigen-specific antibodies prepared in B-cell culture supernatants relative to all other antigen-specific antibodies. In the presence of a very low coating of antigen, only the highest affinity antibodies should be able to bind to any detectable level at equilibrium. (See, e.g., PCT Publication No. WO 03048730A2). In this instance, two mAbs from cohort #1, both of known concentration and known KD, were used as benchmarks in the assay.

Neutravidin plates were made by coating neutravidin at 8 µg/ml in 1×PBS/0.05% sodium azide on Costar 3368 medium binding plates at 50 µl/well with overnight incubation at 4° C. The next day the plates were blocked with 1×PBS/1% skim milk. Biotinylated his-tagged-HER-3 ECD (50 µl/well) was bound to 96-well neutravidin plates at five concentrations: 125, 62.5, 31.2, 15.6, and 7.8 ng/ml in 1×PBS/1% skim milk for 1 hour at room temperature. Each plate was washed 5 times with water. Hybridoma supernatants diluted 1:31 in 1×PBS/1% skim milk/0.05% azide were added at 50 ul/well. After 20 hours incubation at room temperature on a shaker, the plates were again washed 5 times with dH2O. Next, a secondary detection antibody, goat anti human IgG Fc HRP (Horse Radish Peroxidase) at 400 ng/ml in 1×PBS/1% skim milk was added at 50 µl/well. After 1 hour at room temperature, the plates were again washed 5 times with dH2O and 50 µL of one-component TMB substrate were added to each well. The reaction was stopped after 30 minutes by addition of 50 µl of 1M hydrochloric acid to each well and the plates were read at wavelength 450 nm. OD readings from an antigen concentration that yielded OD values in the linear range were used in for data analysis.

Plotting the high antigen data (which comparatively estimate specific antibody concentrations; see above for details) versus the limited antigen OD illustrated that the relatively higher affinity antibodies, e.g., those that bound had higher OD in the limited antigen assay while having lower amounts of IgG HER-3 antibody in the supernatant. Hybridomas from cohorts #3 and #4 for the 33 best performing antibodies in these sets of assays were advanced to cloning by limiting dilution hybridoma plating.

Alternatively, FACS analysis of HER-3 expression of RatI/pLXSN and RatI/HER-3 cells showed similar results (no crossreactivity with endogenous rat epitopes. In detail, $1 \times 10^5$ cells were harvested with 10 mM EDTA in PBS, washed once with FACS buffer (PBS, 3% FCS, 0.4% azide) and seeded on a 96-well round bottom plate. The cells were spun for 3 minutes at 1000 rpm to remove supernatant and then resuspended with the specific HER-family antibodies (3 µg/ml). Cell suspensions were incubated on ice for 45 minutes, washed twice with FACS buffer and resuspended with secondary antibody (100 µl/well) donkey-anti-human-PE (Jackson Immunoresearch, PA) diluted 1:50 in FACS buffer. The cell suspensions were incubated on ice and in the dark for 30 minutes, washed twice with FACS buffer and analyzed (FACS, Beckman Coulter).

Example 8: Structural Analysis of Anti-HER-3 Antibodies

The following discussion provides structural information related to antibodies prepared as described herein. In order to analyze structures of the antibodies, genes encoding the heavy and light chain fragments were amplified out of the particular hybridoma. Sequencing was accomplished as follows:

The $V_H$ and $V_L$ transcripts were amplified from individual hybridoma clones in 96 well plate using reverse transcriptase polymerase chain reaction (RT-PCR). Poly(A)+-mRNA was isolated from approximately $2 \times 10^5$ hybridoma cells using a Fast-Track kit (Invitrogen). Four PCR reactions were run for each Hybridoma: two for light chain (kappa (κ), and two for gamma heavy chain (γ). The QIAGEN OneStep room temperature-PCR kit was used for amplification (Qiagen, Catalog No. 210212). In the coupled room temperature-PCR reactions, cDNAs were synthesized with blend of room temperature enzymes (Omniscript and Sensiscript) using antisense sequence specific primer corresponded to C-κ, or to a consensus of the CH1 regions of Cγ genes. Reverse transcription was performed at 50° C. for 1 hr followed by PCR amplification of the cDNA by HotStarTaq DNA Polymerase for high specificity and sensitivity. Each PCR reaction used a mixture of 5'-sense primers; primer sequences were based on the leader sequences of $V_H$ and $V_K$ available at the Vbase website (http://vbase.mrc-cpe.cam.ac.uk/).

PCR reactions were run at 94° C. for 15 min, initial hot start followed by 40 cycles of 94° C. for 30 sec (denaturation), 60° C. for 30 sec (annealing) and 72° C. for 1 min (elongation).

PCR products were purified and directly sequenced using forward and reverse PCR primers using the ABI PRISM BigDye terminator cycle sequencing ready reaction Kit (Perkin Elmer). Both strands were sequenced using Prism dye-terminator sequencing kits and an ABI 377 sequencing machine.

Sequence Analysis:

Analyses of human V heavy and V kappa cDNA sequences of the HER-3 antibodies were accomplished by aligning the HER-3 sequences with human germline V heavy and V kappa sequences using Abgenix in-house software (5AS). The software identified the usage of the V gene, the D gene and the J gene as well as nucleotide insertions at the recombination junctions and somatic mutations. Amino acid sequences were also generated in silico to identify somatic mutations. Similar results could be obtained with commercially available sequence analysis software and publicly available information on the sequence of human V, D, and J genes, e.g., Vbase (http://vbase.mrc-cpe.cam.ac.uk/).

Molecular Cloning of mAb U1-59:

Total RNA was extracted from the tissue culture well containing multiple hybridomas lineages, including the hybridoma lineage secreting antibody U1-59. A heavy chain variable region was amplified using 5'-leader VH family specific primers, with 3'-C-gamma primer. A major band was amplified using a VH4 primer, no other bands were visible. The VH4-34 gamma fragment was cloned into pCDNA expression vector in frame with a human gamma 1 constant region gene.

An IgM heavy chain variable region was amplified using 5' VH family specific primers with 3' mu constant region primer. A major band was amplified using VH2 primer, no other bands were visible. The VH2-5 mu fragment was cloned into pCDNA expression vector in frame with a human mu constant region gene. V kappa chains were amplified and sequenced. Four kappa chain RT-PCR products were identified. The products were sequenced and after sequence analysis via in silico translation, only three of them had open-reading frames. These three functional kappa chains were cloned out of the oligoclonal U1-59 hybridoma well identified based on V kappa gene usage as (1) VK1 A3-JK2, (2) VK1 A20-JK3 and (3) B3-JK1. All V-kappa were cloned into pCDNA expression vector in frame with a human kappa light chain constant region gene.

Transfections:

Each heavy chain was transfected with each of the kappa chains in transient transfections for a total of 6 heavy chain/kappa light chain pairs. The transfection of the gamma chain with the A20 kappa chain gave poor antibody expression, while no antibody was secreted or detected when the A20 kappa chain was co-transfected with the mu chain. A total of three IgG sups and two IgM sups were available for HER-3 binding assay.

| Chain | VH | D | J | Constant | ORF |
|---|---|---|---|---|---|
| Heavy | VH4-34 | D1-20 | JH2 | Gamma | Yes |
| Heavy | VH2-5 | D6-6 | JH4b | Mu | Yes |
| Light | A3 | | JK2 | Kappa | Yes |
| Light | A20 | | JK3 | Kappa | Yes |
| Light | B3 | | JK1 | Kappa | Yes |
| Light | A27 | | JK3 | Kappa | NO |

Binding activity to HER-3+ cell lines was detected in FACS with the IgG1 mAb consisting of the VH4-34 and the B3 kappa chain. No other VH/Vk combinations gave fluorescence signal above background in FACS using HER-3+ cell lines.

Binding Competition of the Anti-HER-3 Antibodies:

Multiplexed competitive antibody binning was performed as published in Jia et al. (2004) *J Immunol Methods.* 288, 91-98 to assess clusters of HER-3 antibodies that competed for binding to HER-3. Tested HER-3 antibodies from cohort 1 clustered into 5 bins based on competition for binding.

| Bin#1 | Bin#2 | Bin#3 | Bin#4 | Bin#5 |
|---|---|---|---|---|
| U1-42 | U1-48 | U1-52 | U1-38 | U1-45 |
| U1-44 | U1-50 | | U1-39 | U1-40 |
| U1-62 | U1-51 | | | U1-41 |
| U1-46 | | | | U1-43 |

-continued

| Bin#1 | Bin#2 | Bin#3 | Bin#4 | Bin#5 |
|---|---|---|---|---|
| U1-47 | U1-49 | | | U1-61 |
| U1-58 | | | | U1-53 |
| | | | | U1-55 |

Epitope Characterization of Anti-HER-3 Antibodies:

The epitopes of human anti-HER-3 antibodies were characterized. First a dot blot analysis of the reduced, denatured HER-3-His tagged purified ECD protein showed absence of binding by the anti-HER-3 antibodies tested (U1-59, U1-61, U1-41, U1-46, U1-53, U1-43, U1-44, U1-47, U1-52, U1-40, U1-49)) demonstrating that all had epitopes sensitive to reduction of disulfide bonds, suggesting that all had discontinuous epitopes. Next, the antibodies were mapped to defined domains in the HER-3 molecule by engineering various human-rat HER-3 chimeric molecules, based on the division of the HER-3 extra-cellular domain into four domains:

1) L1 (D1): the minor ligand-binding domain,
2) S1 (D2): the first cysteine-rich domain,
3) L2 (D3): the major ligand-binding domain, and
4) S2 (D4): the sec cysteine-rich domain.

The extra-cellular domain (ECD) of Human HER-3 cDNA was amplified from RAT1-HER-3 cells. The rat HER-3 cDNAs was amplified by RT-PCR from rat liver RNA and confirmed by sequencing. The cDNAs expressing the ECD of human and rat HER-3 were cloned into mammalian expression vectors as V5-His fusion proteins. Domains from the human HER-3 ECD were swapped into the scaffold provided by the rat HER-3 ECD by using the Mfe1, BstX1 and DraIII internal restriction sites. By this means, various chimeric rat/human HER-3 ECD HIS fusion proteins (amino acids 1-160, 161-358, 359-575, 1-358, 359-604) were constructed and expressed via transient transfection of HEK 293T cells. Expression of the constructs was confirmed using a rat polyclonal antibody against human HER-3. The human monoclonal antibodies were tested in ELISA for binding to the secreted chimeric ECDs.

Two of the human antibodies, including antibody U1-59, cross-reacted with rat HER-3. To assign binding domains, these mAbs were tested against a truncated form of HER-3 consisting of L1-S1-V5his tagged protein purified from the supernatant of HEK 293T cells transfected with a plasmid DNA encoding the expression of the L1-S1 extra-cellular domains of HER-3. mAb U1-59 bound to the L1-S1 protein in ELISA, implying that its epitope is in L1-S1. mAb 2.5.1 did not bind to the L1-S1 protein, implying that its epitope is in L2-S2. Further mapping of antibody U1-59 was accomplished using SELDI time of flight mass spectroscopy with on-chip proteolytic digests of mAb-HER-3 ECD complexes.

Mapping U1-59 Epitopes Using SELDI:

Further mapping of antibody U1-59 was accomplished using a SELDI time of flight mass spectroscopy with on-chip proteolytic digests of mAb-HER-3 ECD complexes. Protein A was covalently bound to a PS20 protein chip array and used to capture mAb U1-59. Then the complex of the PS20 protein chip and the monoclonal antibody was incubated with HER-3-His purified antigen. Next the antibody-antigen complex was digested with high concentration of Asp-N. The chip was washed, resulting in retention of only the HER-3 peptide bound to the antibody on the chip. The epitope was determined by SELDI and identified by mass of the fragment. The identified 6814 D fragment corresponds to two possible expected peptides generated from a partial digest of the HER-3-his ECD. Both overlapping peptides map to the domain S1. By coupling SELDI results with binding to a HER-3 deletion construct, the epitope was mapped to residues 251 to 325.

The location of the binding domains in the extracellular part of HER-3 that are recognized by the human anti-HER-3 mAbs are summarized in TABLE 4. The epitope domain mapping results were consistent with results from antibody competition binding competition bins, with antibodies that cross-competed each other for binding to HER-3 also mapping to the same domains on HER-3.

TABLE 4

A summary of mAb binding domains based on ELISA assay results

| MAb | Rat XR | Binding domain | mAb | Rat XR | Binding domain |
|---|---|---|---|---|---|
| U1-59 | Yes | S1 | U1-2 | No | L2 |
| U1-61 | No | L2 | U1-7 | No | L2 |
| U1-41 | No | L2 | U1-9 | No | L2 |
| U1-46 | No | S1 | U1-10 | No | L2 |
| U1-53 | No | L2 | U1-12 | No | L2 |
| U1-43 | No | L2 | U1-13 | No | L2 |
| U1-44 | No | S1 | U1-14 | No | L2 |
| U1-47 | No | S1 | U1-15 | No | L2 |
| U1-52 | Yes | L2S2 | U1-19 | No | L2 |
| U1-40 | No | L2 | U1-20 | No | L2 |
| U1-49 | No | L1 | U1-21 | No | L2 |
| U1-21 | No | L2 | U1-28 | No | L2 |
| U1-22 | No | L2 | (U1-31) | No | L2 |
| U1-23 | No | L2 | U1-32 | No | L2 |
| U1-24 | No | L2 | (U1-35) | No | L2 |
| U1-25 | No | L2 | U1-36 | No | L2 |
| U1-26 | No | L2 | (U1-37) | No | L2 |
| U1-27 | No | L2 | | | |

XR = cross-reactive

Example 9: Determination of Canonical Classes of Antibodies

Antibody structure has been described in terms of "canonical classes" for the hypervariable regions of each immunoglobulin chain (Chothia et al. (1987) *J. Mol. Biol.* 196:901-17). The atomic structures of the Fab and VL fragments of a variety of immunoglobulins were analyzed to determine the relationship between their amino acid sequences and the three-dimensional structures of their antigen binding sites. Chothia, et al. found that there were relatively few residues that, through their packing, hydrogen bonding or the ability to assume unusual phi, psi or omega conformations, were primarily responsible for the main-chain conformations of the hypervariable regions. These residues were found to occur at sites within the hypervariable regions and in the conserved β-sheet framework. By examining sequences of immunoglobulins having unknown structure, Chothia, et al. show that many immunoglobulins have hypervariable regions that are similar in size to one of the known structures and additionally contained identical residues at the sites responsible for the observed conformation.

Their discovery implied that these hypervariable regions have conformations close to those in the known structures. For five of the hypervariable regions, the repertoire of conformations appeared to be limited to a relatively small number of discrete structural classes. These commonly occurring main-chain conformations of the hypervariable regions were termed "canonical structures." Further work by Chothia et al. (*Nature* (1989) 342:877-83) and others (Martin et al. (1996) *J. Mol. Biol.* 263:800-15) confirmed that there is a small repertoire of main-chain conformations for at least five of the six hypervariable regions of antibodies.

The CDRs of each antibody described above were analyzed to determine their canonical class. As is known, canonical classes have only been assigned for CDR1 and CDR2 of the antibody heavy chain, along with CDR1, CDR2 and CDR3 of the antibody light chain. The tables below summarize the results of the analysis. The canonical class data is in the form of HCDR1-HCDR2-LCDR1-LCDR2-LCDR3, wherein "HCDR" refers to the heavy chain CDR and "LCDR" refers to the light chain CDR. Thus, for example, a canonical class of 1-3-2-1-5 refers to an antibody that has a HCDR1 that falls into canonical class 1, a HCDR2 that falls into canonical class 3, a LCDR1 that falls into canonical class 2, a LCDR2 that falls into canonical class 1, and a LCDR3 that falls into canonical class 5.

Assignments were made to a particular canonical class where there was 70% or greater identity of the amino acids in the antibody with the amino acids defined for each canonical class. The amino acids defined for each antibody can be found, for example, in the articles by Chothia, et al. referred to above. TABLE 5 and TABLE 6 report the canonical class data for each of the HER-3 antibodies. Where there was less than 70% identity, the canonical class assignment is marked with an asterisk ("*") to indicate that the best estimate of the proper canonical class was made, based on the length of each CDR and the totality of the data. Where there was no matching canonical class with the same CDR length, the canonical class assignment is marked with a letter s and a number, such as "s18", meaning the CDR is of size 18. Where there was no sequence data available for one of the heavy or light chains, the canonical class is marked with "Z".

TABLE 5

| Antibody (sorted) | H1-H2-L1-L2-L3 | H3length |
|---|---|---|
| U1-38 | 3-1-4-1-1 | 9 |
| U1-39 | 1-1-4-1*-1 | 6 |
| U1-40 | 3-1-4-1-1 | 15 |
| U1-41 | 3-1-2-1-1 | 15 |
| U1-42 | 1-2-2-1-1 | 9 |
| U1-43 | 3-1-2-1-1 | 17 |
| U1-44 | 1-2-2-1-1 | 9 |
| U1-45 | 1-2*-2-1-1 | 16 |
| U1-46 | 3-s18-Z-Z-Z | 17 |
| U1-47 | 3-s18-2-1-1 | 16 |
| U1-48 | 1-1-Z-Z-Z | 16 |
| U1-49 | 1-3-4-1-1 | 17 |
| U1-50 | 3-1-2-1-1 | 17 |
| U1-51 | 1-1-3-1-1 | 19 |
| U1-52 | 3-1-8-1-1 | 15 |
| U1-53 | 1-3-2-1-1 | 10 |
| U1-55 | 3-1-4-1-1 | 15 |
| U1-57 | 3-1-4-1-1 | 15 |
| U1-58 | 1-3-2-1-1 | 12 |
| U1-59 | 1-1-3-1-1 | 9 |
| U1-61.1 | 3-1*-2-1-1 | 16 |
| U1-62 | 1-2-8-1-1 | 12 |
| U1-2 | 3-1-2-1-1 | 12 |
| U1-7 | 3-1-2-1-1 | 12 |
| U1-9 | 3-1-2-1-1 | 12 |
| U1-10 | 3-1-2-1-1 | 12 |
| U1-12 | 3-1-2-1-1 | 12 |
| U1-13 | 3-1-4-1-1 | 7 |
| U1-14 | 3-1-2-1-1 | 12 |
| U1-15 | 3-1-8-1-1 | 14 |
| U1-19 | 3-1-Z-Z-Z | 12 |
| U1-20 | 3-1-2-1-1 | 19 |
| U1-21 | 3-1-2-1-1 | 12 |

TABLE 5-continued

| Antibody (sorted) | H1-H2-L1-L2-L3 | H3length |
|---|---|---|
| U1-22 | 3-1-2-1-1 | 12 |
| U1-23 | 3-1-2-1-1 | 12 |
| U1-24 | 3-1-2-1-1 | 12 |
| U1-25 | 3-1-2-1-1 | 12 |
| U1-26 | 3-1-2-1-1 | 12 |
| U1-27 | 3-1-2-1-1 | 12 |
| U1-28 | 3-1-2-1-1 | 12 |
| U1-31 | 1-2-2-1-1 | 13 |
| U1-32 | 3-1-2-1-1 | 12 |
| U1-35 | 1-3-2-1-1 | 14 |
| U1-36 | 3-1-2-1-1 | 12 |
| U1-37 | 1-2-Z-Z-Z | 13 |

TABLE 6 is an analysis of the number of antibodies per class. The number of antibodies having the particular canonical class designated in the left column is shown in the right column. The four mAbs lacking one chain sequence data and thus having "Z" in the canonical assignment are not included in this counting.

The most commonly seen structure is 3-1-2-1-1: Twenty-one out of forty-one mAbs having both heavy and light chain sequences had this combination.

TABLE 6

| H1-H2-L1-L2-L3 | Count |
|---|---|
| 1-1-3-1-1 | 2 |
| 1-1-4-1*-1 | 1 |
| 1-2-2-1-1 | 4 |
| 1-2-8-1-1 | 1 |
| 1-3-2-1-1 | 3 |
| 1-3-4-1-1 | 1 |
| 3-1-2-1-1 | 21 |
| 3-1-4-1-1 | 5 |
| 3-1-8-1-1 | 2 |
| 3-s18-2-1-1 | 1 |

Example 10: Determination of Antibody Affinity

Affinity measurements of anti-HER-3 antibodies were performed by indirect FACS Scatchard analysis. Therefore, $10^5$ cells of interest or SK-Br 3 cells were harvested with 10 mM EDTA in PBS, washed once with FACS buffer (PBS, 3% FCS, 0.4% azide) and seeded on a 96-well round bottom plate. The cells were spun for 3 min at 1000 rpm to remove supernatant and then resuspended with α-HER-3 antibody (3 μg/ml) or with antibody dilutions (100 μl/well) starting with 20 μg/ml human monoclonal antibody in FACS buffer, diluted in 1:2 dilution steps. Cell suspensions were incubated on ice for 1 hr, washed twice with FACS buffer and resuspended with secondary antibody (100 μl/well) donkey-anti-human-PE (Jackson) diluted 1:50 in FACS buffer. The cell suspensions were incubated on ice and in the dark for 30 min, washed twice with FACS buffer and analyzed (FACS, Beckman Coulter). According to the FACS Scatchard analysis, the fluorescence mean was calculated for each measurement. Background staining (=without $1^{st}$ antibody) was subtracted from each fluorescence mean. Scatchard plot with x-value=fluorescence mean and y-value=fluorescence mean/concentration of mAb (nM) was generated. The KD was taken as the absolute value of 1/m of linear equation. Affinity measurements for certain antibodies selected in this manner are provided in TABLE 7.

TABLE 7

| Clone | KD (nm) |
|---|---|
| U1-38 | n.d. |
| U1-39 | 102 |
| U1-40 | 6.7 |
| U1-41 | 0.18 |
| U1-42 | n.d. |
| U1-43 | 0.57 |
| U1-44 | 4 |
| U1-52 | 16.8 |
| U1-61 | 0.13 |
| U1-62 | 20.4 |
| U1-46 | 13.8 |
| U1-47 | 9.38 |
| U1-49 | 1 |
| U1-50 | 39.3 |
| U1-51 | 131.6 |
| U1-53 | 0.082 |
| U1-55.1 | 3.7 |
| U1-58 | 6.4 |
| U1-59 | 3.69 |
| U1-24 | 0.06 |
| U1-7 | 0.02 |

Example 11: Anti-HER-3 Antibodies Induce HER-3 Receptor Endocytosis

HER-3 has been identified as a factor that can influence initiation and progression of hyperproliferative diseases through serving as an important gatekeeper of HER family mediated cell signaling. Thus, if HER-3 is effectively cleared from the cell surface/membrane by receptor internalization, cell signaling and therefore transformation and/or maintenance of cells in malignancy can be ultimately diminished or suppressed.

In order to investigate whether anti-HER-3 antibodies are capable of inducing accelerated endocytosis of HER-3, the relative amount of HER-3 molecules on the cell surface after 0.5 and 4 hr incubation of the cells with anti-HER-3 antibodies were compared. $3 \times 10^5$ cells were seeded in normal growth medium in 24-well dish and left to grow overnight. Cells were preincubated with 10 µg/ml anti-HER-3 mAbs in normal growth medium for the indicated times at 37° C. Cells were detached with 10 mM EDTA and incubated with 10 µg/ml anti-HER-3 mAbs in wash buffer (PBS, 3% FCS, 0.04% azide) for 45 min at 4° C. Cells were washed twice with wash buffer, incubated with donkey-anti-human-PE secondary antibody (Jackson) diluted 1:100 for 45 min at 4° C., washed twice with wash buffer and analyzed by FACS (BeckmanCoulter, EXPO). Percent internalization was calculated based on the reduction of the mean fluorescence intensity of anti-HER-3 treated samples relative to control-treated samples. These experiments demonstrated that treatment of cells with anti-HER-3 antibodies led to internalization of the receptor. See, FIG. 5 of US Publication No. 20080124345.

Example 12: Inhibition of Ligand Binding to Human Cancer Cells SKBr3 by Human Anti-HER-3 Antibodies Radioligand competition experiments were performed in order to quantitate the ability of the anti-HER-3 antibodies to inhibit ligand binding to HER-3 in a cell based assay. Therefore, the HER-3 receptor binding assay was performed with $4 \times 10^5$ SK-BR-3 cells which were incubated with varying concentrations of antibodies for 30 min on ice. 1.25 nM $[^{125}I]$-α-HRG/$[^{125}I]$-β-HRG were added to each well and the incubation was continued for 2 hr on ice. The plates were washed five times, air-dried and counted in a scintillation counter. The antibodies were capable of specifically reducing the binding of $[^{125}I]$-α-HRG/$[^{125}I]$-β-HRG to cells expressing endogenous HER-3. See, FIGS. 6a-6e of US Publication No. 20080124345.

Example 13: Inhibition of Ligand-Induced HER-3 Phosphorylation by Human Anti-HER-3 Antibodies ELISA experiments were performed in order to investigate whether the antibodies are able to block ligand β-HRG-mediated activation of HER-3. Ligand-mediated HER-3 activation was detected by increased receptor tyrosine phosphorylation.

Day 1: 1×96 well dish was coated with 20 µg/ml Collagen I in 0.1 M acetic acid for 4 hr at 37° C. $2.5 \times 10^5$ cells were seeded in normal growth medium Day 2: Cells were starved in 100 µl serum free medium for 24 hr.

Day 3: Cells were preincubated with 10 µg/ml anti-HER-3 mAbs for 1 hr at 37° C. and then treated with 30 ng/ml β-HRG-EGF domain (R&D Systems) for 10 min. Medium was flicked out and cells were fixed with 4% formaldehyde solution in PBS for 1 hr at room temperature. Formaldehyde solution was removed and cells were washed with wash buffer (PBS/0.1% Tween 20). Cells were quenched with 1% $H_2O_2$, 0.1% $NaN_3$ in wash buffer and incubated for 20 min at room temperature, then blocked with NET-Gelantine for 5 hr at 4° C. Primary antibody phospho-HER-3 (Tyr1289) (polyclonal rabbit; Cell signaling #4791; 1:300) was added overnight at 4° C.

Day 4: The plate was washed 3× with wash buffer, then incubated with anti-rabbit-POD diluted 1:3000 in PBS–0.5% BSA was added to each well and incubated for 1.5 hr at room temperature. The plate was washed 3× with wash buffer and once with PBS. Tetramethylbenzidine (TMB, Calbiochem) was added and monitored at 650 nm. The reaction was stopped by addition of 100 µl 250 nM HCl and the absorbance was read at 450 nm with a reference wavelength of 650 nm using a Vmax plate reader (Thermo Lab Systems).

These experiments demonstrated that anti-HER-3 antibodies were able to reduce ligand-mediated HER-3 activation as indicated by decreased receptor tyrosine phosphorylation. See, FIG. 7a of US Publication No. 20080124345.

To test potency of mAb U1-53 to inhibit ligand induced HER-3 activation, MCF-7 cells were starved for 24 hr, incubated with mAb U1-53 for 1 hr at 37° C. and stimulated with 10 nM HRG-β for 10 min. Lysates were transferred to 1B4 (mouse anti-HER-3 mAb) ELISA plates and phosphorylation of HER-3 was analyzed with antibody 4G10. Phosphorylation of HER-3 was almost completely inhibited in a dose dependent manner with an $IC_{50}$ of 0.14 nM. See, FIG. 7b of US Publication No. 20080124345.

Example 14: Inhibition of Ligand-Induced p42/p44 MAP-Kinase Phosphorylation by Human Anti-HER-3 Antibodies Next ELISA experiments were performed in order to investigate whether the antibodies are able to block ligand β-HRG-mediated activation of p42/p44 MAP-Kinase. Ligand-mediated HER-3 activation was detected by increased protein (Thr202/Tyr204) phosphorylation.

Day 1: 1×96 well dish was coated with 20 μg/ml Collagen I in 0.1 M acetic acid for 4 hr at 37° C. 3×10⁵ cells were seeded in normal growth medium Day 2: Cells were starved in 100 μl serum free medium for 24 hr.

Day 3: Cells were preincubated with 5 μg/ml anti-HER-3 mAbs for 1 hr at 37° C. and then treated with 20 ng/ml β-HRG-EGF domain (R&D Systems) for 10 min. Medium was flicked out and cells were fixed with 4% formaldehyde solution in PBS for 1 hr at room temperature. Formaldehyde solution was removed and cells were washed with wash buffer (PBS/0.1% Tween 20). Cells were quenched with 1% $H_2O_2$, 0.1% $NaN_3$ in wash buffer and incubated for 20 min at room temperature, then blocked with PBS/0.5% BSA for 5 hr at 4° C. Primary antibody phospho-p44/p42 MAP Kinase (Thr202/Tyr204) (polyclonal rabbit; Cell signaling #9101; 1:3000) was added overnight at 4° C.

Day 5: The plate was washed 3× with wash buffer, then incubated with anti-rabbit-HRP diluted 1:5000 in PBS– 0.5% BSA was added to each well and incubated for 1.5 hr at room temperature. The plate was washed 3× with wash buffer and once with PBS. Tetramethylbenzidine (TMB, Calbiochem) was added and monitored at 650 nm. The reaction was stopped by addition of 100 μl 250 nM HCl and the absorbance was read at 450 nm with a reference wavelength of 650 nm using a Vmax plate reader (Thermo Lab Systems). These experiments revealed that the antibodies were able to reduce ligand-mediated p42/p44 MAP-Kinase activation as indicated by decreased phosphorylation. See, FIG. 8 of US Publication No. 20080124345.

Example 15: Inhibition of β-HRG-Induced Phospho-AKT Phosphorylation by Human Anti-HER-3 Antibodies In the following ELISA experiment we investigated whether the anti-HER-3 antibodies are able to block ligand β-HRG-mediated activation of AKT-Kinase. Ligand-mediated AKT activation was detected by increased protein (Ser473) phosphorylation.

Day 1: 1×96 well dish was coated with 20 μg/ml Collagen I in 0.1 M acetic acid for 4 hr at 37° C. 3×10⁵ cells were seeded in normal growth medium Day 2: Cells were starved in 100 μl serum free medium for 24 hr.

Day 3: Cells were preincubated with 5 μg/ml anti-HER-3 mAbs for 1 hr at 37° C. and then treated with 20 ng/ml β-HRG-EGF domain (R&D Systems) for 10 min. Medium was flicked out and cells were fixed with 4% formaldehyde solution in PBS for 1 hr at room temperature. Formaldehyde solution was removed and cells were washed with wash buffer (PBS/0.1% Tween 20). Cells were quenched with 1% $H_2O_2$, 0.1% $NaN_3$ in wash buffer and incubated for 20 min at room temperature, then blocked with PBS/0.5% BSA for 5 hr at 4° C. Primary antibody phospho-Akt (Ser473) (polyclonal rabbit; Cell signaling #9217; 1:1000) was added overnight at 4° C.

Day 4: The plate was washed 3× with wash buffer, then incubated with anti-rabbit-HRP diluted 1:5000 in PBS– 0.5% BSA was added to each well and incubated for 1.5 hr at room temperature. The plate was washed 3× with wash buffer and once with PBS. Tetramethylbenzidine (TMB, Calbiochem) was added and monitored at 650 nm. The reaction was stopped by addition of 100 μl 250 nM HCl and the absorbance was read at 450 nm with a reference wavelength of 650 nm using a Vmax plate reader (Thermo Lab Systems). The anti-HER-3 antibodies were able to reduce β-HRG-mediated AKT as indicated by decreased phosphorylation. See, FIG. 9 of US Publication No. 20080124345.

Example 16: Inhibition of α-HRG/β-HRG-Mediated MCF7 Cell Proliferation by Human Anti-HER-3 Antibodies In vitro experiments were conducted in order to determine the ability of the antibodies to inhibit HRG-stimulated cell proliferation. 2000 MCF7 cells were seeded in FCS-containing medium on 96-well plates overnight. Cells were preincubated in quadruplicates with antibody diluted in medium with 0.5% FCS for 1 hr at 37° C. Cells were stimulated with 30 ng/ml α- or 20 ng/ml β-HRG (R&D Systems) by adding ligand directly to antibody solution and were then left to grow for 72 hr. ALAMARBLUE™ (BIOSOURCE) was added and incubated at 37° C. in the dark. Absorbance was measured at 590 nm every 30 min. The data were taken 90 min after addition of alamar blue. These studies showed that representative antibodies could inhibit HRG-induced cell growth in human cancer cells. See, FIG. 10 of US Publication No. 20080124345.

Example 17: Inhibition of β-HRG-Induced MCF7 Cell Migration by Human Anti-HER-3 Antibodies Transmigration experiments were performed in order to investigate whether the antibodies block cell migration. Serum-starved MCF7 cells were preincubated by adding the indicated amount of antibody to the cell suspension and incubating both for 45 min at 37° C. 500 μl cell suspension (50,000 cells) was then placed in the top chamber of collagen I-coated transwells (BD Falcon, 8 μm pores). 750 μl medium (MEM, amino acids, Na-pyruvate, Pen.-Strept., 0.1% BSA, without fetal calf serum) alone or containing the ligands β-HRG-EGF domain (R&D Systems) were used in the bottom chamber. Cells were left to migrate for 8 hr at 37° C. and were stained with DAPI. Stained nuclei were counted manually; percent inhibition was expressed as inhibition relative to a control antibody. These experiments demonstrated that representative anti-HER-3 antibodies could reduce HRG-induced cell migration. See, FIG. 11 of US Publication No. 20080124345.

Example 18: Colony Formation Assay (Soft Agar Assay)

Soft agar assays were conducted in order to investigate the ability of the anti-HER-3 antibodies to inhibit anchorage independent cell growth. The soft agar colony formation assay is a standard in vitro assay to test for transformed cells, as only such transformed cells can grow in soft agar.

750 to 2000 cells (depending on the cell line) were preincubated with indicated antibodies at 10 μg/ml in IMDM medium (Gibco) for 30 min and resuspended in 0.4% Difco noble agar. The cell suspension was plated on 0.75% agarose underlayer containing 20% FCS in quadruplicate in a 96-well plate. Colonies were allowed to form for 14 days, and were then stained with 50 μl MTT (0.5 mg/ml in PBS) overnight, and counted with a Scanalyzer HTS camera system (Lemnatec, Wuerselen). Anti-HER-3 antibodies were able to reduce anchorage independent cell growth of MDA-MB361 and NCI-ADR breast cancer cells, MKN-28 gastric cancer cells, HT144 melanoma cells, Skov3 ovary carcinoma cells, PPC-1 prostate cancer cells, BX-PC3 pancreas cancer cells, A431 epidermoid carcinoma cells, and lung carcinoma cells. See, FIGS. 12a-12i of US Publication No. 20080124345.

Figure 13:
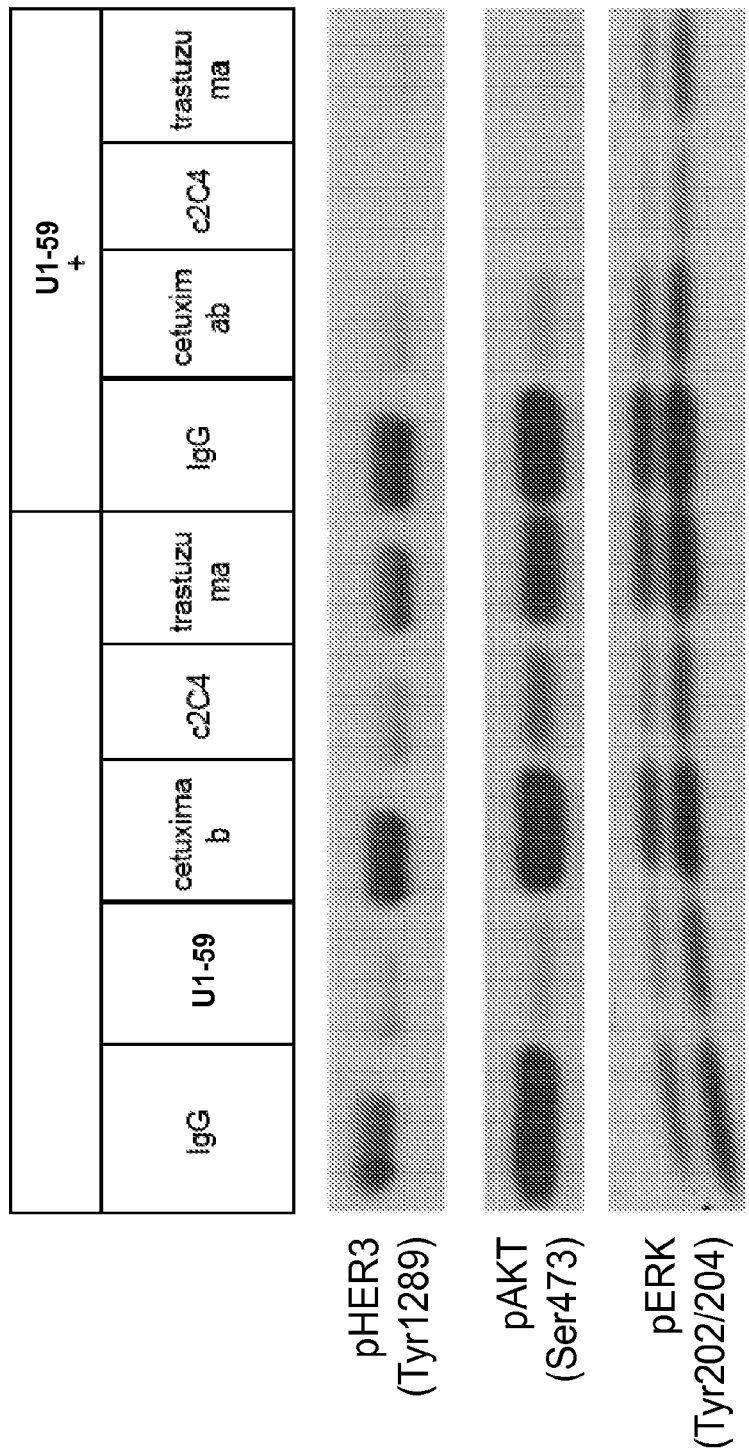
FIG. 13 is a picture of a Western blot showing the effects of a human anti-HER-3 antibody, either alone or in combination with cetuximab, c2C4, or trastuzumab, on phosphorylation of HER-3 (top panel), Akt (middle panel), and ERK (bottom panel) in MDA-MB-175VII breast cancer cells.

Example 19: Human Anti-HER-3 Antibodies Inhibit Human Breast Carcinoma Growth in Nude Mice The anti-tumor efficacy of therapeutic antibodies is often evaluated in human xenograft tumor studies. In these studies, human tumors grow as xenografts in immunocompromised mice and therapeutic efficacy is measured by the degree of tumor growth inhibition. In order to determine, if the anti-HER-3 antibodies interfere with tumor growth of human breast cancer cells in nude mice, $5 \times 10^6$ T47D cells were implanted in female NMRI nude/nude mice. Tumors were subcutaneous, grown on the back of the animal. Treatments began when tumors reached a mean volume of 20 mm$^3$; eight days post implantation. Prior to first treatment, mice were randomized and statistical tests performed to assure uniformity in starting tumor volumes (mean, median and standard deviation) across treatment groups. Treatment started with a loading dose of 50 mg/kg followed by 25 mg/kg injections once a week by intraperitoneal injection. A control arm received doxorubicin (pharmaceutical grade). All animals were supplemented with 0.5 mg/kg/week oestrogen injected i.p. Details of the treatment groups are given in TABLE 8 below. These studies demonstrated that administration of an anti-HER-3 antibody resulted in reduction of tumor growth. See, FIG. 13 of US Publication No. 20080124345.

TABLE 8

| Gr. | N | 1$^{st}$ Compound | Loading (mg/kg) | Weekly dose (mg/kg) | Route | Schedule |
|---|---|---|---|---|---|---|
| 1. | 10 | PBS | — | — | i.p. | once/week |
| 2. | 10 | Doxorubicin | — | 8 mg/kg | i.v. | once/week* |
| 3. | 10 | U1-53 | 50 mg/kg 20 ml/kg | 25 mg/kg 10 ml/kg | i.p. | once/week |

*doxorubin treatment as described by Boven et al., Cancer Research, 1992.

Example 20: Human Anti-HER-3 Antibodies Inhibit Human Pancreatic Tumor Growth in SCID Mice To test the therapeutic potential of anti-HER-3 antibodies in other solid tumor types the anti-HER-3 antibodies, U1-53 and U1-59, were tested in mice with established tumors derived from the human pancreatic tumor cell line BxPC3. As controls sets of mice treated with either the vehicle control, PBS, or the established therapeutic antibody, Erbitux, were included. $5 \times 10^6$ BxPC3 cells were inoculated subcutaneously without Matrigel into CB17 SCiD mice. Mice bearing established tumors with a mean volume of 140 mm$^2$ received 50 mg/kg of U1-53, U1-59, Erbitux or the equivalent volume of PBS via intraperitoneal injection. Thereafter the mice received once weekly 25 mg/kg injections for the duration of the study.

Figure 14:
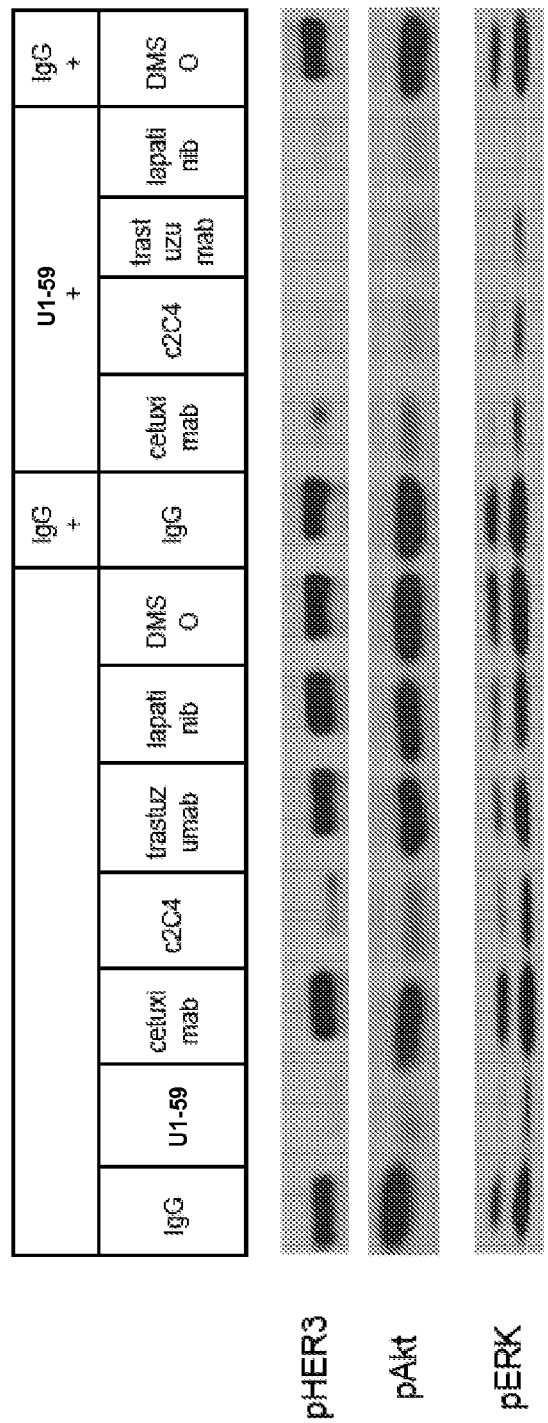
FIG. 14 is a picture of a Western blot showing the effects of a human anti-HER-3 antibody, either alone or in combination with cetuximab, c2C4, trastuzumab, or lapatinib, on phosphorylation of HER-3 (top panel), Akt (middle panel), and ERK (bottom panel) in HRG stimulated SkBr-3 breast cancer cells.

U1-53 and U1-59 reduced the growth of the human pancreatic tumors in a cytostatic fashion. See, FIG. 14 of US Publication No. 20080124345. Notably, in this experiment, U1-53 and U1-59 were more effective than the EGF-R-targeting antibody Erbitux at delaying tumor growth. These studies demonstrated the therapeutic efficacy of anti-HER-3 antibodies in comparison to a benchmark therapeutic agent.

Example 21: Combining the Human Anti-HER-3 Antibodies with Anti-EGF-R Antibodies Increases Anti-Tumor Activity The monotherapy of hyperproliferative diseases with targeted antibodies is often hampered by problems such as, on the one hand, the development of resistance to drugs, and on the other hand, a change in the antigenicity. For example, loss of antigenicity after prolonged treatment may render tumor cells insensitive to therapeutic antibodies, since those tumor cells that do not express or have lost the targeted antigen have a selective growth advantage. These problems might be evaded by using the antibodies in combination with a therapeutic antibody that targets a different receptor on the tumor cells, or another antineoplastic agent. Intervening in multiple signaling pathways or even related pathways but at multiple intervention steps might also provide therapeutic benefit. These combined treatment modalities are likely to be more efficacious, because they combine two anti-cancer agents, each operating via a different mechanism of action.

In order to demonstrate the feasibility of the anti-HER-3 antibodies U1-53 and U1-59 as suitable combination agents, we compared monotherapeutic administrations of U1-53 or U1-59 with those in which either U1-53 or U1-59 was combined with the anti-EGR specific antibody, Erbitux. $5 \times 10^6$ BxPC3 cells were inoculated subcutaneously with Matrigel into CB17 SCID mice. After tumor volumes had reached 200 mm$^3$, mice were randomized into individual treatment groups. Weekly intraperitoneal administrations of U1-53, U1-59 and Erbitux as single agents or combinations of either anti-HER-3 antibodies with Erbitux or as a cocktail of two anti HER-3 antibodies were performed. All antibodies were dosed at a single loading dose of 50 mg/kg/week, followed by weekly injections of 25 mg/kg for six weeks. Control arms received bi-weekly administrations of Gemcitabine (120 mg/kg), weekly pooled human IgG or weekly vehicle (PBS) injections. The regimens are detailed in TABLE 9 below.

TABLE 9

| Gr. | N | Compound | Loading dose (mg/kg) | weekly dose (mg/kg) | Route | Schedule |
|---|---|---|---|---|---|---|
| 1 | 12 | PBS | 20 ml/kg | 10 ml/kg | q7d | i.p. |
| 2 | 12 | Pooled human IgG | 50 mg/kg | 25 mg/kg | q7d | i.p. |
| 3 | 12 | U1-53 | 50 mg/kg | 25 mg/kg | q7d | i.p. |
| 4 | 12 | U1-59 | 50 mg/kg | 25 mg/kg | q7d | i.p. |
| 5 | 12 | Erbitux | 50 mg/kg | 25 mg/kg | q7d | i.p. |
| 6 | 12 | U1-53 + Erbitux | 25 mg/kg each | 12.5 mg/kg each | q7d | i.p. |
| 7 | 12 | U1-59 + Erbitux | 25 mg/kg each | 12.5 mg/kg each | q7d | i.p. |
| 8 | 12 | U1-53 + U1-59 | 25 mg/kg each | 12.5 mg/kg each | q7d | i.p. |
| 9 | 12 | Gemcitabine | none | 120 mg/kg | 2x weekly | i.p. |

Figure 15:
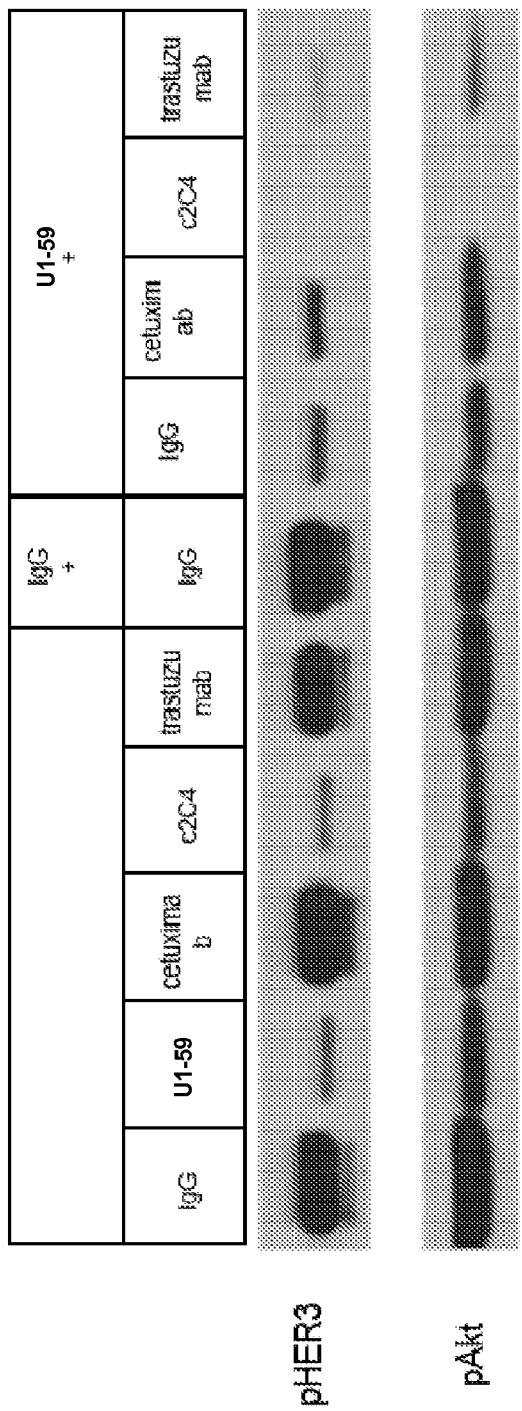
FIG. 15 is a picture of a Western blot showing the effects of a human anti-HER-3 antibody, either alone or in combination with cetuximab, pertuzumab (c2C4), or trastuzumab, on phosphorylation of HER-3 (top panel) or Akt (bottom panel) in HRG stimulated Ls174T colon cancer cells.

Antibodies U1-53 and U1-59, when administered as single agents, delayed the growth of the human pancreatic tumors to the same degree as Gemcitabine, which is often used as a standard anti-pancreatic cancer chemotherapy. Co-administration of Erbitux with U1-53 or U1-59 resulted in a significantly greater reduction of tumor growth than observed with either single agent administration of U1-53, U1-59 or Erbitux. Thus, a beneficial therapeutic response can be achieved by combining the anti-HER-3 antibodies with suitable antibodies that target separate tumor antigens. See, FIG. 15 of US Publication No. 20080124345.

In summary, the anti-HER-3 antibodies had potent therapeutic efficacy against human tumors in vivo. They can be effectively combined with other anti-neoplastic therapeutics for increased anti-tumor activity.

Example 22: Human Anti-HER-3 Antibodies Inhibit Human Melanoma Tumor Growth in Nu/Nu Mice Members of the erbB family of receptors, including HER-3, are abnormally expressed in a large variety of epithelial cancers and they are known to play important roles in the growth and survival of many these solid tumors. These tumors include melanomas, head and neck squamous cell cancers, non-small cell lung cancers and prostate, glioma, gastric, breast, colorectal, pancreatic, ovarian cancers. In order to verify, that the anti-HER-3 antibodies are not restricted in their anti-cancer activity to individual tumor types, e.g., pancreatic cancers (see, Example 21), but can be used as therapeutics against many HER-3-dependent tumors, we tested U1-53 and U1-59 in additional xenograft studies. Human melanoma cells ($5 \times 10^5$), HT144, were injected subcutaneously into CB17 SCID mice, followed by immediate subsequent intraperitoneal injection of 50 mg/kg of U1-53 and U1-59, the equivalent volume of PBS or Dacarbacin (DITC) at 200 mg/kg. Thereafter, mice received 25 mg/kg of U1-53 or U1-59 once weekly, whereas DITC was given once every two weeks at 200 mg/kg.

Figure 16:
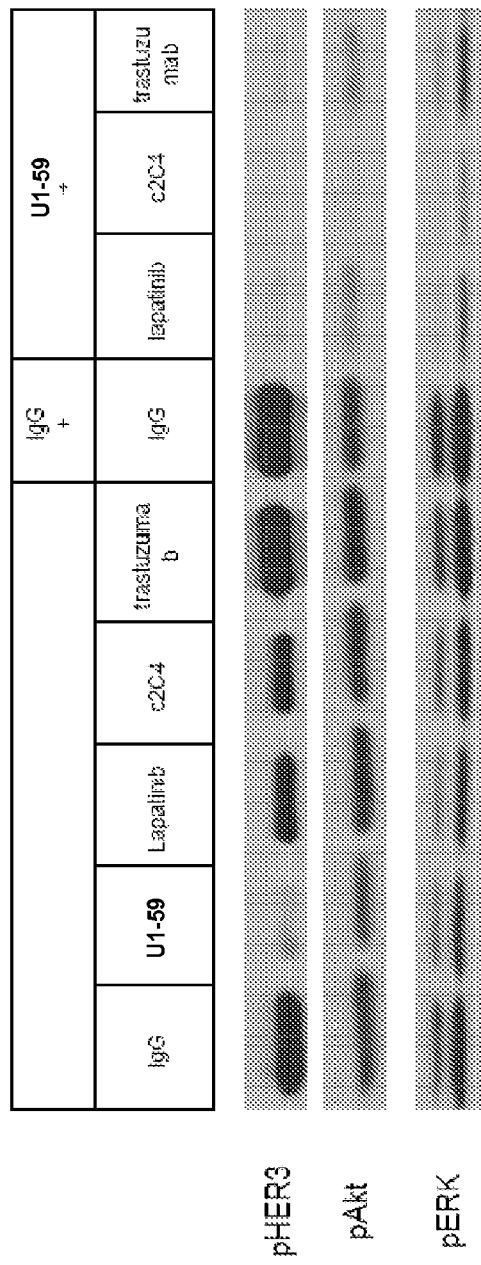
FIG. 16 is a picture of a Western blot showing the effects of a human anti-HER-3 antibody, either alone or in combination with cetuximab, c2C4, or trastuzumab, on phosphorylation of HER-3 (top panel), Akt (middle panel), and ERK (bottom panel) in HRG stimulated HCC 1569 breast cancer cells.

The median tumor volumes from each treatment group were calculated. Administration of the antibodies resulted in growth reduction of the human melanomas when compared to tumors that had been treated with the vehicle control. See, FIG. 16 of US Publication No. 20080124345. These results demonstrate that the antibodies are not restricted in their therapeutic potential and target a wide variety of HER-3 expressing cancers.

Example 23: Human Anti-HER-3 Antibodies Inhibit Growth of Colon Carcinoma Xenografts in Mice HT-29 human colon carcinoma cells were suspended in medium with 2:1 ratio of Matrigel to a final concentration of $10 \times 10^6$ cells/ml. 0.2 ml of cell suspension were injected s.c. into the right flank of 4-5-week-old CD1 nu/nu mice. A total of 95 mice were used.

The mice were randomly assigned to control and treatment groups. The treatment started on the same day. Duration of treatment was 29 days. Upon completion of the study, three tumors per group were collected 3 hours after administration of treatment. The tumours were fast-frozen and kept at −80° C.

Figure 17:
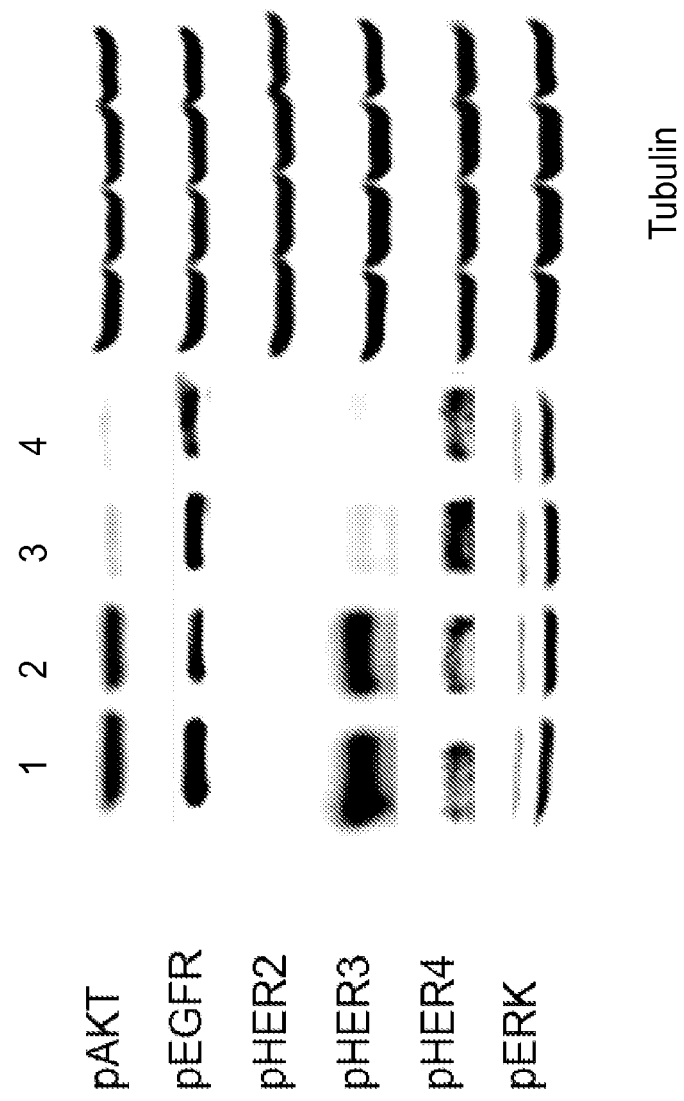
FIG. 17 is a picture of a Western blot showing the effects of a human anti-HER-3 antibody, either alone or in combination with panitumumab, on phosphorylation of Akt, PGFR, HER-2, HER-3, HER-4, and ERK in A549 alveolar epithelial cells. Lane 1, IgG control; lane 2, panitumumab, alone; lane 3, U1-59, alone; lane 4, U1-59, in combination with panitumumab. Tubulin was used as a control for equal loading.

The following treatment protocol was carried out:
Control group: non-specific human IgG 25 mg/kg, twice weekly, intraperitoneal
Treatment group: antibody U1-53, 25 mg/kg, twice weekly, intraperitoneal
Treatment group: antibody U1-7, 25 mg/kg, twice weekly, intraperitoneal
Treatment group: antibody U1-59, 25 mg/kg, twice weekly, intraperitoneal
Treatment group 5-FU: 5-fluorouracil, 50 mg/kg, 9 d×5, intraperitoneal The median tumor volumes from each group were calculated. Administration of the antibodies resulted in growth reduction of the HT-29 colon carcinoma tumors when compared to tumors that had been treated with non-specific human IgG1. See, FIG. 17 of US Publication No. 20080124345.

Example 24: Human Anti-HER-3 Antibodies Inhibit Lung Cancer Growth in Mice

Calu-3 human non-small cell lung cancer cells were suspended in medium with 1:1 ratio of Matrigel to a final concentration of $5 \times 10^6$ cells/ml. 0.05 ml of cell suspension were injected s.c. into the right flank of 9-week-old female CB17 scid mice. A total of 60 mice were used.

The mice were randomly selected to control and treatment groups. Treatment started on the same day. The duration of treatment was 32 days.

Figure 18:
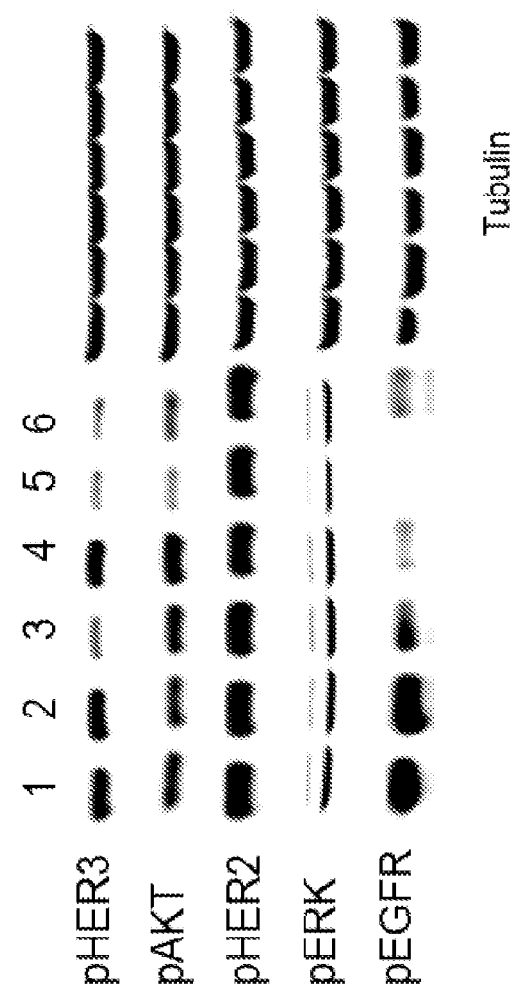
FIG. 18 is a picture of a Western blot showing the effects of a human anti-HER-3 antibody, either alone or in combination with panitumumab or lapatinib, on phosphorylation of HER-3, Akt, HER-2, ERK, and EGF-R in Calu3 NSCLC cells. Lane 1, IgG control; lane 2, panitumumab alone; lane 3, U1-59 alone; lane 4, lapatinib alone; lane 5, U1-59 in combination with panitumumab; lane 6, U1-59 in combination with lapatinib.

The following treatment protocol was carried out:
PBS Vehicle Group
hG control group: non-specific human IgG: 25 mg/kg, twice weekly, intraperitoneal
Treatment group antibody U1-53, 25 mg/kg, twice weekly, intraperitoneal
Treatment group antibody U1-7, 25 mg/kg, twice weekly, intraperitoneal
Treatment group antibody U1-59, 25 mg/kg, twice weekly, intraperitoneal The median tumor volumes from each control and treatment group were calculated. Administration of the antibodies resulted in growth reduction of the human non-small lung cancer xenografts when compared to tumors that had been treated with the PBS vehicle control or non-specific human IgG. See, FIG. 18 of US Publication No. 20080124345.

Example 25: Human Anti-HER-3 Antibodies Inhibit Human Pancreatic Tumor Growth in Balb/C-Mice Human pancreatic BxPC3 tumor cells were suspended in medium with a 2:1 ratio of Matrigel to a final concentration of $5 \times 10^6$ cells per ml. 0.2 ml of cell suspension were injected s.c. into the right flank of 5-7-week-old female BalbC nu/nu mice. A total of 100 mice were used.

The mice were randomly distributed into control and treatment groups. The treatment started on the same day. The treatment duration was 27 days.

The following treatment protocol was carried out:
hIgG control group: non-specific human IgG2, 25 mg/kg, twice weekly, intraperitoneal
Treatment group antibody U1-53, 25 mg/kg, twice weekly, intraperitoneal
Treatment group antibody U1-7, 25 mg/kg, twice weekly, intraperitoneal
Treatment group antibody U1-59, 25 mg/kg, weekly, intraperitoneal
Gemzar treatment group, gemcitabine, 80 mg/kg, weekly, intraperitoneal The median tumor volumes from each control and treatment group were calculated. Administration of the antibodies resulted in growth reduction of the human pancreatic tumors when compared to tumors that had been treated with non-specific human IgG or with Gemzar. See, FIG. 19 of US Publication No. 20080124345.

The inhibition of HER-3 in the human pancreatic tumors could also be shown in a pharmacodynamic experiment. The BxPC3 tumor xenografts were grown as described above. 3 mice were treated with 500 µg of an IgG1 control antibody and 3 mice were treated with 500 µg of the anti-HER-3 antibody U1-59. The mice were treated on day 1 and day 4 and then sacrificed on day 5 to measure the antibody-dependent inhibition of HER-3 phosphorylation (pHER-3).

The tumors were homogenized in a standard RIPA buffer with protease inhibitors. 50 µg clear lysate was separated on a 4-20% Tris-glycine gel, transferred onto a nitrocellulose membrane and blocked in 3% bovine serum albumin (BSA). Immunoblotting was performed using an anti-pHER-3 antibody (antibody 21D3, Cell Signaling technology). An anti-actin antibody (AB a-2066, Sigma) was used as a control.

Expression was detected by enhanced chemiluminescence (Amersham Biosciences, Piscataway, N.J.). The images were captured with the Versadoc 5000 Imaging System (BioRad, Hercules, Calif.). After administration of the human anti-HER-3-antibody U1-59, phosphorylation of HER-3 was no longer detectable. See, FIG. 20 of US Publication No. 20080124345. Thus, the antibodies were capable of significantly reducing HER-3 activation in human pancreatic tumor cells.

Figure 2:
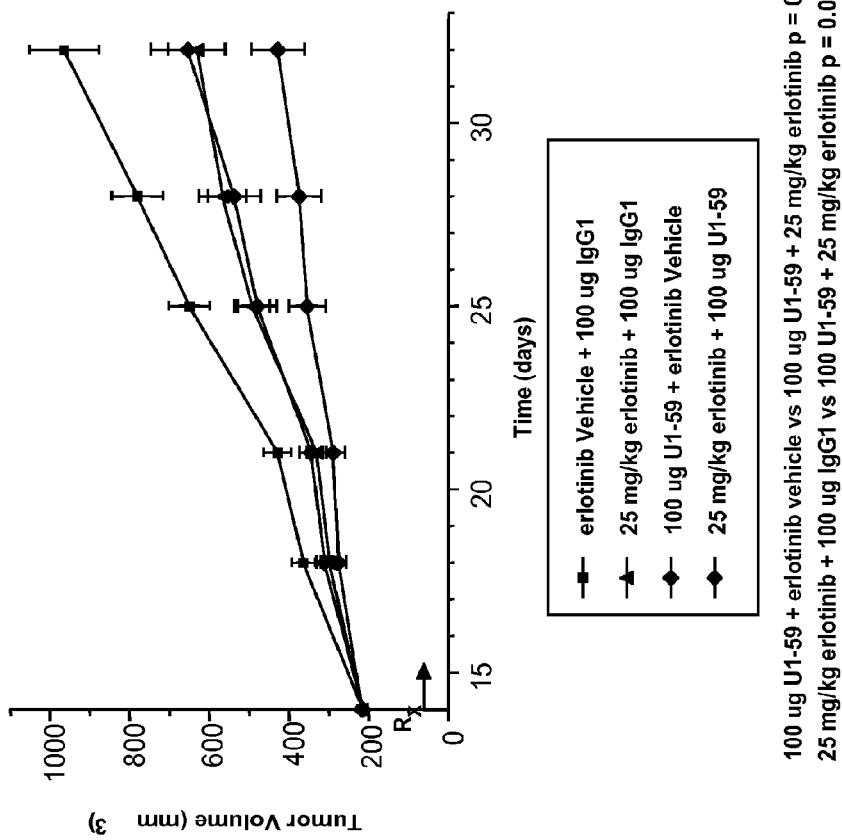
FIG. 2 is a graph plotting the effects of a human anti-HER-3 antibody and erlotinib, either alone or in combination, on Calu-3 growth.

Example 26: U1-59 Inhibits Tumor Growth in Combination with a Second Agent in Xenograft Studies Calu-3 NSCLC tumor xenograft models were used to evaluate the effectiveness of an anti-HER-3 antibody (U1-59), either alone or in combination with panitumamab or erlotinib. To determine in vivo efficacy, mice bearing ~200 mm³ Calu-3 NSCLC xenografts were treated twice a week with anti-HER family inhibitors or control. Other experiments were done with A549 cells. In the combination studies with panitumumab, IgG1 was used as a negative control for U1-59, and IgG2 was used as a negative control for panitumumab. As shown in FIG. 1, while 100 µg of U1-59 or 100 µg of panitumumab alone greatly reduced tumor growth as compared to control, the combination of 100 µg of each of the two agents completely inhibited tumor growth ($p<0.0001$ for the combination vs. either agent alone). In the combination studies with erlotinib, IgG1 was used as a negative control for U1-59, and erlotinib vehicle was used as a negative control for erlotinib. As shown in FIG. 2, the combination of 100 µg U1-59 and 25 µg erlotinib had a greater inhibitory effect than either agent alone. The combination of UI-59 with erlotinib was significantly more effective than U1-59 alone ($p=0.0376$).

Figure 3:
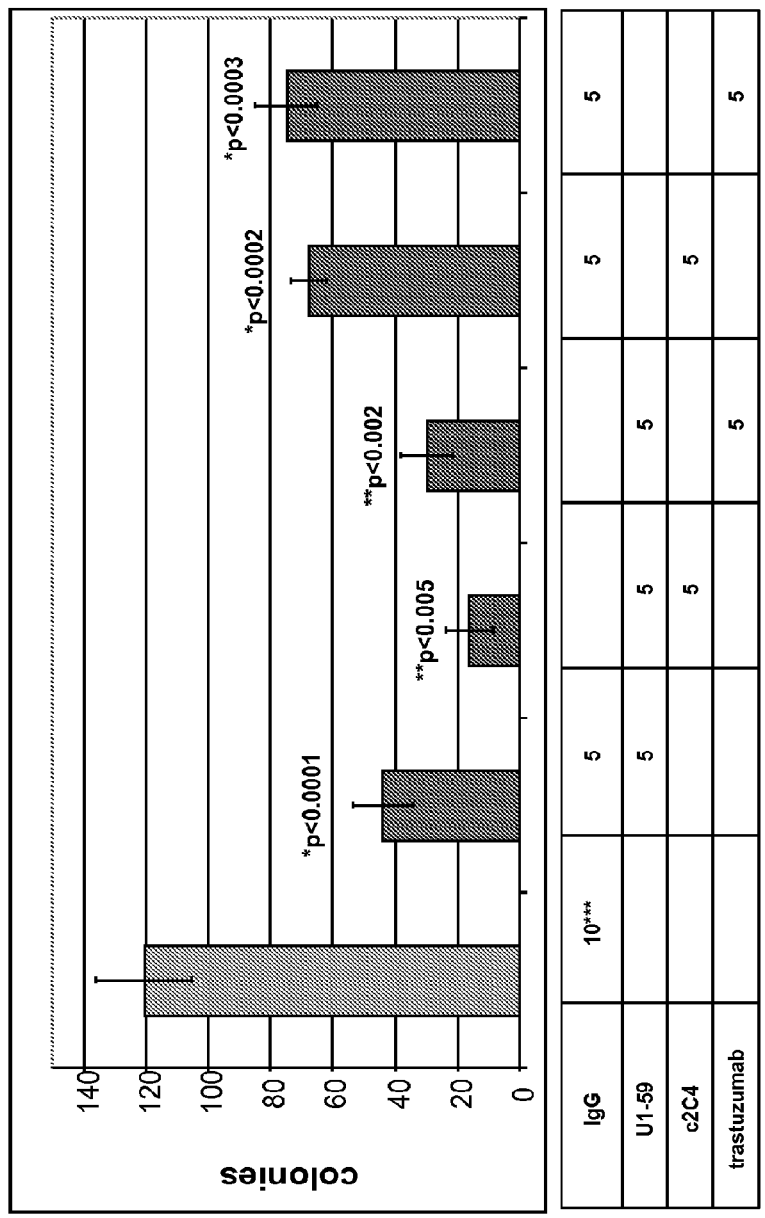
FIG. 3 is a graph plotting the effects of a human anti-HER-3 antibody, either alone or in combination with c2C4 (a HER2 dimerization inhibitor), or trastuzumab on basal anchorage-independent growth of SkBr-3 breast cancer cells.
Figure 4:
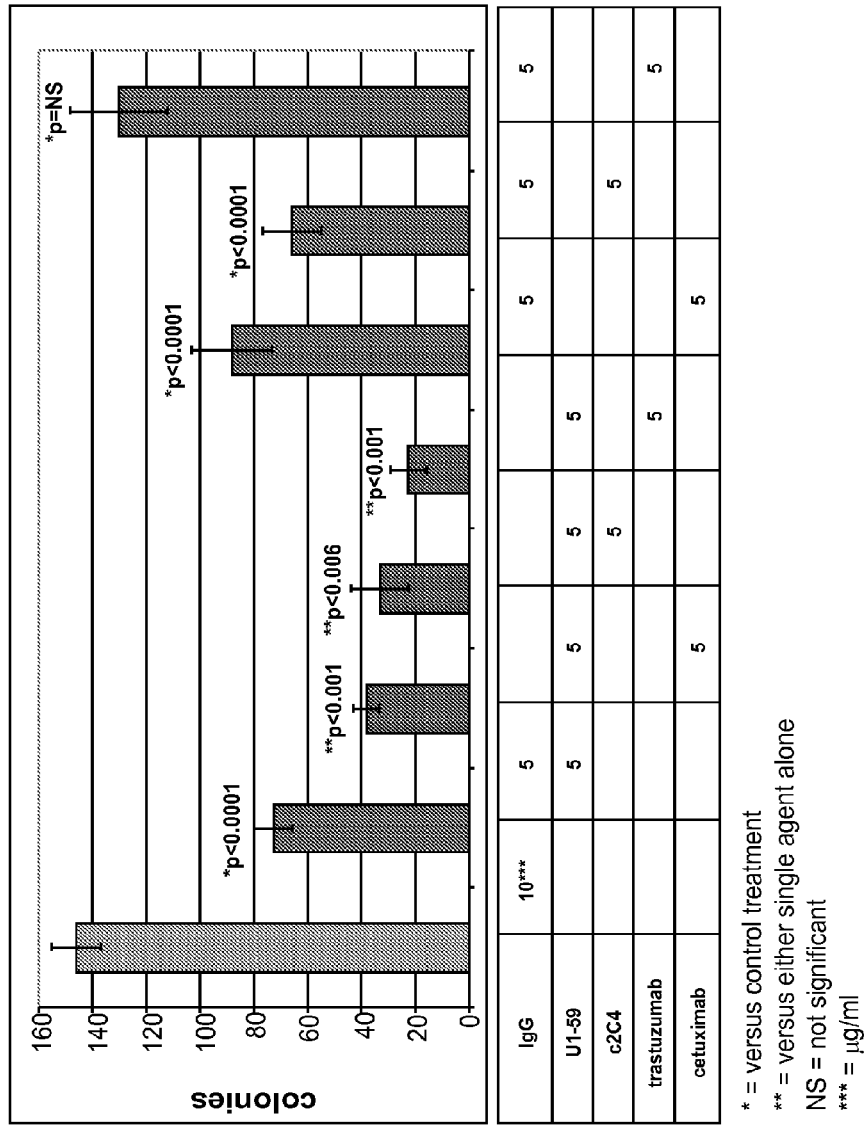
FIG. 4 is a graph plotting the effects of a human anti-HER-3 antibody, either alone or in combination with c2C4, trastuzumab, or cetuximab, on HRG stimulated anchorage-independent growth of SkBr-3 breast cancer cells.
Figure 5:
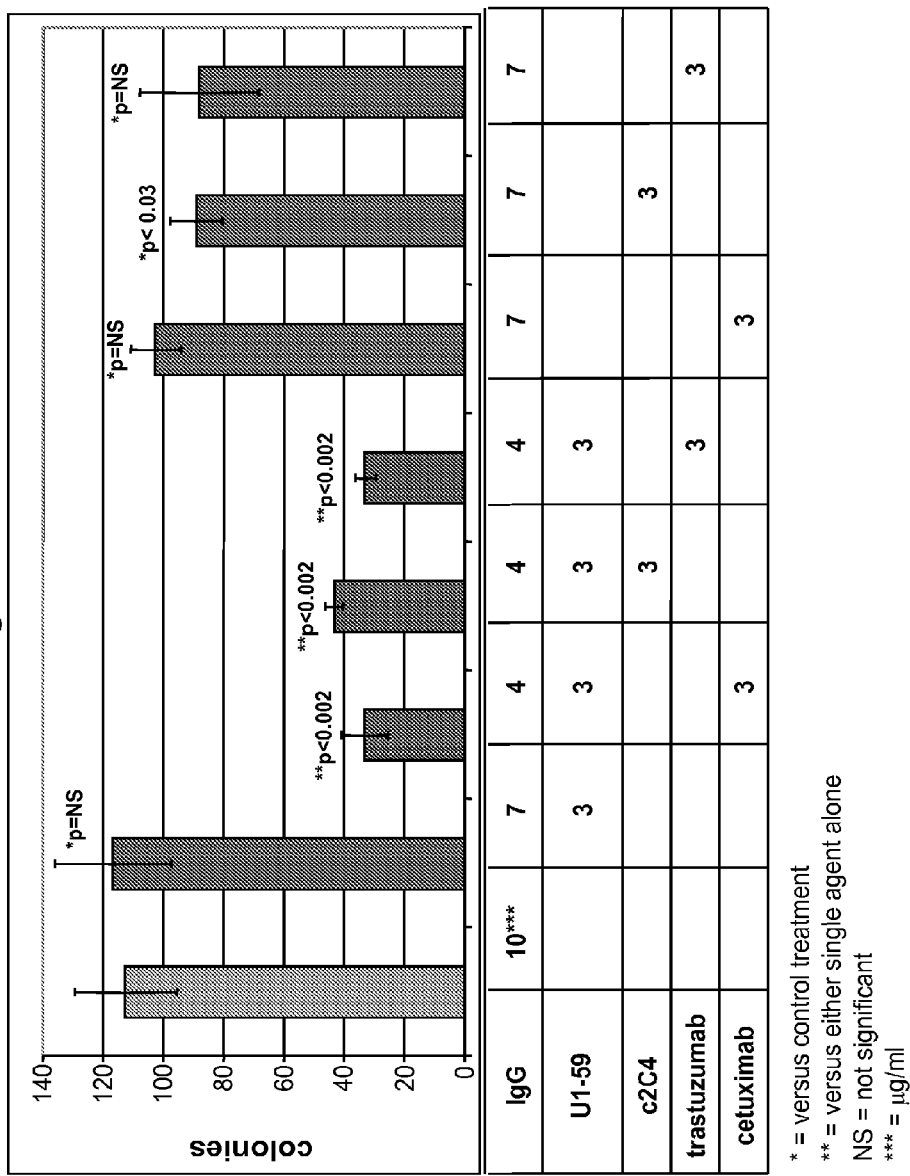
FIG. 5 is a graph plotting the effects of a human anti-HER-3 antibody, either alone or in combination with 2C4), trastuzumab, or cetuximab, on basal anchorage-independent growth of MDA-MB-435 ovarian cancer cells.

Example 27: U1-59 in Combination with HER Inhibitors Inhibits Anchorage-Independent Growth of Breast and Ovarian Cancer Cells Experiments were conducted to evaluate the effect of U1-59 in combination with the HER inhibitors pertuzumab, trastuzumab, or cetuximab on anchorage-independent growth of SkBr-3 (basal or HRG stimulated) and MDA-MB-435 (basal) cancer cells. IgG was used as a negative control for all studies. Tumor cell colonies formed in the absence or presence of HRG for 6 to 10 days and were stained with MTT for 4 to 6 hours and quantified. U1-59 as a single agent did not inhibit colony growth of MDA-MB 435 cells, but inhibited colony growth by 50% in the SkBr-3 cells ($p<0.001$), and up to 95% when combined with other HER inhibitors ($p<0.05$). For example, the combination of 5 µg/ml pertuzumab or trastuzumab with 5 µg/ml U1-59 reduced anchorage-independent growth in basal SkBr-3 breast cancer cells significantly more than either agent alone (FIG. 3), pertuzumab, trastuzumab, or cetuximab in combination with U1-59 were significantly ($p<0.006$) more effective than U1-59 alone in HRG stimulated SkBr-3 cells (FIG. 4). Similarly, combinations of U1-59 with either pertuzumab, trastuzumab or cetuximab inhibited colony formation of basal ovarian cancer cells (MDA-MB-435) significantly better ($p<0.002$) than U1-59 alone (FIG. 5).

Figure 6A:
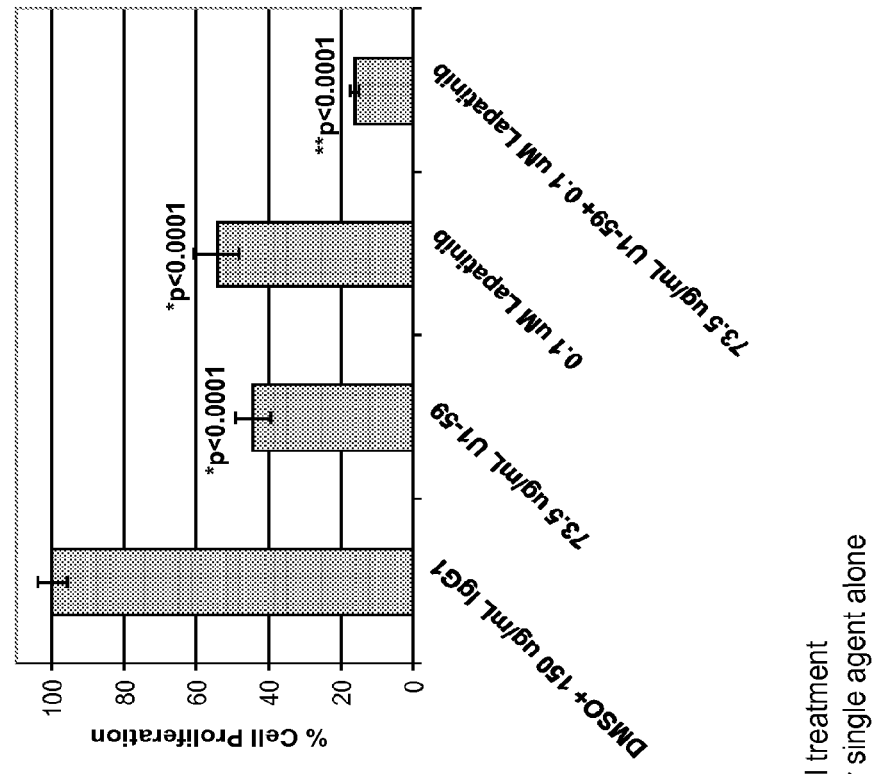
Figure 6B:
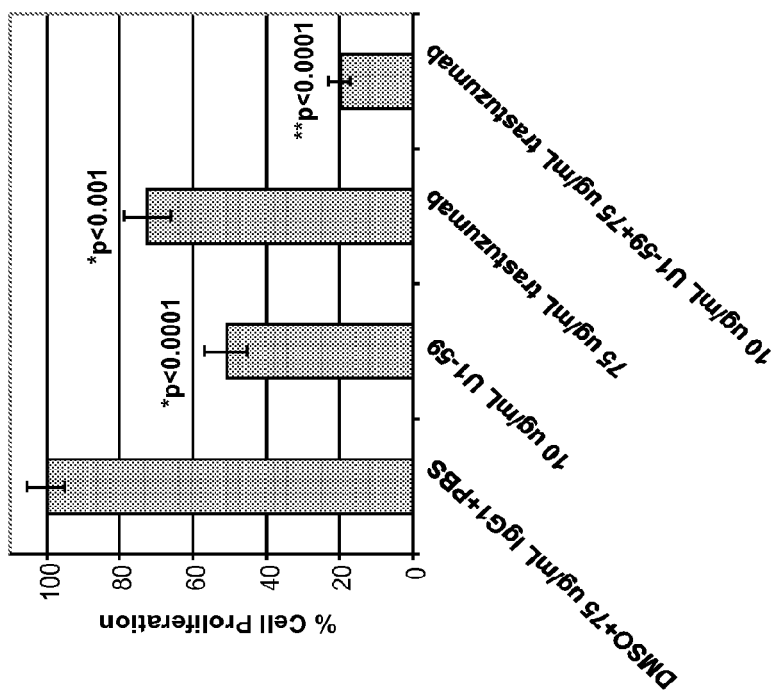

Example 28: U1-59 in Combination with HER-2 Inhibitors or Chemotherapeutic Agents Reduces Cancer Cell Proliferation Studies were conducted to evaluate the effect of U1-59 in combination with HER-2 inhibitors or chemotherapeutic agents on cancer cell proliferation. In particular, the following experiments were conducted in MDA-MB-175 VII breast cancer cells:

U1-59 and Trastuzumab
    Control=DMSO+75 µg/ml IgG1+PBS
    10 µg/ml U1-59
    75 µg/ml Trastuzumab
    10 µg/ml U1-59+75 µg/ml Trastuzumab
U1-59 and Lapatinib
    Control=DMSO+150 µg/ml IgG1
    73.5 µg/ml U1-59
    0.1 µM Lapatinib
    73.5 µg/ml U1-59+0.1 µM Lapatinib
U1-59 and Gemcitibine
    Control=DMSO+75 µg/ml IgG1+PBS
    10 µg/ml U1-59
    1 µg/ml Gemcitibine
    10 µg/ml U1-59+1 µg/ml Gemcitibine
U1-59 and Cisplatin
    Control=DMSO+75 µg/ml IgG1+PBS
    10 µg/ml U1-59
    1 µg/ml Cisplatin
    10 µg/ml U1-59+1 µg/ml Cisplatin MDA-MB-175VII breast cancer cells were incubated with U1-59 and/or the other agents for 1 hour prior to HRG stimulation. After four days, the growth of treated cells was measured with ALOMAR BLUE™. In these assays, U1-59 reduced HRG-stimulated MDA-MB-175VII proliferation up to 40% ($p<0.05$) as a single agent, and up to 80% ($p<0.05$) when combined with trastuzumab or lapatinib (FIGS. 6A and 6B). Of note, additive activity also was observed in MDA-MB-175VII cells when U1-59 was combined with standard of care chemotherapeutics (gemcitabine and cisplatin; $p<0.05$ vs. either single agent alone) (FIGS. 6C and 6D). In each of these experiments, the combination of U1-59 with the HER-2 inhibitor was more effective at reducing proliferation of MDA-MB175VII cells than either agent alone.

Figure 7:
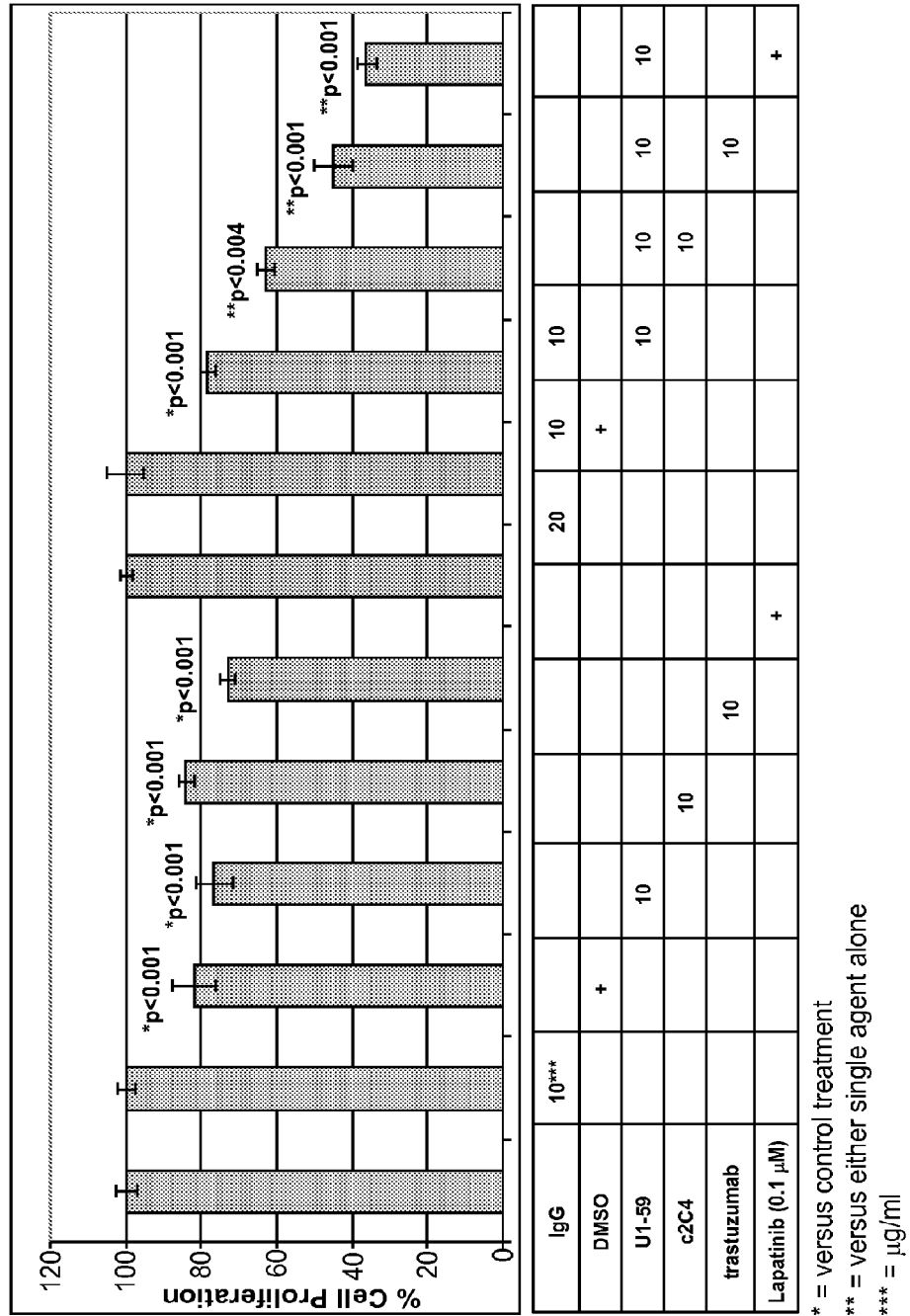
FIG. 7 is a graph plotting the effects of a human anti-HER-3 antibody, either alone or in combination with c2C4, trastuzumab, or lapatinib, on HRG stimulated proliferation of ZR-75-30 breast cancer cells.
Figure 8:
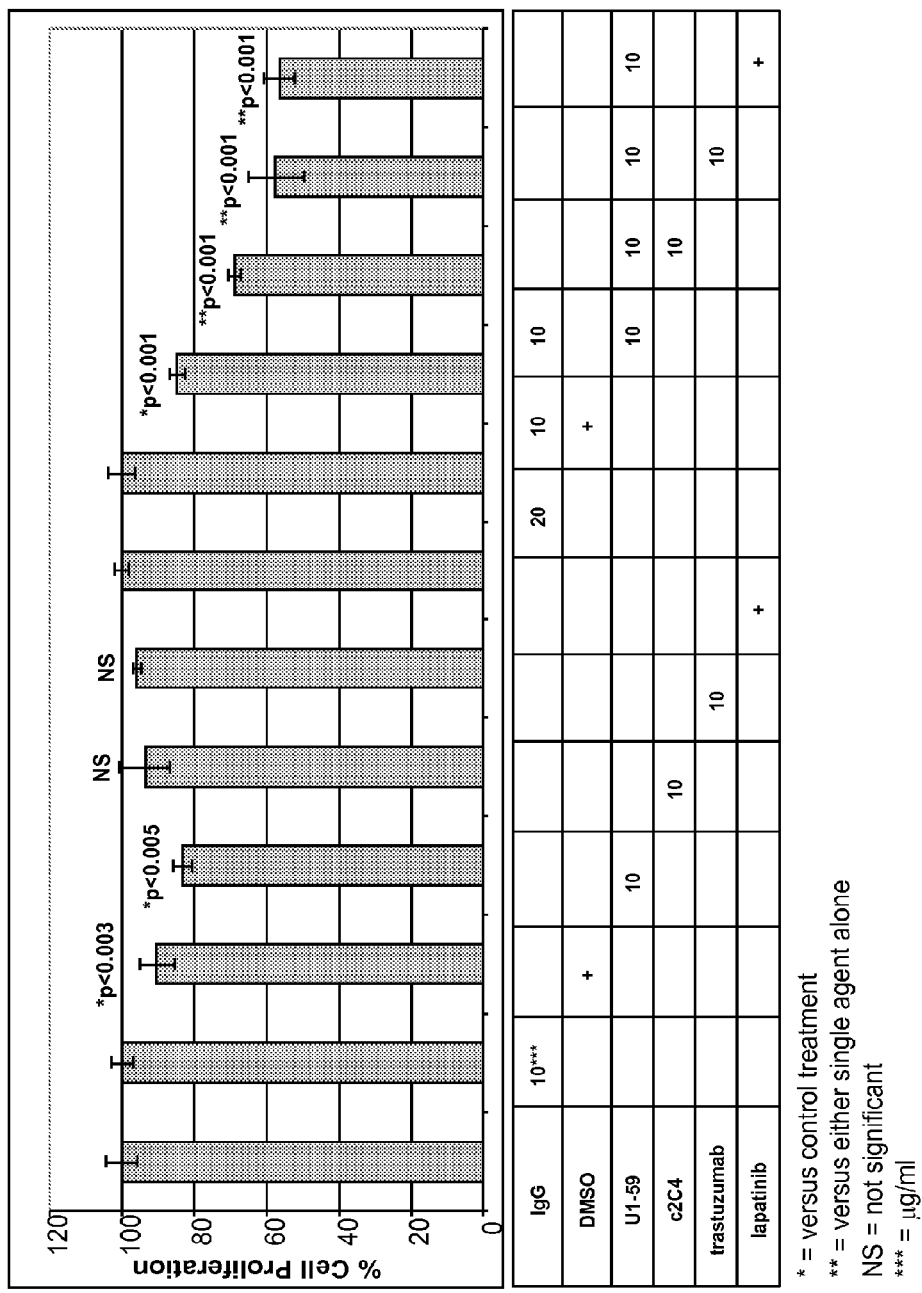
FIG. 8 is a graph plotting the effects of a human anti-HER-3 antibody, either alone or in combination with c2C4, trastuzumab, or lapatinib, on HRG stimulated proliferation of BT474 breast cancer cells.
Figure 9:
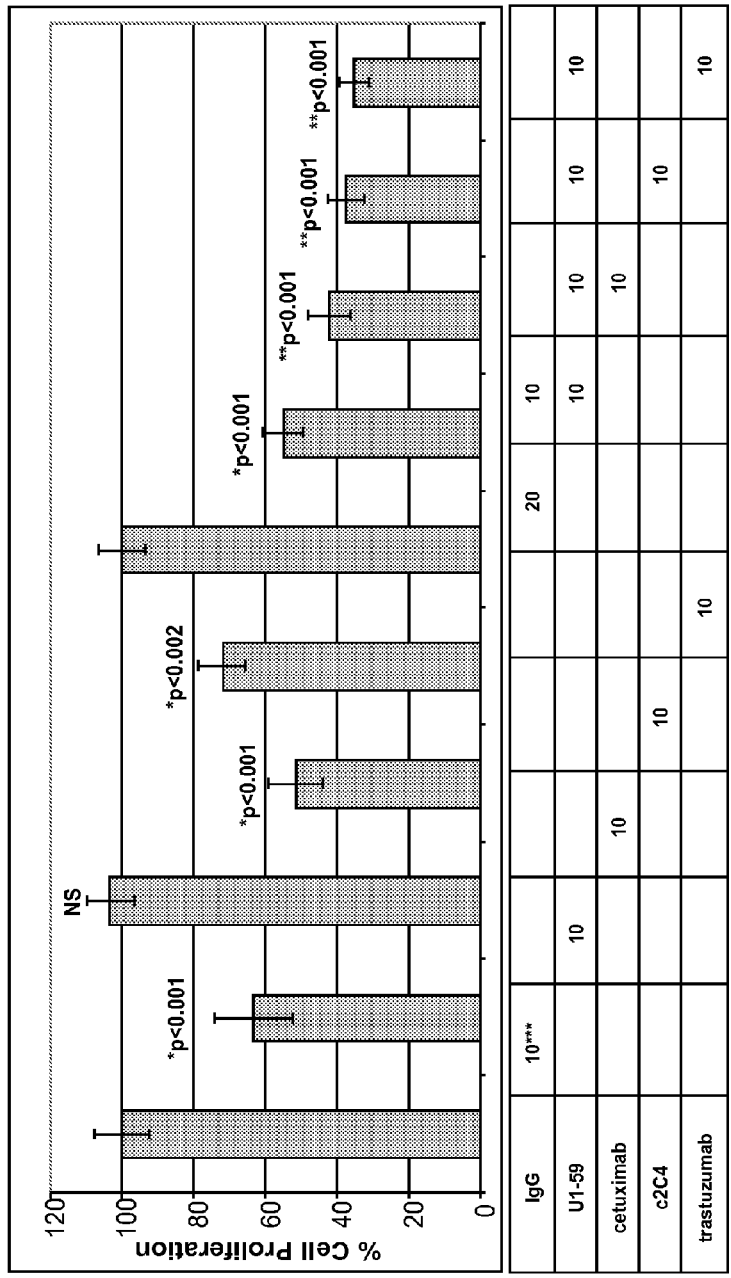
FIG. 9 is a graph plotting the effects of a human anti-HER-3 antibody, either alone or in combination with cetuximab, c2C4, or trastuzumab, on proliferation of HRG stimulated DLD-1 colon cancer cells.
Figure 10:
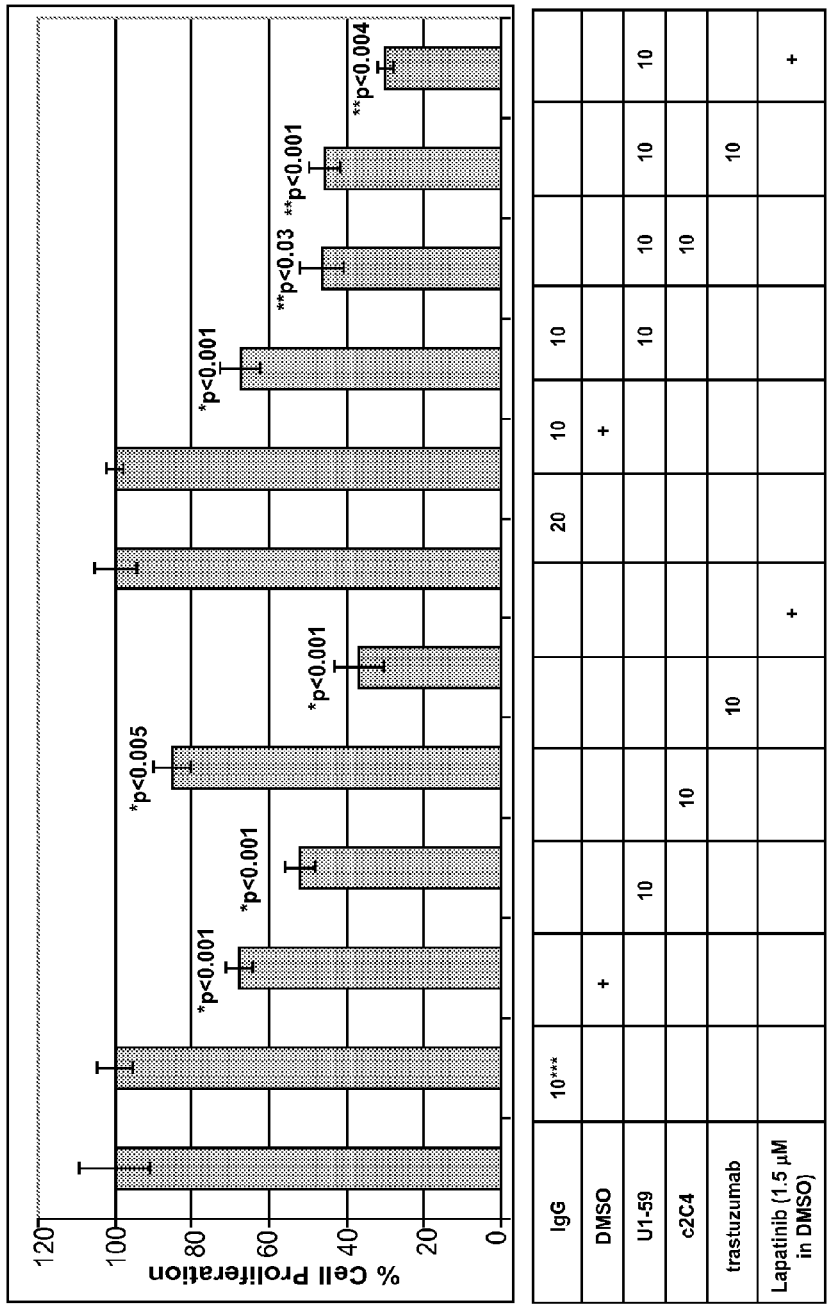
FIG. 10 is a graph plotting the effects of a human anti-HER-3 antibody, either alone or in combination with c2C4, or trastuzumab, or lapatinib on HRG stimulated proliferation of HCC-1569 breast cancer cells.
Figure 11:
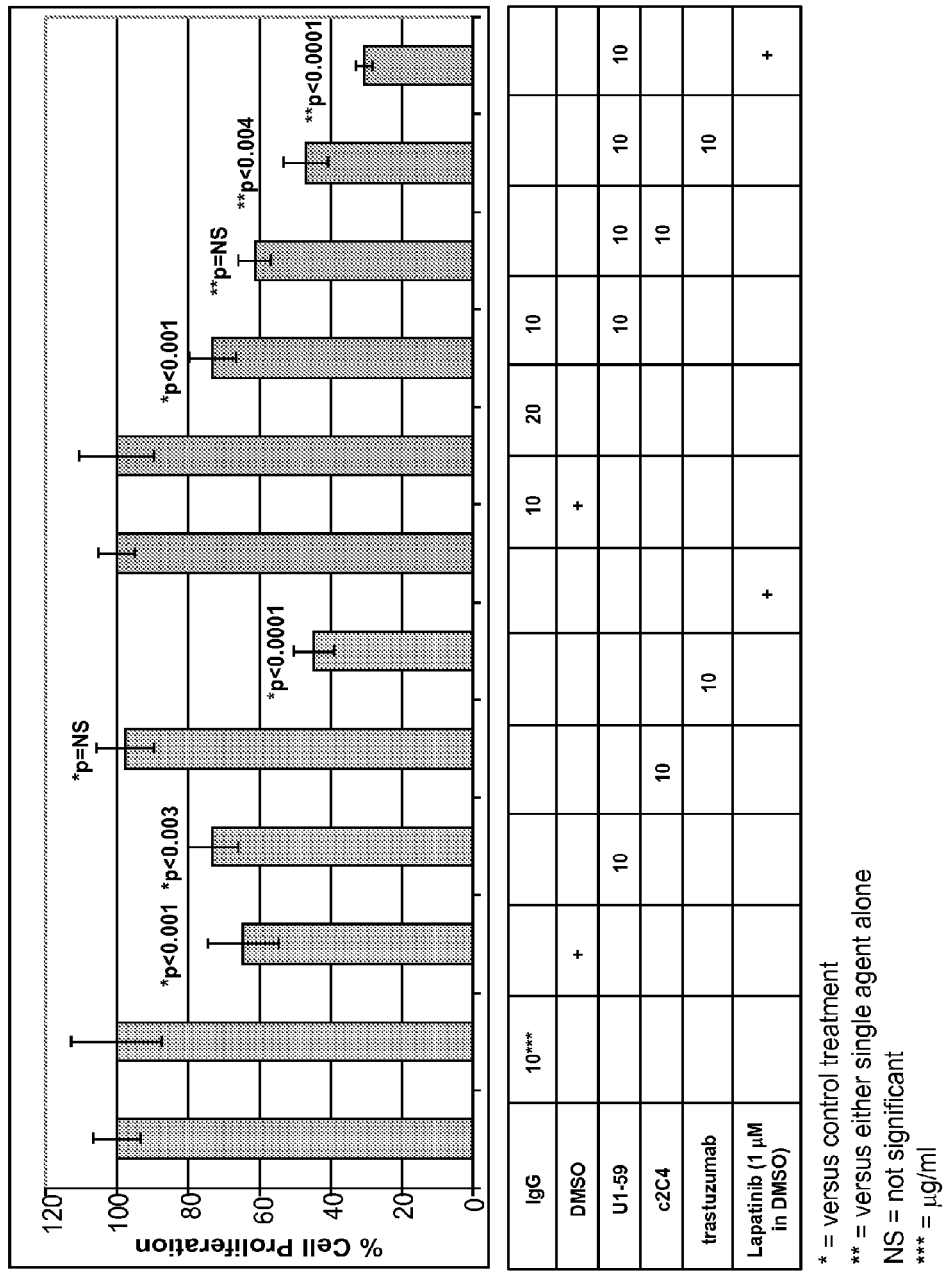
FIG. 11 is a graph plotting the effects of a human anti-HER-3 antibody, either alone or in combination with 2C4, trastuzumab, or lapatinib, on HRG stimulated proliferation of SkBr-3 breast cancer cells.

Similar experiments were conducted with U1-59 and pertuzumab, trastuzumab, or lapatinib in HRG stimulated ZR-75-30 breast cancer cells and HRG stimulated BT474 breast cancer cells (FIGS. 7 and 8, respectively). In each case, the combination of U1-59 and lapatinib had the greatest inhibitory effect on cell proliferation. Compared to single agent treatment alone, the combination of U1-59 with pertuzumab or trastuzumab or lapatinib was significantly ($p<0.004$) more effective than U1-59 alone. Combining U1-59 with one or more of pertuzumab, trastuzumab, and cetixumab in HRG stimulated DLD-1 colon cancer cells and HRG stimulated HCC-1569 breast cancer cells had similar effects, as shown in FIGS. 9 and 10. In addition, combinations of U1-59 with trastuzumab or lapatinib in HRG stimulated SkBr-3 breast cancer cells also were more effective than U1-59 alone (p<0.004) (FIG. 11).

Figure 12:
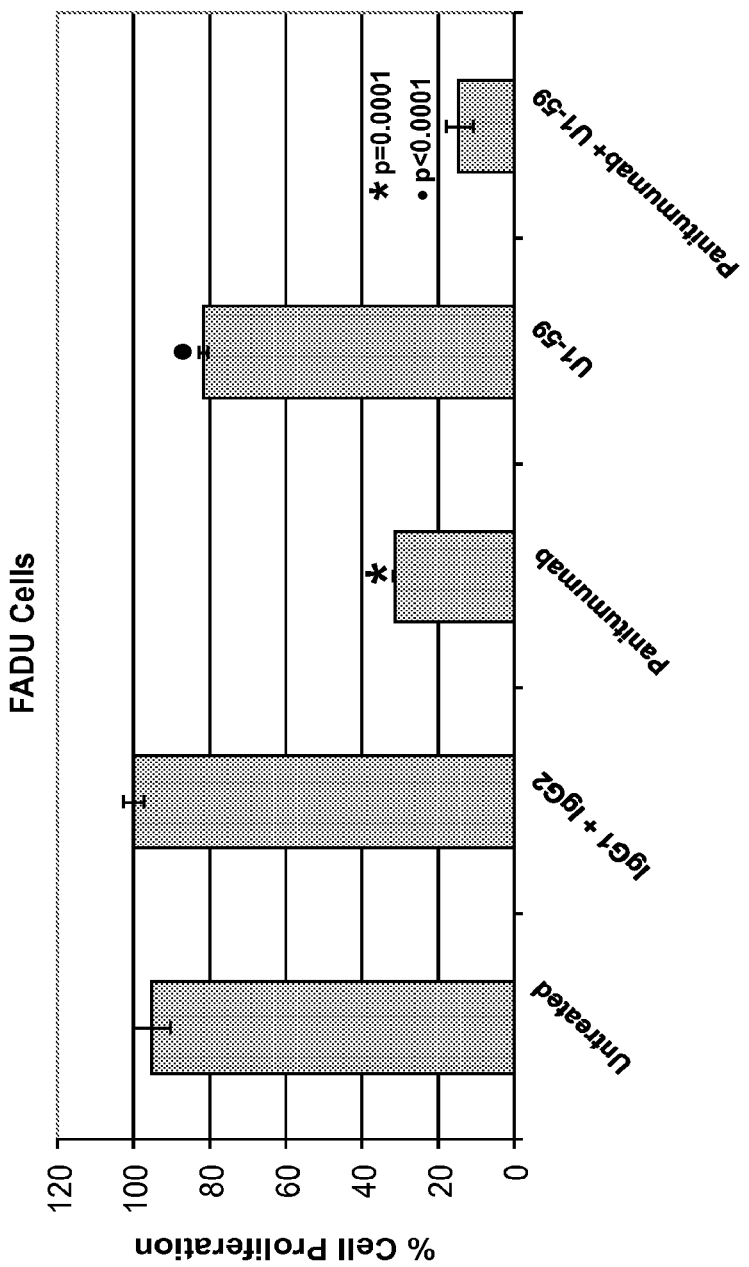
FIG. 12 is a graph plotting the effects of a human anti-HER-3 antibody, either alone or in combination with panitumumab on proliferation of FaDu head and neck cancer cells.

In additional experiments, Head and Neck cancer cells (FaDu) were cultured in growth medium (MEM+10% FBS+1×PSG) and treated with IgG controls, U1-59, panitumumab or a combination of U1-59 with panitumab. After incubation for 5 days at 37° C., proliferation was measured with ALOMAR BLUE™. As a single agent, U1-59 reduced proliferation of FaDu cells by 15% to 20%, whereas the combination of U1-59 with panitumumab resulted in more than 80% reduction. The combination of U1-59 with panitumumab resulted in a significant (p=0.001 vs. best single agent activity) improvement over the use of either agent alone (FIG. 12).

Example 29: U1-59 in Combination with Other HER Inhibitors Inhibits Signal Transduction The effect of U1-59 either alone or in combination with cetuximab, pertuzumab, trastuzumab, or lapatinib on signal transduction was measured in unstimulated MDA-MB-175VII breast cancer cells, HRG stimulated SkBr-3 breast cancer cells, HRG stimulated Ls174T colon cancer cells, and HRG stimulated HCC-1569 breast cancer cells. Cells were treated with agents as indicated in FIGS. 13-16, and phosphorylation of HER-3, Akt, and ERK was evaluated by Western blotting with phospho-specific antibodies. The combination of U1-59 with either pertuzumab, trastuzumab, or lapatinib further reduced phosphorylation of HER-3, Akt and ERK in all cell types tested as compared to single agent treatments. The combination of U1-59 with cetuximab appeared to synergize less efficiently in these assays.

Similar studies were conducted in A549 alveolar epithelial cells (FIG. 17) and Calu3 NSCLC cells (FIG. 18) treated with U1-59 alone or U1-59 in combination with panitumumab or lapatinib, using Western blotting to evaluate phosphorylation of Akt, EGF-R, HER-2, HER-3, HER-4, and ERK. The combination of U1-59 with panitumumab had the greatest apparent effect on HER-3 phosphorylation in A549 cells, while the combination was more effective with regard to Akt and EGF-R phosphorylation in Calu3 cells.

Additional experiments were conducted to evaluate the in vitro efficacy and anchorage-independent growth of A549 cells treated with 10 µg/mL U1-59, other HER family Abs, or control mAb in serum containing medium. Tumor cell colonies formed in the absence of exogenous ligand for 10 days and were stained with MTT and quantified using a Scanalyzer HTS camera imaging system. U1-59 inhibited colony growth by 50% (p<0.001) in the A549 cell line and resulted in tumor stasis in the A549 NSCLC xenograft model vs. IgG control or other HER mAbs (p<0.05).

These results demonstrate that U1-59 inhibits proximal and distal HER-3 oncogenic signaling in breast cell lines in vitro, and that breast cancer cells are sensitive to U1-59 treatment as a single agent and in combination with anti-HER agents.

Example 30: U1-59 Sensitizes Lapatinib for in Vivo Activity

Figure 19:
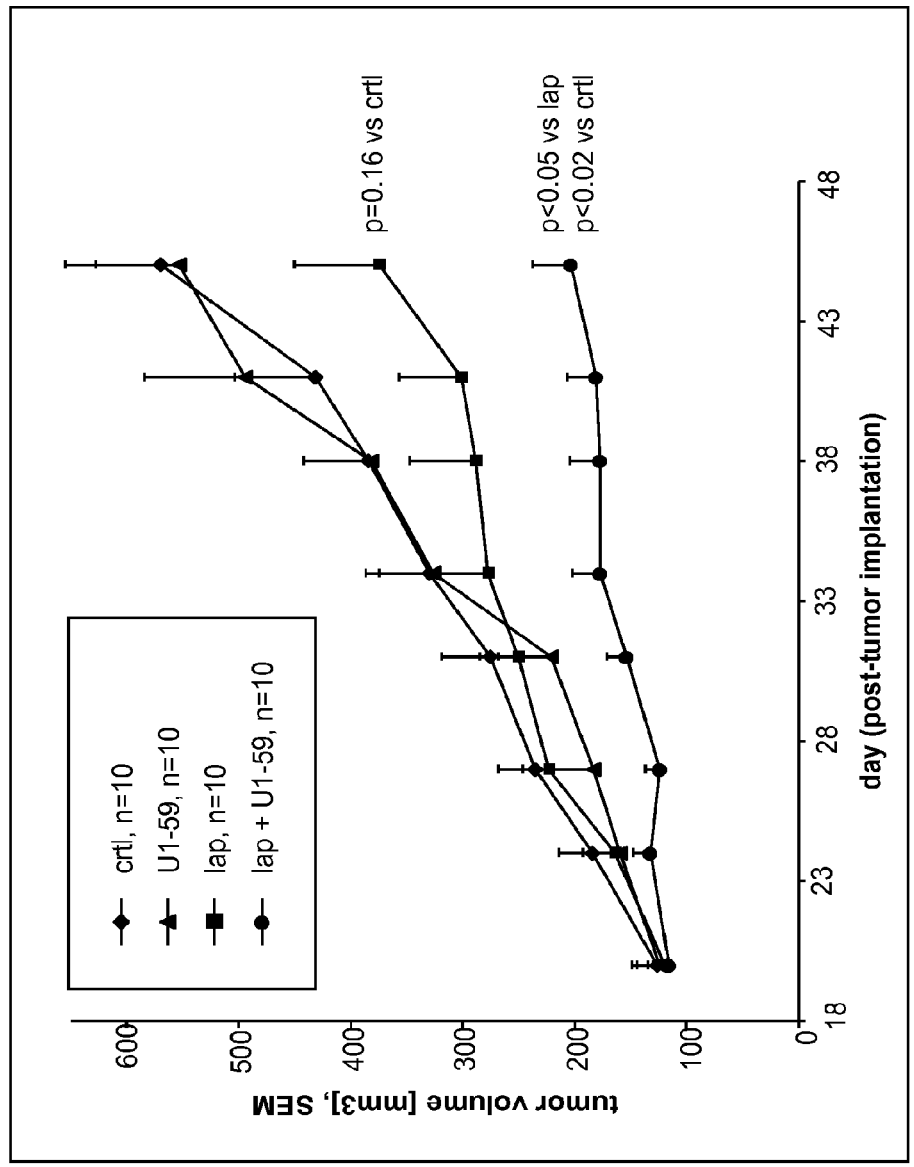
FIG. 19 is a graph plotting the effects of a human anti-HER-3 antibody and lapatinib, either alone or in combination, on breast cancer xenograft tumor (HCC-1569) growth.

To evaluate the combined effects of U1-59 and lapatinib in vivo, mice were implanted with human breast cancer cells (HCC-1569) and treated with U1-59 and lapatinib either alone or in combination. Tumors were allowed to reach sizes greater than or equal to 100 mm$^3$, and mice were subsequently treated with control, lapatinib, U1-59, or a combination of U1-59 and lapantinib. As shown in FIG. 19, U1-59 alone did not inhibit HCC-1569 tumor growth, and lapatinib alone caused some, but not significant tumor growth inhibition compared to the control (p=0.16). The combination of lapatinib with U1-59, however, resulted in significant inhibition of tumor growth (p<0.02 vs. control or p<0.05 vs. lapatinib).

These results indicate that the combination of U1-59 and lapatinib resulted in synergistic inhibition of HCC-1569 tumor growth in vivo. This result is particularly interesting and encouraging as it shows that even tumor types that may not respond to U1-59 or lapatinib alone, can be very effectively treated with the combination of both.

Example 31: Use of Anti-HER-3 Antibodies as Diagnostic Agents

Anti-HER-3 mAb can be used in the diagnostic of malignant diseases. HER-3 is expressed on tumor cells in a very distinct way compared to normal tissue and, therefore, an expression analysis of HER-3 would assist in the primary diagnosis of solid tumors, staging and grading of solid tumors, assessment of prognostic criteria for proliferative diseases and neoplasias and risk management in patients with HER-3 positive tumors.

A. Detection of HER-3 Antigen in a Sample

An Enzyme-Linked Immunosorbent Assay (ELISA) for the detection of HER-3 antigen in a sample is developed. In the assay, wells of a microtiter plate, such as a 96-well microtiter plate or a 384-well microtiter plate, are adsorbed for several hr with a first fully human monoclonal antibody directed against the HER-3 antigen. The immobilized antibody serves as a capture antibody for any of the HER-3 antigen that may be present in a test sample. The wells are rinsed and treated with a blocking agent such as milk protein or albumin to prevent nonspecific adsorption of the analyte.

Subsequently the wells are treated with a test sample suspected of containing the HER-3 antigen, or with a solution containing a standard amount of the HER-3 antigen. Such a sample is, for example, a serum sample from a subject suspected of having levels of circulating HER-3 antigen considered to be diagnostic of a pathology. After rinsing away the test sample or standard, the wells are treated with a second fully human monoclonal anti-HER-3 antibody that is labelled by conjugation with biotin. The labeled anti-HER-3 antibody serves as a detecting antibody. After rinsing away excess secondary antibody, the wells are treated with avidin-conjugated horseradish peroxidase (HRP) and a suitable chromogenic substrate. The concentration of the HER-3 antigen in the test samples is determined by comparison with a standard curve developed from the standard samples.

B. Detection of HER-3-Antigen in Immunohistochemistry (IHC)

In order to determine HER-3-antigen in tissue sections by IHC, Paraffin-embedded tissues are first deparaffinized in xylene for 2×5 min and then hydrated with 100% Ethanol 2×3 min, 95% Ethanol 1 min and rinsed in distilled water. Antigenic epitopes masked by formalin-fixation and paraffin-embedding are exposed by epitope unmasking, enzymatic digestion or saponin. For epitope unmasking paraffin sections are heated in a steamer, water bath or microwave oven for 20-40 min in a epitope retrieval solution as for example 2N HCl solution (pH 1.0). In the case of an enzyme digestion, tissue sections are incubated at 37° C. for 10-30 minutes in different enzyme solutions such as proteinase K, trypsin, pronase, pepsin etc.

After rinsing away the epitope retrieval solution or excess enzyme, tissue sections are treated with a blocking buffer to prevent unspecific interactions. The primary antibody is incubated at appropriate dilutions in dilution buffer for 1 hour at room temperature or overnight. Excess primary antibody is rinsed away and sections are incubated in peroxidase blocking solution for 10 min at room temperature. After another washing step, tissue sections are incubated with a secondary antibody labelled with a group that might serve as an anchor for an enzyme. Examples therefore are biotin labelled secondary antibodies that are recognized by streptavidin coupled horseradish peroxidase. Detection of the antibody/enzyme complex is achieved by incubating with a suitable chromogenic substrate.

C. Determination of HER-3 Antigen Concentration in Serum of Patients

A sandwich ELISA is developed to quantify HER-3 levels in human serum. The two fully human monoclonal anti-HER-3 antibodies used in the sandwich ELISA, recognized different domains on the HER-3 molecule and do not compete for binding, for example (see, Example 8). The ELISA is performed as follows: 50 µl of capture anti-HER-3 antibody in coating buffer (0.1 M NaHCO$_3$, pH 9.6) at a concentration of 2 µg/ml were coated on ELISA plates (Fisher). After incubation at 4° C. overnight, the plates are treated with 200 µl of blocking buffer (0.5% BSA, 0.1% Tween 20, 0.01% Thimerosal in PBS) for 1 hr at 25° C. The plates were washed (3×) using 0.05% Tween 20 in PBS (washing buffer, WB). Normal or patient sera (Clinomics, Bioreclaimation) are diluted in blocking buffer containing 50% human serum. The plates are incubated with serum samples overnight at 4° C., washed with WB, and then incubated with 100 µl/well of biotinylated detection anti-HER-3 antibody for 1 hr at 25° C. After washing, the plates are incubated with HRP-Streptavidin for 15 min, washed as before, and then treated with 100 µl/well of o-phenylenediamine in H$_2$O$_2$ (Sigma developing solution) for color generation. The reaction is stopped with 50 µl/well of H$_2$SO$_4$ (2 M) and analyzed using an ELISA plate reader at 492 nm. The concentration of HER-3 antigen in serum samples is calculated by comparison to dilutions of purified HER-3 antigen using a four parameter curve fitting program.

Staging of Cancer in a Patient:

Based on the results set forth and discussed under items A, B and C, it is possible to stage a cancer in a subject based on expression levels of the HER-3 antigen. For a given type of cancer, samples of blood are taken from subjects diagnosed as being at various stages in the progression of the disease, and/or at various points in the therapeutic treatment of the cancer. The concentration of the HER-3 antigen present in the blood samples is determined using a method that specifically determines the amount of the antigen that is present. Such a method includes an ELISA method, such as the method described under items A and B. Using a population of samples that provides statistically significant results for each stage of progression or therapy, a range of concentrations of the HER-3 antigen that may be considered characteristic of each stage is designated.

In order to stage the progression of the cancer in a subject under study, or to characterize the response of the subject to a course of therapy, a sample of blood is taken from the subject and the concentration of the HER-3 antigen present in the sample is determined. The concentration so obtained is used to identify in which range of concentrations the value falls. The range so identified correlates with a stage of progression or a stage of therapy identified in the various populations of diagnosed subjects, thereby providing a stage in the subject under study.

Anti-HER-3 antibodies as described herein are used for treatment of certain hyperproliferative or HER-3 associated disorders based on a number of factors, such as HER-3 expression, for example. Tumor types such as breast cancer, gastrointestinal cancer, pancreatic cancer, prostate cancer, ovarian cancer, stomach cancer, endometrial cancer, salivary gland cancer, lung cancer, kidney cancer, colon cancer, colorectal cancer, thyroid cancer, bladder cancer, glioma, melanoma, and other HER-3 expressing or overexpressing cancers are examples of indications that are treated with a combination therapy as described herein, although indications are not limited to those in the preceding list. In addition, the following groups of patients may benefit from treatment as described herein:

Patients not eligible for treatment with anti-HER-2 mAb
    Patients with resistance to anti-HER-1 mAb or small molecule anti-EGF-R inhibitor
    Patients with NSCLC resistant to erlotinib or gefitinib Anti-HER-3 antibodies are used in combination with one or more additional agents in a so called "combination therapy." Such combination therapy includes, but is not limited to, the agents disclosed herein. Combination therapy with anti-HER-3 antibodies and other agents can extend patient survival, increase time to tumor progression, or enhance quality of patient life. Protocol and administration design will address therapeutic efficacy as well as the ability to reduce the usual doses of standard therapies, such as chemotherapy or radiation therapy, for example.

Treatment of Humans with Anti-HER-3 Antibodies:

To determine the in vivo effects of anti-HER-3 antibody treatment in human patients with tumors, such human patients are injected over a certain amount of time with an effective amount of anti-HER-3 antibody. At periodic times during the treatment, the human patients are monitored to determine whether their tumors progress, in particular, whether the tumors grow and metastasize.

A tumor patient treated with the anti-HER-3 antibodies has a lower level of tumor growth and/or metastasis compared to the level of tumor growth and metastasis in tumor patients treated with the current standard of care therapeutics.

Treatment with Anti-HER-3 Antibody Conjugates:

To determine the in vivo effects of anti-HER-3 antibody conjugates, human patients or animals exhibiting tumors are injected over a certain amount of time with an effective amount of anti-HER-3 antibody conjugate. For example, the anti-HER-3 antibody conjugate administered is DM1-anti-HER-3 antibody conjugate, an auristatin-anti-HER-3 antibody conjugate or radioisotope-anti-HER-3 antibody conjugate. At periodic times during the treatment, the human patients or animals are monitored to determine whether their tumors progress, in particular, whether the tumors grow and metastasize.

A human patient or animal exhibiting tumors and undergoing treatment with, for example, DM1-anti-HER-3 antibody or radioisotope-anti-HER-3 antibody conjugates has a lower level of tumor growth and metastasis when compared to a control patient or animal exhibiting tumors and undergoing treatment with an alternate therapy. Control DM1-antibodies that may be used in animals include conjugates comprising DM1 linked to antibodies of the same isotype of the anti-HER-3 antibodies, but more specifically, not having the ability to bind to HER-3 tumor antigen. Control radioisotope-antibodies that may be used in animal tests include conjugates comprising radioisotope linked to antibodies of the same isotype of the anti-HER-3 antibodies, but more specifically, not having the ability to bind to HER-3 tumor antigen. Note: the control conjugates would not be administered to humans.

Example 33: Identifying First in Human Doses and Schedule of an Anti-HER-3 mAb Based on Preclinical Pharmacokinetic, Pharmacodynamic, and Efficacy Data Studies were conducted to use preclinical modeling to predict a minimally effective dose regimen for objective response using preclinical pharmacokinetics (PK), BxPC3 xenograft mice anti-tumor efficacy, and pharmacodynamic (PD) data.

Mice bearing ~200 mm$^3$ established BxPC3 pancreatic xenografts were treated twice per week with U1-59 at 25, 100, 200, 500 µg/mouse. Inhibition of pHER in the BxPC3 xenograft tumors was analyzed by western blotting. A PK/PD/Efficacy model (based on Simeoni et al. (2004) *Cancer Res.* 64:1094-1101) was used to prospectively select dose and schedule for further testing. To confirm the PK/PD/Efficacy model, BxPC3 pancreatic tumor-bearing mice were treated with 400 µg/mouse biweekly and 200 µg/mouse biweekly, weekly and twice a week. Interspecies scaling based on body weight (BW) was used to predict U1-59 PK parameters in human on the basis of the serum concentrations obtained in mice, rat and monkeys. The relationship between drug concentration, inhibition of pHER-3 in animals, and interspecies PK scaling was used to select the minimally effective dose for the first in human study.

U1-59 treatment of BxPC3 xenografts resulted in a statistically significant inhibition of tumor growth and pHER-3 levels in a dose and schedule dependent manner (p<0.05). Treatment with U1-59 at 400 µg/mouse biweekly and 200 µg/mouse biweekly, weekly and twice a week resulted in a 50%, 33%, 74% and 70% inhibition of tumor growth (p<0.05), a 30%, 58%, 23% and 20% inhibition of pHER-3 (quantitative Western blot) versus the IgG control treated group, respectively. Serum concentrations of U1-59 at necropsy for the respective dose groups were (mean (SD)) of 2.07 (0.97), 0.45 (0.21), 3.08 (0.82) and 34.9 (9.1) µg/mL, respectively. The estimated trough concentration needed to achieve 90% maximal pHER-3 inhibition (IC$_{90}$) was estimated to be ~3 µg/ml. The PK/PD/efficacy model developed predicted the mean tumor volume ($R^2$=0.925). The clearance (CL) and initial volume of distribution (Vd) in man were estimated to be 11 mL/day/kg and 28 mL/kg. Comparison of simulated human PK profiles suggested that biweekly doses of >3 mg/kg, which should exhibit linear PK, may result in >90% pHER-3 inhibition during two week dosing interval.

The anti-tumor efficacy in the BxPC3 pancreatic xenograft model was correlated with an increased serum concentration of U1-59 and a decrease in pHER-3 levels, allowing for development of a PK/PD/Efficacy relationship. This relationship was used to determine a dose and schedule for U1-59 to investigate in a first in human (FIH) study.

Example 34: Reactivation Studies

Figure 20:
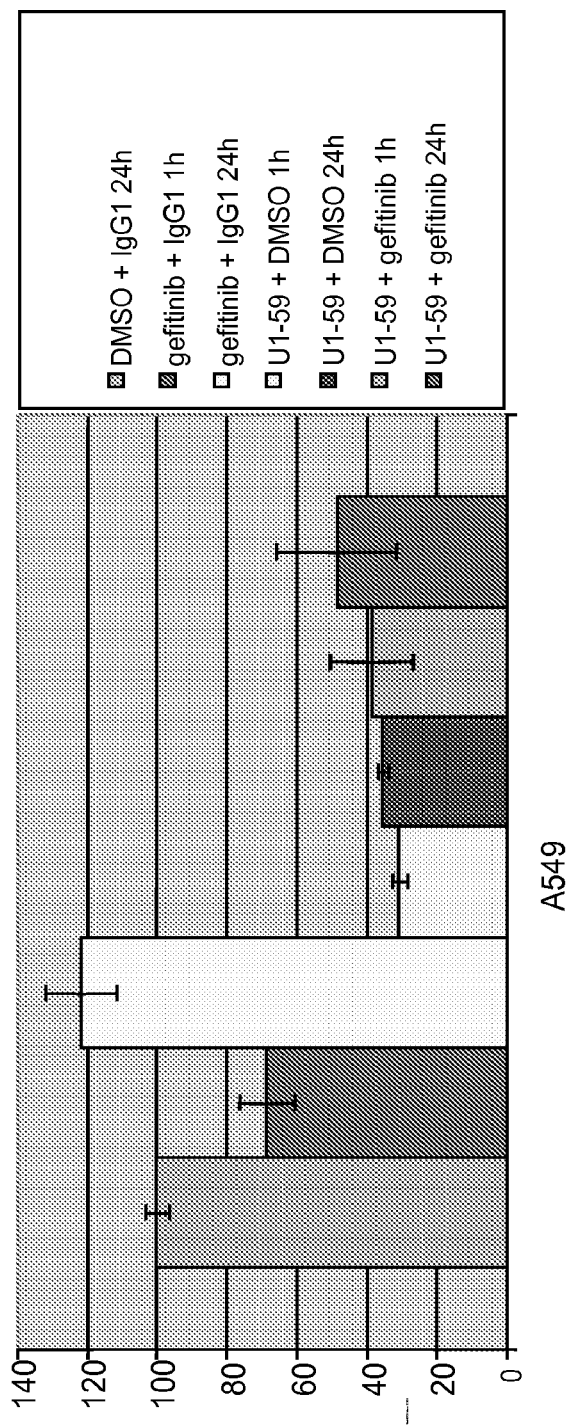
FIG. 20 shows that treatment of A549 NSCLC cells with U1-59 inhibits HER3 phosphorylation and reduces reactivation after treatment with gefitinib. A549 cells were treated with gefitinib, U1-59 or both, and HER3 phosphorylation was evaluated by ELISA analysis. Treatment with gefitinib for 1 hour resulted in partial inhibition of HER phosphorylation, which was reversed to control levels after 24 hours. In contrast, treatment with U1-59 led to greater inhibition of HER phosphorylation that was sustained after 24 hours. Combined treatment with both agents prevented the reversal of inhibition seen after 24 hours in cells treated with gefitinib alone. Experiments were performed in triplicate wells and repeated at least 2 times. Results are expressed as mean±SD.

A549 cells were plated in Ham's F-12 medium (Gibco), all media supplemented with 10% FBS (Hyclone, Logan, Utah) and 1× L-glutamine (Gibco). Cells were serum-starved overnight. The media were changed into fresh serum-free media and cells were treated with 50 µg/ml U1-59 or 5 µM gefitinib alone, or combination of U1-59 and gefitinib, for 1 or 24 hours at 37° C. Cells were washed with cold PBS after their respective treatment time points and lysed using RIPA buffer (20 mM Tris-HCl pH 7.5, 1% Igepal, 1% sodium deoxycholate, 150 mM NaCl, 0.1% SDS, 1% Triton X-100) containing 200 µM phenylmethanesulfonylfluoride (PMSF) (Fluka Biochemica), 200 µM Halt protease inhibitor cocktail kit (Pierce Biotechnology), and 200 µM sodium orthovanadate (Sigma-Aldrich, St. Louis, Mo.). The lysates were passed through QIA shredder columns (Qiagen) and the flow-through quantitated using a spectrophotometer (Beckman Coulter, Fullerton, Calif.). Proteins, 50 µg per well, were analyzed in duplicate for pHER3 using ELISA Duoset (R&D systems) according to manufacturer's protocol. The results are shown in FIG. 20.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 10

CDR Sequences

| AB-Chain | PAT ID: | SEQ ID: | CDR1 | SEQ ID: | CDR2 | SEQ ID: | CDR3 |
|---|---|---|---|---|---|---|---|
| heavy | U1-1 | 235 | GGSINSGDYYWS | 258 | YIYYSGSTYYNPSLKS | 283 | ADYDFWSGYFDY |
| light | U1-1 | 318 | RSQGIRNDALG | 343 | AASSLQS | 360 | LQHNSYPWT |
| heavy | U1-2 | 236 | GGSISSGDYYWS | 259 | YIYYSGSTYYNPSLRS | 283 | ADYDFWSGYFDY |
| light | U1-2 | 318 | RASQGIRNDLG | 343 | AASSLQS | 361 | LQHNGYPWT |
| heavy | U1-3 | 237 | GGSISSGGYYWS | 258 | YIYYSGSTYYNPSLKS | 284 | DGYDSSGYYHGYFDY |

TABLE 10-continued

| CDR Sequences | | | | | | | | |
|---|---|---|---|---|---|---|---|---|
| AB-Chain | PAT ID: | SEQ ID: | CDR1 | SEQ ID: | CDR2 | SEQ ID: | CDR3 |
| light | U1-3 | 319 | KSSQSVLYSSNNKNYLA | 344 | WASTRES | 362 | QQYYSTPLT |
| heavy | U1-4 | 236 | GGSISSGDYYWS | 258 | YIYYSGSTYYNPSLKS | 283 | ADYDFWSGYFDY |
| light | U1-4 | 318 | RASQGIRNDLG | 343 | AASSLQS | 363 | LQHNNYPWT |
| heavy | U1-5 | 236 | GGSISSGDYYWS | 258 | YIYYSGSTYYNPSLKS | 283 | ADYDFWSGYFDY |
| light | U1-5 | 318 | RASQGIRNDLG | 343 | AASSLQS | 364 | LQHNTYPWT |
| heavy | U1-6 | 236 | GGSISSGDYYWS | 258 | YIYYSGSTYYNPSLKS | 285 | ADYDFWNGYFDY |
| light | U1-6 | 318 | RASQGIRNDLG | 343 | AASSLQS | 364 | LQHNTYPWT |
| heavy | U1-7 | 236 | GGSISSGDYYWS | 258 | YIYYSGSTYYNPSLKS | 283 | ADYDFWSGYFDY |
| light | U1-7 | 320 | RASQDIRNDLG | 343 | AASSLQS | 360 | LQHNSYPWT |
| heavy | U1-8 | 238 | GYTLTELSMY | 260 | GFDPEDGETIYAQKFQG | 286 | GWNYVFDY |
| light | U1-8 | 321 | RSSQSLLHSNGYNYLD | 345 | LDSHRAS | 365 | MQALQTPLT |
| heavy | U1-9 | 236 | GGSISSGDYYWS | 258 | YIYYSGSTYYNPSLKS | 285 | ADYDFWNGYFDY |
| light | U1-9 | 320 | RASQDIRNDLG | 343 | AASSLQS | 360 | LQHNSYPWT |
| heavy | U1-10 | 236 | GGSISSGDYYWS | 258 | YIYYSGSTYYNPSLKS | 283 | ADYDFWSGYFDY |
| light | U1-10 | 318 | RASQGIRNDLG | 343 | AASSLQS | 363 | LQHNNYPWT |
| heavy | U1-11 | 236 | GGSISSGDYYWS | 258 | YIYYSGSTYYNPSLKS | 283 | ADYDFWSGYFDY |
| light | U1-11 | 318 | RASQGIRNDLG | 343 | AASSLQS | 364 | LQHNTYPWT |
| heavy | U1-12 | 236 | GGSISSGDYYWS | 258 | YIYYSGSTYYNPSLKS | 283 | ADYDFWSGYFDY |
| light | U1-12 | 318 | RASQGIRNDLG | 343 | AASSLQS | 363 | LQHNNYPWT |
| heavy | U1-13 | 237 | GGSISSGGYYWS | 258 | YIYYSGSTYYNPSLKS | 287 | EDDGMDV |
| light | U1-13 | 322 | RSSQSLLHSNGYNYLE | 346 | LGSNRAS | 366 | MQALQTPIT |
| heavy | U1-14 | 236 | GGSISSGDYYWS | 258 | YIYYSGSTYYNPSLKS | 283 | ADYDFWSGYFDY |
| light | U1-14 | 318 | RASQGIRNDLG | 343 | AASSLQS | 364 | LQHNTYPWT |
| heavy | U1-15 | 239 | GGSVSSGGYYWS | 261 | YIYYSGSTNYNPSLKS | 288 | DGDVDTAMVDAFDI |
| light | U1-15 | 323 | RASQSLSGNYLA | 347 | GASSRAT | 367 | QQYDRSPLT |

TABLE 10-continued

CDR Sequences

| AB-Chain | PAT ID: | SEQ ID: | CDR1 | SEQ ID: | CDR2 | SEQ ID: | CDR3 |
|---|---|---|---|---|---|---|---|
| heavy | U1-16 | 236 | GGSISSGDYYWS | 258 | YIYYSGSTYYNPSLKS | 283 | ADYDFWSGYFDY |
| light | U1-16 | 318 | RASQGIRADLG | 343 | AASSLQS | 360 | LQHNSYPWT |
| heavy | U1-17 | 236 | GGSISSGDYYWS | 262 | YIYYSGSTYYNSSLKS | 283 | ADYDFWSGYFDY |
| light | U1-17 | 318 | RASQGIRNDLG | 343 | AASSLQS | 360 | LQHNSYPWT |
| heavy | U1-18 | 236 | GGSISSGDYYWS | 258 | YIYYSGSTYYNPSLKS | 283 | ADYDFWSGYFDY |
| light | U1-18 | 318 | RSQGIRNDALG | 343 | AASSLQS | 360 | LQHNSYPWT |
| heavy | U1-19 | 236 | GGSISSGDYYWS | 258 | YIYYSGSTYYNPSLKS | 289 | GDYDFWSGEFDY |
| light | U1-19 | | sequence not available | | | | |
| heavy | U1-20 | 237 | GGSISSGGYYWS | 263 | YIYDSGSTYYNPSLKS | 290 | DQGQDGYSYGYGYYYGMDV |
| light | U1-20 | 324 | QASQDISNYLN | 348 | VASNLET | 368 | QQCDNLPLT |
| heavy | U1-21 | 236 | GGSISSGDYYWS | 258 | YIYYSGSTYYNPSLKS | 283 | ADYDFWSGYFDY |
| light | U1-21 | 320 | RASQDIRNDLG | 349 | AASRLQS | 360 | LQHNSYPWT |
| heavy | U1-22 | 236 | GGSISSGDYYWS | 258 | YIYYSGSTYYNPSLKS | 283 | ADYDFWSGYFDY |
| light | U1-22 | 318 | RASQGIRNDLG | 350 | AASSLQN | 360 | LQHNSYPWT |
| heavy | U1-23 | 236 | GGSISSGDYYWS | 258 | YIYYSGSTYYNPSLKS | 283 | ADYDFWSGYFDY |
| light | U1-23 | 318 | RASQGIRNDLG | 343 | AASSLQS | 360 | LQHNSYPWT |
| heavy | U1-24 | 236 | GGSISSGDYYWS | 258 | YIYYSGSTYYNPSLKS | 285 | ADYDFWNGYFDY |
| light | U1-24 | 318 | RASQGIRNDLG | 343 | AASSLQS | 363 | LQHNNYPWT |
| heavy | U1-25 | 236 | GGSISSGDYYWS | 258 | YIYYSGSTYYNPSLKS | 283 | ADYDFWSGYFDY |
| light | U1-25 | 318 | RASQGIRNDLG | 350 | AASSLQN | 360 | LQHNSYPWT |
| heavy | U1-26 | 236 | GGSISSGDYYWS | 258 | YIYYSGSTYYNPSLKS | 291 | ADYDFWSGYFDF |
| light | U1-26 | 318 | RASQGIRNDLG | 343 | AASSLQS | 361 | LQHNGYPWT |
| heavy | U1-27 | 236 | GGSISSGDYYWS | 258 | YIYYSGSTYYNPSLKS | 291 | ADYDFWSGYFDF |
| light | U1-27 | 318 | RASQGIRNDLG | 343 | AASSLQS | 361 | LQHNGYPWT |
| heavy | U1-28 | 236 | GGSISSGDYYWS | 258 | YIYYSGSTYYNPSLKS | 292 | ADYDFWSGYFDS |

TABLE 10-continued

| | | | CDR Sequences | | | | |
|---|---|---|---|---|---|---|---|
| AB-Chain | PAT ID: | SEQ ID: | CDR1 | SEQ ID: | CDR2 | SEQ ID: | CDR3 |
| light | U1-28 | 318 | RASQGIRNDLG | 343 | AASSLQS | 361 | LQHNGYPWT |
| heavy | U1-29 | 240 | GFTFNSYDMH | 264 | VIWYDGSNKYYADSVKG | 293 | DRLCTNGVCYEDYGMDV |
| light | U1-29 | 324 | QASQDISNYLN | 351 | DASNLET | 369 | QHYDTLPLT |
| heavy | U1-30 | 236 | GGSISSGDYYWS | 265 | YIYYSGTTYYNPSLKS | 283 | ADYDFWSGYFDY |
| light | U1-30 | 325 | RAGQGIRNDLG | 343 | AASSLQS | 360 | LQHNSYPWT |
| heavy | U1-31 | 241 | GYTFTNYGIS | 266 | WISAYDGYRNYAQKLQG | 294 | DVQDYGDYDYFDY |
| light | U1-31 | 326 | RASQSISSYLN | 343 | AASSLQS | 370 | QQSYSTPIT |
| heavy | U1-32 | 236 | GGSISSGDYYWS | 265 | YIYYSGTTYYNPSLKS | 283 | ADYDFWSGYFDY |
| light | U1-32 | 325 | RAGQGIRNDLG | 343 | AASSLQS | 360 | LQHNSYPWT |
| heavy | U1-33 | 236 | GGSISSGDYYWS | 258 | YIYYSGSTYYNPSLKS | 295 | ADYDFWSGHFDC |
| light | U1-33 | 327 | RASQGIRDDLG | 352 | AESSLQS | 371 | LQHHSYPWT |
| heavy | U1-34 | 241 | GYTFTNYGIS | 266 | WISAYDGYRNYAQKLQG | 294 | DVQDYGDYDYFDY |
| light | U1-34 | 326 | RASQSISSYLN | 343 | AASSLQS | 370 | QQSYSTPIT |
| heavy | U1-35 | 242 | GFTFSDYYMS | 267 | YISSSGNNIYHADSVKG | 296 | ERYSGYDDPDGFDI |
| light | U1-35 | 328 | QASQDISNYLS | 351 | DASNLET | 372 | QQYDNPPCS |
| heavy | U1-36 | 243 | GGSISSGYYYWS | 268 | YIYYSGTTYYNPSFKS | 297 | ADYDFWSGHFDY |
| light | U1-36 | 318 | RASQGIRNDLG | 343 | AASSLQS | 360 | LQHNSYPWT |
| heavy | U1-37 | 244 | GYTFTSYGIS | 269 | WISAYDGHTNYAQKLQG | 298 | DPHDYSNYEAFDF |
| light | U1-37 | 326 | RASQSISSYLN | 343 | AASSLQS | 370 | QQSYSTPIT |
| heavy | U1-38 | 245 | GFSLSTSGVGVG | 270 | LIYWNDDKRYSPSLKS | 299 | RDEVRGFDY |
| light | U1-38 | 329 | RSSQSLVYSDGYTYLH | 353 | KVSNWDS | 373 | MQGAHWPIT |
| heavy | U1-39 | 246 | GFTVSSNYMS | 271 | VIYSGGSTYYADSVKG | 300 | GQWLDV |
| light | U1-39 | 321 | RSSQSLLHSNGYNYLD | 354 | LGFHRAS | 374 | RQALQTPLT |
| heavy | U1-40 | 237 | GGSISSGGYYWS | 272 | YIYSSGSTYYNPSLKS | 301 | DRELELYYYYGMDV |
| light | U1-40 | 330 | RSSQSLLYSNGYNYLD | 346 | LGSNRAS | 365 | MQALQTPLT |

TABLE 10-continued

CDR Sequences

| AB-Chain | PAT ID: | SEQ ID: | CDR1 | SEQ ID: | CDR2 | SEQ ID: | CDR3 |
|---|---|---|---|---|---|---|---|
| heavy | U1-41 | 237 | GGSISSGGYYWS | 258 | YIYYSGSTYYNPSLKS | 302 | DRELEGYSNYYGVDV |
| light | U1-41 | 331 | RASQAISNYLN | 343 | AASSLQS | 375 | QQNNSLPIT |
| heavy | U1-42 | 247 | GYSFTSYWIG | 273 | IIYPGDSDTRYSPSFQG | 303 | HENYGDYNY |
| light | U1-42 | 332 | RASQSIRSYLN | 343 | AASSLQS | 376 | QQSNGSPLT |
| heavy | U1-43 | 237 | GGSISSGGYYWS | 259 | YIYYSGSTYYNPSLKS | 304 | DREREWDDYGDPQGMDV |
| light | U1-43 | 333 | RASQSISSYLH | 343 | AASSLQS | 377 | QQSYSNPLT |
| heavy | U1-44 | 247 | GYSFTSYWIG | 274 | IIWPGDSDTIYSPSFQG | 303 | HENYGDYNY |
| light | U1-44 | 332 | RASQSIRSYLN | 343 | AASSLQS | 378 | QQSISSPLT |
| heavy | U1-45 | 248 | GYTFTSYDIN | 275 | WMNPNSGDTGYAQVFQG | 305 | FGDLPYDYSYYEWFDP |
| light | U1-45 | 326 | RASQSISSYLN | 343 | AASSLQS | 379 | QQSYSTPLT |
| heavy | U1-46 | 249 | GDSVSSNSAAWN | 276 | RTYYRSKWYNDYAVSVKS | 306 | DLYDFWSGYPYYYGMDV |
| light | U1-46 | | sequence not available | | | | |
| heavy | U1-47 | 249 | GDSVSSNSAAWN | 276 | RTYYRSKWYNDYAVSVKS | 307 | DYYGSGSFYYYYGMDV |
| light | U1-47 | 326 | RASQSISSYLN | 355 | AASNLQS | 380 | QQSYSTPRT |
| heavy | U1-48 | 250 | GGSISSYYWS | 277 | HIYTSGSTNYNPSLKS | 308 | EAIFGVGPYYYYGMDV |
| light | U1-48 | | sequence not available | | | | |
| heavy | U1-49 | 251 | GYTFTGYYMH | 278 | WINPNIGGTNCAQKFQG | 309 | GGRYSSSWSYYYYGMDV |
| light | U1-49 | 334 | KSSQSLLLSDGGTYLY | 356 | EVSNRFS | 381 | MQSMQLPIT |
| heavy | U1-50 | 239 | GGSVSSGGYYWS | 261 | YIYYSGSTNYNPSLKS | 310 | GGDSNYEDYYYYGMDV |
| light | U1-50 | 335 | RASQSISIYLH | 343 | AASSLQS | 382 | QQSYTSPIT |
| heavy | U1-51 | 250 | GGSISSYYWS | 261 | YIYYSGSTNYNPSLKS | 311 | DSSYYDSSGYYLYYYAMDV |
| light | U1-51 | 319 | KSSQSVLYSSNNKNYLA | 344 | WASTRES | 383 | QQYYTTPLT |
| heavy | U1-52 | 237 | GGSISSGGYYWS | 279 | NIYYSGSTYYNPSLKS | 312 | GGTGTNYYYYYGMDV |
| light | U1-52 | 336 | RASQSVSSSYLA | 357 | GASSWAT | 384 | QQYGSSPLT |

TABLE 10-continued

CDR Sequences

| AB-Chain | PAT ID: | SEQ ID: | CDR1 | SEQ ID: | CDR2 | SEQ ID: | CDR3 |
|---|---|---|---|---|---|---|---|
| heavy | U1-53 | 252 | GFTFSIYSMN | 280 | YISSSSSTIYYADSVKG | 313 | DRGDFDAFDI |
| light | U1-53 | 337 | QASQDITNYLN | 351 | DASNLET | 385 | QQCENFPIT |
| heavy | U1-55.1 | 253 | GGSVSSGGYYWN | 281 | YINYSGSTNYNPSLKS | 301 | DRELELYYYYYGMDV |
| light | U1-55.1 | | same as U1-55 | | | | |
| heavy | U1-55 | | will be same as U1-55.1 | | | | |
| light | U1-55 | 338 | RSSQSLLYSNGYKYLD | 346 | LGSNRAS | 366 | MQALQTPIT |
| heavy | U1-57.1 | | same as U1-57 | | | | |
| light | U1-57.1 | 338 | RSSQSLLYSNGYKYLD | 346 | LGSNRAS | 366 | MQALQTPIT |
| heavy | U1-57 | 254 | GGSVSSGGYYWN | 281 | YINYSGSTNYNPSLKS | 301 | DRELELYYYYYGMDV |
| light | U1-57 | | will be same as U1-57.1 | | | | |
| heavy | U1-58 | 255 | GFTFSSYGMH | 264 | VIWYDGSNKYYADSVKG | 314 | AARLDYYYGMDV |
| light | U1-58 | 339 | RASQSINSYLN | 358 | GASGLQS | 386 | QQSYSSPLT |
| heavy | U1-59 | 256 | GGSFSGYYWS | 282 | EINHSGSTNYNPSLKS | 315 | DKWTWYFDL |
| light | U1-59 | 340 | RSSQSVLYSSSNRNYLA | 344 | WASTRES | 387 | QQYYSTPRT |
| heavy | U1-61.1 | 257 | GVSISSGGYYWS | 258 | YIYYSGSTYYNPSLKS | 316 | DSESEYSSSSNYGMDV |
| light | U1-61.1 | | same as U1-61.1 | | | | |
| heavy | U1-61 | 257 | GVSISSGGYYWS | 258 | YIYYSGSTYYNPSLKS | 316 | DSESEYSSSSNYGMDV |
| light | U1-61 | 341 | RASQTISSYLN | 359 | AASSLQG | 377 | QQSYSNPLT |
| heavy | U1-62 | 247 | GYSFTSYWIG | 273 | IIYPGDSDTRYSPSFQG | 317 | QMAGNYYYGMDV |
| light | U1-62 | 342 | RASQSVISIYLA | 347 | GASSRAT | 388 | QQYGSSPCS |

What is claimed is:

1. A method of treating a cancer associated with HER-3 in a subject, comprising administering to the subject a first agent and a second agent, wherein said first agent is an isolated antigen-binding protein which binds to HER-3, comprising:
   (a) a heavy chain amino acid sequence that comprises a CDRH1 having the sequence of SEQ ID NO:236, a CDRH2 having the sequence of SEQ ID NO:258, and a CDRH3 having the sequence of SEQ ID NO:283; and a light chain amino acid sequence that comprises a CDRL1 having the sequence of SEQ ID NO:320, a CDRL2 having the sequence of SEQ ID NO:343, and a CDRL3 having the sequence of SEQ ID NO:360;
   (b) a heavy chain amino acid sequence that comprises a CDRH1 having the sequence of SEQ ID NO:236, a CDRH2 having the sequence of SEQ ID NO:258, and a CDRH3 having the sequence of SEQ ID NO:285; and a light chain amino acid sequence that comprises a CDRL1 having the sequence of SEQ ID No:320, a CDRL2 having the sequence of SEQ ID NO:343, and a CDRL3 having the sequence of SEQ ID NO:360;
   (c) a heavy chain amino acid sequence that comprises a CDRH1 having the sequence of SEQ ID NO:251, a CDRH2 having the sequence of SEQ ID NO:278, and a CDRH3 having the sequence of SEQ ID NO:309; and a light chain amino acid sequence that comprises a CDRL1 having the sequence of SEQ ID NO:334, a CDRL2 having the sequence of SEQ ID NO:356, and a CDRL3 having the sequence of SEQ ID NO:381; or
   (d) a heavy chain amino acid sequence that comprises a CDRH1 having the sequence of SEQ ID NO:256, a CDRH2 having the sequence of SEQ ID NO:282, and a CDRH3 having the sequence of SEQ ID NO:315; and a light chain amino acid sequence that comprises a CDRL1 having the sequence of SEQ ID NO:340, a CDRL2 having the sequence of SEQ ID NO:344, and a CDRL3 having the sequence of SEQ ID NO:387;
   and said second agent is cetuximab.

2. The method of claim 1, wherein said first agent is an antigen-binding protein that binds to HER-3, and comprises the heavy chain amino acid sequence of SEQ ID NO:42 and the light chain amino acid sequence of SEQ ID NO:44.

3. The method of claim 1, wherein said first agent is an antigen-binding protein that binds to HER-3, and comprises the heavy chain amino acid sequence of SEQ ID NO:54 and the light chain amino acid sequence of SEQ ID NO: 56.

4. The method of claim 1, wherein said first agent is an antigen-binding protein that binds to HER-3, and comprises the heavy chain amino acid sequence of SEQ ID NO:70 and the light chain amino acid sequence of SEQ ID NO:72.

5. The method of claim 1, wherein said first agent is an antigen-binding protein that binds to HER-3, and comprises the heavy chain amino acid sequence of SEQ ID NO:92 and the light chain amino acid sequence of SEQ ID NO:94.

6. The method of claim 1, wherein said first agent is an antigen-binding protein that binds to HER-3, and comprises the heavy chain amino acid sequence of SEQ ID NO:96 and the light chain amino acid sequence of SEQ ID NO:98.

7. The method of claim 1, wherein said antigen-binding protein is directed against the extracellular domain of HER-3.

8. The method of claim 1, wherein binding of said antigen-binding protein to HER-3 reduces HER-3-mediated signal transduction.

9. The method of claim 1, wherein binding of said antigen-binding protein to HER-3 reduces HER-3 phosphorylation.

10. The method of any one of claim 1, wherein binding of said antigen-binding protein to HER-3 reduces cell proliferation.

11. The method of any one of claim 1, wherein binding of said antigen-binding protein to HER-3 reduces cell migration.

12. The method of any one of claim 1, wherein binding of said antigen-binding protein to HER-3 increases the down-regulation of HER-3.

13. The method of any one of claim 1, wherein said antigen-binding protein that binds to HER-3 is an antibody.

14. The method of claim 13, wherein said antibody is a monoclonal antibody, a recombinant antibody, a human antibody, a chimeric antibody, a multispecific antibody, or an antibody fragment thereof.

15. The method of claim 14, wherein said antibody fragment is a Fab fragment, a Fab' fragment, a F(ab')2 fragment, a Fv fragment, a diabody, or a single chain antibody molecule.

16. The method of claim 14, wherein said antibody is of the IgG1-, IgG2-, IgG3- or IgG4-type.

17. The method of claim 1, wherein said antigen-binding protein is coupled to an effector group.

18. The method of claim 17, wherein said effector group is a radioisotope or radionuclide, a toxin, or a therapeutic or chemotherapeutic group.

19. The method of claim 18, wherein said therapeutic or chemotherapeutic group is selected from the group consisting of calicheamicin, auristatin-PE, geldanamycin, maytansine and derivatives thereof.

20. The method of claim 1, optionally comprising administering a further therapeutic agent and/or radiation therapy.

21. The method of claim 20, wherein the further therapeutic agent is an anti-neoplastic agent.

22. The method of claim 21, wherein the anti-neoplastic agent is an anti-tumor antibody or a chemotherapeutic agent.

23. The method of claim 22, wherein the chemotherapeutic agent is selected from the group consisting of capecitabine, anthracycline, doxorubicin, cyclophosphamide, paclitaxel, docetaxel, cisplatin, gemcitabine, and carboplatin.

24. The method of claim 1, wherein said first agent and said second agent are administered by intravenous, subcutaneous, intramuscular or oral administration.

25. The method of claim 1, wherein said cancer is selected from the group consisting of breast cancer, ovarian cancer, prostate cancer, colon cancer, renal cancer, lung cancer, pancreatic cancer, epidermoid carcinoma, fibrosarcoma, melanoma, head and neck cancer, nasopharyngeal carcinoma, and squamous cell carcinoma.

26. The method of claim 25, comprising administering said first agent at a dose of about 1 to about 20 mg/kg body weight, at least once every 6 weeks.

27. The method of claim 25, comprising administering said second agent at a dose of about 1 to about 20 mg/kg body weight, at least once every 6 weeks.

28. The method of claim 25, further comprising, after the administering, monitoring the therapeutic outcome.

29. A method of treating a cancer associated with HER-3 in a subject, comprising administering to the subject a first agent and a second agent, wherein said first agent is an isolated binding protein which binds to HER-3, comprising a heavy chain amino acid sequence selected from the group consisting of SEQ ID NOs:42, 54, 70, 92, and 96, and a light chain, and said second agent is cetuximab.

30. A method of treating a cancer associated with HER-3 in a subject, comprising administering to the subject a first agent and a second agent, wherein said first agent is an isolated binding protein which binds to HER-3, comprising a light chain amino acid sequence selected from the group consisting of SEQ ID NOs:44, 56, 72, 94, and 98, and a heavy chain, and said second agent is cetuximab.

31. A method of treating a cancer associated with HER-3 in a subject, comprising administering to the subject a first agent and a second agent, wherein said first agent is an antigen-binding protein that binds to HER-3 and comprises the heavy chain amino acid sequence of SEQ ID NO:70 and the light chain amino acid sequence of SEQ ID NO:72, and wherein said second agent is cetuximab.

* * * * *